(12) United States Patent
Culiat

(10) Patent No.: US 10,752,663 B2
(45) Date of Patent: Aug. 25, 2020

(54) METHODS AND COMPOSITIONS FOR REGENERATING TISSUES

(71) Applicant: NELLONE THERAPEUTICS, INC., Oak Ridge, TN (US)

(72) Inventor: Cymbeline T. Culiat, Oak Ridge, TN (US)

(73) Assignee: NELLONE THERAPEUTICS, INC., Oak Ridge, TN (US)

( * ) Notice: Subject to any disclaimer, the term of this patent is extended or adjusted under 35 U.S.C. 154(b) by 0 days.

(21) Appl. No.: 15/690,093

(22) Filed: Aug. 29, 2017

(65) Prior Publication Data

US 2018/0057550 A1 Mar. 1, 2018

Related U.S. Application Data

(60) Provisional application No. 62/380,920, filed on Aug. 29, 2016.

(51) Int. Cl.
*A61K 38/17* (2006.01)
*C07K 14/47* (2006.01)

(52) U.S. Cl.
CPC ...... *C07K 14/4705* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 7,052,856 B2 | 5/2006 | Ting | |
| 7,910,542 B2 | 3/2011 | Culiat | |
| 8,722,625 B2 | 5/2014 | Culiat | |
| 8,877,176 B2 | 11/2014 | Culiat | |
| 9,920,104 B2 | 3/2018 | Culiat | |
| 2006/0025367 A1 | 2/2006 | Simari | |
| 2006/0053503 A1 | 3/2006 | Culiat | |
| 2006/0111313 A1 | 3/2006 | Ting et al. | |
| 2006/0228392 A1 | 10/2006 | Ting | |
| 2006/0292670 A1 | 12/2006 | Ting et al. | |
| 2007/0128697 A1 | 6/2007 | Ting et al. | |
| 2007/0134291 A1 | 6/2007 | Ting | |
| 2009/0087415 A1 | 4/2009 | Culiat | |
| 2011/0236325 A1* | 9/2011 | Mitchell | A61K 38/17 424/59 |
| 2014/0205577 A1 | 7/2014 | Culiat | |

FOREIGN PATENT DOCUMENTS

| | | |
|---|---|---|
| WO | 2002100426 | 12/2002 |
| WO | 2004024893 | 3/2004 |
| WO | 2004072100 A2 | 8/2004 |
| WO | 2006089023 | 8/2006 |
| WO | 2008073631 | 6/2008 |
| WO | 2008109274 | 9/2008 |
| WO | 2009042859 | 4/2009 |
| WO | 2009045800 | 4/2009 |
| WO | 2011091244 | 7/2011 |

OTHER PUBLICATIONS

Siu et al., Tissue Eng. Part A, 2012, vol. 18(3-4):252-261.*
Nakamura et al., J. Biol. Chem., 2012, vol. 287(5):3282-3291.*
Lehto, et al. Skeletal Muscle Injury—Molecular Changes in the Collagen During Healing. 1985. Research in Experimental Medicine. 185:95-106.
Lecker, et al. Multiple types of skeletal muscle atrophy involve a common program of changes in gene expression. 2004. The FASEB Journal. vol. 18, No. 1, pp. 39-51.
Martin, "Wound Healing—Aiming for Perfect Skin Regeneration," Science. 1997. vol. 276. 75-81.
Ruszczak, Effect of collagen matrices on dermal wound healing. 2003. Advanced Drug Delivery Reviews. 55:1595-1611.
Hannes Hentze, et al., "Teratoma Formation by Human Embryonic Stem Cells: Evaluation of Essential Parameters for Future Safety Studies," Stem Cell Research, 2009, pp. 198-210, vol. 2.
Karin Norrman, et al., "Quantitative Comparison of Constitutive Promoters in Human ES Cells," PLoS One, 2010, pp. 1-10, vol. 5, Issue 8.
Capucine Trollet, et al., "Gene Therapy for Muscular Dystrophy: Current Progress and Future Prospects," Expert Opinion Biol. Ther., 2009, pp. 849-866, vol. 9, Issue 7.
Luigi Naldini, et al., "Ex vivo Gene Transfer and correction for Cell-Based Therapies," Nature Reviews Genetics, 2011, pp. 301-315, vol. 12.
H. K. Raymon, et al., "Application of ex Vivo Gene Therapy in the Treatment of Parkinson's Disease," Experimental Neurology, 1997, pp. 82-91, vol. 144.
J. Prieto, et al., "Cells as Vehicles for Therapeutic Genes to Treat Liver Diseases," Gene Therapy, 2008, pp. 765-771, vol. 15.
Franke et al., "Systematic Association Mapping Identifies NELL1 as a Novel IBD Disease Gene," PLoS One, 2007, pp. 1-13, vol. 8(e691) and supplemental documents.
Aghaloo et al., "A Study of the Role of Nell-1 Gene Modified Goat Bone Marrow Stromal Cells in Promoting New Bone Formation," Molecular Therapy, 2007, pp. 1872-1880, vol. 15(10).
Liu et al., "Characterizing the Role of the Nell1 Gene in Cardiovascular Development," U.S. Department of Energy Journal of Undergraduate Research, 2007, pp. 63-70.
Liu, L.Y. et al., Characterizing the Role of the Nell1 Gene in Cardiovascular Development, American Association for the Advancement of Science, San Francisco, CA, Presentation on Feb. 15-17, 2007 (Abstract).
Desai, J., et al. "Nell1, A Gene Coding for a Novel PKC-binding Protein is a Candidate for Late-Gestation Recessive Lethal Mutations at the l7R6 Locus," 16th International Mouse Genome Conference, San Antonio, TX, Presentation on Nov. 17-21, 2002 (Abstract).

(Continued)

*Primary Examiner* — Xiaozhen Xie
(74) *Attorney, Agent, or Firm* — Womble Bond Dickinson (US) LLP

(57) ABSTRACT

Provided are methods for promoting the healing of injuries to tendons and ligaments by administering a NELL1 protein or a nucleic acid encoding a NELL1 protein to a subject in need thereof. Also provided are NELL1 compositions and methods for promoting tissue regeneration, promoting the healing of wounds, and enhancing fibroblast migration, proliferation, or both migration and proliferation.

7 Claims, 10 Drawing Sheets

Specification includes a Sequence Listing.

(56) References Cited

OTHER PUBLICATIONS

Desai, J., et al., "Nell1-deficient Mice have Reduced Expression of Extracellular Matrix Proteins Causing Cranial and Vertebral Defects," 20th International Mouse Genome Conference, Charleston, SC, Presentation on No. 14, 2006 (Abstract).
Desai, J., et al., "Characterization of Mouse Nell1: A Gene Coding for a Novel PKC-binding Protein," Women in Science Meeting, ORNL, Oak Ridge, TN, Presentation on May 1, 2006 (Abstract).
Liu, L., et al., "Characterizing the Role of the Nell1 Gene in Cardiovascular Development," Oak Ridge Science Semester Poster Presentation, ORNL, Oak Ridge, TN, Presentation on Aug. 11, 2006 (Poster).
Tsutsumi, S., et al., "The Novel Gene Encoding a Putative Transmembrane Protein is Mutated in Gnathodiaphyseal Dysplasia (GDD)," Am. J. Hum. Genet, 2004, pp. 1255-1261, vol. 74.
Zhang, X., et al., "Nell-1 Induces Acrania-Like Cranioskeletal Deformities During Mouse Embryonic Development," Lab Invest, 2006, pp. 633-644, vol. 86, Issue 7.
Zhang, X., et al., "Overexpression of Nell1, a Craniosynostosis-Associated Gene, Induces Apoptosis in Osteoblasts During Craniofacial Development," J Bone Miner Res, 2003, pp. 2126-2134, vol. 18, Issue 12.
Ting, K., et al., "Human NELL-1 Expressed in Unilateral Coronal Synostosis," J Bone Miner Res, 1999, pp. 80-89, vol. 14, Issue 1.
Aghaloo, T., et al., "Nell-1-Induced Bone Regeneration in Calvarial Defects," Am J Pathol, 2006, pp. 903-915, vol. 169, Issue 3.
Zhang, X., et al., "Craniosynostosis in Transgenic Mice Overexpressing Nell-1," J Clin Invest, 2002, pp. 861-870, vol. 110, Issue 6.
Cowan, C.M., et al., "Nell-1 Induced Bone Formation Within the Distracted Intermaxillary Suture," Bone, 2006, pp. 48-58, vol. 38, Issue 1.
Desai, J., et al., "Nell1-Deficient Mice Have Reduced Expression of Extracellular Matrix Proteins Causing Cranial and Vertebral Defects," Hum Mol. Genet, 2006, pp. 1329-1341, vol. 15, Issue 8.
Maeda, K. et al., Brain Specific Human Genes, NELL1 and NELL2, are Predominantly Expressed in Neuroblastoma and Other Embryonal Neuroephithelial Tumors, Neurol Med Chir (Tokyo), 2001, pp. 582-588, vol. 41, Issue 12.
Luce, M.J., et al., "The Neuronal EGF-related Genes NELL1 and NELL2 are Expressed in Hemopoietic Cells and Developmentally Regulated in the B Lineage," Gene, 1999, pp. 121-126, vol. 231, Issue 1-2.
Kuroda, S. et al., "Biochemical Characterization and Expression Analysis of Neural Thrombospondin-1-like Proteins NELL1 and NELL2," Biochem Biophys Res Commun, 1999, pp. 79-86, vol. 265, Issue 1.
Watanabe, T.K., et al., "Cloning and Characterization of Two Novel Human cDNAs (NELL1 and NELL2) Encoding Proteins with Six EGF-Like Repeats," Genomics, 1996, pp. 273-276, vol. 38.
Shen, Y., et al. "Knock Down of NELL2 in Wilms' Tumor Cell Line," Journal of the William Jarvie Society, 2006, p. 41, vol. 49, Abstract.
Santini, M. P. et al., "Signalling Pathways in Cardiac Rengeneration," Novartis Found Symp, 2006, pp. 228-243, vol. 274.
Rubart, M., et al., "Cell-Based Approaches for Cardiac Repair," Ann NY Acad Sci, 2006, pp. 34-38, vol. 1080.
Ott, H.C., et al., "From Cardiac Repair to Cardiac Regeneration—Ready to Translate?," Expert Opin Biol Ther., 2006, pp. 867-878, vol. 6, Issue 9.
Rosenthal, N., et al., "Growth Factor Enhancement of Cardiac Regeneration," Cell Transplant. 15 (Suppl1): S41-S45, 2006.
Kuroda, S., et al., "Involvement of Epidermal Growth Factor-Like Domain of NELL Proteins in the Novel Protein-Protein Interaction with Protein Kinase C," Biochem Biophys Res Commun, 1999, pp. 752-757, vol. 265, Issue 3.
Haider, H.K.H., "Bone Marrow Cells for Cardiac Regeneration and Repair: Current Status and Issues," Expert Rev Cardiovasc Ther., 2006, pp. 557-568, vol. 4, Issue 4.
Orlic, D., et al., "Transplanted Adult Bone Marrow Cells Repair Myocardial Infarcts in Mice," Ann NY Acad Sci, 2001, pp. 221-230, vol. 938, Issue 1.
Lu, S.S., et al., "The Osteoinductive Properties of Nell-1 in a Rat Spinal Fusion Model," The Spine Journal, 2007, pp. 50-60, vol. 7, Issue 1.
The Reporter, No. 78 (Jun. 2006), published by Oak Ridge National Laboratory, accessible on line at http://www.oml.gov/info/reporter/no78/June06 dw.htm.
Ekser, et al., "Clinical Xenotransplantation: the Next Medical Revolution?" The Lancet, 2012, vol. 379, pp. 672-683.
Diwan, A.D., et al., "Current Concepts in Interverterbral Disk Restoration," Orthopedic Clinics of North America, 2000, pp. 453-464, vol. 31, No. 3.
Rinchik, E.M., et al., "Functional Annotation of Mammalian Genomic DNA Sequence by Chemical Mutagenesis: A Fine-Structure Genetic Mutation Map of a 1- to 2-cM Segment of Mouse Chromosome 7 Corresponding to Human Chromosome 11p14p15," PNAS, 2002, pp. 844-849, vol. 99, Issue 2.
Culiat, C.T., et al., Nell1: A Candidate Gene for ENU-Induced Recessive Lethal Mutaitons at the 17R6 Locus and Potential Mouse Models for Human Neonatal Unilateral Coronal Synostosis (UCS),: International Mammalian Genome Society, 15th International Mouse Genome Conference, 2001.
Culiat, C.T., et al., "Nell1: A Candidate Gene for ENU-Induced Recessive Lethal Mutations at the 17R6 Locus and Potential Mouse Models for Human Neonatal Unilateral Coronal Synostosis (UCS)," Jan. 27-31, 2002 (abstract).
Bareggi, R., et al., "Protein Kinase C (PKC) Isoenzymes Exhibit Specific Expression in the Vertebral Column of Human Fetuses," J. Biol. Res. 1995, pp. 83-91, LXXI.
Yamamoto, et al., "Regulation of Bone Morphogenetic Proteins in Early Embryonic Development," Naturwissenschaften, 2004, pp. 519-534, vol. 91.
Cowan, et al., "Synergistic Effects of Nell-1 and BMP-2 on the Osteogenic Differentiation of Myoblasts," J. Bone Mineral Res., 2007, pp. 918-930, vol. 22.
Schmitt, et al., "BMP2 Initiates Chondrogenic Lineage Development of Adult Human Mesenchymal Stem Cells in High-Density Culture," Differentiation, 2003, pp. 567-577, vol. 71, Issue 9-10.
Pettit, et al., "The Development of Site-Specific Drug-Delivery Systems for Protein and Peptide Biopharmaceuticals," Trends in Biotechnology, 1998, pp. 343-349, vol. 16.
Wells, J.A., "Additivity of Mutational Effects in Proteins," Biochemistry, 1990, pp. 8509-8517, vol. 29, Issue 37.
Ngo, et al., "Computational Complexity, Protein Structure Prediction, and the Levinthal Paradox," In Merz and La Grand (Eds.) The Protein Folding Problem and Tertiary Structure Prediction, Birkhause: Boston, 1994, pp. 491-495.
Lin, et al., "Coagulation Dysregulation as a Barrier to Xenotransplantation in the Primate," Transplant Immunology, 2009, pp. 75-80, vol. 21.
Strauer, et al., "Stem Cell Therapy in Perspective," Circulation, 2003, pp. 929-934, vol. 107.
Lian Li, et al., "Effects of Administration Route on Migration and distribution of Neural Progenitor Cells Transplanted into Rats with Focal Cerebral Ischemia, and MRI Study," J. Cerebral Blood Flow and Met., 2010, pp. 653-663, vol. 30.
Yang, et al., "In vitro and in vivo Induction of Bone Formation based on ex vivo Gene Therapy Using Rat Adipose-Derived Adult Stem Cells Expressing BMP-7," Cytotherapy, 2005, pp. 273-281, vol. 7, Issue 3.
Kuroda, et al., "Biochemical Characterization and Expression Analysis of Neural Thrombospondin-1-like Proteins NELL1 and NELL2," Biochemical and Biophysical Res. Comm,1999, pp. 79-86, vol. 265.
Zhang, et al., "Craniosynostosis in Trangenic Mice Overexpressing Nell-1," Journal of Clinical Investigation, 2002, pp. 861-870, vol. 110.
James, et al., "A New Function of Nell-1 Protein in Repressing Adipogenic Differentiation," Biochemical and Biophyscial Res. Comm., 2011, pp. 126-131, vol. 411.

(56) References Cited

OTHER PUBLICATIONS

Narang, et al., "Biological and Biomaterial Approaches for Improved Islet Transplantation," Pharmacological Reviews, 2006, pp. 194-243, vol. 58, Issue 2.
Rich, "Single-center study of 83 horses with suspensory injuries treated with adipose-derived stem and regenerative cells," Stem Cell Discovery, 2014, vol. 4, pp. 44-53.
Nakamura, et al., "Oligomerization-induced conformational change in the C-terminal region of Nel-like Molecule 1 (NELL1) protein is necessary for the efficient mediation of murine MC3T3-E1 cell adhesion and spreading," The Journal of Biological Chemistry, 2014, vol. 289, No. 14, pp. 9781-9794.
Hasebe, et al., "The C-terminal region of NELL1 mediates osteoblastic cell adhesion through integrin $\alpha 3\beta 1$," FEBS Letters, 2012, vol. 586, pp. 2500-2506.
Hasebe, et al., "Efficient production and characterization of recombinant human NELL1 protein in human embryonic kidney 293-F cells," Mol Biotechnol, 2012, vol. 51, Iss. 1, pp. 58-66.
Askarinam et al., "Human Perivascular Stem Cells Show Enhanced Osteogenesis and Vasculogenesis with Nel-Like Molecule 1 Protein," 2013, Tissue Engineering: Part A, 19(11-12):1386-1397.
Bassetto et al., "Regenerative Medicine for Tendon Regeneration and Repair: The Role of Bioscaffolds and Mechanical Loading," 2011, Biomaterials Science and Engineering, Ch. 18, Ed. R. Pignatello, InTech, pp. 369-386.
Bi et al., "Identification of tendon stem/progenitor cells and the role of the extracellular matrix in their niche," Nov. 2007, Nature Medicine, 13:1219-1227.
Briggs, "Tackling Tendon and Ligament Injuries," Jun. 3, 2011, The Horse, 7 pp.
Caudill, "Stem Cell Therapy," The American Quarter Horse Racing Journal, www.americashorsedaily.com, Oct. 15, 2015, 6 pp.
Connizzo et al., "Regulatory Role of Collagen V in Establishing Mechanical Properties of Tendons and Ligaments is Tissue Dependent," Jun. 2015, J Orthopaedic Research, 33:882-888.
Davis et al., "MMP inhibition as a potential method to augment the healing of skeletal muscle and tendon extracellular matrix," 2013, J Appl Physiol, 115:884-891.
Endo et al., "High-throughput, genome-scale protein production method based on the wheat germ cell-free expression system," 2003, Biotechnol. Adv. 21(8):695-713.
Estrada et al., "Comparison of healing in forelimb and hindlimb surgically induced core lesions of the equine superficial digital flexor tendon," 2014, Vet Comp Orthop Traumatol, 27(05):358-365.
Fortier et al., "Regenerative Medicine for Tendinous and Ligamentous Injuries of Sport Horses," 2008, Vet Clin Equine, 24:191-201.
Gelfand et al., "Surrogate Endpoints for the Treatment of Venous Leg Ulcers," 2002, J Invest Dermatol, 119:1420-1425.
Gomez et al., "Effects of 3 biologic dressings on healing of cutaneous wounds on the limbs of horse," 2004, The Canadian Journal of Veterinary Research, 68:49-55.
Godwin et al., "Implantation of bone marrow-derived mesenchymal stem cells demonstrates improved outcome in horses with overstrain injury of the superficial digital flexor tendon," 2012, Equine Veterinary Journal, 44:25-32.
Hamilton, "Functional role of periostin in development and wound repair: implications for connective tissue disease," 2008, J Cell Commun Signal, 2:9-17.
Ituarte et al., "Anti-inflammatory Properties of Nell-1 on Human Articular Chondrocytes In Vivo," ORS 2014 Annual Meeting, Poster No. 0362.
James et al., "NELL-1 in the treatment of osteoporotic bone loss," 2015, Nature Communications, 6:7362, 14 pp.
Jin et al., "Hypermethylation of the nel-like 1 gene is a common and early event and is associated with poor prognosis in early-stage esophageal adenocarcinoma," 2007, Oncogene, 26:6332-6340.
Juneja et al., "Defects in Tendon, Ligament, and Enthesis in Response to Genetic Alterations in Key Proteoglycans and Glycoproteins: A Review," 2013, Arthritis 2013:1-30.

Lee et al., "Effect of Nell-1 Delivery on Chondrocyte Proliferation and Cartilaginous Extracellular Matrix Deposition," 2010, Tissue Engineering: Part A, 16(5):1791-1800.
Li et al., "Neural EGFL-like 1 is a Downstream Regulator of Runt-Related Transcription Factor 2 in Chondrogenic Differentiation and Maturation," May 2017, Am J Pathol, 187(5):963-972.
Li et al., "Nell-1 Enhances Bone Regeneration in a Rat Critical-Sized Femoral Segmental Defect Model," Feb. 2011, Plast Reconstr Surg, 127(2):580-587.
Lui, "Stem cell technology for tendon regeneration: current status, challenges, and future research directions," 2015, Stem Cells and Cloning: Advances and Applications, 8:163-174.
Madin et al., "A highly efficient and robust cell-free protein synthesis system prepared from wheat embryos: Plants apparently contain a suicide system directed at ribosomes," Jan. 18, 2000, Proc Natl Acad Sci USA, 97(2):559-564.
Matsuhashi et al., "New Gene, nel, Encoding a Mr 93 K Protein With EGF-Like Repeats Is Strongly Expressed in Neural Tissues of Early Stage Chick Embryos," 1995, Developmental Dynamics, 203:212-222.
Mitchell et al., "Nell1 Protein Reduces the Number of Sunburned Cells and Modulates the Inflammatory Response after UV-induced Damage in a 3D Human Skin Model," Mar. 16-20, 2012, 70th Annual Meeting of the American Academy of Dermatology, San Diego, CA.
Morgan et al., "Effects of extracorporeal shock wave therapy on wounds of the distal portion of the limbs in horses," May 1, 2009, J Am Vet Med Assoc, 234(9):1154-1161.
Mori et al., "A Genome-Wide Search Identifies Epigenetic Silencing of Somatostatin, Tachykini-1, and 5 Other Genes in Colon Cancer," 2006, Gastroenterology, 131:797-808.
Nemoto et al., "Tenascin-C Expression in Equine Tendon-derived Cells During Proliferation and Migration," 2013, J Equine Sci, 24(2):17-24.
Nixon et al., "Effect of adipose-derived nucleated cell fractions on tendon repair in horses with collagenase-induced tendinitis," Jul. 2008, Am J Vet Res, 69(7):928-937.
Oke, "Regenerative Therapy Trends and Techniques in Horses," May 18, 2016, Article #37581, pp. 1-4.
Pakvasa et al., "Neural EGF-like protein 1 (NELL1-): Signaling crosstalk in mesenchymal stem cells and applications in regenerative medicine," 2017, Genes & Diseases, 4:127-137.
Pauly et al., "BMP2 and BMP7 affect human rotator cuff tendon cells in vitro," 2011, J Shoulder Elbow Surg, pp. 1-10.
Richardson et al., "Stem cells in veterinary medicine—Attempts at regenerating equine tendon after injury," Oct. 2007, Trends in Biotechnology, pp. 1-10.
Sawasaki et al., "Construction of an efficient expression vector for coupled transcription/translation in a wheat germ cell-free system," 2000, Nucleic Acids Symposium Series, 44:9-10.
Sawasaki et al., "A cell-free protein synthesis system for high-throughput proteomics," Nov. 12, 2002, Proc Natl Acad Sci USA, 99(23):14652-14657.
Schramme et al., "A surgical tendonitis model in horses: Technique, clinical, ultrasonographic and histological characterization," 2010, Vet Comp Orthop Traumatol, 23(04):231-239.
Schumacher et al., "Kinetics of healing of grafted and nongrafted wounds on the distal portion of the forelimbs of horses," 1992, Am J Vet Res 53(9):1568-1571—Abstract only.
Schwarting et al., "Bone Morphogenetic Protein 7 (BMP-7) Influences Tendon-Bone Integration In Vitro," Feb. 2, 2015, PLoS One, 10(2):1-17.
September et al., "Tendon and ligament injuries: the genetic component," 2007, Br J Sports Med, 41:241-246.
Shen et al., "Nell-1 Promotes Cell Adhesion and Differentiation via Integrin$\beta 1$," 2012, J of Cellular Biochemistry, 113:3620-3628.
Shen et al., "BMP2-Induced Inflammation Can Be Suppressed by the Osteoinductive Growth Factor NELL-1," Nov. 2013, Tissue Eng Part A, 19(21-22):2390-2401.
Siu et al., "Nell-1 Protein Promotes Bone Formation in a Sheep Spinal Fusion Model," 2011, Tissue Eng, Part A, 17(7-8):1123-1135.

(56) References Cited

OTHER PUBLICATIONS

Sun et al., "Targeted Deletion of Collagen V in Tendons and Ligaments Results in a Classic Ehlers-Danlos Syndrome Joint Phenotype," May 2015, Am J Pathol 185(5):1436-1447.

Tan, "A Review and Update on Tendon and Ligament Injuries in Horses," Mar. 30, 2016, The Horse, pp. 1-7.

Taylor et al., "Gene expression markers of tendon fibroblasts in normal and diseased tissue compared to monolayer and three dimensional culture systems," 2009, BMC Musculoskeletal Disorders, 10:27, 10 pp.

Tempfer et al., "Perivascular cells of the supraspinatus tendon express both tendon- and stem cell-related markers," Histochem Cell Biol, 2009, 131:733-741.

Theoret, "Wound Repair in the Horse: Problems and Proposed Innovative Solutions," 2004, Clin Tech Equine Pract, 3:134-140.

Thomas, A-Cell Therapy Offers Renewed Hope for Horses Incurring Tendon and Ligament Injuries, Sep. 12, 2005, The Chronicle of the Horse, pp. 134-137.

Turner et al., "Human NELL1 Protein Augments Constructive Tissue Remodeling with Biologic Scaffolds," 2013, Cells Tissues Organs, 2013, DOI: 10.1159/000356491.

Watts et al., "A collagenase gel/physical defect model for controlled induction of superficial digital tendonitis," 2012, Equine Veterinary Journal, 44(5):576-586.

Xue et al., "NELL1 promotes high-quality bone regeneration in rat femoral distraction osteogenesis model," 2011, Bone, 48:485-495.

Yang et al., "Tendon and Ligament Regeneration and Repair: Clinical Relevance and Developmental Paradigm," Sep. 2013, Birth Defects Res C Embryo Today, 99(3):203-222.

Zhang et al., "Bioactivity and circulation time of PEGylated NELL-1 in mice and the potential for osteoporosis therapy," 2014, Biomaterials, 35:6614-6621.

Zhu et al., "NEL-like molecule-1-modified bone marrow mesenchymal stem cells/poly lactic-co-glycolic acid composite improves repair of large osteochondral defects in mandibular condyle," 2011, Osteoarthritis and Cartilage, 19:743-750.

\* cited by examiner

SEQUENCE LISTING

```
<160> NUMBER OF SEQ ID NOS: 19

<210> SEQ ID NO 1
<211> LENGTH: 3255
<212> TYPE: DNA
<213> ORGANISM: Homo sapiens
<220> FEATURE:
<221> NAME/KEY: CDS
<222> LOCATION: (154)..(2586)

<400> SEQUENCE: 1
atatgcgagc gcagcacccg gcgctgccga gccacctccc ccgccgcccg ctagcaagtt      60
tggcggctcc aagccaggcg cgcctcagga tccaggctca tttgcttcca cctagcttcg     120
gtgccccctg ctaggcgggg accctcgaga gcg atg ccg atg gat ttg att tta     174
```

|                                                                                              |      |
|----------------------------------------------------------------------------------------------|------|
|                       Met Pro Met Asp Leu Ile Leu<br>                        1              5 | |
| gtt gtg tgg ttc tgt gtg tgc act gcc agg aca gtg gtg ggc ttt ggg<br>Val Val Trp Phe Cys Val Cys Thr Ala Arg Thr Val Val Gly Phe Gly<br>          10               15                  20 | 222 |
| atg gac cct gac ctt cag atg gat atc gtc acc gag ctt gac ctt gtg<br>Met Asp Pro Asp Leu Gln Met Asp Ile Val Thr Glu Leu Asp Leu Val<br> 25                    30                  35 | 270 |
| aac acc acc ctt gga gtt gct cag gtg tct gga atg cac aat gcc agc<br>Asn Thr Thr Leu Gly Val Ala Gln Val Ser Gly Met His Asn Ala Ser<br>40                  45               50               55 | 318 |
| aaa gca ttt tta ttt caa gac ata gaa aga gag atc cat gca gct cct<br>Lys Ala Phe Leu Phe Gln Asp Ile Glu Arg Glu Ile His Ala Ala Pro<br>               60               65               70 | 366 |
| cat gtg agt gag aaa tta att cag ctg ttc cgg aac aag agt gaa ttc<br>His Val Ser Glu Lys Leu Ile Gln Leu Phe Arg Asn Lys Ser Glu Phe<br>         75                80               85 | 414 |
| acc att ttg gcc act gta cag cag aag cca tcc act tca gga gtg ata<br>Thr Ile Leu Ala Thr Val Gln Gln Lys Pro Ser Thr Ser Gly Val Ile<br>         90                95              100 | 462 |
| ctg tcc att cga gaa ctg gag cac agc tat ttt gaa ctg gag agc agt<br>Leu Ser Ile Arg Glu Leu Glu His Ser Tyr Phe Glu Leu Glu Ser Ser<br>105                 110               115 | 510 |
| ggc ctg agg gat gag att cgg tat cac tac ata cac aat ggg aag cca<br>Gly Leu Arg Asp Glu Ile Arg Tyr His Tyr Ile His Asn Gly Lys Pro<br>120                125              130             135 | 558 |
| agg aca gag gca ctt cct tac cgc atg gca gat gga caa tgg cac aag<br>Arg Thr Glu Ala Leu Pro Tyr Arg Met Ala Asp Gly Gln Trp His Lys<br>               140               145              150 | 606 |
| gtt gca ctg tca gtt agc gcc tct cat ctc ctg ctc cat gtc gac tgt<br>Val Ala Leu Ser Val Ser Ala Ser His Leu Leu Leu His Val Asp Cys<br>          155               160               165 | 654 |
| aac agg att tat gag cgt gtg ata gac cct cca gat acc aac ctt ccc<br>Asn Arg Ile Tyr Glu Arg Val Ile Asp Pro Pro Asp Thr Asn Leu Pro<br>               170               175              180 | 702 |
| cca gga atc aat tta tgg ctt ggc cag cgc aac caa aag cat ggc tta<br>Pro Gly Ile Asn Leu Trp Leu Gly Gln Arg Asn Gln Lys His Gly Leu<br>185                190               195 | 750 |
| ttc aaa ggg atc atc caa gat ggg aag atc atc ttt atg ccg aat gga<br>Phe Lys Gly Ile Ile Gln Asp Gly Lys Ile Ile Phe Met Pro Asn Gly<br>200                205              210             215 | 798 |
| tat ata aca cag tgt cca aat cta aat cac act tgc cca acc tgc agt<br>Tyr Ile Thr Gln Cys Pro Asn Leu Asn His Thr Cys Pro Thr Cys Ser<br>               220               225              230 | 846 |
| gat ttc tta agc ctg gtg caa gga ata atg gat tta caa gag ctt ttg<br>Asp Phe Leu Ser Leu Val Gln Gly Ile Met Asp Leu Gln Glu Leu Leu<br>          235               240               245 | 894 |
| gcc aag atg act gca aaa cta aat tat gca gag aca aga ctt agt caa<br>Ala Lys Met Thr Ala Lys Leu Asn Tyr Ala Glu Thr Arg Leu Ser Gln<br>250                255              260 | 942 |
| ttg gaa aac tgt cat tgt gag aag act tgt caa gtg agt gga ctg ctc<br>Leu Glu Asn Cys His Cys Glu Lys Thr Cys Gln Val Ser Gly Leu Leu<br>          265               270              275 | 990 |
| tat cga gat caa gac tct tgg gta gat ggt gac cat tgc agg aac tgc<br>Tyr Arg Asp Gln Asp Ser Trp Val Asp Gly Asp His Cys Arg Asn Cys<br>280                285              290             295 | 1038 |
| act tgc aaa agt ggt gcc gtg gaa tgc cga agg atg tcc tgt ccc cct<br>Thr Cys Lys Ser Gly Ala Val Glu Cys Arg Arg Met Ser Cys Pro Pro<br>               300               305              310 | 1086 |

-continued

| | |
|---|---|
| ctc aat tgc tcc cca gac tcc ctc cca gtg cac att gct ggc cag tgc<br>Leu Asn Cys Ser Pro Asp Ser Leu Pro Val His Ile Ala Gly Gln Cys<br>315                320                325 | 1134 |
| tgt aag gtc tgc cga cca aaa tgt atc tat gga gga aaa gtt ctt gca<br>Cys Lys Val Cys Arg Pro Lys Cys Ile Tyr Gly Gly Lys Val Leu Ala<br>330                335                340 | 1182 |
| gaa ggc cag cgg att tta acc aag agc tgt cgg gaa tgc cga ggt gga<br>Glu Gly Gln Arg Ile Leu Thr Lys Ser Cys Arg Glu Cys Arg Gly Gly<br>345                350                355 | 1230 |
| gtt tta gta aaa att aca gaa atg tgt cct cct ttg aac tgc tca gaa<br>Val Leu Val Lys Ile Thr Glu Met Cys Pro Pro Leu Asn Cys Ser Glu<br>360                365                370                375 | 1278 |
| aag gat cac att ctt cct gag aat cag tgc tgc cgt gtc tgt aga ggt<br>Lys Asp His Ile Leu Pro Glu Asn Gln Cys Cys Arg Val Cys Arg Gly<br>380                385                390 | 1326 |
| cat aac ttt tgt gca gaa gga cct aaa tgt ggt gaa aac tca gag tgc<br>His Asn Phe Cys Ala Glu Gly Pro Lys Cys Gly Glu Asn Ser Glu Cys<br>395                400                405 | 1374 |
| aaa aac tgg aat aca aaa gct act tgt gag tgc aag agt ggt tac atc<br>Lys Asn Trp Asn Thr Lys Ala Thr Cys Glu Cys Lys Ser Gly Tyr Ile<br>410                415                420 | 1422 |
| tct gtc cag gga gac tct gcc tac tgt gaa gat att gat gag tgt gca<br>Ser Val Gln Gly Asp Ser Ala Tyr Cys Glu Asp Ile Asp Glu Cys Ala<br>425                430                435 | 1470 |
| gct aag atg cat tac tgt cat gcc aat act gtg tgt gtc aac ctt cct<br>Ala Lys Met His Tyr Cys His Ala Asn Thr Val Cys Val Asn Leu Pro<br>440                445                450                455 | 1518 |
| ggg tta tat cgc tgt gac tgt gtc cca gga tac att cgt gtg gat gac<br>Gly Leu Tyr Arg Cys Asp Cys Val Pro Gly Tyr Ile Arg Val Asp Asp<br>460                465                470 | 1566 |
| ttc tct tgt aca gaa cac gat gaa tgt ggc agc ggc cag cac aac tgt<br>Phe Ser Cys Thr Glu His Asp Glu Cys Gly Ser Gly Gln His Asn Cys<br>475                480                485 | 1614 |
| gat gag aat gcc atc tgc acc aac act gtc cag gga cac agc tgc acc<br>Asp Glu Asn Ala Ile Cys Thr Asn Thr Val Gln Gly His Ser Cys Thr<br>490                495                500 | 1662 |
| tgc aaa ccg ggc tac gtg ggg aac ggg acc atc tgc aga gct ttc tgt<br>Cys Lys Pro Gly Tyr Val Gly Asn Gly Thr Ile Cys Arg Ala Phe Cys<br>505                510                515 | 1710 |
| gaa gag ggc tgc aga tac ggt gga acg tgt gtg gct ccc aac aaa tgt<br>Glu Glu Gly Cys Arg Tyr Gly Gly Thr Cys Val Ala Pro Asn Lys Cys<br>520                525                535 | 1758 |
| gtc tgt cca tct gga ttc aca gga agc cac tgc gag aaa gat att gat<br>Val Cys Pro Ser Gly Phe Thr Gly Ser His Cys Glu Lys Asp Ile Asp<br>540                545                550 | 1806 |
| gaa tgt tca gag gga atc att gag tgc cac aac cat tcc cgc tgc gtt<br>Glu Cys Ser Glu Gly Ile Ile Glu Cys His Asn His Ser Arg Cys Val<br>555                560                565 | 1854 |
| aac ctg cca ggg tgg tac cac tgt gag tgc aga agc ggt ttc cat gac<br>Asn Leu Pro Gly Trp Tyr His Cys Glu Cys Arg Ser Gly Phe His Asp<br>570                575                580 | 1902 |
| gat ggg acc tat tca ctg tcc ggg gag tcc tgt att gac att gat gaa<br>Asp Gly Thr Tyr Ser Leu Ser Gly Glu Ser Cys Ile Asp Ile Asp Glu<br>585                590                595 | 1950 |
| tgt gcc tta aga act cac acc tgt tgg aac gat tct gcc tgc atc aac<br>Cys Ala Leu Arg Thr His Thr Cys Trp Asn Asp Ser Ala Cys Ile Asn<br>600                605                610                615 | 1998 |
| ctg gca ggg ggc ttt gac tgt ctc tgc ccc tct ggg ccc tcc tgc tct<br>Leu Ala Gly Gly Phe Asp Cys Leu Cys Pro Ser Gly Pro Ser Cys Ser<br>620                625                630 | 2046 |

```
ggt gac tgt cct cat gaa ggg ggg ctg aag cac aat ggc cag gtg tgg      2094
Gly Asp Cys Pro His Glu Gly Gly Leu Lys His Asn Gly Gln Val Trp
            635                 640                 645 acc ttg aaa gaa gac agg tgt tct gtc tgc tcc tgc aag gat ggc aag      2142
Thr Leu Lys Glu Asp Arg Cys Ser Val Cys Ser Cys Lys Asp Gly Lys
        650                 655                 660 ata ttc tgc cga cgg aca gct tgt gat tgc cag aat cca agt gct gac      2190
Ile Phe Cys Arg Arg Thr Ala Cys Asp Cys Gln Asn Pro Ser Ala Asp
    665                 670                 675 cta ttc tgt tgc cca gaa tgt gac acc aga gtc aca agt caa tgt tta      2238
Leu Phe Cys Cys Pro Glu Cys Asp Thr Arg Val Thr Ser Gln Cys Leu
680                 685                 690                 695 gac caa aat ggt cac aag ctg tat cga agt gga gac aat tgg acc cat      2286
Asp Gln Asn Gly His Lys Leu Tyr Arg Ser Gly Asp Asn Trp Thr His
            700                 705                 710 agc tgt cag cag tgt cgg tgt ctg gaa gga gag gta gat tgc tgg cca      2334
Ser Cys Gln Gln Cys Arg Cys Leu Glu Gly Glu Val Asp Cys Trp Pro
        715                 720                 725 ctc act tgc ccc aac ttg agc tgt gag tat aca gct atc tta gaa ggg      2382
Leu Thr Cys Pro Asn Leu Ser Cys Glu Tyr Thr Ala Ile Leu Glu Gly
    730                 735                 740 gaa tgt tgt ccc cgc tgt gtc agt gac ccc tgc cta gct gat aac atc      2430
Glu Cys Cys Pro Arg Cys Val Ser Asp Pro Cys Leu Ala Asp Asn Ile
745                 750                 755 acc tat gac atc aga aaa act tgc ctg gac agc tat ggt gtt tca cgg      2478
Thr Tyr Asp Ile Arg Lys Thr Cys Leu Asp Ser Tyr Gly Val Ser Arg
            760                 765                 770                 775 ctt agt ggc tca gtg tgg acg atg gct gga tct ccc tgc aca acc tgt      2526
Leu Ser Gly Ser Val Trp Thr Met Ala Gly Ser Pro Cys Thr Thr Cys
        780                 785                 790 aaa tgc aag aat gga aga gtc tgt tgt tct gtg gat ttt gag tgt ctt      2574
Lys Cys Lys Asn Gly Arg Val Cys Cys Ser Val Asp Phe Glu Cys Leu
    795                 800                 805 caa aat aat tga agtatttaca gtggactcaa cgcagaagaa tggacgaaat          2626
Gln Asn Asn
        810 gaccatccaa cgtgattaag gataggaatc ggtagtttgg ttttttttgtt tgttttgttt   2686 ttttaaccac agataattgc caaagttttcc acctgaggac ggtgtttgga ggttgccttt   2746 tggacctacc actttgctca ttcttgctaa cctagtctag gtgacctaca gtgccgtgca    2806 tttaagtcaa tggttgttaa aagaagtttc ccgtgttgta aatcatgttt cccttatcag    2866 atcatttgca aatacattta aatgatctca tggtaaatgt tgatgtattt tttggtttat    2926 tttgtgtact aacataatag agagagactc agctcctttt atttattttg ttgatttatg    2986 gatcaaattc taaataaag ttgcctgttg tgacttttgt cccatctact gcatacttag    3046 tgctgagatc cctgtaaaat gttttgatga aaatatgtat gtagagtcca gtcgcattat    3106 acatacattt catagtgctg aaccttctta aatgcctact cattcagctt aaacaggctg    3166 aagccaagta tgacaaagag gggaagggcc aaaaacataa tcaagaata attttaaaga    3226 gaattcttgt ctctcttgca aaaaaaaaa                                      3255

<210> SEQ ID NO 2
<211> LENGTH: 810
<212> TYPE: PRT
<213> ORGANISM: Homo sapiens

<400> SEQUENCE: 2
```

```
Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
                20                  25                  30

Val Thr Glu Leu Asp Leu Val Asn Thr Thr Leu Gly Val Ala Gln Val
            35                  40                  45

Ser Gly Met His Asn Ala Ser Lys Ala Phe Leu Phe Gln Asp Ile Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
            195                 200                 205

Ile Ile Phe Met Pro Asn Gly Tyr Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Glu Met Cys
        355                 360                 365

Pro Pro Leu Asn Cys Ser Glu Lys Asp His Ile Leu Pro Glu Asn Gln
    370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
            405                 410                 415

Glu Cys Lys Ser Gly Tyr Ile Ser Val Gln Gly Asp Ser Ala Tyr Cys
```

```
                420             425             430
Glu Asp Ile Asp Glu Cys Ala Ala Lys Met His Tyr Cys His Ala Asn
            435             440             445
Thr Val Cys Val Asn Leu Pro Gly Leu Tyr Arg Cys Asp Cys Val Pro
        450             455             460
Gly Tyr Ile Arg Val Asp Asp Phe Ser Cys Thr Glu His Asp Glu Cys
465             470             475             480
Gly Ser Gly Gln His Asn Cys Asp Glu Asn Ala Ile Cys Thr Asn Thr
                485             490             495
Val Gln Gly His Ser Cys Thr Cys Lys Pro Gly Tyr Val Gly Asn Gly
            500             505             510
Thr Ile Cys Arg Ala Phe Cys Glu Glu Gly Cys Arg Tyr Gly Gly Thr
        515             520             525
Cys Val Ala Pro Asn Lys Cys Val Cys Pro Ser Gly Phe Thr Gly Ser
        530             535             540
His Cys Glu Lys Asp Ile Asp Glu Cys Ser Glu Gly Ile Ile Glu Cys
545             550             555             560
His Asn His Ser Arg Cys Val Asn Leu Pro Gly Trp Tyr His Cys Glu
                565             570             575
Cys Arg Ser Gly Phe His Asp Asp Gly Thr Tyr Ser Leu Ser Gly Glu
            580             585             590
Ser Cys Ile Asp Ile Asp Glu Cys Ala Leu Arg Thr His Thr Cys Trp
        595             600             605
Asn Asp Ser Ala Cys Ile Asn Leu Ala Gly Gly Phe Asp Cys Leu Cys
        610             615             620
Pro Ser Gly Pro Ser Cys Ser Gly Asp Cys Pro His Glu Gly Gly Leu
625             630             635             640
Lys His Asn Gly Gln Val Trp Thr Leu Lys Glu Asp Arg Cys Ser Val
                645             650             655
Cys Ser Cys Lys Asp Gly Lys Ile Phe Cys Arg Arg Thr Ala Cys Asp
            660             665             670
Cys Gln Asn Pro Ser Ala Asp Leu Phe Cys Cys Pro Glu Cys Asp Thr
        675             680             685
Arg Val Thr Ser Gln Cys Leu Asp Gln Asn Gly His Lys Leu Tyr Arg
        690             695             700
Ser Gly Asp Asn Trp Thr His Ser Cys Gln Gln Cys Arg Cys Leu Glu
705             710             715             720
Gly Glu Val Asp Cys Trp Pro Leu Thr Cys Pro Asn Leu Ser Cys Glu
                725             730             735
Tyr Thr Ala Ile Leu Glu Gly Glu Cys Cys Pro Arg Cys Val Ser Asp
            740             745             750
Pro Cys Leu Ala Asp Asn Ile Thr Tyr Asp Ile Arg Lys Thr Cys Leu
        755             760             765
Asp Ser Tyr Gly Val Ser Arg Leu Ser Gly Ser Val Trp Thr Met Ala
        770             775             780
Gly Ser Pro Cys Thr Thr Cys Lys Cys Lys Asn Gly Arg Val Cys Cys
785             790             795             800
Ser Val Asp Phe Glu Cys Leu Gln Asn Asn
                805             810

<210> SEQ ID NO 3
<211> LENGTH: 3114
<212> TYPE: DNA
<213> ORGANISM: Homo sapiens
```

```
<220> FEATURE:
<221> NAME/KEY: CDS
<222> LOCATION: (154)..(2445)

<400> SEQUENCE: 3
atatgcgagc gcagcacccg gcgctgccga gccacctccc ccgccgcccg ctagcaagtt      60
tggcggctcc aagccaggcg cgcctcagga tccaggctca tttgcttcca cctagcttcg     120
gtgccccctg ctaggcgggg accctcgaga gcg atg ccg atg gat ttg att tta     174
                                    Met Pro Met Asp Leu Ile Leu
                                    1               5 gtt gtg tgg ttc tgt gtg tgc act gcc agg aca gtg gtg ggc ttt ggg     222
Val Val Trp Phe Cys Val Cys Thr Ala Arg Thr Val Val Gly Phe Gly
        10                  15                  20 atg gac cct gac ctt cag atg gat atc gtc acc gag ctt gac ctt gtg     270
Met Asp Pro Asp Leu Gln Met Asp Ile Val Thr Glu Leu Asp Leu Val
 25                  30                  35 aac acc acc ctt gga gtt gct cag gtg tct gga atg cac aat gcc agc     318
Asn Thr Thr Leu Gly Val Ala Gln Val Ser Gly Met His Asn Ala Ser
 40                  45                  50                  55 aaa gca ttt tta ttt caa gac ata gaa aga gag atc cat gca gct cct     366
Lys Ala Phe Leu Phe Gln Asp Ile Glu Arg Glu Ile His Ala Ala Pro
                 60                  65                  70 cat gtg agt gag aaa tta att cag ctg ttc cgg aac aag agt gaa ttc     414
His Val Ser Glu Lys Leu Ile Gln Leu Phe Arg Asn Lys Ser Glu Phe
             75                  80                  85 acc att ttg gcc act gta cag cag aag cca tcc act tca gga gtg ata     462
Thr Ile Leu Ala Thr Val Gln Gln Lys Pro Ser Thr Ser Gly Val Ile
         90                  95                 100 ctg tcc att cga gaa ctg gag cac agc tat ttt gaa ctg gag agc agt     510
Leu Ser Ile Arg Glu Leu Glu His Ser Tyr Phe Glu Leu Glu Ser Ser
    105                 110                 115 ggc ctg agg gat gag att cgg tat cac tac ata cac aat ggg aag cca     558
Gly Leu Arg Asp Glu Ile Arg Tyr His Tyr Ile His Asn Gly Lys Pro
120                 125                 130                 135 agg aca gag gca ctt cct tac cgc atg gca gat gga caa tgg cac aag     606
Arg Thr Glu Ala Leu Pro Tyr Arg Met Ala Asp Gly Gln Trp His Lys
                140                 145                 150 gtt gca ctg tca gtt agc gcc tct cat ctc ctg ctc cat gtc gac tgt     654
Val Ala Leu Ser Val Ser Ala Ser His Leu Leu Leu His Val Asp Cys
            155                 160                 165 aac agg att tat gag cgt gtg ata gac cct cca gat acc aac ctt ccc     702
Asn Arg Ile Tyr Glu Arg Val Ile Asp Pro Pro Asp Thr Asn Leu Pro
        170                 175                 180 cca gga atc aat tta tgg ctt ggc cag cgc aac caa aag cat ggc tta     750
Pro Gly Ile Asn Leu Trp Leu Gly Gln Arg Asn Gln Lys His Gly Leu
    185                 190                 195 ttc aaa ggg atc atc caa gat ggg aag atc atc ttt atg ccg aat gga     798
Phe Lys Gly Ile Ile Gln Asp Gly Lys Ile Ile Phe Met Pro Asn Gly
200                 205                 210                 215 tat ata aca cag tgt cca aat cta aat cac act tgc cca acc tgc agt     846
Tyr Ile Thr Gln Cys Pro Asn Leu Asn His Thr Cys Pro Thr Cys Ser
                220                 225                 230 gat ttc tta agc ctg gtg caa gga ata atg gat tta caa gag ctt ttg     894
Asp Phe Leu Ser Leu Val Gln Gly Ile Met Asp Leu Gln Glu Leu Leu
            235                 240                 245 gcc aag atg act gca aaa cta aat tat gca gag aca aga ctt agt caa     942
Ala Lys Met Thr Ala Lys Leu Asn Tyr Ala Glu Thr Arg Leu Ser Gln
        250                 255                 260 ttg gaa aac tgt cat tgt gag aag act tgt caa gtg agt gga ctg ctc     990
```

|  |  |  |  |  |  |  |  |  |  |  |  |  |
|---|---|---|---|---|---|---|---|---|---|---|---|---|
| Leu | Glu | Asn | Cys | His | Cys | Glu | Lys | Thr | Cys | Gln | Val | Ser | Gly | Leu | Leu |
|  | 265 |  |  |  | 270 |  |  |  | 275 |  |  |  |

```
tat cga gat caa gac tct tgg gta gat ggt gac cat tgc agg aac tgc     1038
Tyr Arg Asp Gln Asp Ser Trp Val Asp Gly Asp His Cys Arg Asn Cys
280             285             290             295 act tgc aaa agt ggt gcc gtg gaa tgc cga agg atg tcc tgt ccc cct     1086
Thr Cys Lys Ser Gly Ala Val Glu Cys Arg Arg Met Ser Cys Pro Pro
                300             305             310 ctc aat tgc tcc cca gac tcc ctc cca gtg cac att gct ggc cag tgc     1134
Leu Asn Cys Ser Pro Asp Ser Leu Pro Val His Ile Ala Gly Gln Cys
            315             320             325 tgt aag gtc tgc cga cca aaa tgt atc tat gga gga aaa gtt ctt gca     1182
Cys Lys Val Cys Arg Pro Lys Cys Ile Tyr Gly Gly Lys Val Leu Ala
        330             335             340 gaa ggc cag cgg att tta acc aag agc tgt cgg gaa tgc cga ggt gga     1230
Glu Gly Gln Arg Ile Leu Thr Lys Ser Cys Arg Glu Cys Arg Gly Gly
    345             350             355 gtt tta gta aaa att aca gaa atg tgt cct cct ttg aac tgc tca gaa     1278
Val Leu Val Lys Ile Thr Glu Met Cys Pro Pro Leu Asn Cys Ser Glu
360             365             370             375 aag gat cac att ctt cct gag aat cag tgc tgc cgt gtc tgt aga ggt     1326
Lys Asp His Ile Leu Pro Glu Asn Gln Cys Cys Arg Val Cys Arg Gly
                380             385             390 cat aac ttt tgt gca gaa gga cct aaa tgt ggt gaa aac tca gag tgc     1374
His Asn Phe Cys Ala Glu Gly Pro Lys Cys Gly Glu Asn Ser Glu Cys
            395             400             405 aaa aac tgg aat aca aaa gct act tgt gag tgc aag agt ggt tac atc     1422
Lys Asn Trp Asn Thr Lys Ala Thr Cys Glu Cys Lys Ser Gly Tyr Ile
        410             415             420 tct gtc cag gga gac tct gcc tac tgt gaa gat att gat gag tgt gca     1470
Ser Val Gln Gly Asp Ser Ala Tyr Cys Glu Asp Ile Asp Glu Cys Ala
    425             430             435 gct aag atg cat tac tgt cat gcc aat act gtg tgt gtc aac ctt cct     1518
Ala Lys Met His Tyr Cys His Ala Asn Thr Val Cys Val Asn Leu Pro
440             445             450             455 ggg tta tat cgc tgt gac tgt gtc cca gga tac att cgt gtg gat gac     1566
Gly Leu Tyr Arg Cys Asp Cys Val Pro Gly Tyr Ile Arg Val Asp Asp
                460             465             470 ttc tct tgt aca gaa cac gat gaa tgt ggc agc ggc cag cac aac tgt     1614
Phe Ser Cys Thr Glu His Asp Glu Cys Gly Ser Gly Gln His Asn Cys
            475             480             485 gat gag aat gcc atc tgc acc aac act gtc cag gga cac agc tgc acc     1662
Asp Glu Asn Ala Ile Cys Thr Asn Thr Val Gln Gly His Ser Cys Thr
        490             495             500 tgc aaa ccg ggc tac gtg ggg aac ggg acc atc tgc aga gct ttc tgt     1710
Cys Lys Pro Gly Tyr Val Gly Asn Gly Thr Ile Cys Arg Ala Phe Cys
    505             510             515 gaa gag ggc tgc aga tac ggt gga acg tgt gtg gct ccc aac aaa tgt     1758
Glu Glu Gly Cys Arg Tyr Gly Gly Thr Cys Val Ala Pro Asn Lys Cys
520             525             530             535 gtc tgt cca tct gga ttc aca gga agc cac tgc gag aaa gac att gat     1806
Val Cys Pro Ser Gly Phe Thr Gly Ser His Cys Glu Lys Asp Ile Asp
                540             545             550 gaa tgt gcc tta aga act cac acc tgt tgg aac gat tct gcc tgc atc     1854
Glu Cys Ala Leu Arg Thr His Thr Cys Trp Asn Asp Ser Ala Cys Ile
            555             560             565 aac ctg gca ggg ggc ttt gac tgt ctc tgc ccc tct ggg ccc tcc tgc     1902
Asn Leu Ala Gly Gly Phe Asp Cys Leu Cys Pro Ser Gly Pro Ser Cys
        570             575             580
```

```
tct ggt gac tgt cct cat gaa ggg ggg ctg aag cac aat ggc cag gtg      1950
Ser Gly Asp Cys Pro His Glu Gly Gly Leu Lys His Asn Gly Gln Val
    585                 590                 595 tgg acc ttg aaa gaa gac agg tgt tct gtc tgc tcc tgc aag gat ggc      1998
Trp Thr Leu Lys Glu Asp Arg Cys Ser Val Cys Ser Cys Lys Asp Gly
600                 605                 610                 615 aag ata ttc tgc cga cgg aca gct tgt gat tgc cag aat cca agt gct      2046
Lys Ile Phe Cys Arg Arg Thr Ala Cys Asp Cys Gln Asn Pro Ser Ala
                620                 625                 630 gac cta ttc tgt tgc cca gaa tgt gac acc aga gtc aca agt caa tgt      2094
Asp Leu Phe Cys Cys Pro Glu Cys Asp Thr Arg Val Thr Ser Gln Cys
                635                 640                 645 tta gac caa aat ggt cac aag ctg tat cga agt gga gac aat tgg acc      2142
Leu Asp Gln Asn Gly His Lys Leu Tyr Arg Ser Gly Asp Asn Trp Thr
            650                 655                 660 cat agc tgt cag cag tgt cgg tgt ctg gaa gga gag gta gat tgc tgg      2190
His Ser Cys Gln Gln Cys Arg Cys Leu Glu Gly Glu Val Asp Cys Trp
        665                 670                 675 cca ctc act tgc ccc aac ttg agc tgt gag tat aca gct atc tta gaa      2238
Pro Leu Thr Cys Pro Asn Leu Ser Cys Glu Tyr Thr Ala Ile Leu Glu
680                 685                 690                 695 ggg gaa tgt tgt ccc cgc tgt gtc agt gac ccc tgc cta gct gat aac      2286
Gly Glu Cys Cys Pro Arg Cys Val Ser Asp Pro Cys Leu Ala Asp Asn
                700                 705                 710 atc acc tat gac atc aga aaa act tgc ctg gac agc tat ggt gtt tca      2334
Ile Thr Tyr Asp Ile Arg Lys Thr Cys Leu Asp Ser Tyr Gly Val Ser
                715                 720                 725 cgg ctt agt ggc tca gtg tgg acg atg gct gga tct ccc tgc aca acc      2382
Arg Leu Ser Gly Ser Val Trp Thr Met Ala Gly Ser Pro Cys Thr Thr
            730                 735                 740 tgt aaa tgc aag aat gga aga gtc tgt tgt tct gtg gat ttt gag tgt      2430
Cys Lys Cys Lys Asn Gly Arg Val Cys Cys Ser Val Asp Phe Glu Cys
        745                 750                 755 ctt caa aat aat tga agtatttaca gtggactcaa cgcagaagaa tggacgaaat      2485
Leu Gln Asn Asn
760 gaccatccaa cgtgattaag gataggaatc ggtagtttgg ttttttttgtt tgttttgttt   2545 ttttaaccac agataattgc caaagtttcc acctgaggac ggtgtttgga ggttgccttt    2605 tggacctacc actttgctca ttcttgctaa cctagtctag gtgacctaca gtgccgtgca    2665 tttaagtcaa tggttgttaa aagaagtttc ccgtgttgta aatcatgttt cccttatcag    2725 atcatttgca aatacattta aatgatctca tggtaaatgt tgatgtattt tttggtttat    2785 tttgtgtact aacataatag agagagactc agctccttt atttattttg ttgatttatg     2845 gatcaaattc taaataaag ttgcctgttg tgacttttgt cccatctact gcatacttag     2905 tgctgagatc cctgtaaaat gttttgatga aaatatgtat gtagagtcca gtcgcattat    2965 acatacattt catagtgctg aaccttctta aatgcctact cattcagctt aaacaggctg    3025 aagccaagta tgacaaagag gggaagggcc aaaaacataa tcaaagaata attttaaaga    3085 gaattcttgt ctctcttgca aaaaaaaaa                                       3114

<210> SEQ ID NO 4
<211> LENGTH: 763
<212> TYPE: PRT
<213> ORGANISM: Homo sapiens

<400> SEQUENCE: 4

Met Pro Met Asp Leu Ile Leu Val Val Trp Phe Cys Val Cys Thr Ala
```

-continued

```
1               5                   10                  15
Arg Thr Val Val Gly Phe Gly Met Asp Pro Asp Leu Gln Met Asp Ile
                20                  25                  30

Val Thr Glu Leu Asp Leu Val Asn Thr Thr Leu Gly Val Ala Gln Val
                35                  40                  45

Ser Gly Met His Asn Ala Ser Lys Ala Phe Leu Phe Gln Asp Ile Glu
                50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
                100                 105                 110

Tyr Phe Glu Leu Glu Ser Ser Gly Leu Arg Asp Glu Ile Arg Tyr His
                115                 120                 125

Tyr Ile His Asn Gly Lys Pro Arg Thr Glu Ala Leu Pro Tyr Arg Met
                130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
                180                 185                 190

Arg Asn Gln Lys His Gly Leu Phe Lys Gly Ile Ile Gln Asp Gly Lys
                195                 200                 205

Ile Ile Phe Met Pro Asn Gly Tyr Ile Thr Gln Cys Pro Asn Leu Asn
                210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
                260                 265                 270

Cys Gln Val Ser Gly Leu Leu Tyr Arg Asp Gln Asp Ser Trp Val Asp
                275                 280                 285

Gly Asp His Cys Arg Asn Cys Thr Cys Lys Ser Gly Ala Val Glu Cys
                290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
                340                 345                 350

Cys Arg Glu Cys Arg Gly Gly Val Leu Val Lys Ile Thr Glu Met Cys
                355                 360                 365

Pro Pro Leu Asn Cys Ser Glu Lys Asp His Ile Leu Pro Glu Asn Gln
                370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
                420                 425                 430
```

```
Glu Asp Ile Asp Glu Cys Ala Ala Lys Met His Tyr Cys His Ala Asn
            435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ala Leu Arg Thr His Thr Cys
545                 550                 555                 560
Trp Asn Asp Ser Ala Cys Ile Asn Leu Ala Gly Gly Phe Asp Cys Leu
                565                 570                 575
Cys Pro Ser Gly Pro Ser Cys Ser Gly Asp Cys Pro His Glu Gly Gly
            580                 585                 590
Leu Lys His Asn Gly Gln Val Trp Thr Leu Lys Glu Asp Arg Cys Ser
        595                 600                 605
Val Cys Ser Cys Lys Asp Gly Lys Ile Phe Cys Arg Arg Thr Ala Cys
    610                 615                 620
Asp Cys Gln Asn Pro Ser Ala Asp Leu Phe Cys Cys Pro Glu Cys Asp
625                 630                 635                 640
Thr Arg Val Thr Ser Gln Cys Leu Asp Gln Asn Gly His Lys Leu Tyr
                645                 650                 655
Arg Ser Gly Asp Asn Trp Thr His Ser Cys Gln Gln Cys Arg Cys Leu
            660                 665                 670
Glu Gly Glu Val Asp Cys Trp Pro Leu Thr Cys Pro Asn Leu Ser Cys
        675                 680                 685
Glu Tyr Thr Ala Ile Leu Glu Gly Glu Cys Cys Pro Arg Cys Val Ser
    690                 695                 700
Asp Pro Cys Leu Ala Asp Asn Ile Thr Tyr Asp Ile Arg Lys Thr Cys
705                 710                 715                 720
Leu Asp Ser Tyr Gly Val Ser Arg Leu Ser Gly Ser Val Trp Thr Met
                725                 730                 735
Ala Gly Ser Pro Cys Thr Thr Cys Lys Cys Lys Asn Gly Arg Val Cys
            740                 745                 750
Cys Ser Val Asp Phe Glu Cys Leu Gln Asn Asn
        755                 760

<210> SEQ ID NO 5
<211> LENGTH: 2791
<212> TYPE: DNA
<213> ORGANISM: Equus caballus
<220> FEATURE:
<221> NAME/KEY: CDS
<222> LOCATION: (1)..(2376)

<400> SEQUENCE: 5 atg ggc ttt ggg atg gac ccc gac ctt caa atg gat att atc acc gag      48
Met Gly Phe Gly Met Asp Pro Asp Leu Gln Met Asp Ile Ile Thr Glu
1               5                   10                  15
```

|  |  |
|---|---|
| ctc gac ctc gtg aac acc acc ctt gga gtc act cag gtg tcc gga ctg<br>Leu Asp Leu Val Asn Thr Thr Leu Gly Val Thr Gln Val Ser Gly Leu<br>20 25 30 | 96 |
| cac aat gcc agc aaa gca ttt tta ttt caa gat gta gag aga gag atc<br>His Asn Ala Ser Lys Ala Phe Leu Phe Gln Asp Val Glu Arg Glu Ile<br>35 40 45 | 144 |
| cat gca gcc cca cac gtg agt gag aaa tta att cag ctg ttc cgg aat<br>His Ala Ala Pro His Val Ser Glu Lys Leu Ile Gln Leu Phe Arg Asn<br>50 55 60 | 192 |
| aag agt gaa ttc acc ttt ttg gcc act gtg cag cag aag ccg tca act<br>Lys Ser Glu Phe Thr Phe Leu Ala Thr Val Gln Gln Lys Pro Ser Thr<br>65 70 75 80 | 240 |
| tca gga gtg ata ctg tcc att cga gaa ctg gaa aac agt tat ttt gaa<br>Ser Gly Val Ile Leu Ser Ile Arg Glu Leu Glu Asn Ser Tyr Phe Glu<br>85 90 95 | 288 |
| ctg gag agc agt ggc ctg aga gat gag att cga tat cac tac aca cac<br>Leu Glu Ser Ser Gly Leu Arg Asp Glu Ile Arg Tyr His Tyr Thr His<br>100 105 110 | 336 |
| aag ggg aag ccc agg aca gag gca ctt ccc tac cgg atg gcg gac gga<br>Lys Gly Lys Pro Arg Thr Glu Ala Leu Pro Tyr Arg Met Ala Asp Gly<br>115 120 125 | 384 |
| cgg tgg cac aag gtg gcg ctg tca gtt agc gcc tct cat ctc ctg ctc<br>Arg Trp His Lys Val Ala Leu Ser Val Ser Ala Ser His Leu Leu Leu<br>130 135 140 | 432 |
| cac atc gac tgc aac agg att tat gaa cgt gtg ata gac act cct gag<br>His Ile Asp Cys Asn Arg Ile Tyr Glu Arg Val Ile Asp Thr Pro Glu<br>145 150 155 160 | 480 |
| acc aac ctc ccc cca gga agc aat ttg tgg ctg ggt cag cga aac caa<br>Thr Asn Leu Pro Pro Gly Ser Asn Leu Trp Leu Gly Gln Arg Asn Gln<br>165 170 175 | 528 |
| aag cac ggc tta ttc aaa gga atc atc caa gat gga aaa atc atc ttc<br>Lys His Gly Leu Phe Lys Gly Ile Ile Gln Asp Gly Lys Ile Ile Phe<br>180 185 190 | 576 |
| atg ccg aat gga tac ata aca cag tgt ccg aac ctg aat cgc act tgc<br>Met Pro Asn Gly Tyr Ile Thr Gln Cys Pro Asn Leu Asn Arg Thr Cys<br>195 200 205 | 624 |
| cca acg tgc agt gat ttc tta agc ctg gtg caa gga atc atg gat tta<br>Pro Thr Cys Ser Asp Phe Leu Ser Leu Val Gln Gly Ile Met Asp Leu<br>210 215 220 | 672 |
| caa gag ctt ctg gcc aag atg act gcg aaa cta aat tat gca gag aca<br>Gln Glu Leu Leu Ala Lys Met Thr Ala Lys Leu Asn Tyr Ala Glu Thr<br>225 230 235 240 | 720 |
| cga ctt agt caa ttg gaa aac tgc cac tgc gag aag acc tgt caa gtg<br>Arg Leu Ser Gln Leu Glu Asn Cys His Cys Glu Lys Thr Cys Gln Val<br>245 250 255 | 768 |
| agt gga ctg ctc tat aga gac cag gac tcc tgg gtt gat ggc gat cac<br>Ser Gly Leu Leu Tyr Arg Asp Gln Asp Ser Trp Val Asp Gly Asp His<br>260 265 270 | 816 |
| tgt agg aac tgc acg tgc aaa agc ggc gct gtg gaa tgt cgg agg atg<br>Cys Arg Asn Cys Thr Cys Lys Ser Gly Ala Val Glu Cys Arg Arg Met<br>275 280 285 | 864 |
| tct tgt ccc cct ctc aat tgc tcc cca gac tcc ctc cct gtg cac gtt<br>Ser Cys Pro Pro Leu Asn Cys Ser Pro Asp Ser Leu Pro Val His Val<br>290 295 300 | 912 |
| gcc ggc cag tgc tgt aag gtc tgc cga cca aaa tgt atc tac gga ggg<br>Ala Gly Gln Cys Cys Lys Val Cys Arg Pro Lys Cys Ile Tyr Gly Gly<br>305 310 315 320 | 960 |
| aaa gtc ctt gca gaa ggc cag cgg att tta acc aag agc tgt cgg gaa<br>Lys Val Leu Ala Glu Gly Gln Arg Ile Leu Thr Lys Ser Cys Arg Glu<br>325 330 335 | 1008 |

-continued

```
tgc cga ggt gga gtt tta gtg aaa att aca gaa gcg tgc cct cct ttg    1056
Cys Arg Gly Gly Val Leu Val Lys Ile Thr Glu Ala Cys Pro Pro Leu
        340                 345                 350 aac tgc tca gac aag gat cac att ctc cca gag aat cag tgc tgc agc    1104
Asn Cys Ser Asp Lys Asp His Ile Leu Pro Glu Asn Gln Cys Cys Ser
355                 360                 365 gtc tgc aga ggt cat aac ttt tgt gcg gaa gga cct aaa tgt ggt gaa    1152
Val Cys Arg Gly His Asn Phe Cys Ala Glu Gly Pro Lys Cys Gly Glu
        370                 375                 380 aat tca gag tgc aaa aac tgg aat aca aaa gct act tgc gag tgc aag    1200
Asn Ser Glu Cys Lys Asn Trp Asn Thr Lys Ala Thr Cys Glu Cys Lys
385                 390                 395                 400 aat ggt tat atc tct gtc cag ggg gac tcc gcc tac tgt gaa gat atc    1248
Asn Gly Tyr Ile Ser Val Gln Gly Asp Ser Ala Tyr Cys Glu Asp Ile
            405                 410                 415 gat gag tgt gct gct aag atg cat tac tgt cgt gcc aat act gtg tgt    1296
Asp Glu Cys Ala Ala Lys Met His Tyr Cys Arg Ala Asn Thr Val Cys
        420                 425                 430 gtc aac ctg cct ggg tta tat cgg tgt gac tgt gtc ccg gga tac att    1344
Val Asn Leu Pro Gly Leu Tyr Arg Cys Asp Cys Val Pro Gly Tyr Ile
        435                 440                 445 cgc gtg gat gat ttc tct tgt aca gaa cat gac gaa tgt ggc agc ggg    1392
Arg Val Asp Asp Phe Ser Cys Thr Glu His Asp Glu Cys Gly Ser Gly
    450                 455                 460 cag cac aac tgt gat gag aat gcc atc tgc acc aac act gtc cag gga    1440
Gln His Asn Cys Asp Glu Asn Ala Ile Cys Thr Asn Thr Val Gln Gly
465                 470                 475                 480 cac agc tgc acc tgc aaa ccg ggc tac gtg ggg aat ggg acc agc tgc    1488
His Ser Cys Thr Cys Lys Pro Gly Tyr Val Gly Asn Gly Thr Ser Cys
            485                 490                 495 aga gcg ttc tgc gaa gag ggc tgc aga tat ggg gga aca tgc gtg gct    1536
Arg Ala Phe Cys Glu Glu Gly Cys Arg Tyr Gly Gly Thr Cys Val Ala
        500                 505                 510 cct aac aaa tgt gtc tgt cct tct gga ttc aca gga agc cac tgt gag    1584
Pro Asn Lys Cys Val Cys Pro Ser Gly Phe Thr Gly Ser His Cys Glu
        515                 520                 525 aaa gat att gat gaa tgt aca gag gga atc att gag tgc cac aac cat    1632
Lys Asp Ile Asp Glu Cys Thr Glu Gly Ile Ile Glu Cys His Asn His
530                 535                 540 tcc cgc tgc gtt aac ctg cca ggg tgg tac cac tgt gag tgc aga agc    1680
Ser Arg Cys Val Asn Leu Pro Gly Trp Tyr His Cys Glu Cys Arg Ser
545                 550                 555                 560 ggt ttc cat gac gat ggg acc tat tca ctg tcc ggg gag tcc tgt att    1728
Gly Phe His Asp Asp Gly Thr Tyr Ser Leu Ser Gly Glu Ser Cys Ile
            565                 570                 575 gac att gat gaa tgt gcc tta aga act cac acc tgt tgg aat gat tct    1776
Asp Ile Asp Glu Cys Ala Leu Arg Thr His Thr Cys Trp Asn Asp Ser
        580                 585                 590 gcc tgc atc aac ttg gca ggg ggc ttc gac tgc ctg tgt ccc tca ggg    1824
Ala Cys Ile Asn Leu Ala Gly Gly Phe Asp Cys Leu Cys Pro Ser Gly
        595                 600                 605 cca tcc tgc tct ggt gac tgc ccc cac gaa gga gga ctg aag cgc aac    1872
Pro Ser Cys Ser Gly Asp Cys Pro His Glu Gly Gly Leu Lys Arg Asn
    610                 615                 620 ggg cag gtg tgg acc ctg aaa gaa gac agg tgt tct gtg tgt tcc tgc    1920
Gly Gln Val Trp Thr Leu Lys Glu Asp Arg Cys Ser Val Cys Ser Cys
625                 630                 635                 640 aag gat ggg aag ata ttc tgc cga cgg aca gct tgt gat tgc cag aat    1968
Lys Asp Gly Lys Ile Phe Cys Arg Arg Thr Ala Cys Asp Cys Gln Asn
```

```
                645                 650                 655
cca agc gtt gac ctt ttc tgt tgc cca gag tgt gac acc agg gtc aca    2016
Pro Ser Val Asp Leu Phe Cys Cys Pro Glu Cys Asp Thr Arg Val Thr
            660                 665                 670 agt caa tgt tta gac caa aat gga cac aag ctc tat cga agt gga gac    2064
Ser Gln Cys Leu Asp Gln Asn Gly His Lys Leu Tyr Arg Ser Gly Asp
        675                 680                 685 aat tgg act cac agc tgt cag cag tgc cgg tgt ctg gaa gga gag gta    2112
Asn Trp Thr His Ser Cys Gln Gln Cys Arg Cys Leu Glu Gly Glu Val
    690                 695                 700 gat tgc tgg cca ctc act tgc ccc aga ttg agc tgt gag tac aca gcc    2160
Asp Cys Trp Pro Leu Thr Cys Pro Arg Leu Ser Cys Glu Tyr Thr Ala
705                 710                 715                 720 atc ttg gaa ggg gag tgt tgt cca cgc tgt gtc agc gac ccc tgc ctg    2208
Ile Leu Glu Gly Glu Cys Cys Pro Arg Cys Val Ser Asp Pro Cys Leu
            725                 730                 735 gcg gat aac atc gtc tat gac atc aga gaa act tgc ctg gac agc tat    2256
Ala Asp Asn Ile Val Tyr Asp Ile Arg Glu Thr Cys Leu Asp Ser Tyr
        740                 745                 750 gga gtt tca agg ctt agt ggc tca gtg tgg aca ttg gct gga tct ccc    2304
Gly Val Ser Arg Leu Ser Gly Ser Val Trp Thr Leu Ala Gly Ser Pro
    755                 760                 765 tgc acg acc tgc aaa tgc aag aat gga agt gtc tgc tgt tct gtg gat    2352
Cys Thr Thr Cys Lys Cys Lys Asn Gly Ser Val Cys Cys Ser Val Asp
770                 775                 780 ttg gag tgt ctt cat aat aat tga aggatttaaa atggactcat gatcgccaga    2406
Leu Glu Cys Leu His Asn Asn
785                 790 gaaaaatgga caaatgacca tccatgatga tgaagaaca ggagttggtg ttttttttac    2466
cacagacaat taccaaagtc tccgtctgag gaaggtgttt gcaggttgcc ttttggacct    2526
cccactctgc tcattcttgc taacctagtc taggtgacct acagtgcatt tcagtctatg    2586
gttgttaaaa gaagttttcc gtgttgtaaa tcacgttttcc cttaccaggt cattgcaaat    2646
acatttaaat gatttcatgg taaatgttga tgtattttt gggtttattt tgtgtactaa    2706
cataatagag attcagctgc ttttatttat ttttttcttg acttttggat caaattcaac    2766
aaataaagtt gcctgttgtg atttt                                          2791
```

<210> SEQ ID NO 6
<211> LENGTH: 791
<212> TYPE: PRT
<213> ORGANISM: Equus caballus

<400> SEQUENCE: 6

```
Met Gly Phe Gly Met Asp Pro Asp Leu Gln Met Asp Ile Ile Thr Glu
1               5                   10                  15

Leu Asp Leu Val Asn Thr Thr Leu Gly Val Thr Gln Val Ser Gly Leu
            20                  25                  30

His Asn Ala Ser Lys Ala Phe Leu Phe Gln Asp Val Glu Arg Glu Ile
        35                  40                  45

His Ala Ala Pro His Val Ser Glu Lys Leu Ile Gln Leu Phe Arg Asn
    50                  55                  60

Lys Ser Glu Phe Thr Phe Leu Ala Thr Val Gln Lys Pro Ser Thr
65                  70                  75                  80

Ser Gly Val Ile Leu Ser Ile Arg Glu Leu Glu Asn Ser Tyr Phe Glu
            85                  90                  95

Leu Glu Ser Ser Gly Leu Arg Asp Glu Ile Arg Tyr His Tyr Thr His
```

```
                100                 105                 110
Lys Gly Lys Pro Arg Thr Glu Ala Leu Pro Tyr Arg Met Ala Asp Gly
            115                 120                 125

Arg Trp His Lys Val Ala Leu Ser Val Ser Ala Ser His Leu Leu Leu
            130                 135                 140

His Ile Asp Cys Asn Arg Ile Tyr Glu Arg Val Ile Asp Thr Pro Glu
145                 150                 155                 160

Thr Asn Leu Pro Pro Gly Ser Asn Leu Trp Leu Gly Gln Arg Asn Gln
            165                 170                 175

Lys His Gly Leu Phe Lys Gly Ile Ile Gln Asp Gly Lys Ile Ile Phe
            180                 185                 190

Met Pro Asn Gly Tyr Ile Thr Gln Cys Pro Asn Leu Asn Arg Thr Cys
            195                 200                 205

Pro Thr Cys Ser Asp Phe Leu Ser Leu Val Gln Gly Ile Met Asp Leu
            210                 215                 220

Gln Glu Leu Leu Ala Lys Met Thr Ala Lys Leu Asn Tyr Ala Glu Thr
225                 230                 235                 240

Arg Leu Ser Gln Leu Glu Asn Cys His Cys Glu Lys Thr Cys Gln Val
            245                 250                 255

Ser Gly Leu Leu Tyr Arg Asp Gln Asp Ser Trp Val Asp Gly Asp His
            260                 265                 270

Cys Arg Asn Cys Thr Cys Lys Ser Gly Ala Val Glu Cys Arg Arg Met
            275                 280                 285

Ser Cys Pro Pro Leu Asn Cys Ser Pro Asp Ser Leu Pro Val His Val
            290                 295                 300

Ala Gly Gln Cys Cys Lys Val Cys Arg Pro Lys Cys Ile Tyr Gly Gly
305                 310                 315                 320

Lys Val Leu Ala Glu Gly Gln Arg Ile Leu Thr Lys Ser Cys Arg Glu
            325                 330                 335

Cys Arg Gly Gly Val Leu Val Lys Ile Thr Glu Ala Cys Pro Pro Leu
            340                 345                 350

Asn Cys Ser Asp Lys Asp His Ile Leu Pro Glu Asn Gln Cys Cys Ser
            355                 360                 365

Val Cys Arg Gly His Asn Phe Cys Ala Glu Gly Pro Lys Cys Gly Glu
            370                 375                 380

Asn Ser Glu Cys Lys Asn Trp Asn Thr Lys Ala Thr Cys Glu Cys Lys
385                 390                 395                 400

Asn Gly Tyr Ile Ser Val Gln Gly Asp Ser Ala Tyr Cys Glu Asp Ile
            405                 410                 415

Asp Glu Cys Ala Ala Lys Met His Tyr Cys Arg Ala Asn Thr Val Cys
            420                 425                 430

Val Asn Leu Pro Gly Leu Tyr Arg Cys Asp Cys Val Pro Gly Tyr Ile
            435                 440                 445

Arg Val Asp Asp Phe Ser Cys Thr Glu His Asp Glu Cys Gly Ser Gly
            450                 455                 460

Gln His Asn Cys Asp Glu Asn Ala Ile Cys Thr Asn Thr Val Gln Gly
465                 470                 475                 480

His Ser Cys Thr Cys Lys Pro Gly Tyr Val Gly Asn Gly Thr Ser Cys
            485                 490                 495

Arg Ala Phe Cys Glu Glu Gly Cys Arg Tyr Gly Gly Thr Cys Val Ala
            500                 505                 510

Pro Asn Lys Cys Val Cys Pro Ser Gly Phe Thr Gly Ser His Cys Glu
            515                 520                 525
```

```
Lys Asp Ile Asp Glu Cys Thr Glu Gly Ile Ile Glu Cys His Asn His
      530                 535                 540

Ser Arg Cys Val Asn Leu Pro Gly Trp Tyr His Cys Glu Cys Arg Ser
545                 550                 555                 560

Gly Phe His Asp Asp Gly Thr Tyr Ser Leu Ser Gly Glu Ser Cys Ile
              565                 570                 575

Asp Ile Asp Glu Cys Ala Leu Arg Thr His Thr Cys Trp Asn Asp Ser
          580                 585                 590

Ala Cys Ile Asn Leu Ala Gly Gly Phe Asp Cys Leu Cys Pro Ser Gly
      595                 600                 605

Pro Ser Cys Ser Gly Asp Cys Pro His Glu Gly Leu Lys Arg Asn
      610                 615                 620

Gly Gln Val Trp Thr Leu Lys Glu Asp Arg Cys Ser Val Cys Ser Cys
625                 630                 635                 640

Lys Asp Gly Lys Ile Phe Cys Arg Arg Thr Ala Cys Asp Cys Gln Asn
              645                 650                 655

Pro Ser Val Asp Leu Phe Cys Cys Pro Glu Cys Asp Thr Arg Val Thr
              660                 665                 670

Ser Gln Cys Leu Asp Gln Asn Gly His Lys Leu Tyr Arg Ser Gly Asp
      675                 680                 685

Asn Trp Thr His Ser Cys Gln Gln Cys Arg Cys Leu Glu Gly Glu Val
      690                 695                 700

Asp Cys Trp Pro Leu Thr Cys Pro Arg Leu Ser Cys Glu Tyr Thr Ala
705                 710                 715                 720

Ile Leu Glu Gly Glu Cys Cys Pro Arg Cys Val Ser Asp Pro Cys Leu
                  725                 730                 735

Ala Asp Asn Ile Val Tyr Asp Ile Arg Glu Thr Cys Leu Asp Ser Tyr
              740                 745                 750

Gly Val Ser Arg Leu Ser Gly Ser Val Trp Thr Leu Ala Gly Ser Pro
          755                 760                 765

Cys Thr Thr Cys Lys Cys Lys Asn Gly Ser Val Cys Cys Ser Val Asp
      770                 775                 780

Leu Glu Cys Leu His Asn Asn
785                 790

<210> SEQ ID NO 7
<211> LENGTH: 2285
<212> TYPE: DNA
<213> ORGANISM: Equus caballus
<220> FEATURE:
<221> NAME/KEY: CDS
<222> LOCATION: (1)..(2235)

<400> SEQUENCE: 7 atg ggc ttt ggg atg gac ccc gac ctt caa atg gat att atc acc gag      48
Met Gly Phe Gly Met Asp Pro Asp Leu Gln Met Asp Ile Ile Thr Glu
1               5                   10                  15 ctc gac ctc gtg aac acc acc ctt gga gtc act cag gtg tcc gga ctg      96
Leu Asp Leu Val Asn Thr Thr Leu Gly Val Thr Gln Val Ser Gly Leu
            20                  25                  30 cac aat gcc agc aaa gca ttt tta ttt caa gat gta gag aga gag atc     144
His Asn Ala Ser Lys Ala Phe Leu Phe Gln Asp Val Glu Arg Glu Ile
        35                  40                  45 cat gca gcc cca cac gtg agt gag aaa tta att cag ctg ttc cgg aat     192
His Ala Ala Pro His Val Ser Glu Lys Leu Ile Gln Leu Phe Arg Asn
    50                  55                  60
```

|  |  |
|---|---|
| aag agt gaa ttc acc ttt ttg gcc act gtg cag cag aag ccg tca act<br>Lys Ser Glu Phe Thr Phe Leu Ala Thr Val Gln Gln Lys Pro Ser Thr<br>65                      70                     75                   80 | 240 |
| tca gga gtg ata ctg tcc att cga gaa ctg gaa aac agt tat ttt gaa<br>Ser Gly Val Ile Leu Ser Ile Arg Glu Leu Glu Asn Ser Tyr Phe Glu<br>                      85                   90                   95 | 288 |
| ctg gag agc agt ggc ctg aga gat gag att cga tat cac tac aca cac<br>Leu Glu Ser Ser Gly Leu Arg Asp Glu Ile Arg Tyr His Tyr Thr His<br>                 100                 105                 110 | 336 |
| aag ggg aag ccc agg aca gag gca ctt ccc tac cgg atg gcg gac gga<br>Lys Gly Lys Pro Arg Thr Glu Ala Leu Pro Tyr Arg Met Ala Asp Gly<br>115                    120                    125 | 384 |
| cgg tgg cac aag gtg gcg ctg tca gtt agc gcc tct cat ctc ctg ctc<br>Arg Trp His Lys Val Ala Leu Ser Val Ser Ala Ser His Leu Leu Leu<br>130                    135                    140 | 432 |
| cac atc gac tgc aac agg att tat gaa cgt gtg ata gac act cct gag<br>His Ile Asp Cys Asn Arg Ile Tyr Glu Arg Val Ile Asp Thr Pro Glu<br>145                    150                    155                 160 | 480 |
| acc aac ctc ccc cca gga agc aat ttg tgg ctg ggt cag cga aac caa<br>Thr Asn Leu Pro Pro Gly Ser Asn Leu Trp Leu Gly Gln Arg Asn Gln<br>                     165                 170                 175 | 528 |
| aag cac ggc tta ttc aaa gga atc atc caa gat gga aaa atc atc ttc<br>Lys His Gly Leu Phe Lys Gly Ile Ile Gln Asp Gly Lys Ile Ile Phe<br>                 180                 185                 190 | 576 |
| atg ccg aat gga tac ata aca cag tgt ccg aac ctg aat cgc act tgc<br>Met Pro Asn Gly Tyr Ile Thr Gln Cys Pro Asn Leu Asn Arg Thr Cys<br>         195                 200                 205 | 624 |
| cca acg tgc agt gat ttc tta agc ctg gtg caa gga atc atg gat tta<br>Pro Thr Cys Ser Asp Phe Leu Ser Leu Val Gln Gly Ile Met Asp Leu<br>210                    215                    220 | 672 |
| caa gag ctt ctg gcc aag atg act gcg aaa cta aat tat gca gag aca<br>Gln Glu Leu Leu Ala Lys Met Thr Ala Lys Leu Asn Tyr Ala Glu Thr<br>225                    230                    235                 240 | 720 |
| cga ctt agt caa ttg gaa aac tgc cac tgc gag aag acc tgt caa gtg<br>Arg Leu Ser Gln Leu Glu Asn Cys His Cys Glu Lys Thr Cys Gln Val<br>                     245                 250                 255 | 768 |
| agt gga ctg ctc tat aga gac cag gac tcc tgg gtt gat ggc gat cac<br>Ser Gly Leu Leu Tyr Arg Asp Gln Asp Ser Trp Val Asp Gly Asp His<br>                 260                 265                 270 | 816 |
| tgt agg aac tgc acg tgc aaa agc ggc gct gtg gaa tgt cgg agg atg<br>Cys Arg Asn Cys Thr Cys Lys Ser Gly Ala Val Glu Cys Arg Arg Met<br>         275                 280                 285 | 864 |
| tct tgt ccc cct ctc aat tgc tcc cca gac tcc ctc cct gtg cac gtt<br>Ser Cys Pro Pro Leu Asn Cys Ser Pro Asp Ser Leu Pro Val His Val<br>290                    295                    300 | 912 |
| gcc ggc cag tgc tgt aag gtc tgc cga cca aaa tgt atc tac gga ggg<br>Ala Gly Gln Cys Cys Lys Val Cys Arg Pro Lys Cys Ile Tyr Gly Gly<br>305                    310                    315                 320 | 960 |
| aaa gtc ctt gca gaa ggc cag cgg att tta acc aag agc tgt cgg gaa<br>Lys Val Leu Ala Glu Gly Gln Arg Ile Leu Thr Lys Ser Cys Arg Glu<br>                     325                 330                 335 | 1008 |
| tgc cga ggt gga gtt tta gtg aaa att aca gaa gcg tgc cct cct ttg<br>Cys Arg Gly Gly Val Leu Val Lys Ile Thr Glu Ala Cys Pro Pro Leu<br>                 340                 345                 350 | 1056 |
| aac tgc tca gac aag gat cac att ctc cca gag aat cag tgc tgc agc<br>Asn Cys Ser Asp Lys Asp His Ile Leu Pro Glu Asn Gln Cys Cys Ser<br>         355                 360                 365 | 1104 |
| gtc tgc aga ggt cat aac ttt tgt gcg gaa gga cct aaa tgt ggt gaa<br>Val Cys Arg Gly His Asn Phe Cys Ala Glu Gly Pro Lys Cys Gly Glu<br>370                    375                    380 | 1152 |

```
aat tca gag tgc aaa aac tgg aat aca aaa gct act tgc gag tgc aag      1200
Asn Ser Glu Cys Lys Asn Trp Asn Thr Lys Ala Thr Cys Glu Cys Lys
385                 390                 395                 400 aat ggt tat atc tct gtc cag ggg gac tcc gcc tac tgt gaa gat atc      1248
Asn Gly Tyr Ile Ser Val Gln Gly Asp Ser Ala Tyr Cys Glu Asp Ile
                405                 410                 415 gat gag tgt gct gct aag atg cat tac tgt cgt gcc aat act gtg tgt      1296
Asp Glu Cys Ala Ala Lys Met His Tyr Cys Arg Ala Asn Thr Val Cys
420                 425                 430 gtc aac ctg cct ggg tta tat cgg tgt gac tgt gtc ccg gga tac att      1344
Val Asn Leu Pro Gly Leu Tyr Arg Cys Asp Cys Val Pro Gly Tyr Ile
        435                 440                 445 cgc gtg gat gat ttc tct tgt aca gaa cat gac gaa tgt ggc agc ggg      1392
Arg Val Asp Asp Phe Ser Cys Thr Glu His Asp Glu Cys Gly Ser Gly
    450                 455                 460 cag cac aac tgt gat gag aat gcc atc tgc acc aac act gtc cag gga      1440
Gln His Asn Cys Asp Glu Asn Ala Ile Cys Thr Asn Thr Val Gln Gly
465                 470                 475                 480 cac agc tgc acc tgc aaa ccg ggc tac gtg ggg aat ggg acc agc tgc      1488
His Ser Cys Thr Cys Lys Pro Gly Tyr Val Gly Asn Gly Thr Ser Cys
                485                 490                 495 aga gcg ttc tgc gaa gag ggc tgc aga tat ggc ggg aca tgc gtg gct      1536
Arg Ala Phe Cys Glu Glu Gly Cys Arg Tyr Gly Gly Thr Cys Val Ala
                500                 505                 510 cct aac aaa tgt gtc tgt cct tct gga ttc aca gga agc cac tgt gag      1584
Pro Asn Lys Cys Val Cys Pro Ser Gly Phe Thr Gly Ser His Cys Glu
        515                 520                 525 aaa gac att gat gaa tgt gcc tta aga act cac acc tgt tgg aat gat      1632
Lys Asp Ile Asp Glu Cys Ala Leu Arg Thr His Thr Cys Trp Asn Asp
530                 535                 540 tct gcc tgc atc aac ttg gca ggg ggc ttc gac tgc ctg tgt ccc tca      1680
Ser Ala Cys Ile Asn Leu Ala Gly Gly Phe Asp Cys Leu Cys Pro Ser
545                 550                 555                 560 ggg cca tcc tgc tct ggt gac tgc ccc cac gaa gga gga ctg aag cgc      1728
Gly Pro Ser Cys Ser Gly Asp Cys Pro His Glu Gly Gly Leu Lys Arg
                565                 570                 575 aac ggg cag gtg tgg acc ctg aaa gaa gac agg tgt tct gtg tgt tcc      1776
Asn Gly Gln Val Trp Thr Leu Lys Glu Asp Arg Cys Ser Val Cys Ser
                580                 585                 590 tgc aag gat ggg aag ata ttc tgc cga cgg aca gct tgt gat tgc cag      1824
Cys Lys Asp Gly Lys Ile Phe Cys Arg Arg Thr Ala Cys Asp Cys Gln
        595                 600                 605 aat cca agc gtt gac ctt ttc tgt tgc cca gag tgt gac acc agg gtc      1872
Asn Pro Ser Val Asp Leu Phe Cys Cys Pro Glu Cys Asp Thr Arg Val
610                 615                 620 aca agt caa tgt tta gac caa aat gga cac aag ctc tat cga agt gga      1920
Thr Ser Gln Cys Leu Asp Gln Asn Gly His Lys Leu Tyr Arg Ser Gly
625                 630                 635                 640 gac aat tgg act cac agc tgt cag cag tgc cgg tgt ctg gaa gga gag      1968
Asp Asn Trp Thr His Ser Cys Gln Gln Cys Arg Cys Leu Glu Gly Glu
                645                 650                 655 gta gat tgc tgg cca ctc act tgc ccc aga ttg agc tgt gag tac aca      2016
Val Asp Cys Trp Pro Leu Thr Cys Pro Arg Leu Ser Cys Glu Tyr Thr
                660                 665                 670 gcc atc ttg gaa ggg gag tgt tgt cca cgc tgt gtc agc gac ccc tgc      2064
Ala Ile Leu Glu Gly Glu Cys Cys Pro Arg Cys Val Ser Asp Pro Cys
        675                 680                 685 ctg gcg gat aac atc gtc tat gac atc aga gaa act tgc ctg gac agc      2112
Leu Ala Asp Asn Ile Val Tyr Asp Ile Arg Glu Thr Cys Leu Asp Ser
```

```
              690                 695                 700
tat gga gtt tca agg ctt agt ggc tca gtg tgg aca ttg gct gga tct          2160
Tyr Gly Val Ser Arg Leu Ser Gly Ser Val Trp Thr Leu Ala Gly Ser
705                 710                 715                 720 ccc tgc acg acc tgc aaa tgc aag aat gga agt gtc tgc tgt tct gtg          2208
Pro Cys Thr Thr Cys Lys Cys Lys Asn Gly Ser Val Cys Cys Ser Val
                725                 730                 735 gat ttg gag tgt ctt cat aat aat tga aggatttaaa atggactcat                2255
Asp Leu Glu Cys Leu His Asn Asn
                740 gatcgccaga gaaaaatgga caaatgacca                                         2285

<210> SEQ ID NO 8
<211> LENGTH: 744
<212> TYPE: PRT
<213> ORGANISM: Equus caballus

<400> SEQUENCE: 8

Met Gly Phe Gly Met Asp Pro Asp Leu Gln Met Asp Ile Ile Thr Glu
1               5                   10                  15

Leu Asp Leu Val Asn Thr Thr Leu Gly Val Thr Gln Val Ser Gly Leu
                20                  25                  30

His Asn Ala Ser Lys Ala Phe Leu Phe Gln Asp Val Glu Arg Glu Ile
            35                  40                  45

His Ala Ala Pro His Val Ser Glu Lys Leu Ile Gln Leu Phe Arg Asn
        50                  55                  60

Lys Ser Glu Phe Thr Phe Leu Ala Thr Val Gln Gln Lys Pro Ser Thr
65                  70                  75                  80

Ser Gly Val Ile Leu Ser Ile Arg Glu Leu Glu Asn Ser Tyr Phe Glu
                85                  90                  95

Leu Glu Ser Ser Gly Leu Arg Asp Glu Ile Arg Tyr His Tyr Thr His
                100                 105                 110

Lys Gly Lys Pro Arg Thr Glu Ala Leu Pro Tyr Arg Met Ala Asp Gly
            115                 120                 125

Arg Trp His Lys Val Ala Leu Ser Val Ser Ala Ser His Leu Leu Leu
        130                 135                 140

His Ile Asp Cys Asn Arg Ile Tyr Glu Arg Val Ile Asp Thr Pro Glu
145                 150                 155                 160

Thr Asn Leu Pro Pro Gly Ser Asn Leu Trp Leu Gly Gln Arg Asn Gln
                165                 170                 175

Lys His Gly Leu Phe Lys Gly Ile Ile Gln Asp Gly Lys Ile Ile Phe
            180                 185                 190

Met Pro Asn Gly Tyr Ile Thr Gln Cys Pro Asn Leu Asn Arg Thr Cys
        195                 200                 205

Pro Thr Cys Ser Asp Phe Leu Ser Leu Val Gln Gly Ile Met Asp Leu
    210                 215                 220

Gln Glu Leu Leu Ala Lys Met Thr Ala Lys Leu Asn Tyr Ala Glu Thr
225                 230                 235                 240

Arg Leu Ser Gln Leu Glu Asn Cys His Cys Glu Lys Thr Cys Gln Val
                245                 250                 255

Ser Gly Leu Leu Tyr Arg Asp Gln Asp Ser Trp Val Asp Gly Asp His
            260                 265                 270

Cys Arg Asn Cys Thr Cys Lys Ser Gly Ala Val Glu Cys Arg Arg Met
        275                 280                 285

Ser Cys Pro Pro Leu Asn Cys Ser Pro Asp Ser Leu Pro Val His Val
```

-continued

```
                290                 295                 300
Ala Gly Gln Cys Cys Lys Val Cys Arg Pro Lys Cys Ile Tyr Gly Gly
305                 310                 315                 320

Lys Val Leu Ala Glu Gly Gln Arg Ile Leu Thr Lys Ser Cys Arg Glu
                325                 330                 335

Cys Arg Gly Gly Val Leu Val Lys Ile Thr Glu Ala Cys Pro Pro Leu
                340                 345                 350

Asn Cys Ser Asp Lys Asp His Ile Leu Pro Glu Asn Gln Cys Cys Ser
                355                 360                 365

Val Cys Arg Gly His Asn Phe Cys Ala Glu Gly Pro Lys Cys Gly Glu
                370                 375                 380

Asn Ser Glu Cys Lys Asn Trp Asn Thr Lys Ala Thr Cys Glu Cys Lys
385                 390                 395                 400

Asn Gly Tyr Ile Ser Val Gln Gly Asp Ser Ala Tyr Cys Glu Asp Ile
                405                 410                 415

Asp Glu Cys Ala Ala Lys Met His Tyr Cys Arg Ala Asn Thr Val Cys
                420                 425                 430

Val Asn Leu Pro Gly Leu Tyr Arg Cys Asp Cys Val Pro Gly Tyr Ile
                435                 440                 445

Arg Val Asp Asp Phe Ser Cys Thr Glu His Asp Glu Cys Gly Ser Gly
                450                 455                 460

Gln His Asn Cys Asp Glu Asn Ala Ile Cys Thr Asn Thr Val Gln Gly
465                 470                 475                 480

His Ser Cys Thr Cys Lys Pro Gly Tyr Val Gly Asn Gly Thr Ser Cys
                485                 490                 495

Arg Ala Phe Cys Glu Glu Gly Cys Arg Tyr Gly Gly Thr Cys Val Ala
                500                 505                 510

Pro Asn Lys Cys Val Cys Pro Ser Gly Phe Thr Gly Ser His Cys Glu
                515                 520                 525

Lys Asp Ile Asp Glu Cys Ala Leu Arg Thr His Thr Cys Trp Asn Asp
                530                 535                 540

Ser Ala Cys Ile Asn Leu Ala Gly Gly Phe Asp Cys Leu Cys Pro Ser
545                 550                 555                 560

Gly Pro Ser Cys Ser Gly Asp Cys Pro His Glu Gly Gly Leu Lys Arg
                565                 570                 575

Asn Gly Gln Val Trp Thr Leu Lys Glu Asp Arg Cys Ser Val Cys Ser
                580                 585                 590

Cys Lys Asp Gly Lys Ile Phe Cys Arg Arg Thr Ala Cys Asp Cys Gln
                595                 600                 605

Asn Pro Ser Val Asp Leu Phe Cys Cys Pro Glu Cys Asp Thr Arg Val
                610                 615                 620

Thr Ser Gln Cys Leu Asp Gln Asn Gly His Lys Leu Tyr Arg Ser Gly
625                 630                 635                 640

Asp Asn Trp Thr His Ser Cys Gln Gln Cys Arg Cys Leu Glu Gly Glu
                645                 650                 655

Val Asp Cys Trp Pro Leu Thr Cys Pro Arg Leu Ser Cys Glu Tyr Thr
                660                 665                 670

Ala Ile Leu Glu Gly Glu Cys Cys Pro Arg Cys Val Ser Asp Pro Cys
                675                 680                 685

Leu Ala Asp Asn Ile Val Tyr Asp Ile Arg Glu Thr Cys Leu Asp Ser
                690                 695                 700

Tyr Gly Val Ser Arg Leu Ser Gly Ser Val Trp Thr Leu Ala Gly Ser
705                 710                 715                 720
```

```
              Pro Cys Thr Thr Cys Lys Cys Lys Asn Gly Ser Val Cys Cys Ser Val
                          725                 730                 735

Asp Leu Glu Cys Leu His Asn Asn
                          740

<210> SEQ ID NO 9
<211> LENGTH: 2812
<212> TYPE: DNA
<213> ORGANISM: Mus musculus
<220> FEATURE:
<221> NAME/KEY: CDS
<222> LOCATION: (40)..(2472)

<400> SEQUENCE: 9
gcgttggtgc gccctgcttg gcgggggggcc tccggagcg atg ccg atg gat gtg           54
                                            Met Pro Met Asp Val
                                             1               5 att tta gtt ttg tgg ttc tgt gtg tgc acc gcc agg aca gtg ctg ggc          102
Ile Leu Val Leu Trp Phe Cys Val Cys Thr Ala Arg Thr Val Leu Gly
             10                  15                  20 ttt ggg atg gac cct gac ctt cag atg gac atc atc act gaa ctt gac          150
Phe Gly Met Asp Pro Asp Leu Gln Met Asp Ile Ile Thr Glu Leu Asp
         25                  30                  35 ctt gtg aac acc acc ctg ggc gtc act cag gtg gct gga cta cac aat          198
Leu Val Asn Thr Thr Leu Gly Val Thr Gln Val Ala Gly Leu His Asn
     40                  45                  50 gcc agt aag gca ttt ctg ttt caa gat gta cag aga gag atc cac tca          246
Ala Ser Lys Ala Phe Leu Phe Gln Asp Val Gln Arg Glu Ile His Ser
 55                  60                  65 gcc cct cat gtg agt gag aag ctg atc cag cta ttc cgg aat aag agt          294
Ala Pro His Val Ser Glu Lys Leu Ile Gln Leu Phe Arg Asn Lys Ser
 70                  75                  80                  85 gag ttt acc ttt ttg gct aca gtg cag cag aag ccg tcc acc tca ggg          342
Glu Phe Thr Phe Leu Ala Thr Val Gln Gln Lys Pro Ser Thr Ser Gly
             90                  95                 100 gtg ata ctg tcg atc cgg gag ctg gaa cac agc tat ttt gaa ctg gag          390
Val Ile Leu Ser Ile Arg Glu Leu Glu His Ser Tyr Phe Glu Leu Glu
        105                 110                 115 agc agt ggc cca aga gaa gag ata cgc tat cat tac atc cat ggc ggc          438
Ser Ser Gly Pro Arg Glu Glu Ile Arg Tyr His Tyr Ile His Gly Gly
        120                 125                 130 aag ccc agg act gag gcc ctt ccc tac cgc atg gcc gat gga cag tgg          486
Lys Pro Arg Thr Glu Ala Leu Pro Tyr Arg Met Ala Asp Gly Gln Trp
        135                 140                 145 cac aag gtc gcg ctg tct gtg agc gcc tct cac ctc cta ctc cat gtc          534
His Lys Val Ala Leu Ser Val Ser Ala Ser His Leu Leu Leu His Val
150                 155                 160                 165 gac tgc aat agg att tat gag cgt gtg ata gat cct ccg gag acc aac          582
Asp Cys Asn Arg Ile Tyr Glu Arg Val Ile Asp Pro Pro Glu Thr Asn
                170                 175                 180 ctt cct cca gga agc aat cta tgg ctt ggg caa cgt aat caa aag cat          630
Leu Pro Pro Gly Ser Asn Leu Trp Leu Gly Gln Arg Asn Gln Lys His
            185                 190                 195 ggc ttt ttc aaa gga atc atc caa gat ggc aag atc atc ttc atg ccg          678
Gly Phe Phe Lys Gly Ile Ile Gln Asp Gly Lys Ile Ile Phe Met Pro
            200                 205                 210 aac ggc ttc atc aca cag tgc ccc aac cta aat cgc act tgc cca aca          726
Asn Gly Phe Ile Thr Gln Cys Pro Asn Leu Asn Arg Thr Cys Pro Thr
        215                 220                 225 tgc agt gat ttc ctg agc ctg gtt caa gga ata atg gat ttg caa gag          774
```

-continued

| | | |
|---|---|---|
| Cys Ser Asp Phe Leu Ser Leu Val Gln Gly Ile Met Asp Leu Gln Glu<br>230       235       240       245 | | |
| ctt ttg gcc aag atg act gca aaa ctg aat tat gca gag acg aga ctt<br>Leu Leu Ala Lys Met Thr Ala Lys Leu Asn Tyr Ala Glu Thr Arg Leu<br>       250       255       260 | 822 | |
| ggt caa ctg gaa aat tgc cac tgt gag aag acc tgc caa gtg agt ggg<br>Gly Gln Leu Glu Asn Cys His Cys Glu Lys Thr Cys Gln Val Ser Gly<br>    265        270        275 | 870 | |
| ctg ctc tac agg gac caa gac tcc tgg gta gat ggt gac aac tgc agg<br>Leu Leu Tyr Arg Asp Gln Asp Ser Trp Val Asp Gly Asp Asn Cys Arg<br>      280        285        290 | 918 | |
| aac tgc aca tgc aaa agt ggt gct gtg gag tgc cga agg atg tcc tgt<br>Asn Cys Thr Cys Lys Ser Gly Ala Val Glu Cys Arg Arg Met Ser Cys<br>295       300       305 | 966 | |
| ccc cca ctc aac tgt tcc cca gac tca ctt cct gtg cat att tct ggc<br>Pro Pro Leu Asn Cys Ser Pro Asp Ser Leu Pro Val His Ile Ser Gly<br>310       315       320       325 | 1014 | |
| caa tgt tgt aaa gtt tgc aga cca aaa tgt atc tat gga gga aaa gtt<br>Gln Cys Cys Lys Val Cys Arg Pro Lys Cys Ile Tyr Gly Gly Lys Val<br>        330       335       340 | 1062 | |
| ctt gct gag ggc cag cgg att tta acc aag acc tgc cgg gaa tgt cga<br>Leu Ala Glu Gly Gln Arg Ile Leu Thr Lys Thr Cys Arg Glu Cys Arg<br>    345        350        355 | 1110 | |
| ggt gga gtc ttg gta aaa atc aca gaa gct tgc cct cct ttg aac tgc<br>Gly Gly Val Leu Val Lys Ile Thr Glu Ala Cys Pro Pro Leu Asn Cys<br>      360        365        370 | 1158 | |
| tca gag aag gat cat att ctt ccg gag aac cag tgc tgc agg gtc tgc<br>Ser Glu Lys Asp His Ile Leu Pro Glu Asn Gln Cys Cys Arg Val Cys<br>375       380       385 | 1206 | |
| cga ggt cat aac ttc tgt gca gaa gca cct aag tgt gga gaa aac tcg<br>Arg Gly His Asn Phe Cys Ala Glu Ala Pro Lys Cys Gly Glu Asn Ser<br>390       395       400       405 | 1254 | |
| gaa tgc aaa aat tgg aat aca aaa gcg act tgt gag tgc aag aat gga<br>Glu Cys Lys Asn Trp Asn Thr Lys Ala Thr Cys Glu Cys Lys Asn Gly<br>        410       415       420 | 1302 | |
| tac atc tct gtc cag ggc aac tct gca tac tgt gaa gat atc gat gag<br>Tyr Ile Ser Val Gln Gly Asn Ser Ala Tyr Cys Glu Asp Ile Asp Glu<br>    425        430        435 | 1350 | |
| tgt gca gca aag atg cac tac tgt cat gcc aac acg gtg tgt gtc aac<br>Cys Ala Ala Lys Met His Tyr Cys His Ala Asn Thr Val Cys Val Asn<br>      440        445        450 | 1398 | |
| ttg ccg ggg tta tat cgc tgt gac tgc atc cca gga tac atc cgt gtg<br>Leu Pro Gly Leu Tyr Arg Cys Asp Cys Ile Pro Gly Tyr Ile Arg Val<br>455       460       465 | 1446 | |
| gat gac ttc tct tgt acg gag cat gat gat tgt ggc agc gga caa cac<br>Asp Asp Phe Ser Cys Thr Glu His Asp Asp Cys Gly Ser Gly Gln His<br>470       475       480       485 | 1494 | |
| aac tgt gac aaa aat gcc atc tgt acc aac aca gtc cag gga cac agc<br>Asn Cys Asp Lys Asn Ala Ile Cys Thr Asn Thr Val Gln Gly His Ser<br>        490       495       500 | 1542 | |
| tgt acc tgc cag cca ggc tac gtg gga aat ggt act gtc tgc aaa gca<br>Cys Thr Cys Gln Pro Gly Tyr Val Gly Asn Gly Thr Val Cys Lys Ala<br>    505        510        515 | 1590 | |
| ttc tgt gaa gag ggt tgc aga tac gga ggt acc tgt gtg gcc cct aac<br>Phe Cys Glu Glu Gly Cys Arg Tyr Gly Gly Thr Cys Val Ala Pro Asn<br>      520        525        530 | 1638 | |
| aaa tgt gtc tgt cct tct gga ttc aca gga agc cac tgt gag aaa gat<br>Lys Cys Val Cys Pro Ser Gly Phe Thr Gly Ser His Cys Glu Lys Asp<br>535       540       545 | 1686 | |

| | | |
|---|---|---|
| att gat gaa tgt gca gag gga ttc gtt gag tgc cac aac cac tcc cgc<br>Ile Asp Glu Cys Ala Glu Gly Phe Val Glu Cys His Asn His Ser Arg<br>550                555                    560                565 | 1734 |
| tgc gtt aac ctt cca ggg tgg tac cac tgt gag tgc aga agc ggt ttc<br>Cys Val Asn Leu Pro Gly Trp Tyr His Cys Glu Cys Arg Ser Gly Phe<br>                  570                    575                    580 | 1782 |
| cat gac gat ggg acc tat tca ctg tcc ggg gag tcc tgc att gat att<br>His Asp Asp Gly Thr Tyr Ser Leu Ser Gly Glu Ser Cys Ile Asp Ile<br>                585                    590                    595 | 1830 |
| gat gaa tgt gcc tta aga act cac act tgt tgg aat gac tct gcc tgc<br>Asp Glu Cys Ala Leu Arg Thr His Thr Cys Trp Asn Asp Ser Ala Cys<br>600                605                    610 | 1878 |
| atc aac tta gca gga gga ttt gac tgc ctg tgt ccc tct ggg ccc tcc<br>Ile Asn Leu Ala Gly Gly Phe Asp Cys Leu Cys Pro Ser Gly Pro Ser<br>                615                    620                    625 | 1926 |
| tgc tct ggt gac tgt ccc cac gaa ggg ggg ctg aag cat aat ggg cag<br>Cys Ser Gly Asp Cys Pro His Glu Gly Gly Leu Lys His Asn Gly Gln<br>630                635                    640                    645 | 1974 |
| gtg tgg att ctg aga gaa gac agg tgt tca gtc tgt tcc tgt aag gat<br>Val Trp Ile Leu Arg Glu Asp Arg Cys Ser Val Cys Ser Cys Lys Asp<br>                650                    655                    660 | 2022 |
| ggg aag ata ttc tgc cgg cgg aca gct tgt gat tgc cag aat cca aat<br>Gly Lys Ile Phe Cys Arg Arg Thr Ala Cys Asp Cys Gln Asn Pro Asn<br>                  665                    670                    675 | 2070 |
| gtt gac ctt ttc tgc tgc cca gag tgt gac acc agg gtc act agc caa<br>Val Asp Leu Phe Cys Cys Pro Glu Cys Asp Thr Arg Val Thr Ser Gln<br>680                685                    690 | 2118 |
| tgt tta gat caa agc gga cag aag ctc tat cga agt gga gac aac tgg<br>Cys Leu Asp Gln Ser Gly Gln Lys Leu Tyr Arg Ser Gly Asp Asn Trp<br>                695                    700                    705 | 2166 |
| acc cac agc tgc cag cag tgc cga tgt ctg gaa gga gag gca gac tgc<br>Thr His Ser Cys Gln Gln Cys Arg Cys Leu Glu Gly Glu Ala Asp Cys<br>710                715                    720                    725 | 2214 |
| tgg cct cta gct tgc cct agt ttg agc tgt gaa tac aca gcc atc ttt<br>Trp Pro Leu Ala Cys Pro Ser Leu Ser Cys Glu Tyr Thr Ala Ile Phe<br>                  730                    735                    740 | 2262 |
| gaa gga gag tgt tgt ccc cgc tgt gtc agt gac ccc tgc ctg gct gat<br>Glu Gly Glu Cys Cys Pro Arg Cys Val Ser Asp Pro Cys Leu Ala Asp<br>                745                    750                    755 | 2310 |
| aat att gcc tat gac atc aga aaa act tgc ctg gac agc tct ggt att<br>Asn Ile Ala Tyr Asp Ile Arg Lys Thr Cys Leu Asp Ser Ser Gly Ile<br>                760                    765                    770 | 2358 |
| tcg agg ctg agc ggc gca gtg tgg aca atg gct gga tct ccc tgt aca<br>Ser Arg Leu Ser Gly Ala Val Trp Thr Met Ala Gly Ser Pro Cys Thr<br>775                780                    785 | 2406 |
| acc tgt caa tgc aag aat ggg aga gtc tgc tgc tct gtg gat ctg gtg<br>Thr Cys Gln Cys Lys Asn Gly Arg Val Cys Cys Ser Val Asp Leu Val<br>790                795                    800                    805 | 2454 |
| tgt ctt gag aat aac tga agattttaaa tggactcatc acatgagaaa<br>Cys Leu Glu Asn Asn<br>                810 | 2502 |
| atggacaaaa tgaccatcca acctgaggaa gaggaggggc tgatttcttt ttcttttaa | 2562 |
| ccacagtcaa ttaccaaagt ctccatcaga ggaaggcgtt tgggttgcct ttaccacttt | 2622 |
| gctcatcctt gctgacctag tctagatgcc tgcagtaccg tgtatttcgg tcgatggttg | 2682 |
| ttgagtctcc gtgctgtaaa tcacatttcc cttgtcagat catttacaga tacatttaaa | 2742 |
| ggattccatg ataaatgtta aagtacccctt tgtttatttt gtgtaccaac ataatagaga | 2802 |
| cttggcacca | 2812 |

```
<210> SEQ ID NO 10
<211> LENGTH: 810
<212> TYPE: PRT
<213> ORGANISM: Mus musculus

<400> SEQUENCE: 10

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Glu Lys Asp His Ile Leu Pro Glu Asn Gln
```

```
            370                 375                 380
Cys Cys Arg Val Cys Arg Gly His Asn Phe Cys Ala Glu Ala Pro Lys
385                 390                 395                 400
Cys Gly Glu Asn Ser Glu Cys Lys Asn Trp Asn Thr Lys Ala Thr Cys
                405                 410                 415
Glu Cys Lys Asn Gly Tyr Ile Ser Val Gln Gly Asn Ser Ala Tyr Cys
                420                 425                 430
Glu Asp Ile Asp Glu Cys Ala Ala Lys Met His Tyr Cys His Ala Asn
                435                 440                 445
Thr Val Cys Val Asn Leu Pro Gly Leu Tyr Arg Cys Asp Cys Ile Pro
        450                 455                 460
Gly Tyr Ile Arg Val Asp Asp Phe Ser Cys Thr Glu His Asp Asp Cys
465                 470                 475                 480
Gly Ser Gly Gln His Asn Cys Asp Lys Asn Ala Ile Cys Thr Asn Thr
                485                 490                 495
Val Gln Gly His Ser Cys Thr Cys Gln Pro Gly Tyr Val Gly Asn Gly
                500                 505                 510
Thr Val Cys Lys Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
        530                 535                 540
His Cys Glu Lys Asp Ile Asp Glu Cys Ala Glu Gly Phe Val Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
                580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
        610                 615                 620
Pro Ser Gly Pro Ser Cys Ser Gly Asp Cys Pro His Glu Gly Gly Leu
625                 630                 635                 640
Lys His Asn Gly Gln Val Trp Ile Leu Arg Glu Asp Arg Cys Ser Val
                645                 650                 655
Cys Ser Cys Lys Asp Gly Lys Ile Phe Cys Arg Arg Thr Ala Cys Asp
                660                 665                 670
Cys Gln Asn Pro Asn Val Asp Leu Phe Cys Cys Pro Glu Cys Asp Thr
                675                 680                 685
Arg Val Thr Ser Gln Cys Leu Asp Gln Ser Gly Gln Lys Leu Tyr Arg
        690                 695                 700
Ser Gly Asp Asn Trp Thr His Ser Cys Gln Cys Arg Cys Leu Glu
705                 710                 715                 720
Gly Glu Ala Asp Cys Trp Pro Leu Ala Cys Pro Ser Leu Ser Cys Glu
                725                 730                 735
Tyr Thr Ala Ile Phe Glu Gly Glu Cys Cys Pro Arg Cys Val Ser Asp
                740                 745                 750
Pro Cys Leu Ala Asp Asn Ile Ala Tyr Asp Ile Arg Lys Thr Cys Leu
                755                 760                 765
Asp Ser Ser Gly Ile Ser Arg Leu Ser Gly Ala Val Trp Thr Met Ala
        770                 775                 780
Gly Ser Pro Cys Thr Thr Cys Gln Cys Lys Asn Gly Arg Val Cys Cys
785                 790                 795                 800
```

<210> SEQ ID NO 11
<211> LENGTH: 2915
<212> TYPE: DNA
<213> ORGANISM: Rattus norvegicus
<220> FEATURE:
<221> NAME/KEY: CDS
<222> LOCATION: (59)..(2491)

<400> SEQUENCE: 11

```
aagcactggt tcttgttag cgttggtgcg ccctgcttgg cgggggttct ccggagcg      58 atg ccg atg gat gtg att tta gtt ttg tgg ttc tgt gta tgc acc gcc    106
Met Pro Met Asp Val Ile Leu Val Leu Trp Phe Cys Val Cys Thr Ala
1               5                   10                  15 agg aca gtg ttg ggc ttt ggg atg gac cct gac ctt cag ctg gac atc    154
Arg Thr Val Leu Gly Phe Gly Met Asp Pro Asp Leu Gln Leu Asp Ile
            20                  25                  30 atc tca gag ctc gac ctg gtg aac acc acc ctg gga gtc acg cag gtg    202
Ile Ser Glu Leu Asp Leu Val Asn Thr Thr Leu Gly Val Thr Gln Val
        35                  40                  45 gct gga ctg cac aac gcc agt aaa gca ttt cta ttt caa gat gta cag    250
Ala Gly Leu His Asn Ala Ser Lys Ala Phe Leu Phe Gln Asp Val Gln
    50                  55                  60 aga gag atc cat tcg gcc cct cac gtg agt gag aag ctg atc cag cta    298
Arg Glu Ile His Ser Ala Pro His Val Ser Glu Lys Leu Ile Gln Leu
65                  70                  75                  80 ttc cgg aat aag agc gag ttc acc ttt ttg gct aca gtg cag cag aaa    346
Phe Arg Asn Lys Ser Glu Phe Thr Phe Leu Ala Thr Val Gln Gln Lys
                85                  90                  95 cca tcc acc tca ggg gtg ata ctg tcc atc cgg gag ctg gag cac agc    394
Pro Ser Thr Ser Gly Val Ile Leu Ser Ile Arg Glu Leu Glu His Ser
            100                 105                 110 tat ttt gaa ctg gag agc agt ggc cca aga gaa gag ata cgc tac cat    442
Tyr Phe Glu Leu Glu Ser Ser Gly Pro Arg Glu Glu Ile Arg Tyr His
        115                 120                 125 tac ata cat ggt gga aag ccc agg act gag gcc ctt ccc tac cgc atg    490
Tyr Ile His Gly Gly Lys Pro Arg Thr Glu Ala Leu Pro Tyr Arg Met
    130                 135                 140 gca gac gga caa tgg cac aag gtc gcg ctg tca gtg agc gcc tct cac    538
Ala Asp Gly Gln Trp His Lys Val Ala Leu Ser Val Ser Ala Ser His
145                 150                 155                 160 ctc ctg ctc cac atc gac tgc aat agg att tac gag cgt gtg ata gac    586
Leu Leu Leu His Ile Asp Cys Asn Arg Ile Tyr Glu Arg Val Ile Asp
                165                 170                 175 cct ccg gag acc aac ctt cct cca gga agc aat ctg tgg ctt ggg caa    634
Pro Pro Glu Thr Asn Leu Pro Pro Gly Ser Asn Leu Trp Leu Gly Gln
            180                 185                 190 cgt aac caa aag cat ggc ttt ttc aaa gga atc atc caa gat ggt aag    682
Arg Asn Gln Lys His Gly Phe Phe Lys Gly Ile Ile Gln Asp Gly Lys
        195                 200                 205 atc atc ttc atg ccg aat ggt ttc atc aca cag tgt ccc aac ctc aat    730
Ile Ile Phe Met Pro Asn Gly Phe Ile Thr Gln Cys Pro Asn Leu Asn
    210                 215                 220 cgc act tgc cca aca tgc agt gac ttc ctg agc ctg gtt caa gga ata    778
Arg Thr Cys Pro Thr Cys Ser Asp Phe Leu Ser Leu Val Gln Gly Ile
225                 230                 235                 240 atg gat ttg caa gag ctt ttg gcc aag atg act gca aaa ctg aat tat    826
Met Asp Leu Gln Glu Leu Leu Ala Lys Met Thr Ala Lys Leu Asn Tyr
```

-continued

|  |  |  | 245 |  |  |  | 250 |  |  |  | 255 |  |  |  |  |
|---|---|---|---|---|---|---|---|---|---|---|---|---|---|---|---|
| gca | gag | acg | aga | ctt | ggt | caa | ctg | gaa | aat | tgc | cac | tgt | gag | aag | acc | 874 |
| Ala | Glu | Thr | Arg | Leu | Gly | Gln | Leu | Glu | Asn | Cys | His | Cys | Glu | Lys | Thr |
|  |  | 260 |  |  |  |  | 265 |  |  |  |  | 270 |  |  |  |

| tgc | caa | gtg | agt | ggg | ctg | ctc | tac | agg | gac | caa | gac | tcc | tgg | gtg | gat | 922 |
| Cys | Gln | Val | Ser | Gly | Leu | Leu | Tyr | Arg | Asp | Gln | Asp | Ser | Trp | Val | Asp |
|  |  |  | 275 |  |  |  |  | 280 |  |  |  |  | 285 |  |  |

| ggt | gac | aac | tgt | ggg | aac | tgc | acg | tgc | aaa | agt | ggt | gcc | gtg | gag | tgc | 970 |
| Gly | Asp | Asn | Cys | Gly | Asn | Cys | Thr | Cys | Lys | Ser | Gly | Ala | Val | Glu | Cys |
|  | 290 |  |  |  |  | 295 |  |  |  |  | 300 |  |  |  |  |

| cgc | agg | atg | tcc | tgt | ccc | ccg | ctc | aac | tgt | tcc | ccg | gac | tca | ctt | cct | 1018 |
| Arg | Arg | Met | Ser | Cys | Pro | Pro | Leu | Asn | Cys | Ser | Pro | Asp | Ser | Leu | Pro |
| 305 |  |  |  |  | 310 |  |  |  |  | 315 |  |  |  |  | 320 |

| gtg | cac | att | tcc | ggc | cag | tgt | tgt | aaa | gtt | tgc | aga | cca | aaa | tgt | atc | 1066 |
| Val | His | Ile | Ser | Gly | Gln | Cys | Cys | Lys | Val | Cys | Arg | Pro | Lys | Cys | Ile |
|  |  |  |  | 325 |  |  |  |  | 330 |  |  |  |  | 335 |  |

| tat | gga | gga | aaa | gtt | ctt | gct | gag | ggc | cag | cgg | att | tta | acc | aag | acc | 1114 |
| Tyr | Gly | Gly | Lys | Val | Leu | Ala | Glu | Gly | Gln | Arg | Ile | Leu | Thr | Lys | Thr |
|  |  | 340 |  |  |  |  | 345 |  |  |  |  | 350 |  |  |  |

| tgc | cgg | gaa | tgt | cga | ggt | gga | gtc | ttg | gta | aaa | atc | aca | gaa | gct | tgc | 1162 |
| Cys | Arg | Glu | Cys | Arg | Gly | Gly | Val | Leu | Val | Lys | Ile | Thr | Glu | Ala | Cys |
|  |  |  | 355 |  |  |  |  | 360 |  |  |  |  | 365 |  |  |

| cct | cct | ttg | aac | tgc | tca | gca | aag | gat | cat | att | ctt | cca | gag | aat | cag | 1210 |
| Pro | Pro | Leu | Asn | Cys | Ser | Ala | Lys | Asp | His | Ile | Leu | Pro | Glu | Asn | Gln |
|  | 370 |  |  |  |  | 375 |  |  |  |  | 380 |  |  |  |  |

| tgc | tgc | agg | gtc | tgc | cca | ggt | cat | aac | ttc | tgt | gca | gaa | gca | cct | aag | 1258 |
| Cys | Cys | Arg | Val | Cys | Pro | Gly | His | Asn | Phe | Cys | Ala | Glu | Ala | Pro | Lys |
| 385 |  |  |  |  | 390 |  |  |  |  | 395 |  |  |  |  | 400 |

| tgc | gga | gaa | aac | tcg | gaa | tgc | aaa | aat | tgg | aat | aca | aaa | gca | acc | tgt | 1306 |
| Cys | Gly | Glu | Asn | Ser | Glu | Cys | Lys | Asn | Trp | Asn | Thr | Lys | Ala | Thr | Cys |
|  |  |  |  | 405 |  |  |  |  | 410 |  |  |  |  | 415 |  |

| gag | tgc | aag | aat | gga | tac | atc | tct | gtc | cag | ggc | aac | tct | gca | tac | tgt | 1354 |
| Glu | Cys | Lys | Asn | Gly | Tyr | Ile | Ser | Val | Gln | Gly | Asn | Ser | Ala | Tyr | Cys |
|  |  |  | 420 |  |  |  |  | 425 |  |  |  |  | 430 |  |  |

| gaa | gat | att | gat | gag | tgt | gca | gct | aaa | atg | cac | tat | tgt | cat | gcc | aac | 1402 |
| Glu | Asp | Ile | Asp | Glu | Cys | Ala | Ala | Lys | Met | His | Tyr | Cys | His | Ala | Asn |
|  |  | 435 |  |  |  |  | 440 |  |  |  |  | 445 |  |  |  |

| acc | gtg | tgt | gtc | aac | ttg | ccg | ggg | ttg | tat | cgc | tgt | gac | tgc | gtc | cca | 1450 |
| Thr | Val | Cys | Val | Asn | Leu | Pro | Gly | Leu | Tyr | Arg | Cys | Asp | Cys | Val | Pro |
| 450 |  |  |  |  | 455 |  |  |  |  | 460 |  |  |  |  |  |

| ggg | tac | atc | cgt | gtg | gat | gac | ttc | tct | tgt | acg | gag | cat | gat | gat | tgt | 1498 |
| Gly | Tyr | Ile | Arg | Val | Asp | Asp | Phe | Ser | Cys | Thr | Glu | His | Asp | Asp | Cys |
| 465 |  |  |  |  | 470 |  |  |  |  | 475 |  |  |  |  | 480 |

| ggc | agc | gga | caa | cac | aac | tgc | gac | aaa | aat | gcc | atc | tgt | acc | aac | aca | 1546 |
| Gly | Ser | Gly | Gln | His | Asn | Cys | Asp | Lys | Asn | Ala | Ile | Cys | Thr | Asn | Thr |
|  |  |  |  | 485 |  |  |  |  | 490 |  |  |  |  | 495 |  |

| gtc | cag | gga | cac | agc | tgc | acc | tgc | cag | ccg | ggt | tac | gtg | gga | aat | ggc | 1594 |
| Val | Gln | Gly | His | Ser | Cys | Thr | Cys | Gln | Pro | Gly | Tyr | Val | Gly | Asn | Gly |
|  |  |  | 500 |  |  |  |  | 505 |  |  |  |  | 510 |  |  |

| acc | atc | tgc | aaa | gca | ttc | tgt | gaa | gag | ggt | tgc | aga | tac | gga | ggt | acc | 1642 |
| Thr | Ile | Cys | Lys | Ala | Phe | Cys | Glu | Glu | Gly | Cys | Arg | Tyr | Gly | Gly | Thr |
|  |  | 515 |  |  |  |  | 520 |  |  |  |  | 525 |  |  |  |

| tgt | gtg | gct | cct | aac | aag | tgt | gtc | tgt | cct | tct | gga | ttc | acg | gga | agc | 1690 |
| Cys | Val | Ala | Pro | Asn | Lys | Cys | Val | Cys | Pro | Ser | Gly | Phe | Thr | Gly | Ser |
|  | 530 |  |  |  |  | 535 |  |  |  |  | 540 |  |  |  |  |

| cac | tgt | gag | aaa | gat | att | gat | gaa | tgc | gca | gag | gga | ttc | gtt | gaa | tgc | 1738 |
| His | Cys | Glu | Lys | Asp | Ile | Asp | Glu | Cys | Ala | Glu | Gly | Phe | Val | Glu | Cys |
| 545 |  |  |  |  | 550 |  |  |  |  | 555 |  |  |  |  | 560 |

| cac | aac | tac | tcc | cgc | tgt | gtt | aac | ctg | cca | ggg | tgg | tac | cac | tgt | gag | 1786 |

```
                His Asn Tyr Ser Arg Cys Val Asn Leu Pro Gly Trp Tyr His Cys Glu
                            565                 570                 575 tgc aga agc ggt ttc cat gac gat ggg acc tac tca ctg tcc ggg gag           1834
Cys Arg Ser Gly Phe His Asp Asp Gly Thr Tyr Ser Leu Ser Gly Glu
            580                 585                 590 tcc tgc att gat atc gat gaa tgt gcc tta aga act cac act tgt tgg           1882
Ser Cys Ile Asp Ile Asp Glu Cys Ala Leu Arg Thr His Thr Cys Trp
                595                 600                 605 aat gac tct gcc tgc atc aac tta gca gga gga ttt gac tgc ctg tgt           1930
Asn Asp Ser Ala Cys Ile Asn Leu Ala Gly Gly Phe Asp Cys Leu Cys
        610                 615                 620 ccc tct ggg ccc tcc tgc tct ggt gac tgt ccc cac gaa gga ggg ctg           1978
Pro Ser Gly Pro Ser Cys Ser Gly Asp Cys Pro His Glu Gly Gly Leu
625                 630                 635                 640 aag cat aat ggg cag gtg tgg att ctg aga gaa gac agg tgt tca gtc           2026
Lys His Asn Gly Gln Val Trp Ile Leu Arg Glu Asp Arg Cys Ser Val
                645                 650                 655 tgt tcc tgc aag gat ggg aag ata ttc tgc cgg cgg aca gct tgt gat           2074
Cys Ser Cys Lys Asp Gly Lys Ile Phe Cys Arg Arg Thr Ala Cys Asp
            660                 665                 670 tgc cag aat cca aat gtt gac ctt ttt tgc tgc cca gag tgc gat acc           2122
Cys Gln Asn Pro Asn Val Asp Leu Phe Cys Cys Pro Glu Cys Asp Thr
        675                 680                 685 agg gtc acc agc caa tgt tta gat caa agt gga cag aag ctc tat cga           2170
Arg Val Thr Ser Gln Cys Leu Asp Gln Ser Gly Gln Lys Leu Tyr Arg
    690                 695                 700 agt gga gac aac tgg acc cac agc tgc cag cag tgc cga tgt ctg gaa           2218
Ser Gly Asp Asn Trp Thr His Ser Cys Gln Gln Cys Arg Cys Leu Glu
705                 710                 715                 720 gga gag gca gac tgc tgg cct ctg gct tgc cct agt ttg ggc tgt gaa           2266
Gly Glu Ala Asp Cys Trp Pro Leu Ala Cys Pro Ser Leu Gly Cys Glu
                725                 730                 735 tac aca gcc atg ttt gaa ggg gag tgt tgt ccc cga tgt gtc agt gac           2314
Tyr Thr Ala Met Phe Glu Gly Glu Cys Cys Pro Arg Cys Val Ser Asp
            740                 745                 750 ccc tgc ctg gct ggt aat att gcc tat gac atc aga aaa act tgc ctg           2362
Pro Cys Leu Ala Gly Asn Ile Ala Tyr Asp Ile Arg Lys Thr Cys Leu
        755                 760                 765 gac agc ttt ggt gtt tcg agg ctg agc gga gcc gtg tgg aca atg gct           2410
Asp Ser Phe Gly Val Ser Arg Leu Ser Gly Ala Val Trp Thr Met Ala
    770                 775                 780 gga tct cct tgt aca acc tgc aaa tgc aag aat ggg aga gtc tgc tgc           2458
Gly Ser Pro Cys Thr Thr Cys Lys Cys Lys Asn Gly Arg Val Cys Cys
785                 790                 795                 800 tct gtg gat ctg gag tgt att gag aat aac tga agattttaaa tggactcgtc        2511
Ser Val Asp Leu Glu Cys Ile Glu Asn Asn
                805                 810 acgtgagaaa atgggcaaaa tgatcatccc acctgaggaa gaagaggggc tgatttcttt        2571 ttcttttaa ccacagtcaa ttaccaaagt ctccatctga ggaaggcgtt tggattgcct         2631
ttgccacttt gctcatcctt gctgacctag tctagatgcc tgcagtaccg tgcatttcgg        2691
tcgatggttg ttgagtctca gtgttgtaaa tcgcatttcc ctcgtcagat catttacaga        2751
tacatttaaa ggggttccat gataaatgtt aatgtaactt tgtttatttt tgtgtactga        2811
cataatagag acttggcacc atttatttat ttttcttgat ttttggatca aattctaaaa        2871
ataaagttgc ctgttgcgaa aaaaaaaaaa aaaaaaaaa aaaa                          2915

<210> SEQ ID NO 12
```

-continued

```
<211> LENGTH: 810
<212> TYPE: PRT
<213> ORGANISM: Rattus norvegicus

<400> SEQUENCE: 12

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Gly Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Ala Lys Asp His Ile Leu Pro Glu Asn Gln
    370                 375                 380

Cys Cys Arg Val Cys Pro Gly His Asn Phe Cys Ala Glu Ala Pro Lys
```

```
385                 390                 395                 400
Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
                420                 425                 430

Glu Asp Ile Asp Glu Cys Ala Ala Lys Met His Tyr Cys His Ala Asn
                435                 440                 445

Thr Val Cys Val Asn Leu Pro Gly Leu Tyr Arg Cys Asp Cys Val Pro
            450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Ile Cys Lys Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
            530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
            595                 600                 605

Asn Asp Ser Ala Cys Ile Asn Leu Ala Gly Gly Phe Asp Cys Leu Cys
            610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
                660                 665                 670

Cys Gln Asn Pro Asn Val Asp Leu Phe Cys Cys Pro Glu Cys Asp Thr
                675                 680                 685

Arg Val Thr Ser Gln Cys Leu Asp Gln Ser Gly Gln Lys Leu Tyr Arg
            690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Gly Cys Glu
                725                 730                 735

Tyr Thr Ala Met Phe Glu Gly Glu Cys Cys Pro Arg Cys Val Ser Asp
                740                 745                 750

Pro Cys Leu Ala Gly Asn Ile Ala Tyr Asp Ile Arg Lys Thr Cys Leu
            755                 760                 765

Asp Ser Phe Gly Val Ser Arg Leu Ser Gly Ala Val Trp Thr Met Ala
            770                 775                 780

Gly Ser Pro Cys Thr Thr Cys Lys Cys Lys Asn Gly Arg Val Cys Cys
785                 790                 795                 800

Ser Val Asp Leu Glu Cys Ile Glu Asn Asn
                805                 810
```

<210> SEQ ID NO 13
<211> LENGTH: 810
<212> TYPE: PRT
<213> ORGANISM: Felis catus

<400> SEQUENCE: 13

```
Met Pro Arg Asp Val Ile Leu Val Val Trp Phe Cys Val Cys Thr Ala
1               5                   10                  15

Arg Thr Val Val Gly Phe Gly Thr Asp Pro Asp Leu Gln Val Asp Ile
            20                  25                  30

Ile Ala Glu Leu Asp Leu Val Asn Thr Thr Ala Gly Val Thr Gln Val
        35                  40                  45

Ser Gly Leu His Asn Ala Ser Lys Ala Tyr Leu Phe Gln Glu Thr Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Ser Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Ile Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Val Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Asn Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Asp Ala Cys
        355                 360                 365

Pro Pro Leu Asn Cys Ser Glu Lys Asp His Ile Leu Pro Glu Asn Gln
```

```
                370             375             380
Cys Cys Ser Val Cys Arg Gly His Asn Phe Cys Ala Glu Gly Pro Thr
385             390             395             400
Cys Gly Glu Asn Ser Glu Cys Lys Asn Trp Asn Thr Lys Ala Thr Cys
                405             410             415
Glu Cys Lys Asn Gly Tyr Ile Ser Val Gln Gly Asp Ser Ala Tyr Cys
                420             425             430
Glu Asp Ile Asp Glu Cys Ala Ala Lys Met His Tyr Cys His Ala Asn
            435             440             445
Thr Val Cys Val Asn Leu Pro Gly Leu Tyr Arg Cys Asp Cys Val Pro
    450             455             460
Gly Tyr Ile Arg Val Asp Asp Phe Ser Cys Thr Glu His Asp Glu Cys
465             470             475             480
Gly Ser Gly Gln His Asn Cys Asp Glu Asn Ala Ile Cys Thr Asn Thr
            485             490             495
Val Gln Gly His Ser Cys Thr Cys Lys Pro Gly Tyr Val Gly Asn Gly
        500             505             510
Thr Ile Cys Arg Ala Phe Cys Gln Glu Gly Cys Arg Tyr Gly Gly Thr
        515             520             525
Cys Val Ser Pro Asn Lys Cys Val Cys Pro Ser Gly Phe Thr Gly Ser
    530             535             540
His Cys Glu Lys Asp Ile Asp Glu Cys Thr Glu Gly Ile Ile Glu Cys
545             550             555             560
His Asn His Ser Arg Cys Val Asn Leu Pro Gly Trp Tyr His Cys Glu
            565             570             575
Cys Arg Ser Gly Phe His Asp Asp Gly Thr Tyr Ser Leu Ser Gly Glu
            580             585             590
Ser Cys Ile Asp Ile Asp Glu Cys Ala Leu Arg Thr His Thr Cys Trp
        595             600             605
Asn Asp Ser Ala Cys Ile Asn Leu Ala Gly Gly Phe Asp Cys Leu Cys
    610             615             620
Pro Ser Gly Pro Ser Cys Ser Gly Asp Cys Pro His Glu Gly Gly Leu
625             630             635             640
Lys Arg Asn Gly Gln Val Trp Thr Leu Lys Glu Asp Arg Cys Ser Val
            645             650             655
Cys Ser Cys Lys Asp Gly Lys Ile Phe Cys Arg Arg Thr Ala Cys Asp
            660             665             670
Cys Gln Asn Pro Ser Val Asp Leu Phe Cys Cys Pro Glu Cys Asp Thr
        675             680             685
Arg Val Thr Ser Gln Cys Leu Asp Gln Asn Gly His Lys Leu Tyr Arg
    690             695             700
Ser Gly Asp Asn Trp Thr His Ser Cys Gln Cys Arg Cys Leu Glu
705             710             715             720
Gly Glu Val Asp Cys Trp Pro Leu Thr Cys Pro Asn Leu Ser Cys Glu
            725             730             735
Tyr Thr Ala Met Leu Glu Gly Glu Cys Cys Pro Arg Cys Val Ser Asp
            740             745             750
Pro Cys Leu Ala Asp Asn Ile Ala Tyr Asp Ile Arg Lys Thr Cys Leu
        755             760             765
Asp Ser Tyr Gly Ile Ser Arg Leu Ser Gly Ala Val Trp Thr Met Ala
    770             775             780
Gly Ser Pro Cys Thr Thr Cys Lys Cys Lys Asn Gly Ser Val Cys Cys
785             790             795             800
```

Ser Val Asp Leu Glu Cys Leu His Asn Asn
             805                 810

<210> SEQ ID NO 14
<211> LENGTH: 763
<212> TYPE: PRT
<213> ORGANISM: Felis catus

<400> SEQUENCE: 14

Met Pro Arg Asp Val Ile Leu Val Val Trp Phe Cys Val Cys Thr Ala
1               5                   10                  15

Arg Thr Val Val Gly Phe Gly Thr Asp Pro Asp Leu Gln Val Asp Ile
            20                  25                  30

Ile Ala Glu Leu Asp Leu Val Asn Thr Thr Ala Gly Val Thr Gln Val
        35                  40                  45

Ser Gly Leu His Asn Ala Ser Lys Ala Tyr Leu Phe Gln Glu Thr Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Ser Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Ile Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Val Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Asn Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Asp Ala Cys

```
            355                 360                 365
    Pro Pro Leu Asn Cys Ser Glu Lys Asp His Ile Leu Pro Glu Asn Gln
        370                 375                 380

Cys Cys Ser Val Cys Arg Gly His Asn Phe Cys Ala Glu Gly Pro Thr
    385                 390                 395                 400

Cys Gly Glu Asn Ser Glu Cys Lys Asn Trp Asn Thr Lys Ala Thr Cys
                    405                 410                 415

Glu Cys Lys Asn Gly Tyr Ile Ser Val Gln Gly Asp Ser Ala Tyr Cys
                420                 425                 430

Glu Asp Ile Asp Glu Cys Ala Ala Lys Met His Tyr Cys His Ala Asn
                435                 440                 445

Thr Val Cys Val Asn Leu Pro Gly Leu Tyr Arg Cys Asp Cys Val Pro
            450                 455                 460

Gly Tyr Ile Arg Val Asp Asp Phe Ser Cys Thr Glu His Asp Glu Cys
    465                 470                 475                 480

Gly Ser Gly Gln His Asn Cys Asp Glu Asn Ala Ile Cys Thr Asn Thr
                    485                 490                 495

Val Gln Gly His Ser Cys Thr Cys Lys Pro Gly Tyr Val Gly Asn Gly
                500                 505                 510

Thr Ile Cys Arg Ala Phe Cys Gln Glu Gly Cys Arg Tyr Gly Gly Thr
                515                 520                 525

Cys Val Ser Pro Asn Lys Cys Val Cys Pro Ser Gly Phe Thr Gly Ser
            530                 535                 540

His Cys Glu Lys Asp Ile Asp Glu Cys Ala Leu Arg Thr His Thr Cys
    545                 550                 555                 560

Trp Asn Asp Ser Ala Cys Ile Asn Leu Ala Gly Gly Phe Asp Cys Leu
                    565                 570                 575

Cys Pro Ser Gly Pro Ser Cys Ser Gly Asp Cys Pro His Glu Gly Gly
                580                 585                 590

Leu Lys Arg Asn Gly Gln Val Trp Thr Leu Lys Glu Asp Arg Cys Ser
                595                 600                 605

Val Cys Ser Cys Lys Asp Gly Lys Ile Phe Cys Arg Arg Thr Ala Cys
            610                 615                 620

Asp Cys Gln Asn Pro Ser Val Asp Leu Phe Cys Cys Pro Glu Cys Asp
    625                 630                 635                 640

Thr Arg Val Thr Ser Gln Cys Leu Asp Gln Asn Gly His Lys Leu Tyr
                    645                 650                 655

Arg Ser Gly Asp Asn Trp Thr His Ser Cys Gln Gln Cys Arg Cys Leu
                660                 665                 670

Glu Gly Glu Val Asp Cys Trp Pro Leu Thr Cys Pro Asn Leu Ser Cys
                675                 680                 685

Glu Tyr Thr Ala Met Leu Gly Glu Cys Cys Pro Arg Cys Val Ser
            690                 695                 700

Asp Pro Cys Leu Ala Asp Asn Ile Ala Tyr Asp Ile Arg Lys Thr Cys
    705                 710                 715                 720

Leu Asp Ser Tyr Gly Ile Ser Arg Leu Ser Gly Ala Val Trp Thr Met
                    725                 730                 735

Ala Gly Ser Pro Cys Thr Thr Cys Lys Cys Lys Asn Gly Ser Val Cys
                740                 745                 750

Cys Ser Val Asp Leu Glu Cys Leu His Asn Asn
                755                 760

<210> SEQ ID NO 15
```

-continued

```
<211> LENGTH: 901
<212> TYPE: PRT
<213> ORGANISM: Canis familiaris

<400> SEQUENCE: 15

Met Thr Ser Thr Ser Phe Leu Leu Trp Leu Gly Cys Val His Asn Thr
1               5                   10                  15

Lys Phe Pro Phe Pro Leu Val Leu Val Thr Arg Ala Ile Val Val Val
            20                  25                  30

Val Val Glu Val Val Gly Val Gly Ser Pro Gly Val Arg Ile Arg Ser
        35                  40                  45

Thr Gly Cys Asp Ile Leu Leu Leu Tyr Glu Val Leu Glu His Leu Leu
50                  55                  60

Gly Ile Arg Phe Leu Cys Val Asp Gln Gly Glu Asn Ser Cys His His
65                  70                  75                  80

Gly Gln Cys Ala Cys Arg Leu Gln Val Ile Val Pro Lys Ala Leu Met
                85                  90                  95

Ser Val Phe Glu Ala Lys Thr Ala Val Cys Phe Phe Pro Val Val Gly
            100                 105                 110

Phe Gly Thr Asp Pro Asp Leu Gln Met Asp Ile Ile Thr Glu Leu Asp
        115                 120                 125

Leu Val Asn Ile Ser Leu Gly Val Thr Gln Val Ser Gly Leu His Asn
130                 135                 140

Ala Ser Lys Ala Tyr Val Phe Gln Asp Thr Ala Arg Glu Ile His Ala
145                 150                 155                 160

Ala Pro His Val Ser Glu Lys Leu Ile Gln Leu Phe Arg Asn Lys Ser
                165                 170                 175

Asp Phe Thr Phe Leu Ala Thr Val Gln Gln Lys Pro Ser Thr Ser Gly
            180                 185                 190

Val Ile Leu Ser Ile Arg Glu Leu Glu His Ser Tyr Phe Glu Leu Glu
        195                 200                 205

Ser Ser Gly Leu Arg Asp Glu Ile Arg Tyr His Tyr Met His Asn Gly
210                 215                 220

Lys Pro Arg Thr Glu Ala Leu Pro Tyr Arg Leu Ala Asp Gly Gln Trp
225                 230                 235                 240

His Lys Val Ala Leu Ser Val Ser Ala Ser His Leu Leu His Ile
                245                 250                 255

Asp Cys Asn Arg Ile Tyr Glu Arg Val Ile Asp Pro Pro Glu Thr Asn
            260                 265                 270

Leu Pro Pro Gly Ser Asn Leu Trp Leu Gly Gln Arg Asn Gln Lys His
        275                 280                 285

Gly Phe Phe Lys Gly Ile Ile Gln Asp Gly Lys Ile Ile Phe Met Pro
290                 295                 300

Asn Gly Tyr Ile Thr Gln Cys Pro Asn Leu Asn Arg Thr Cys Pro Thr
305                 310                 315                 320

Cys Ser Asp Phe Leu Ser Leu Val Gln Gly Ile Met Asp Leu Gln Glu
                325                 330                 335

Leu Leu Ala Lys Met Thr Ala Lys Leu Asn Tyr Ala Glu Thr Arg Leu
            340                 345                 350

Ser Gln Leu Glu Asn Cys His Cys Glu Lys Thr Cys Gln Val Ser Gly
        355                 360                 365

Leu Leu Tyr Arg Asp Gln Asp Ser Trp Val Asp Gly Asp His Cys Arg
370                 375                 380

Asn Cys Thr Cys Lys Gly Gly Ala Val Glu Cys Arg Arg Met Ser Cys
```

```
385                 390                 395                 400
Pro Pro Leu Asn Cys Ser Pro Asp Ser Leu Pro Val His Ile Ala Gly
                405                 410                 415
Gln Cys Cys Lys Val Cys Arg Pro Lys Cys Ile Tyr Gly Gly Arg Val
                420                 425                 430
Leu Ala Glu Gly Gln Arg Ile Leu Thr Lys Ser Cys Arg Glu Cys Arg
                435                 440                 445
Gly Gly Val Leu Val Lys Ile Thr Asp Ala Cys Pro Pro Leu Asn Cys
                450                 455                 460
Ser Glu Lys Asp His Ile Leu Pro Glu Asn Gln Cys Cys Ser Val Cys
465                 470                 475                 480
Arg Gly His Asn Phe Cys Ala Glu Gly Pro Lys Cys Gly Glu Asn Ser
                    485                 490                 495
Glu Cys Lys Asn Trp Asn Thr Lys Ala Thr Cys Glu Cys Lys Asn Gly
                500                 505                 510
Tyr Ile Ser Val Gln Gly Asp Ser Ala Tyr Cys Glu Asp Ile Asp Glu
                515                 520                 525
Cys Ala Ala Lys Met His Tyr Cys His Ala Asn Thr Val Cys Val Asn
530                 535                 540
Leu Pro Gly Leu Tyr Arg Cys Asp Cys Val Pro Gly Tyr Ile Arg Val
545                 550                 555                 560
Asp Asp Phe Ser Cys Thr Glu His Asp Glu Cys Gly Ser Gly Gln His
                565                 570                 575
Asn Cys Asp Glu Asn Ala Ile Cys Thr Asn Thr Val Arg Gly His Ser
                580                 585                 590
Cys Thr Cys Lys Pro Gly Tyr Val Gly Asn Gly Thr Ile Cys Arg Ala
                595                 600                 605
Phe Cys Gln Glu Gly Cys Arg Tyr Gly Gly Ser Cys Val Ser Pro Asn
                610                 615                 620
Lys Cys Val Cys Pro Ser Gly Phe Thr Gly Ser His Cys Glu Lys Asp
625                 630                 635                 640
Ile Asp Glu Cys Thr Glu Gly Ile Ile Glu Cys His Asn His Ser Arg
                645                 650                 655
Cys Val Asn Leu Pro Gly Trp Tyr His Cys Glu Cys Arg Ser Gly Phe
                660                 665                 670
His Asp Asp Gly Thr Tyr Ser Leu Ser Gly Glu Ser Cys Ile Asp Ile
                675                 680                 685
Asp Glu Cys Ala Leu Arg Thr His Thr Cys Trp Asn Asp Ser Ala Cys
                690                 695                 700
Ile Asn Leu Ala Gly Gly Phe Asp Cys Leu Cys Pro Ser Gly Pro Ser
705                 710                 715                 720
Cys Ser Gly Asp Cys Pro His Glu Gly Leu Lys Arg Asn Gly Gln
                725                 730                 735
Val Trp Thr Leu Lys Glu Asp Arg Cys Ser Val Cys Ser Cys Lys Asp
                740                 745                 750
Gly Lys Ile Leu Cys Arg Arg Thr Ala Cys Asp Cys Gln Asn Pro Ser
                755                 760                 765
Val Asp Leu Phe Cys Cys Pro Glu Cys Asp Thr Arg Val Thr Ser Gln
                770                 775                 780
Cys Leu Asp Gln Asn Gly His Lys Leu Tyr Arg Ser Gly Asp Asn Trp
785                 790                 795                 800
Thr His Ser Cys Gln Gln Cys Arg Cys Leu Glu Gly Glu Val Asp Cys
                    805                 810                 815
```

```
Trp Pro Leu Thr Cys Pro Asn Leu Ser Cys Glu Tyr Thr Ala Ile Leu
            820             825                 830

Glu Gly Glu Cys Cys Pro Arg Cys Val Ser Asp Pro Cys Leu Ala Asp
        835                 840                 845

Asn Ile Ala Tyr Asp Ile Arg Lys Thr Cys Leu Asp Ser Tyr Gly Ile
850                 855                 860

Ser Arg Leu Ser Gly Ser Val Trp Thr Met Ala Gly Ser Pro Cys Thr
865             870                 875                 880

Thr Cys Lys Cys Lys Asn Gly Ser Val Cys Cys Ser Val Asp Leu Glu
                885                 890                 895

Cys Leu His Asn Asn
            900

<210> SEQ ID NO 16
<211> LENGTH: 810
<212> TYPE: PRT
<213> ORGANISM: Ovis aries

<400> SEQUENCE: 16

Met Pro Arg Gly Val Ile Leu Val Val Cys Phe Cys Val Cys Ala Ala
1               5                   10                  15

Arg Thr Val Val Gly Phe Gly Met Asp Pro Asp Leu Gln Leu Asp Ile
            20                  25                  30

Ile Thr Glu Leu Asp Leu Val Asn Thr Thr Leu Gly Val Thr Gln Val
        35                  40                  45

Ser Gly Leu His Asn Thr Ser Lys Ala Phe Leu Phe Gln Asp Ala Glu
50                  55                  60

Arg Glu Ile His Ala Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Met His Ser Gly Arg Pro Arg Thr Glu Ala Leu Pro Tyr Arg Leu
    130                 135                 140

Ala Asp Gly Gln Trp His Arg Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
```

```
            275                 280                 285
Gly Asp His Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                    325                 330                 335

Tyr Gly Gly Lys Val Leu Ala Glu Gly Gln Arg Ile Leu Ser Lys Asn
                340                 345                 350

Cys Gln Glu Cys Arg Gly Gly Val Leu Val Lys Ile Thr Glu Ala Cys
            355                 360                 365

Pro Leu Leu Asn Cys Ser Glu Lys Asp His Ile Leu Pro Glu Asn Gln
        370                 375                 380

Cys Cys Ser Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asp Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
    450                 455                 460

Gly Tyr Ile Arg Val Asp Asp Phe Ser Cys Thr Glu His Asp Asp Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
            500                 505                 510

Thr Ile Cys Arg Ala Phe Cys Glu Glu Gly Cys Arg Tyr Gly Gly Thr
        515                 520                 525

Cys Met Ala Pro Asn Lys Cys Val Cys Pro Ser Gly Phe Thr Gly Ser
    530                 535                 540

His Cys Glu Lys Asp Ile Asp Glu Cys Ala Glu Gly Ile Ile Glu Cys
545                 550                 555                 560

His Ser His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Val Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys Arg Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Ser Val Asp Leu Phe Cys Cys Pro Glu Cys Asp Thr
        675                 680                 685

Arg Val Thr Ser Gln Cys Leu Asp Gln Asn Gly Asn Lys Leu Tyr Arg
    690                 695                 700
```

```
Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Ser Leu Ser Cys Glu
            725                 730                 735

Tyr Thr Thr Ile Leu Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
            755                 760                 765

Asp Ser Tyr Gly Leu Ser Arg Leu Ser Gly Ser Val Trp Thr Met Ala
            770                 775                 780

Gly Ser Pro Cys Thr Thr Cys Lys Cys Lys Asn Gly Ser Val Cys Cys
785                 790                 795                 800

Ser Val Asp Leu Glu Cys Leu His Asn Asn
            805                 810

<210> SEQ ID NO 17
<211> LENGTH: 610
<212> TYPE: PRT
<213> ORGANISM: Homo sapiens

<400> SEQUENCE: 17

Phe Gly Met Asp Pro Asp Leu Gln Met Asp Ile Val Thr Glu Leu Asp
1               5                   10                  15

Leu Val Asn Thr Thr Leu Gly Val Ala Gln Val Ser Gly Met His Asn
                20                  25                  30

Ala Ser Lys Ala Phe Leu Phe Gln Asp Ile Glu Arg Glu Ile His Ala
            35                  40                  45

Ala Pro His Val Ser Glu Lys Leu Ile Gln Leu Phe Arg Asn Lys Ser
        50                  55                  60

Glu Phe Thr Ile Leu Ala Thr Val Gln Gln Lys Pro Ser Thr Ser Gly
65                  70                  75                  80

Val Ile Leu Ser Ile Arg Glu Leu Glu His Ser Tyr Phe Glu Leu Glu
                85                  90                  95

Ser Ser Gly Leu Arg Asp Glu Ile Arg Tyr His Tyr Ile His Asn Gly
            100                 105                 110

Lys Pro Arg Thr Glu Ala Leu Pro Tyr Arg Met Ala Asp Gly Gln Trp
        115                 120                 125

His Lys Val Ala Leu Ser Val Ser Ala Ser His Leu Leu Leu His Val
130                 135                 140

Asp Cys Asn Arg Ile Tyr Glu Arg Val Ile Asp Pro Pro Asp Thr Asn
145                 150                 155                 160

Leu Pro Pro Gly Ile Asn Leu Trp Leu Gly Gln Arg Asn Gln Lys His
                165                 170                 175

Gly Leu Phe Lys Gly Ile Ile Gln Asp Gly Lys Ile Ile Phe Met Pro
            180                 185                 190

Asn Gly Tyr Ile Thr Gln Cys Pro Asn Leu Asn His Thr Cys Pro Thr
        195                 200                 205

Cys Ser Asp Phe Leu Ser Leu Val Gln Gly Ile Met Asp Leu Gln Glu
    210                 215                 220

Leu Leu Ala Lys Met Thr Ala Lys Leu Asn Tyr Ala Glu Thr Arg Leu
225                 230                 235                 240

Ser Gln Leu Glu Asn Cys His Cys Glu Lys Thr Cys Gln Val Ser Gly
                245                 250                 255

Leu Leu Tyr Arg Asp Gln Asp Ser Trp Val Asp Gly Asp His Cys Arg
```

```
            260                 265                 270
Asn Cys Thr Cys Lys Ser Gly Ala Val Glu Cys Arg Arg Met Ser Cys
            275                 280                 285

Pro Pro Leu Asn Cys Ser Pro Asp Ser Leu Pro Val His Ile Ala Gly
            290                 295                 300

Gln Cys Cys Lys Val Cys Arg Pro Lys Cys Ile Tyr Gly Gly Lys Val
305                 310                 315                 320

Leu Ala Glu Gly Gln Arg Ile Leu Thr Lys Ser Cys Arg Glu Cys Arg
                    325                 330                 335

Gly Gly Val Leu Val Lys Ile Thr Glu Met Cys Pro Pro Leu Asn Cys
                340                 345                 350

Ser Glu Lys Asp His Ile Leu Pro Glu Asn Gln Cys Cys Arg Val Cys
            355                 360                 365

Arg Gly His Asn Phe Cys Ala Glu Gly Pro Lys Cys Gly Glu Asn Ser
            370                 375                 380

Glu Cys Lys Asn Trp Asn Thr Lys Ala Thr Cys Glu Cys Lys Ser Gly
385                 390                 395                 400

Tyr Ile Ser Val Gln Gly Asp Ser Ala Tyr Cys Glu Asp Ile Asp Glu
                    405                 410                 415

Cys Ala Ala Lys Met His Tyr Cys His Ala Asn Thr Val Cys Val Asn
                420                 425                 430

Leu Pro Gly Leu Tyr Arg Cys Asp Cys Val Pro Gly Tyr Ile Arg Val
            435                 440                 445

Asp Asp Phe Ser Cys Thr Glu His Asp Glu Cys Gly Ser Gly Gln His
            450                 455                 460

Asn Cys Asp Glu Asn Ala Ile Cys Thr Asn Thr Val Gln Gly His Ser
465                 470                 475                 480

Cys Thr Cys Lys Pro Gly Tyr Val Gly Asn Gly Thr Ile Cys Arg Ala
                    485                 490                 495

Phe Cys Glu Glu Gly Cys Arg Tyr Gly Gly Thr Cys Val Ala Pro Asn
                500                 505                 510

Lys Cys Val Cys Pro Ser Gly Phe Thr Gly Ser His Cys Glu Lys Asp
            515                 520                 525

Ile Asp Glu Cys Ser Glu Gly Ile Ile Glu Cys His Asn His Ser Arg
            530                 535                 540

Cys Val Asn Leu Pro Gly Trp Tyr His Cys Glu Cys Arg Ser Gly Phe
545                 550                 555                 560

His Asp Asp Gly Thr Tyr Ser Leu Ser Gly Glu Ser Cys Ile Asp Ile
                    565                 570                 575

Asp Glu Cys Ala Leu Arg Thr His Thr Cys Trp Asn Asp Ser Ala Cys
                580                 585                 590

Ile Asn Leu Ala Gly Gly Phe Asp Cys Leu Cys Pro Ser Gly Pro Ser
            595                 600                 605

Cys Ser
    610

<210> SEQ ID NO 18
<211> LENGTH: 610
<212> TYPE: PRT
<213> ORGANISM: Equus caballus

<400> SEQUENCE: 18

Phe Gly Met Asp Pro Asp Leu Gln Met Asp Ile Ile Thr Glu Leu Asp
1               5                   10                  15
```

```
Leu Val Asn Thr Thr Leu Gly Val Thr Gln Val Ser Gly Leu His Asn
            20                  25                  30
Ala Ser Lys Ala Phe Leu Phe Gln Asp Val Glu Arg Glu Ile His Ala
        35                  40                  45
Ala Pro His Val Ser Glu Lys Leu Ile Gln Leu Phe Arg Asn Lys Ser
50                  55                  60
Glu Phe Thr Phe Leu Ala Thr Val Gln Gln Lys Pro Ser Thr Ser Gly
65                  70                  75                  80
Val Ile Leu Ser Ile Arg Glu Leu Glu Asn Ser Tyr Phe Glu Leu Glu
                85                  90                  95
Ser Ser Gly Leu Arg Asp Glu Ile Arg Tyr His Tyr Thr His Lys Gly
            100                 105                 110
Lys Pro Arg Thr Glu Ala Leu Pro Tyr Arg Met Ala Asp Gly Arg Trp
        115                 120                 125
His Lys Val Ala Leu Ser Val Ser Ala Ser His Leu Leu His Ile
130                 135                 140
Asp Cys Asn Arg Ile Tyr Glu Arg Val Ile Asp Thr Pro Glu Thr Asn
145                 150                 155                 160
Leu Pro Pro Gly Ser Asn Leu Trp Leu Gly Gln Arg Asn Gln Lys His
                165                 170                 175
Gly Leu Phe Lys Gly Ile Ile Gln Asp Gly Lys Ile Ile Phe Met Pro
            180                 185                 190
Asn Gly Tyr Ile Thr Gln Cys Pro Asn Leu Asn Arg Thr Cys Pro Thr
        195                 200                 205
Cys Ser Asp Phe Leu Ser Leu Val Gln Gly Ile Met Asp Leu Gln Glu
210                 215                 220
Leu Leu Ala Lys Met Thr Ala Lys Leu Asn Tyr Ala Glu Thr Arg Leu
225                 230                 235                 240
Ser Gln Leu Glu Asn Cys His Cys Glu Lys Thr Cys Gln Val Ser Gly
                245                 250                 255
Leu Leu Tyr Arg Asp Gln Asp Ser Trp Val Asp Gly Asp His Cys Arg
            260                 265                 270
Asn Cys Thr Cys Lys Ser Gly Ala Val Glu Cys Arg Arg Met Ser Cys
        275                 280                 285
Pro Pro Leu Asn Cys Ser Pro Asp Ser Leu Pro Val His Val Ala Gly
290                 295                 300
Gln Cys Cys Lys Val Cys Arg Pro Lys Cys Ile Tyr Gly Gly Lys Val
305                 310                 315                 320
Leu Ala Glu Gly Gln Arg Ile Leu Thr Lys Ser Cys Arg Glu Cys Arg
                325                 330                 335
Gly Gly Val Leu Val Lys Ile Thr Glu Ala Cys Pro Pro Leu Asn Cys
            340                 345                 350
Ser Asp Lys Asp His Ile Leu Pro Glu Asn Gln Cys Cys Ser Val Cys
        355                 360                 365
Arg Gly His Asn Phe Cys Ala Glu Gly Pro Lys Cys Gly Glu Asn Ser
370                 375                 380
Glu Cys Lys Asn Trp Asn Thr Lys Ala Thr Cys Glu Cys Lys Asn Gly
385                 390                 395                 400
Tyr Ile Ser Val Gln Gly Asp Ser Ala Tyr Cys Glu Asp Ile Asp Glu
                405                 410                 415
Cys Ala Ala Lys Met His Tyr Cys Arg Ala Asn Thr Val Cys Val Asn
            420                 425                 430
Leu Pro Gly Leu Tyr Arg Cys Asp Cys Val Pro Gly Tyr Ile Arg Val
```

```
            435                 440                 445
Asp Asp Phe Ser Cys Thr Glu His Asp Glu Cys Gly Ser Gly Gln His
    450                 455                 460

Asn Cys Asp Glu Asn Ala Ile Cys Thr Asn Thr Val Gln Gly His Ser
465                 470                 475                 480

Cys Thr Cys Lys Pro Gly Tyr Val Gly Asn Gly Thr Ser Cys Arg Ala
                485                 490                 495

Phe Cys Glu Glu Gly Cys Arg Tyr Gly Gly Thr Cys Val Ala Pro Asn
            500                 505                 510

Lys Cys Val Cys Pro Ser Gly Phe Thr Gly Ser His Cys Glu Lys Asp
        515                 520                 525

Ile Asp Glu Cys Thr Glu Gly Ile Ile Glu Cys His Asn His Ser Arg
    530                 535                 540

Cys Val Asn Leu Pro Gly Trp Tyr His Cys Glu Cys Arg Ser Gly Phe
545                 550                 555                 560

His Asp Asp Gly Thr Tyr Ser Leu Ser Gly Glu Ser Cys Ile Asp Ile
                565                 570                 575

Asp Glu Cys Ala Leu Arg Thr His Thr Cys Trp Asn Asp Ser Ala Cys
            580                 585                 590

Ile Asn Leu Ala Gly Gly Phe Asp Cys Leu Cys Pro Ser Gly Pro Ser
        595                 600                 605

Cys Ser
    610

<210> SEQ ID NO 19
<211> LENGTH: 599
<212> TYPE: PRT
<213> ORGANISM: Bos taurus

<400> SEQUENCE: 19

Met Ala Leu Cys Ser Phe Ser Val Val Gly Phe Gly Leu Asp Pro Asp
1               5                   10                  15

Leu Gln Leu Asp Ile Ile Thr Glu Leu Asp Leu Val Asn Thr Thr Leu
            20                  25                  30

Gly Val Thr Gln Val Ser Gly Leu His Asn Thr Ser Lys Ala Phe Leu
        35                  40                  45

Phe Gln Asp Ala Glu Arg Glu Ile His Ala Ala Pro His Val Ser Glu
    50                  55                  60

Lys Leu Ile Gln Leu Phe Arg Asn Lys Ser Glu Phe Thr Phe Leu Ala
65                  70                  75                  80

Thr Val Gln Gln Lys Pro Ser Thr Ser Gly Val Ile Leu Ser Ile Arg
                85                  90                  95

Glu Leu Glu His Ser Tyr Phe Glu Leu Glu Ser Ser Gly Leu Arg Asp
            100                 105                 110

Glu Ile Arg Tyr His Tyr Val His Ser Gly Arg Pro Arg Thr Glu Ala
        115                 120                 125

Leu Pro Tyr Arg Leu Ala Asp Gly Gln Trp His Arg Val Ala Leu Ser
    130                 135                 140

Val Ser Ala Ser His Leu Leu Leu His Ile Asp Cys Asn Arg Ile Tyr
145                 150                 155                 160

Glu Arg Val Ile Asp Pro Pro Glu Thr Asn Leu Pro Gly Ser Asn
                165                 170                 175

Leu Trp Leu Gly Gln Arg Asn Gln Lys His Gly Leu Phe Lys Gly Ile
            180                 185                 190
```

```
Ile Gln Asp Gly Lys Ile Ile Phe Met Pro Asn Gly Tyr Ile Thr Gln
            195                 200                 205
Cys Pro Asn Leu Asn Arg Thr Cys Pro Thr Cys Ser Asp Phe Leu Ser
        210                 215                 220
Leu Val Gln Gly Ile Met Asp Leu Gln Glu Leu Leu Ala Lys Met Thr
225                 230                 235                 240
Ala Lys Leu Asn Tyr Ala Glu Thr Arg Leu Ser Gln Leu Glu Asn Cys
                245                 250                 255
His Cys Glu Lys Thr Cys Gln Val Ser Gly Leu Leu Tyr Arg Asp Gln
            260                 265                 270
Asp Ser Trp Val Asp Gly Asp His Cys Arg Asn Cys Thr Cys Lys Ser
        275                 280                 285
Gly Ala Val Glu Cys Arg Arg Met Ser Cys Pro Pro Leu Asn Cys Ser
290                 295                 300
Pro Asp Ser Leu Pro Val His Ile Ala Gly Glu Cys Cys Lys Val Cys
305                 310                 315                 320
Arg Pro Lys Cys Ile Tyr Gly Gly Lys Val Leu Ala Glu Gly Gln Arg
                325                 330                 335
Ile Leu Ser Lys Ser Cys Gln Glu Cys Arg Gly Gly Val Leu Val Lys
            340                 345                 350
Ile Thr Glu Ala Cys Pro Leu Leu Asn Cys Ser Glu Lys Asp His Ile
        355                 360                 365
Leu Pro Glu Asn Gln Cys Cys Ser Val Cys Arg His Asn Phe Cys
        370                 375                 380
Ala Glu Gly Pro Lys Cys Gly Glu Asn Ser Glu Cys Lys Asn Trp Asn
385                 390                 395                 400
Thr Lys Ala Thr Cys Glu Cys Lys Asn Gly Tyr Ile Ser Val Gln Gly
                405                 410                 415
Asp Ser Ala Tyr Cys Glu Asp Ile Asp Glu Cys Ala Ala Lys Met His
            420                 425                 430
Tyr Cys His Ala Asn Thr Val Cys Val Asn Leu Pro Gly Leu Tyr Arg
        435                 440                 445
Cys Asp Cys Val Pro Gly Tyr Ile Arg Val Asp Asp Phe Ser Cys Thr
450                 455                 460
Glu His Asp Asp Cys Gly Ser Gly Gln His Asn Cys Asp Glu Asn Ala
465                 470                 475                 480
Ile Cys Thr Asn Thr Val Gln Gly His Ser Cys Thr Cys Lys Pro Gly
                485                 490                 495
Tyr Val Gly Asn Gly Thr Ile Cys Arg Gly Met Pro Glu Val Gly Pro
            500                 505                 510
Pro Arg Ala Leu Leu Asn Ser Leu Asp Leu Gly Phe Leu Ser Phe Ser
        515                 520                 525
Lys Glu Ala Leu Ala Val Gly Met Ile Thr Leu Glu Gly Asn Ile Val
        530                 535                 540
Ala Lys Ser Phe Thr Asp Asp Glu Thr Leu Val Glu Arg Gly Arg Glu
545                 550                 555                 560
Lys Val Ile Ala Leu Leu Phe Ser Trp Leu His Lys Glu Lys Leu Ser
                565                 570                 575
Leu Glu Asn Leu Arg Asp Ile Tyr Cys Lys Ala Asn Ser Leu Val Gly
            580                 585                 590
Leu Asp His Leu Pro Gln Arg
        595
```

METHODS AND COMPOSITIONS FOR REGENERATING TISSUES

CROSS REFERENCED APPLICATIONS

This application claims the benefit of U.S. Provisional Application No. 62/380,920, filed Aug. 29, 2016, which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20171103N8850-91060US1SEQLIST_ST25, created on Nov. 3, 2017, and having a size of 158,512 bytes, and was filed with the Response to Notice to Comply with Requirements for Patent Applications Containing Nucleotide Sequence and/or Amino Acid Sequence Disclosures filed on Nov. 7, 2017. The sequence listing contained in this ASCII formatted document is part of the specification and is herein incorporated by reference in its entirety.

FIELD OF THE INVENTION

This application generally relates to the healing of injuries, including those involving tendons and/or ligaments, with a regenerative protein or a nucleic acid encoding the same.

BACKGROUND OF THE INVENTION

The healing of an injury involves a multistep process whereby injured tissue is repaired, specialized tissue is regenerated, and new tissue is reorganized into a functional unit. Wound healing is generally divided into the inflammatory phase, the proliferative phase, and the maturation and remodeling phase. An impairment in any one of these phases can lead to complications. Particular tissues can be more difficult to heal properly due in part to their cellular makeup, limited vasculature, and/or location in highly mobile parts of the body. Injuries to tendons and ligaments, for example, can be particularly challenging to properly heal.

Tendons are soft connective tissues that connect muscle to bone or cartilage, while ligaments connect bone to bone to hold the skeleton and stabilize the joints. They are composed primarily of packed collagen fibers that impart different mechanical properties based on the shape and how they are organized. There is very little cellularity in these tissues—mostly fibroblasts secreting the extracellular material (ECM). Ligaments have a lower collagen content (~75%) with a random pattern, while tendons have more collagen (80-90%) and are highly organized. The ECM of both tissues are composed of Types I and III collagen, with ligaments having a lesser proportion of Type I (90%) and more of type III (10%) in comparison to tendons which have 95-99% Type 1 and 1-5% Type III. Another key difference between these two types of connective tissue is the presence of elastin in ligaments, which is very minimal in tendons. (Lui (2015) *Stem Cells and Cloning: Advances and Applications* 8:163-174).

Considerable basic studies have been devoted to the understanding of the development, structure, and function of these important tissues, because traumatic tendon/ligament injuries are extremely difficult to heal completely. These injuries often result in permanent disability and chronic pain in human patients, while in veterinary animals such as horses or dogs, damage to key tendon and ligaments can adversely affect the quality of life so severely that euthanasia is necessary. Treating tendon/ligament injuries is clinically challenging in both human and veterinary medicine because of the innate poor tissue healing response, likely due to the primary characteristics of these soft tissues including: a) a low proportion of resident progenitor and stem cells; b) limited vasculature or blood vessel supply; and c) a tendency for persistent inflammation because these are located in highly mobile body parts. The constant motion of the injured sites can hinder healing. Even in cases where healing occurs, a fibrovascular scar is formed which does not possess the biomechanical and biochemical properties of normal/original tendon and/or ligament, thereby resulting in significant loss of function for the individual and increased re-injury rates. (Lui (2015); Ross (2014) *Stem Cell Discovery* 4:44-53)

The three most common tendon injuries in man are tearing of the rotator cuff, injuries to the hand flexor tendon, and injuries to the Achilles tendon. These are often treated by surgical repair, physical therapy/rehabilitation and cryotherapy. In 2004, it was estimated that 45% of 32 million musculoskeletal injuries involved tendons and ligaments, and that the incidence was rapidly rising due to increased sports activities and an aging population. (September et al. (2007) *Br J Sports Med* 41:241-246)

The most common tendon and/or ligament injuries in racehorses and performance horses affect the suspensory ligament running behind the cannon bone, and the superficial and deep digital flexor tendons (SDFT and DDFT) running behind the back of the knee (or hock) all the way down to the navicular bone in each foot, acting as a sling for the fetlock to bear weight. (Briggs (2011) *The Horse* Jun. 3, 2011, pp. 1-7). Injuries can be inflammation, sprains, strains, disruptions or tears and lacerations. Tendon/ligament injuries are estimated to be ~46% of all sport horse injuries, and 90% of tendon/ligament injuries are to the SDFT. SDFT damage is confirmed by a veterinarian with a physical exam for lameness and ultrasound. A horse can manifest lameness, heat, sensitivity to touch, tendon swelling or thickening, or a bowed or convex profile. Lameness correlates the degree of inflammation. (Tan (2016) *The Horse* Mar. 30, 2016, pp. 1-7). DDFT injuries are common in the hoof capsule and tendon sheath and are classified as tendon enlargements, changes in shape, focal core lesions, mineralization and marginal tears. Tears are best detected with ultrasound, MRI or tenoscopy.

Ligament injuries in horses are often proximal suspensory desmitis (PSD) in the limbs that result in acute lameness. Hind limb PSD occurs frequently in high-level dressage horses and is not very responsive to conservative therapy which consists of repeated bandaging, administration of anti-inflammatories and analgesics (only 14% return without lameness for less than one year).

The repair or regeneration of tendon/ligament injuries have been a consistent target of the increasing number of regenerative medicine technologies, such as stem cells, platelet rich plasma (PRP), bone marrow aspirate concentrate, growth factors, and bioengineered scaffolds. Techniques such as extracorporeal shock wave therapy, low level laser therapy and mechanical stimulation have also been employed. (Thomas (2005) *The Chronicle of the Horse* 134-137; Fortier and Smith (2008) *Vet Clin Equine* 24:191-201; Briggs (2011); Yang et al. (2013) *Birth Defects Res C Embryo Today* 99(3):203-222; Lui (2015); Tan (2016); Basetto et al. (2011) Biomaterials Science and Engineering,

SUMMARY OF THE INVENTION

Compositions comprising a variant NELL1 peptide or a nucleic acid encoding the same are provided. The variant NELL1 peptide lacks at least one of the carboxy-terminal von Willebrand factor, type C (VWC) domains of a NELL1 protein. In some embodiments of the invention, the variant NELL1 peptide lacks both carboxy-terminal VWC domains. In some of these embodiments, the variant NELL1 peptide lacks the carboxy-terminal 179 amino acid residues. In particular aspects of the invention, the variant NELL1 peptide has at least 75% sequence identity to the disclosed SEQ ID NO: 17 or 18 and one of the following properties: enhanced efficacy in tissue regeneration, promotion of wound healing, easier purification, higher yield, and less aggregate formation, when compared to a full-length NELL1 protein. In some of these embodiments, the variant NELL1 peptide comprises or consists essentially of SEQ ID NO: 17 or 18. Also provided herein are pharmaceutical compositions and kits comprising the variant NELL1 peptide or a nucleic acid encoding the same.

The variant NELL1 peptides or nucleic acids encoding the same find use in regenerating injured tissues, promoting the maturation of a progenitor cell, enhancing the migration and/or proliferation of fibroblast cells, and promoting the healing of a wound, such as an injury to a tendon or a ligament. In particular aspects of the invention, the wound is an open wound. In certain embodiments, the wound comprises an injury to skeletal muscle, cartilage, bone, skin, tendon, ligament or a combination thereof. In some aspects, the variant NELL1 peptide or nucleic acid encoding the same is administered locally to the wound. In particular embodiments, the subject in need of promotion of healing of a wound is a mammal, such as a human or a horse. The variant NELL1 peptide or nucleic acid encoding the same can be administered to the wound about two days after the injury.

Methods for promoting the healing of an injury to a tendon or ligament in a subject in need thereof are provided herein. These presently disclosed methods involve the administration of an effective amount of a NELL1 peptide or a nucleic acid encoding a NELL1 peptide to the subject. The subject can be a mammal, such as a human or a horse. The methods find use in treating various injuries in humans, including injuries to Achilles tendons. Horses, especially racehorses, are particularly prone to tendon and ligament injuries, such as the superficial digital flexor tendon or deep digital flexor tendon, and the presently disclosed methods are useful in promoting the healing of these injuries. The NELL1 peptide or nucleic acid encoding the same can be administered via local injection to the area surrounding the injured tendon or ligament or can be incorporated into a matrix, such as a wound dressing and applied directly to the injured tissue. The NELL1 peptide or nucleic acid encoding the same can be administered to the tendon or ligament injury about seven days after the injury.

Methods for enhancing the migration and/or proliferation of fibroblast cells with a NELL1 peptide or a nucleic acid encoding the same are also provided herein. In particular aspects of the invention, the fibroblast cell is a dermal fibroblast or a ligament fibroblast. In some embodiments, the migration of the fibroblasts towards a wound area is enhanced with a NELL1 peptide or a nucleic acid encoding the same.

The foregoing is a summary and thus contains, by necessity, simplifications, generalizations, and omissions of detail; consequently, those skilled in the art will appreciate that the summary is illustrative and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 2A and 2B) and horse NEL1 variant protein aa3-612 (FIGS. 2C and 2D). FIGS. 2A and 2C depict sodium dodecyl sulfate polyacrylamide gel electrophoresis (SDS-PAGE), whereas FIGS. 2B and 2D depict Western Blots using mouse anti-GST antibody (1 µg/ml) to the GST tag attached to the NELL1 protein, followed by Jackson anti-mouse IgG-HRP (1500×). The lanes in FIG. 2A are as follows: M=molecular markers (kilodaltons or kDa) 10 µl/lane; lane 1=NELL1 protein aa3-791 (5 µl/lane); and lanes 2-5 are loading control proteins at 0.1 µg/lane, 0.2 µg/lane, 0.5 µg/lane, and 1.0 µg/lane, respectively. The lanes in FIG. 2B are as follows: M=molecular markers (kDa); lane 1 is NELL1 aa3-791 protein (5 µl); and lane 2 is GST protein. The lanes in FIG. 2C are as follows: M=molecular markers 10 µl/lane (kDa); lane 1=NELL1 protein aa3-612 (5 µl/lane); and lanes 2-5 are loading control proteins at 0.1 µg/lane, 0.2 µg/lane, 0.5 µg/lane, and 1.0 µg/lane, respectively. The lanes in FIG. 2D are as follows: M=molecular markers (kDa); lane 1 is NELL1 aa3-612 protein (5 µl); and lane 2 is GST protein.

FIG. 3A demonstrates a dose-dependent increase in wound healing on Type 1 diabetic human dermal fibroblasts in an in vitro wound scratch assay with Nell1 variant protein (aa3-612). There is increased migration of the diabetic dermal fibroblasts into the wound area when treated with 100 ng/ml (line b), 200 ng/ml (line c), and 300 ng/ml (line d) of the protein, compared to the untreated controls (line a). FIGS. 3B, 3C, and 3D demonstrates an increased wound healing effect on Type 1 diabetic human dermal fibroblasts, normal human dermal fibroblasts, and normal human ligament fibroblasts, respectively, in an in vitro wound scratch assay by 300 ng/ml of NELL1 variant protein (aa3-612; line C), compared to the full-length NELL1 protein at the same dose (line B) and the untreated control (line A).

DETAILED DESCRIPTION OF THE INVENTION

I. Introduction

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes and are not to be construed as limiting the subject matter described. Finally, for the purposes of the instant disclosure all identifying sequence Accession numbers may be found in the NCBI Reference Sequence (RefSeq) database and/or the NCBI GenBank archival sequence database unless otherwise noted.

II. NELL1

The neural epidermal growth-factor-like (nel) gene was first detected in neural tissue from an embryonic chicken cDNA library, and its human ortholog neural epidermal growth-factor-like 1 (NEL-like 1, NELL1) was discovered later in B-cells. Studies have reported the presence of NELL1 in various fetal and adult organs, including, but not limited to, skeletal and cardiac muscle, skin, the brain, kidneys, colon, thymus, lung, and small intestine.

The human NELL1 gene encodes an 810-amino acid polypeptide. Generally, the arrangement of the functional domains of the NELL1 protein bears resemblance to thrombospondin-1 (THBS1) and consists of a thrombospondin N-terminal domain (TSPN) and several von Willebrand factor, type C (VWC), and epidermal growth-factor (EGF) domains. A domain is a region of a protein with a characteristic primary structure and function.

Additional studies have shown that there are at least two human NELL1 transcript variants encoding different isoforms. In humans, the nel-like 1 isoform 1 precursor transcript variant (set forth in SEQ ID NO: 1) represents the longer transcript (set forth in GenBank Acc. No. NM_006157) and encodes the longer isoform 1 (set forth in SEQ ID NO: 2).

Figure 1:
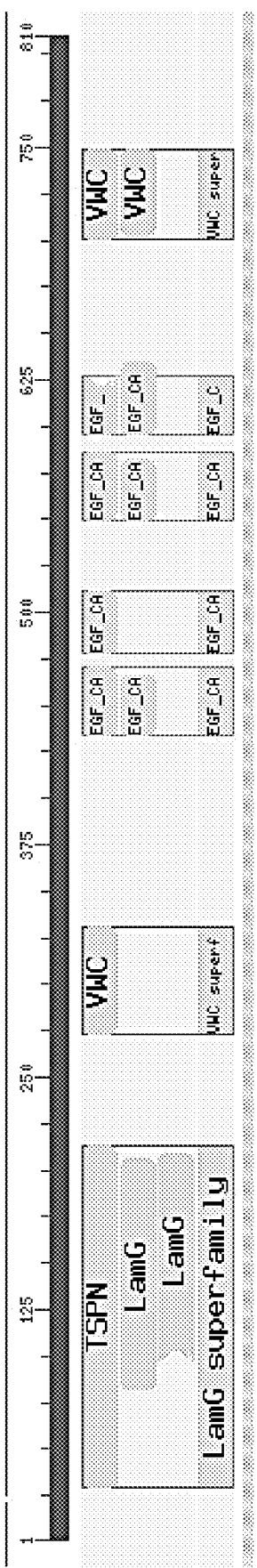
FIG. 1 shows the general structure of the human nel-like 1 isoform 1 (SEQ ID NO: 2).
Figure 2B:
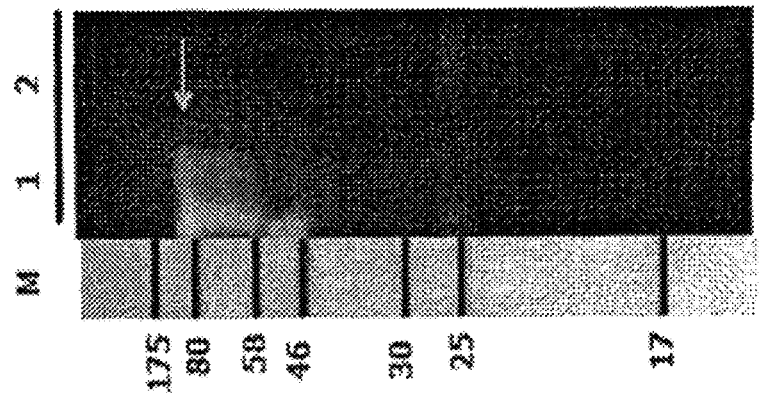
FIGS. 2A-2D depict purified recombinant horse NELL1 protein aa3-791 (full-length.
Figure 2A:
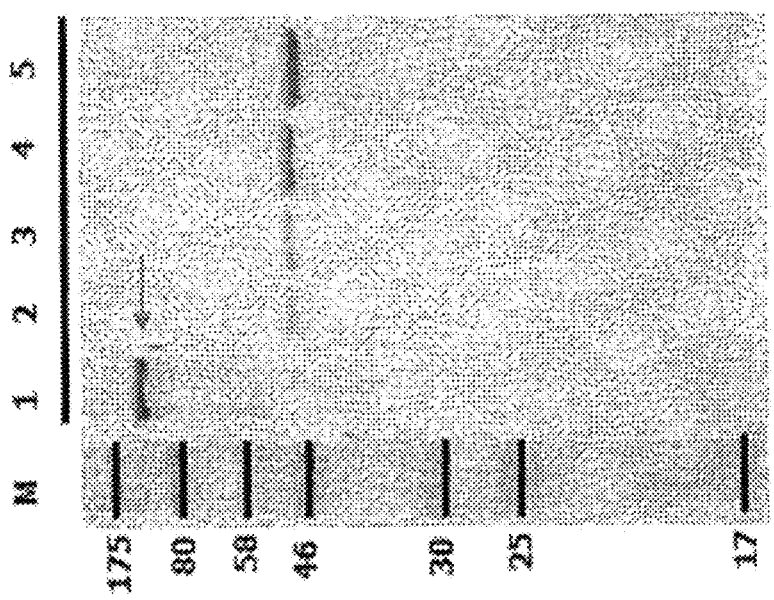
Figure 2D:
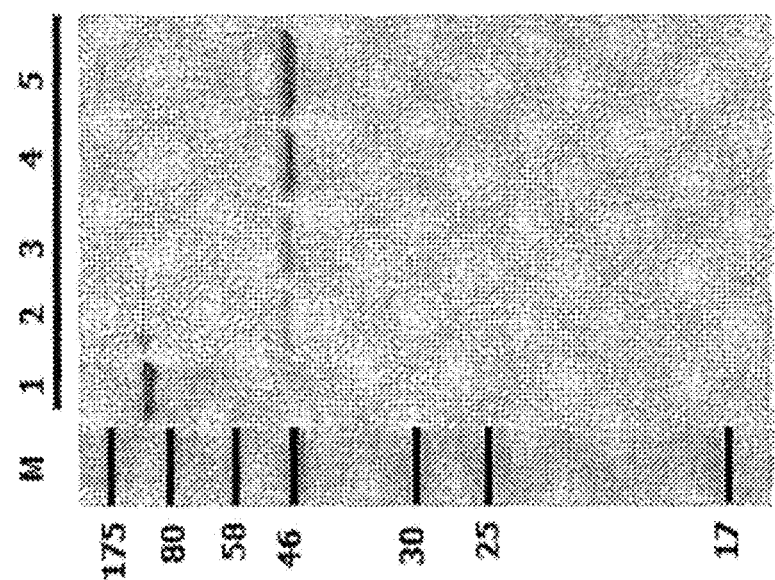
Figure 2C:
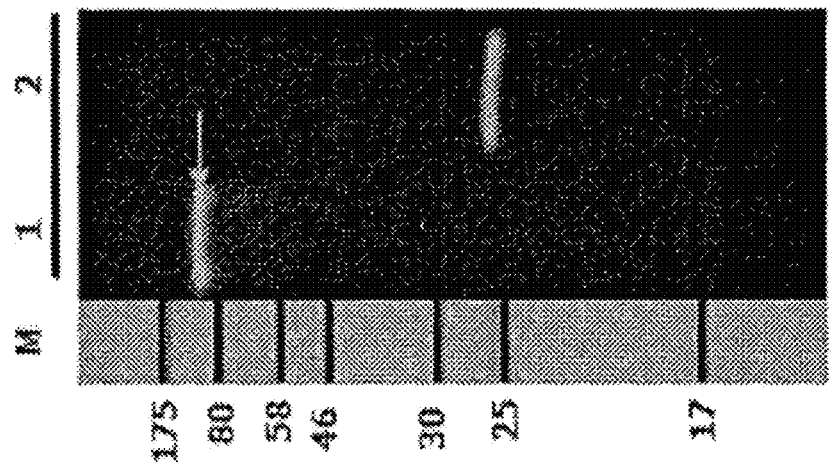

FIG. 1 shows the general structure of human nel-like 1 isoform 1 (SEQ ID NO: 2). The conserved domains reside in seven regions of the isoform 1 peptide and include: (1) a TSPN domain/Laminin G superfamily domain; (2) a VWC domain; (3) four EGF-like domains; and (4) a VWC domain. NELL1 also comprises a secretion signal peptide domain (amino acid residues 1-16 of SEQ ID NO: 2) that is generally involved in transport of the protein to cell organelles where it is processed for secretion outside the cell.

The first conserved domain region comprises amino acids (amino acids 29 to 213 of SEQ ID NO: 2) that are most similar to a thrombospondin N-terminal-like domain. Thrombospondins are a family of related, adhesive glycoproteins, which are synthesized, secreted and incorporated into the (ECM) of a variety of cells, including alpha granules of platelets following thrombin activation and endothelial cells. They interact with a number of blood coagulation factors and anticoagulant factors, and are involved in cell adhesion, platelet aggregation, cell proliferation, angiogenesis, tumor metastasis, vascular smooth muscle growth and tissue repair. The first conserved domain also comprises amino acids (amino acids 82 to 206; amino acids 98 to 209 of SEQ ID NO: 2) that are similar to a Laminin G-like domain. Laminin G-like (LamG) domains usually are $Ca^{2+}$ mediated receptors that can have binding sites for steroids, β1-integrins, heparin, sulfatides, fibulin-1, and α-dystroglycans. Proteins that contain LamG domains serve a variety of purposes, including signal transduction via cell-surface steroid receptors, adhesion, migration and differentiation through mediation of cell adhesion molecules.

Studies show that NELL1 signaling involves an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix (ECM) proteins; such as human laminin α3 chain (hLAMA3), mouse laminin α3 chain (mLAMA3), human collagen 11 α3 chain (hCOLA1), and human thrombospondin-1 (hTSP1). This complex facilitates either activation of tyrosine kinases, inactivation of tyrosine phosphatases, or intracellular recruitment of tyrosine-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2; the laminin G domain is believed to play a role in the interaction between integrins and a 67 kDa laminin receptor (Shen et al. (2012) *J Cell Biochem* 113: 3620-3628).

The second conserved domain (amino acids 273 to 331 of SEQ ID NO: 2) and seventh conserved domain (amino acids 701 to 749 of SEQ ID NO: 2) are similar to von Willebrand factor type C (VWC) domains, also known as chordin-like repeats. An additional VWC domain is also found from amino acid residues 634 to 686 of SEQ ID NO: 2. VWC domains occur in numerous proteins of diverse functions and have been associated with facilitating protein oligomerization.

The third conserved domain (amino acids 434 to 466 of SEQ ID NO: 2), fourth conserved domain (amino acids 478 to 512 of SEQ ID NO: 2), fifth conserved domain (amino acids 549 to 586 of SEQ ID NO: 2), and sixth conserved domain (amino acids 596 to 627 of SEQ ID NO: 2) are similar to a calcium-binding EGF-like domain. Calcium-binding EGF-like domains are present in a large number of membrane-bound and extracellular (mostly animal) proteins. Many of these proteins require calcium for their biological function. Calcium-binding sites have been found to be located at the N-terminus of particular EGF-like domains, suggesting calcium-binding may be crucial for numerous protein-protein interactions. Six conserved core cysteines form three disulfide bridges as in non-calcium-binding EGF domains whose structures are very similar. The calcium-binding EGF-like domains of NELL1 bind protein kinase C beta, which is typically involved in cell signaling pathways in growth and differentiation.

The nel-like 1 isoform 2 precursor transcript variant (set forth in GenBank Acc. No. NM_201551 and SEQ ID NO: 3)

lacks an alternate in-frame exon compared to variant 1. The resulting isoform 2 (set forth in SEQ ID NO: 4), which has the same N- and C-termini as isoform 1 but is shorter compared to isoform 1, has six conserved regions including a TSPN domain/LamG superfamily domain (amino acids 29 to 213 of SEQ ID NO: 4); VWC domains (amino acids 273 to 331 of SEQ ID NO: 4; amino acids 654 to 702 of SEQ ID NO: 4); and calcium-binding EGF-like domains (amino acids 478 to 512 of SEQ ID NO: 4; amino acids 434 to 466 of SEQ ID NO: 4; amino acids 549 to 580 of SEQ ID NO: 4).

NELL1 and its orthologs are found across several species including *Homo sapiens* (man), *Bos taurus* (cow; the nucleic acid sequence of which is set forth in GenBank Acc. No. XM_002699102 and the amino acid sequence is set forth in SEQ ID NO: 19), *Equus caballus* (horse; the nucleic acid sequence of isoforms 1 and 2 are set forth in GenBank Acc. Nos. XM_001504986 and XM_001504987, respectively, and in SEQ ID NO: 5 and 7, respectively; the amino acid sequences are set forth in SEQ ID NO: 6 and 8, respectively), *Macaca mulatta* (rhesus monkey; the nucleic acid sequence of isoforms 1, 2, 3, and 4 are set forth in GenBank Acc. Nos. XM_002799606, XM_001092428, XM_001092540, and XM_001092655, respectively), *Mus musculus* (mouse; the nucleic acid sequence of which is set forth in GenBank Acc. No. NM_001037906 and in SEQ ID NO: 9; the amino acid sequence of which is set forth in SEQ ID NO: 10), *Rattus norvegicus* (rat; the nucleic acid sequence of which is set forth in GenBank Acc. No. NM_031069 and in SEQ ID NO: 11; the amino acid sequence of which is set forth in SEQ ID NO: 12), *Pan troglodytes* (chimpanzee; the nucleic acid sequence of which is set forth in GenBank Acc. No. XM_508331.2), *Felis catus* (cat; the amino acid sequences of isoform 1 and 2 are set forth in GenBank Acc. Nos. XP_003993117.1 and XP_003993118.1, and SEQ ID NOs: 13 and 14, respectively, *Canis lupus familiaris* (dog; the amino acid sequence is set forth in GenBank Acc. No. XP_534090 and SEQ ID NO: 15), and *Ovis aries* (sheep; the amino acid sequence is set forth in GenBank Acc. No. XP_004019490 and SEQ ID NO: 16).

NELL1 is a signaling protein that mediates tissue growth and maturation in a variety of tissues such as bone, cartilage, heart and skeletal muscle—during fetal development and the healing of acute injuries in adult tissues (Desai et al. (2006) *Hum Mol Genet* 15(8):1329-1341; Siu et al. (2011) *Tissue Eng Part A* 17(7-8):1123-1135; Siu et al. (2012) *Tissue Eng Part A* 18(3-4):252-261; Xue et al. (2011) *Bone* 48(3):485-495; Li et al. (2011) *Plast Reconstr Surg* 127(2):580-587; Turner et al. (2013) *Cells Tissues and Organs* 198(4):249-265). During early development, NELL1 regulates the production of many components of the extracellular matrix (ECM) which collectively serve as an architectural framework and communication highway to mediate new tissue formation.

In vitro studies on three-dimensional human skin models exposed to UV radiation demonstrated that NELL1 reduces levels of key pro-inflammatory molecules (e.g. IL1-β, IL8) after adult tissue injury (Mitchell et al. (2012) Abstract, 70$^{th}$ Annual Meeting of the American Academy of Dermatology, San Diego, Calif., March 16-20). Human genome-wide association studies have also suggested that in certain genetic populations NELL1 plays a role in controlling severe inflammatory conditions (Franke et al. (2007) *PLoS ONE* 2(8):e691).

Multiple effects of NELL1 are believed to contribute to its ability to heal injuries to tendons and/or ligaments. Such effects include its pro-angiogenic activity, which stimulates blood vessel formation in areas having poor blood supply. NELL1 accomplishes this via effects on VEGF and perivascular stem cells (Askarinam et al. (2013) *Tissue Eng A* 19(11-12):1386-1397). The effect of NELL1 in perivascular cells is particularly important in tendon regeneration because the capillaries of tendons contain perivascular stem cells that express tendon- and stem/precursor cell-like characteristics which could be the source of the formation/regeneration of new tendon tissue (Tempfer et al. (2009) *Histochem Cell Biol* 131(6):733-741). While not being held by any theory or mechanism of action, it is believed that NELL1 can also stimulate the proliferation and migration of tendon precursor stem cells, fibroblasts or perivascular stem cells, contributing to the healing of tendons (Nemoto et al. (2013) *J Equine Sci* 24(2):17-24).

NELL1 induces the production of molecules in the extracellular matrix that are key structural components of tendons and ligaments or molecules that regulate the production of components and their assembly/organization into the correct functional architecture. Some of the known genes in the NELL1 pathway directly impact tendon or ligament development, structure, function, repair and regeneration after injuries. This list includes tenascin C, collagen V, Bmp7, periostin or osteoblast specific factor 2, and Prg4 (lubricin). Tenascin C is a glycoprotein abundant in tissues with high tensile strength and subject to compression stress. It is believed to be a key factor in tendon healing due to its ability to promote fibroblast/tendon cell proliferation and migration. Tenascin C is a genetic determinant of Achilles heel tendinopathies and ruptures and is linked to tissue response to mechanical loading, probably by regulating cell-ECM interactions (September et al. (2007); Taylor et al. (2009) *BUM Musculoskeletal Disorders* 10(27):1-10; Juneja & Veillette (2013) *Arthritis* 2013:1-30; Nemoto et al. (2013)). Collagen V, specifically Col5a1 and Col5a3, is a component of fibrillary collagen that regulates collagen fiber assembly and diameter in tendons and ligaments (September et al. (2007); Connizzo et al. (2015) *J Orthopaedic Research* 33:882-888; Sun et al. (2015) *Am J Pathol* 185:1436-1447). Bmp7 is a bone morphogenetic protein that serves as a growth factor promoting cell growth and differentiation. It facilitates tendon-bone integration. Other studies show it increases collagen type 1 production and cell activity (Pauly et al. (2012) *J Shoulder Elbow Surg* 21(4):464-473; Schwarting et al. (2015) *PLoS One* 10(2):1-17). Periostin or osteoblast specific factor 2 is a matricellular protein that is abundant in collagen rich connective tissue, where it is essential for proper ECM synthesis, collagen 1 fibrillogenesis, and tendon crosslinking. (Hamilton et al. (2008) *J Cell Commun Signal* 2:9-17; Juneja & Veilette (2013)). Prg4 (lubricin) is a proteoglycan that plays a role in boundary lubrication in articulating joints and tendon gliding. Its absence leads to decreased lubrication, which causes tissue damage, matrix remodeling and dystrophic calcification. (Juneja & Veilette (2013)). NELL1 modulates the inflammatory response via the downregulation of cytokines such as IL-1 beta and IL8 (Mitchell et al. (2012)). Tendon and ligament injuries are prone to prolonged inflammation because the injured sites are often subjected to constant motion. NELL1 downregulates matrix metalloproteinases (e.g. MMP1), which degrade the collagen in tendon ECM. MMPs are needed to maintain ECM homeostasis, but tendon injury can lead to an imbalance or dysregulation so that high levels can further degrade tendon architecture and function. (Mitchell et al. (2012); Davis et al. (2013) *J Applied Physiol* 115(6):884-891).

Disclosed herein is the discovery that NELL1 also enhances the migration and/or the proliferation of fibroblast cells (e.g., ligament fibroblasts, dermal fibroblasts from normal individuals and type 1 diabetic patients). This effect can serve to promote wound healing by increasing the numbers of fibroblasts within a wound area, thus enhancing the contraction and closure of the wound. The proliferation and migration of fibroblasts into the provisional wound matrix/fibrin clot are critical processes that are triggered early in wound healing (e.g., few days after injury in human skin) and have significant roles in supporting other biological processes throughout normal wound healing, including the degradation of the fibrin clot, secretion of new extracellular matrix and collagen-rich structures to support the activities of other cells, and wound contraction. The presently disclosed methods and compositions utilize a NELL1 peptide or a nucleic acid molecule encoding the same to promote the healing of injuries to tendons or ligaments or to enhance the migration and/or proliferation of fibroblasts. Certain NELL1 variants also find broader use in regenerating tissues, promoting healing of wounds, and promoting the maturation of progenitor cells.

A peptide, polypeptide, or protein is a sequence of subunit amino acids, amino acid analogs, or peptidomimetics. A peptidomimetic is a small protein-like chain designed to mimic a peptide. A peptidomimetic typically arises from modification of an existing peptide in order to alter the molecule's properties.

A peptide, polypeptide or protein can also be amino acid polymers in which one or more amino acid residue is an artificial chemical analogue of a corresponding naturally occurring amino acid, as well as to naturally-occurring amino acid polymers. A polypeptide, peptide or protein is inclusive of modifications including, but not limited to, glycosylation, lipid attachment, sulfation, gamma-carboxylation of glutamic acid residues, hydroxylation, phosphorylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of post-translational events, including natural processing events and events brought about by human manipulation which do not occur naturally. Circular, branched and branched circular polypeptides may be synthesized by non-translation natural processes and by entirely synthetic methods, as well.

A NELL1 peptide, NELL1 polypeptide, or NELL1 protein is a naturally-occurring NELL1 protein, or a variant or fragment thereof that retains the ability to promote the healing of injuries to tendons and/or ligaments. In some embodiments, the NELL1 peptide exhibits any one of the activities selected from the group consisting of: stimulation of ECM production (e.g., through the upregulation of at least one of tenascins, proteoglycans, elastin, glycosaminoglycans, including epidermal hyaluronic acid, and collagens), reduction in the levels of inflammatory mediators (e.g., IL-1β and IL-8), reduction in the levels of matrix metalloproteinases (e.g., MMP1), and enhancing the migration and/or proliferation of fibroblasts. In other embodiments, the NELL1 peptide can also exhibit at least one of the activities selected from the group consisting of binding to PKC-beta, stimulation of differentiation of a precursor cell (e.g., skeletal satellite cell, osteoblast precursor, perivascular stem cell, or tendon precursor stem cell) to maturity, and stimulation of angiogenesis. To determine whether a peptide exhibits any one of these activities, any method known in the art useful for measuring these activities can be used.

Suitable assays for determining if a given peptide can stimulate ECM production and reduce the levels of inflammatory mediators or MMPs include assays that measure transcript levels (e.g., quantitative polymerase chain reaction) or levels of the protein (e.g., enzyme-linked immunoassay) directly or indirectly (by measuring the activity of the protein), including those that are described elsewhere herein.

Suitable assays for assessing the binding of NELL1 to PKC beta is described in e.g., Kuroda et al. (1999) *Biochem Biophys Res Comm* 265:752-757. For example, protein-protein interactions can be analyzed by using the yeast two-hybrid system. Briefly, a NELL1 protein can be fused with GAL4 activating domain and the regulatory domain of PKC can be fused with the GAL4 DNA-binding domain.

In other embodiments, the NELL1 peptide stimulates the differentiation of precursor cells, such as skeletal satellite cells, osteoblast precursors, perivascular stem cells, and tendon precursor stem cells, to maturity. The maturity of cells can be assessed cellularly (histology) and molecularly (expression of cell-specific proteins or extracellular matrix materials).

Suitable assays for determining if a peptide is capable of promoting the healing of tendon and/or ligament injuries include those known in the art (Nemoto et al. (2013); Taylor et al. (2009); Yanming et al. (2007) *Nature Medicine* 13:1219-1227; Tempfer et al. (2009)) and disclosed elsewhere herein.

Suitable assays for determining if a NELL1 peptide can promote the migration and/or proliferation of fibroblasts include wound scratch assays known in the art and described elsewhere herein.

The NELL1 peptide may be a naturally-occurring (i.e., wild-type) NELL1 protein or an active variant or fragment thereof. Naturally refers to as found in nature; wild-type; innately or inherently. A naturally-occurring NELL1 peptide may be purified from a natural source or may be a peptide that has been recombinantly or synthetically produced that has the same amino acid sequence as a NELL1 peptide found in nature.

A polynucleotide can be a singular nucleic acid, as well as plural nucleic acids, and refers to a nucleic acid molecule or construct, e.g., messenger RNA (mRNA), complementary DNA (cDNA), plasmid DNA (pDNA), or short interfering RNA (siRNA). A polynucleotide can be single-stranded or double-stranded, linear or circular and can be comprised of DNA, RNA, or a combination thereof. A polynucleotide can comprise a conventional phosphodiester bond or a non-conventional bond (e.g., an amide bond, such as found in peptide nucleic acids (PNA)). A nucleic acid can be any one or more nucleic acid segments, e.g., DNA or RNA fragments, present in a polynucleotide. The polynucleotide can contain modified nucleic acids, such as phosphorothioate, phosphate, ring atom modified derivatives, and the like. The polynucleotide can be a naturally occurring polynucleotide (i.e., one existing in nature without human intervention), a recombinant polynucleotide (i.e., one existing with human intervention), or a synthetically derived polynucleotide.

An isolated material can refer to a nucleic acid, peptide, polypeptide, or protein, which is: (1) substantially or essentially free from components that normally accompany or interact with it as found in its naturally occurring environment. Substantially free or essentially free refer to considerably or significantly free of, or more than about 95% free of, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868, each of which is incorporated by reference herein. Likewise, a naturally occurring nucleic acid (for example, a promoter) becomes isolated if it is introduced by non-naturally occurring means to a locus of the genome not native to that nucleic acid.

Fragments and variants of native (i.e., naturally-occurring) NELL polypeptides can be employed in the various methods and compositions of the invention. A fragment is intended a portion of a polynucleotide or a portion of a polypeptide. Fragments of a polynucleotide may encode polypeptide fragments that retain the biological activity of the native polypeptide. A fragment of a polynucleotide that encodes a biologically active portion of a NELL1 polypeptide will encode at least 15, 25, 30, 50, 100, 150, 200, 250, 300, 350, 400, 450, 500, 550, 600, 650, 700, 750, or 800 contiguous amino acids, or up to the total number of amino acids present in a full-length NELL1 polypeptide. In certain embodiments, the NELL1 fragment is 610 amino acids in length.

A fragment of a native NELL1 polypeptide can be prepared by isolating a portion of a polynucleotide encoding the portion of the NELL1 polypeptide and expressing the encoded portion of the polypeptide (e.g., by recombinant expression in vitro). Polynucleotides that encode fragments of a NELL1 polypeptide can comprise nucleotide sequences comprising at least 15, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, or 2400 contiguous nucleotides, or up to the number of nucleotides present in a full-length NELL1 nucleotide sequence. In some embodiments, the fragment lacks the first amino acid residue, or the first 2, 3, 4, 5, 6, 7, 8, 9, 10, 20, 21, 22, 23, 24, 25, 26, 27, 28, 29, 30, 35, 40, or 45 amino acid residues from the amino terminal end of the NELL1 protein. In some embodiments, the fragment lacks the last 5, 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 220, 230, 240, 250, 260 or more amino acid residues. In certain embodiments, the fragment of a NELL1 protein lacks the most carboxy-terminal 179 amino acid residues from the end of the protein. In other embodiments, the NELL1 protein fragment lacks the first two amino acid residues from the amino terminal end and the last 179 amino acid residues from the carboxy terminal end of the protein. In some embodiments, the NELL1 protein fragment has 610 amino acid residues.

The inventors determined that removal of 179 amino acid residues from the carboxy-terminus of the *Equus caballus* NELL1 isoform 1 protein unexpectedly provided a higher yield and easier purification during manufacture of the protein. Without being bound by any theory or mechanism of action, it is believed that the removal of the carboxy-terminal domains led to decreased formation of aggregates of the protein. Although NELL1 protein naturally oligomerizes into trimers, which are functional, aggregates of NELL1 protein refer to large, higher-ordered macromolecular complexes that prevent or reduce the function of the protein or make the protein products difficult to extract and purify. The NELL1 protein lacking the C-terminal 179 amino acid residues is also unexpectedly more efficacious than full-length NELL1 protein in horse body wound healing studies and fibroblast wound scratch assays. Thus, in specific embodiments, the NELL1 protein fragment lacks the last 179 amino acid residues from the carboxy terminus. In some of these embodiments, the NELL1 protein fragment also lacks the first two amino acid residues from the amino terminus. The sequence of this horse NELL1 fragment is set forth in SEQ ID NO: 18. In other embodiments, the NELL1 protein fragment lacks the first 21 amino acid residues from the amino terminus and the last 179 amino acid residues from the carboxy terminus. The sequence of this human NELL1 fragment is set forth in SEQ ID NO: 17. In certain embodiments, the NELL1 protein fragment lacks at least one of the two carboxy-terminal VWC domains (located at amino acid residues 634-686 and 701-749 of SEQ ID NO: 2). In some of these embodiments, the NELL1 protein fragment lacks both of these carboxy-terminal VWC domains. Compositions comprising these NELL1 fragments are contemplated herein and methods for using these NELL1 fragments for regenerating tissues (e.g., bone, cartilage, heart, vasculature, skeletal muscle), promoting the maturation of progenitor cells for various tissues (e.g., bone, cartilage, heart, vasculature, skeletal muscle, tendons, ligaments), and promoting the migration and/or proliferation of fibroblasts are also contemplated herein.

In those embodiments wherein a variant NELL1 protein lacks at least one C-terminal VWC domain, the variant NELL1 protein exhibits at least one of the following characteristics: enhanced efficacy in tissue regeneration and/or promotion of wound healing, easier purification, higher yield, less aggregate formation, and enhanced efficacy in fibroblast migration and/or proliferation, when compared to a full-length NELL1 protein. An easier purification includes a purification process whereby a single polypeptide species is substantially separated from other polypeptide species or a natural or synthetic milieu comprising the single polypeptide species and other polypeptide species that comprises fewer steps required for substantial separation or wherein the time required for at least one of the steps in the separation is reduced. An easier purification also refers to a purification process which results in a higher yield of the substantially purified or separated polypeptide species. The terms "substantially purified" or "substantially separated" when used in reference to a single polypeptide species refers to a level of purification whereby the single polypeptide species represents at least about 70% of a total population of polypeptide species within a sample, including but not limited to at least about 75%, 80%, 85%, 86%, 87%, 88%, 89%, 90%, 91%, 92%, 93%, 94%, 95%, 96%, 97%, 98%, 99%, or greater of a total population of polypeptide species within a sample. A yield of a protein product from a purification process refers to the overall concentration of the polypeptide within a solution. The higher the concentration of the polypeptide within the solution, the more yield is obtained. If a polypeptide is present within a solution at <0.1 µg/µl, the protein is considered difficult to produce and purify. Thus, in some embodiments, a variant NELL1 protein that lacks at least one C-terminal VWC domain exhibits the ability to be purified using conventional purification means known in the art, such as those methods described elsewhere herein, to a concentration greater than 0.1 μg/μl. In some of these embodiments, a variant NELL1 protein has the ability to be purified using conventional purification means known in the art to a concentration of about 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30 μg/μl, or greater. In certain embodiments, a variant NELL1 protein lacking at least one C-terminal VWC domain exhibits both a higher yield and a greater purity as compared to a full-length NELL1 protein following a purification process.

Variant sequences have a high degree of sequence similarity. For polynucleotides, conservative variants include those sequences that, because of the degeneracy of the genetic code, encode the amino acid sequence of a NELL1 polypeptide. Variants such as these can be identified with the use of well-known molecular biology techniques, such as, for example, polymerase chain reaction (PCR) and hybridization techniques. Variant polynucleotides also include synthetically derived nucleotide sequences, such as those generated, for example, by using site-directed mutagenesis. In some embodiments, the variant polynucleotide still encodes a NELL1 polypeptide or a fragment thereof. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide can also be evaluated by comparison of the percent sequence identity between the polypeptide encoded by a variant polynucleotide and the polypeptide encoded by the reference polynucleotide. Thus, variants include, for example, polynucleotides that encode a polypeptide with a given percent sequence identity to a native NELL1 polypeptide. Percent sequence identity between any two polypeptides can be calculated using sequence alignment programs and parameters described herein. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant polypeptide is a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. The activity of variant NELL1 polypeptides can be assessed using the methods disclosed herein to determine if the variant is biologically active. Such variants may result from, for example, genetic polymorphism or from human manipulation. Biologically active variants of a native NELL1 polypeptide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native polypeptide as determined by sequence alignment programs and parameters described elsewhere herein. A biologically active variant of a polypeptide may differ from that polypeptide by as few as 1-15 amino acid residues, as few as 1-10, such as 6-10, as few as 5, as few as 4, 3, 2, or even 1 amino acid residue.

Biologically active variants of the NELL1 fragments disclosed herein (i.e., those lacking at least one of the two VWC domains at the carboxy terminus of NELL1) are also contemplated herein and may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the active NELL1 fragment (e.g., SEQ ID NO: 17 or 18).

Polypeptides may be altered in various ways including amino acid substitutions, deletions, truncations, and insertions. Methods for such manipulations are generally known in the art. For example, amino acid sequence variants of native NELL1 polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.). Conservative substitutions, such as exchanging one amino acid with another having similar properties, may be preferable.

Generally, the mutations made in the polynucleotide encoding the variant NELL1 polypeptide should not place the sequence out of reading frame, and/or create complementary regions that could produce secondary mRNA structure. See, EP Patent Application Publication No. 75,444.

Variant NELL1 polynucleotides and polypeptides also encompass sequences and polypeptides derived from a mutagenic and recombinogenic procedure such as DNA shuffling. With such a procedure, one or more different NELL1 coding sequences can be manipulated to create peptides that can be evaluated to determine if it retains NELL1 activity. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) Nature 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Variant NELL1 polynucleotides and polypeptides also encompass sequences and polypeptides derived from gene editing systems, such as CRISPR/Cas system.

Sequence identity in the context of two polynucleotides or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have sequence similarity or similarity. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Percentage of sequence identity is the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3; % identity and % similarity for an amino acid sequence using GAP Weight of 8 and Length Weight of 2, and the BLOSUM62 scoring matrix; or any equivalent program thereof. An equivalent program is any sequence comparison program that, for any two sequences in question, generates an alignment having identical nucleotide or amino acid residue matches and an identical percent sequence identity when compared to the corresponding alignment generated by GAP Version 10.

The NELL1 peptide may be made synthetically, i.e. from individual amino acids, or semi-synthetically, i.e. from oligopeptide units or a combination of oligopeptide units and individual amino acids. Suitable methods for synthesizing proteins are described by Stuart and Young in "*Solid Phase Peptide Synthesis*," Second Edition, Pierce Chemical Company (1984), *Solid Phase Peptide Synthesis, Methods Enzymol.*, 289, Academic Press, Inc, New York (1997).

The NELL1 peptide may also be prepared by methods that are well known in the art. One such method includes isolating or synthesizing DNA encoding the NELL1 peptide, and producing the recombinant protein by expressing the DNA, optionally in a recombinant vector, in a suitable host cell. Suitable methods for synthesizing DNA are described by Caruthers et al. (1985) *Science* 230:281-285; and *DNA Structure, Part A: Synthesis and Physical Analysis of DNA*, Lilley, D. M. J. and Dahlberg, J. E. (Eds.), *Methods Enzymol.*, 211, Academic Press, Inc., New York (1992).

In some embodiments of the presently disclosed methods, a nucleic acid molecule encoding a NELL1 peptide is administered to a subject in need thereof in order to regenerate tissue, promote the healing of an injury (e.g., tendon or ligament injury), or to enhance migration and/or proliferation of fibroblasts. As used herein, the terms "encoding" or "encoded" when used in the context of a specified nucleic acid mean that the nucleic acid comprises the requisite information to direct translation of the nucleotide sequence into a specified polypeptide.

In some embodiments of the presently disclosed methods, the NELL1 nucleic acid molecule is operably linked to at least one regulatory element. A regulatory element is a nucleic acid sequence(s) capable of effecting the expression of nucleic acid(s), or the peptide or protein product thereof. Non-limiting examples of regulatory elements include promoters, enhancers, polyadenylation signals, transcription or translation termination signals, ribosome binding sites, or other segments of DNA where regulatory proteins, such as, but not limited to, transcription factors, bind preferentially to control gene expression and thus protein expression.

Regulatory elements may be operably linked to the nucleic acids, peptides, or proteins of the described invention. When two or more elements are operably linked, there exists a functional linkage between the elements. For example, when a promoter and a protein coding sequence are operably linked, the promoter sequence initiates and mediates transcription of the protein coding sequence. The regulatory elements need not be contiguous with the nucleic acids, peptides, or proteins whose expression they control as long as they function to direct the expression thereof. Thus, for example, intervening untranslated yet transcribed sequences may be present between a promoter sequence and a nucleic acid of the described invention and the promoter sequence may still be considered operably linked to the coding sequence.

In certain embodiments, the NELL1 nucleic acid molecule is a recombinant expression cassette or is part of an expression system. The term "recombinant expression cassette" refers to a nucleic acid construct, generated recombinantly or synthetically, with a series of specified nucleic acid elements which permit transcription of a particular nucleic acid (e.g., protein coding sequence) in a host cell. The recombinant expression cassette can be incorporated into a plasmid, chromosome, mitochondrial DNA, virus, or nucleic acid fragment. Typically, the recombinant expression cassette portion of an expression vector includes, among other sequences, a nucleic acid to be transcribed, a promoter, and a transcription termination signal such as a poly-A signal.

The expression cassette or cloning vector can be generated using molecular biology techniques known in the art and utilizing restriction enzymes, ligases, recombinases, and nucleic acid amplification techniques such as polymerase chain reaction that can be coupled with reverse transcription.

In some embodiments, the NELL1 protein is produced using a cell-free expression system such as the wheat germ in vitro translation system.

In some embodiments, the NELL1 nucleic acid molecule is in a host cell that can be used for propagation of the nucleic acid molecule or for expression of the NELL1 peptide and subsequent isolation and/or purification. A host cell is any cell that contains a heterologous nucleic acid molecule. A heterologous polypeptide or nucleotide sequence is a polypeptide or a sequence that originates from a different species, or if from the same species, is substantially modified from its native form in composition and/or genomic locus by deliberate human intervention. The host cell typically supports the replication and/or expression of the vector. Host cells may be prokaryotic cells such as, but not limited to, *Escherichia coli*, or eukaryotic cells such as, but not limited to, yeast, insect, amphibian, plant (e.g., *Nicotiana tabacum* (tobacco), *Oryza sativa* (rice), *Arabidopsis thaliana* (cress)), or mammalian cells. The term as used herein means any cell which may exist in culture or in vivo as part of a unicellular organism, part of a multicellular organism, or a fused or engineered cell culture. A cloning host cell is a host cell that contains a cloning vector.

A recombinant cell or vector is one that has been modified by the introduction of a heterologous nucleic acid or the cell that is derived from a cell so modified. Recombinant cells express genes that are not found in identical form within the native (non-recombinant) form of the cell or express native genes that are otherwise abnormally expressed, under-expressed or not expressed at all as a result of deliberate human intervention. The alteration of a cell or vector by naturally occurring events (e.g., spontaneous mutation, natural transformation transduction/transposition), such as those occurring without deliberate human intervention, does not result in a recombinant cell or vector.

The NELL1 nucleic acid molecule can be introduced into a host cell for propagation of production of NELL1 using any method known in the art, including transfection, transformation, or transduction, so long as the nucleic acid molecule gains access to the interior of the cell. The insertion or introduction of a nucleic acid into a cell refers to transfection or transformation or transduction and includes the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The NELL1 nucleic acid molecule can be introduced to allow for stable transformation or transient transformation. Stable transformation is intended to mean that the nucleotide construct introduced into a cell integrates into a genome of the cell. Transient transformation is intended to mean that a polynucleotide is introduced into the cell and does not integrate into a genome of the cell.

The NELL1 protein can be administered by a cell based gene therapy. For example, autologous, allogeneic or xenogeneic donor cells are genetically modified in vitro to express and secrete NELL1 protein. The genetically modified donor cells are then subsequently implanted into the subject in need of delivery of NELL1 protein in vivo. Examples of suitable cells include, but are not limited to, tenocytes, endothelial cells, fibroblasts (including tendon-derived fibroblasts), or stem/precursor cells, such as adult stem cells, embryonic stem cells, cord blood stem cells, perivascular stem cells, or tendon/stem progenitor cells (TSPCs).

III. Methods

The presently disclosed methods involve the regeneration of tissue, promotion of healing of an injury (e.g., tendon or ligament injury), or the enhancement of fibroblast migration and/or proliferation in a subject in need thereof. NELL1 peptides also find use in enhancing fibroblast migration and/or proliferation in an in vitro or ex vivo setting, for example in a wound scratch assay.

The regeneration of tissue refers to the process of renewal and growth of cells and extracellular matrix components within a particular tissue that results in the production of tissue that has a cellular component and architecture that allows for the normal functions of the particular tissue type. As described elsewhere herein, NELL1 has been demonstrated to stimulate the regeneration of tissues such as bone, cartilage, and skeletal muscle, which is believed to be attributed to at least one of the following effects of NELL1 protein: stimulation of the differentiation of precursor cells to maturity, pro-angiogenic activity, stimulation of ECM production, and reduction in levels of MMPs and inflammatory mediators. As disclosed herein, NELL1 also enhances the migration and/or proliferation of fibroblast cells, which can also contribute to tissue regeneration, particularly in response to a wound or within an area of injury.

As disclosed herein, the administration of NELL1 to fibroblast cells results in an increased migration rate and greater cell numbers within an area of tissue injury. The greater cell numbers can be a result of an enhanced migration rate and/or an increase in proliferation of the fibroblasts. Thus, a NELL1 protein can enhance the migration and/or proliferation of fibroblast cells. An enhancement of fibroblast migration refers to an increase in the rate of movement of fibroblasts from one region to another, for example, chemotactic movement towards a chemical signal or movement towards an area of injury (i.e., a wound). Thus, NELL1 proteins find use in methods of enhancing the migration and/or proliferation of fibroblast cells, in vivo or in vitro. In vitro settings in which NELL1 proteins can enhance the migration and/or proliferation of fibroblast cells include wound scratch assays whereby a confluent or substantially confluent layer of fibroblast cells grown in culture are disturbed through the introduction of a "scratch" or removal of a portion of the fibroblast monolayer, followed by a period of culturing the cells such that the fibroblasts begin to repopulate the "wounded" area either through migration of the fibroblasts into the wounded area or proliferation of the fibroblasts, or a combination of the two.

The promotion of the healing of a wound refers to an increase in the speed with which an injury (i.e., wound) heals or an improved outcome. Healing of an injury is considered to be promoted, for example, if the time of healing of an injury treated with NELL1 compared to an injury not treated with NELL1 is decreased by about 10%, about 25%, about 50%, or about 75%. Alternatively, healing of an injury is considered to be promoted if the extent of re-acquisition of tendon and/or ligament function of an injury treated with NELL1 compared to an injury not treated with NELL1 is improved by about 10%, about 25%, about 50%, or about 75%. Conversely, healing of an injury is considered to be promoted if the degree and/or amount of scar tissue resulting from an injury treated with NELL1 as compared to an injury not treated with NELL1 is reduced by about 10%, about 25%, about 50%, or about 75%. Promotion of healing of an injury to a tendon or ligament can also be considered if there is an improvement in the composition (e.g., proportion and amount of collagen types) and/or architecture (e.g., correct alignment of collagen fibrils/fibers/bundles) of at least about 10%, about 25%, about 50%, or about 75% of an injury treated with NELL1 compared to an injury not treated with NELL1.

The NELL1 peptide or nucleic acid molecule encoding the same is administered to a subject in need thereof to regenerate tissue, particularly to promote healing of an injury (e.g., a tendon and/or ligament injury), or to enhance the migration and/or proliferation of fibroblasts (e.g., dermal fibroblasts, ligament fibroblasts). The terms "subject", "individual", and "patient" are used interchangeably to refer to a member of a species that comprises tendons and ligaments. In certain embodiments, the subject is a mammal, including but not limited to, mouse, rat, cat, goat, sheep, horse, hamster, ferret, pig, dog, platypus, guinea pig, rabbit and a primate, such as, for example, a monkey, ape, or human. In some of these embodiments, the subject is a human or a horse, such as a racehorse. Subjects in need of treatment with a NELL1 peptide or nucleic acid molecule include those having an injury or those that are prone to injuries or an impaired healing process. Subjects that are prone to the development of injuries to a ligament and/or tendon include racehorses and athletes. Subjects in need of treatment with a NELL1 peptide or nucleic acid molecular encoding the same include those that have or are prone to impaired wound healing, impaired neovascularization, or impaired angiogenesis, including but not limited to those subjects with diabetes (type 1 or type 2), vascular diseases, hypercholesterolemia, and aging.

An injury or wound refers to damage or harm to a structure or function of the body caused by intrinsic and/or extrinsic factors. Non-limiting intrinsic or extrinsic factors that can cause an injury or wound include those of chemical, mechanical, thermal, bacterial, or physical means and encompass those that occur as the result of surgical procedures, overuse, or environmental conditions. The wound can be an open wound in which the skin is broken (e.g., lacerations, abrasions, puncture wound) or a closed wound. Particular wounds that can be healed with NELL1 include, but are not limited to, bone injuries (e.g., complete or partial fractures), skin wounds, and skeletal muscle injuries.

Intrinsic factors that can contribute to the development of injuries to tendons and/or ligaments include genetic susceptibility, overuse, poor biomechanics, poor nutrition, and obesity. The extrinsic factors are often related to sports and include excessive forces or loading, poor training techniques, environmental conditions, and surgical procedures. The injury to the tendon and/or ligament can be a closed wound or an open wound, where the skin is lacerated, cut or punctured. The injury can include inflammation, a sprain, strain, tearing, stretching, or laceration of the tendon or ligament.

A tendon is a band of connective tissue that connects muscles to bones or cartilage. A ligament is a band of connective tissue that connects bones to other bones to form joints.

Injuries to tendons include tendinitis (acute tendon injury accompanied by inflammation), tendinosis (chronic tendon injury with degeneration at the cellular level and no inflammation), and other tendinopathies exhibiting chronic tendon injury with no etiological implications. With tendinosis, damage to collagen, cells, and the vascular components of the tendon can occur, such as irregularities of collagen fibrils (e.g., disorientation, degeneration, thinning, non-uniformity in length or diameter, increase in the amount of glycosaminoglycans between the fibrils), rounded tenocytes or other cell abnormalities, and the ingrowth of blood vessels.

The healing of an injury to any type of tendon can be promoted with NELL1, including a hand flexor tendon, a tendon within the rotator cuff, and an Achilles tendon, and within horses, a superficial digital flexor tendon (SDFT) and a deep digital flexor tendon (DDFT) of either the hindlimb(s) or forelimb(s).

Likewise, the healing of an injury to any type of ligament can be promoted with NELL1, including an anterior cruciate ligament (ACL), posterior cruciate ligament (PCL), lateral collateral ligament (LCL), medial collateral ligament (MCL), and in horses, a suspensory ligament of either the hindlimb(s) or forelimb(s). A common ligament injury in horses that can be healed according to the presently disclosed methods is proximal suspensory desmitis, an inflammation of the suspensory ligament just below the hock.

The NELL1 peptide or nucleic acid encoding the same can be administered to subjects in need thereof in the form of a composition further comprising a carrier. The term "carrier" as used herein describes a material that does not cause significant irritation to an organism and does not abrogate the biological activity and properties of the composition of the described invention. Carriers must be of sufficiently high purity and of sufficiently low toxicity to render them suitable for administration to a subject being treated. The carrier can be inert, or it can possess pharmaceutical benefits.

A pharmaceutical composition is a composition that is employed to prevent, reduce in intensity, cure or otherwise treat a target condition or disease.

A pharmaceutically acceptable carrier refers to one or more compatible solid or liquid filler, diluents or encapsulating substances which are suitable for administration to a human or other vertebrate animal.

The formulations may be presented conveniently in unit dosage form and may be prepared by any of the methods well known in the art of pharmacy. All methods include the step of bringing into association the NELL1 peptide or nucleic acid encoding the same ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The NELL1 peptide or nucleic acid encoding the same may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions, may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring the addition of the sterile liquid carrier, for example, saline, water-for-injection, a semi-liquid foam, or gel, immediately prior to use. Extemporaneous injection solutions and suspensions may be prepared from sterile powders, granules and tablets of the kind previously described. Alternatively, a NELL1 peptide or nucleic acid encoding the same is dissolved in a buffered liquid solution that is frozen in a unit-dose or multi-dose container and later thawed for injection or kept/stabilized under refrigeration until use. Any label on, or associated with, the container(s) indicates that the enclosed composition is used for promoting the healing of injuries to tendons and/or ligaments.

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. In some embodiments, the use of a long-term sustained release implant may be particularly suitable for treatment of chronic conditions. Long-term sustained release implants are well-known to those of ordinary skill in the art and include some of the release systems described above.

In some embodiments wherein the pharmaceutical composition is in the form of an implant, the NELL1 peptide or a nucleic acid encoding the same is impregnated into drug eluting devices, scaffolds or matrices that are implanted into an injured area to deliver NELL1 in a controlled release fashion. The protein can also be linked to sutures that are used for tendon and/or ligament surgeries. In those instances wherein the NELL1 peptide is delivered by genetically modified donor cells, the cells can be incorporated into a matrix containing an appropriate microenvironment to maintain, for a given time, the viability and growth of the genetically modified donor cells.

Non-limiting examples of suitable matrices include, but are not limited to, wound dressings, collagen matrix, patches, and hydrogels. The matrix can be applied to the injured tendon and/or ligament that has been exposed post-surgically, for example. After the injured tendon and/or ligament is healed, the matrix can be removed or the matrix incorporating the NELL1 peptide or nucleic acid encoding the same can be replaced intermittently throughout the healing process. In some embodiments, a rapidly degradable (e.g., 3-5 days in horses and 1-2 weeks in rats) scaffold or dressing is used to deliver NELL1 (e.g., calcium alginate). Rapidly degradable scaffolds or dressings allow for the release of a burst of NELL1 in the first phase of healing and activates tissue regeneration instead of scarring pathways. In certain embodiments, the scaffold or dressing is simpler (e.g., consisting essentially of collagen type A), rather than a complex biological carrier, such as those made from urinary bladder or intestinal linings that may comprise various growth factors and collagens. In some embodiments, the wound dressing or matrix used to deliver NELL1 comprises or consists essentially of calcium alginate.

The NELL1 peptide or nucleic acid encoding the same can be administered to a subject by dispensing, supplying, applying, or giving the NELL1 peptide or nucleic acid encoding the same to the subject. Administration may be in vivo or administration directly to tissue ex vivo. Generally, NELL1 peptides, nucleic acid molecules encoding the same, or compositions comprising the NELL1 peptide or nucleic acid may be administered systemically either orally, buccally, parenterally, topically, by inhalation or insufflation (i.e., through the mouth or through the nose), or rectally in dosage unit formulations, optionally containing the conventional nontoxic pharmaceutically acceptable carriers, adjuvants, and vehicles as desired, or may be locally administered by means such as, but not limited to, injection, implantation, grafting, or topical application. Additional administration may be performed, for example, intravenously, transmucosally, transdermally, intramuscularly, subcutaneously, intraperitoneally, intrathecally, intralymphatically, intralesionally, or epidurally.

Any suitable route of administration may be used to deliver the NELL1 peptide or nucleic acid molecule encoding the same for the purposes of tissue regeneration, such as promoting the healing of an injury to a tendon and/or ligament. In certain embodiments, the NELL1 peptide or nucleic acid encoding the same is administered locally to the site of injury or of desired tissue regeneration or fibroblast migration and/or proliferation. In some of these embodiments, the NELL1 peptide, NELL1 nucleic acid molecule, or a composition comprising the NELL1 peptide or NELL1 nucleic acid molecule are administered parenterally. The term "parenteral" as used herein refers to introduction into the body by way of an injection (i.e., administration by injection), including, for example, subcutaneously (i.e., an injection beneath the skin beneath the dermis into the subcutaneous tissue or "superficial fascia"), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. Injectable preparations, such as sterile injectable aqueous or oleaginous suspensions, may be formulated according to the known art using suitable dispersing or wetting agents and suspending agents. According to some such embodiments, the NELL1 peptide or nucleic acid molecule encoding the same is administered by injection.

In certain embodiments, the NELL1 peptide or nucleic acid molecule is administered as a spray onto a tissue, such as a tendon or ligament that has been exposed surgically (e.g., tendon splitting procedures to ease strain). The NELL1 peptide or nucleic acid molecule can also be administered via adhesion to novel materials such as nanoparticles. Lyophilized NELL protein, which may or may not be reconstituted as a liquid or a gel, can be placed directly onto an injured tendon or ligament.

Administering can be performed, for example, once, a plurality of times, and/or over one or more extended periods. Generally, an effective dose of the NELL1 peptide or nucleic acid encoding the same is administered to a subject one or more times. In certain preferred embodiments, the course of treatment will comprise multiple doses of the NELL1 peptide or nucleic acid encoding the same over a period of weeks or months. More specifically, the NELL1 peptide or nucleic acid encoding the same may be administered once every day, every two days, every three days, every four days, every five days, every six days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

An effective amount of a pharmaceutical composition of the invention is any amount that is effective to achieve its purpose. The effective amount, usually expressed in mg/kg can be determined by routine methods during pre-clinical and clinical trials by those of skill in the art.

The NELL1 peptide or nucleic acid encoding the same can be administered immediately after the injury to a tissue (e.g., the tendon and/or ligament) occurred or the administration can be delayed post-injury for about three hours, 12 hours, one day, two days, three days, four days, five days, six days, seven days, eight days, nine days, ten days, two weeks, three weeks, or longer.

The NELL1 peptide or nucleic acid encoding the same can be administered prior to, along with, or subsequent to another treatment for healing the injury (e.g., tendon and/or ligament injury). Non-limiting examples of other treatments include surgery, rehabilitation, cryotherapy, administration of precursor cells, extracellular matrix materials (synthetic or purified), anti-inflammatory agents, and analgesics.

NELL1 can be combined with cells that are important in the formation of new tissues. For example, for tendons and ligaments tenocytes, tendon-derived fibroblasts, tendon stem/progenitor cells (TSPCs) and perivascular stem cells, as well as adult stem cells, such as mesenchymal stem cells, adipose derived stem cells, and bone marrow aspirate, can be used. The combination of NELL1 with cells can be delivered as an injectable mixture or in a complex scaffold (synthetic or natural scaffold) that degrades in the injured site and acts both as a starting architectural guide for new tissue to form and also for releasing correct signals that draw into the injured site growth factors and cells needed for healing. This can be either novel scaffolds or existing commercial products (e.g. mesenchymal stem cells) that have already demonstrated activity in healing injuries, such as those to tendons and/or ligaments but whose activity can be boosted by the addition of NELL1 for more severe or challenging traumatic tissue damage. (Yanming et al. 2007; Tempfer et al. 2009; Nemoto et al. 2013)

NELL1 can be added to formulations or products that are acellular extracellular matrix materials either extracted from natural sources (e.g. linings of urinary bladder, small intestinal submucosa etc.) or manufactured as a synthetic. Acellular products for regenerative medicine that contain extracellular matrix material may not have all the needed signals for tissue regeneration and the addition of NELL1 can enhance the ability of some of these materials to effect cell differentiation and tissue maturation.

In practicing combination therapy, the NELL1 peptide or nucleic acid encoding the same and the additional treatment or therapeutic agent may be administered to the subject simultaneously, either in a single composition, or as two or more distinct compositions using the same or different administration routes. Alternatively, the NELL1 peptide or nucleic acid encoding the same may precede, or follow, the additional treatment or therapeutic agent by, e.g., intervals ranging from minutes to weeks. In at least one embodiment, the NELL1 peptide or nucleic acid encoding the same and the additional treatment or therapeutic agent are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the NELL1 peptide or nucleic acid encoding the same and the additional treatment or therapeutic agent. In some of these embodiments, the NELL1 peptide or nucleic acid is administered along with platelet derived plasma (PRP).

IV. Articles of Manufacture

The invention includes kits comprising a NELL1 peptide or nucleic acid encoding the same comprising one or more containers. The kit can contain a unit dosage of a NELL1 peptide or nucleic acid encoding the same, and may also contain one or more additional agents, such as those agents that promote wound healing, stimulate the regeneration of a tissue, or promote the migration or proliferation of fibroblast cells.

The components of the kit may be provided in one or more liquid solutions, such as a sterile aqueous solution. Alternatively, the components of the kit may be provided in a lyophilized form that is suitable for reconstitution with an aqueous or non-aqueous liquid. Such a liquid may be provided in a separate container.

The kit can further comprise a label or package insert associated with the container(s) providing information regarding the use of the kit, such as for regenerating tissues, promoting the healing of wounds, or promoting the migration or proliferation of fibroblast cells.

IV. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutscher, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding. No unnecessary limitations are to be understood therefrom. The invention is not limited to the exact details shown and described. Variations obvious to one skilled in the art are included in the invention defined by the claims. Any section headings used herein are for organizational purposes and are not to be construed as limiting the subject matter described.

V. Sequence Summary and Sequences

The following Table 1 provides a summary of the included sequences.

TABLE 1

Nucleotide and amino acid sequences disclosed herein.

| SEQ ID NO. | Description |
| --- | --- |
| 1 | Homo sapiens NELL1 isoform 1 transcript variant (nucleotide) |
| 2 | Homo sapiens NELL1 isoform 1 (amino acid) |
| 3 | Homo sapiens NELL1 isoform 2 transcript variant (nucleotide) |
| 4 | Homo sapiens NELL1 isoform 2 (amino acid) |
| 5 | Equus caballus NELL1 isoform 1 (nucleotide) |
| 6 | Equus caballus NELL1 isoform 1 (amino acid) |
| 7 | Equus caballus NELL1 isoform 2 (nucleotide) |
| 8 | Equus caballus NELL1 isoform 2 (amino acid) |
| 9 | Mus musculus NELL1 (nucleotide) |
| 10 | Mus musculus NELL1 (amino acid) |
| 11 | Rattus norvegicus NELL1 (nucleotide) |
| 12 | Rattus norvegicus NELL1 (amino acid) |
| 13 | Felis catus NELL1 isoform 1 (amino acid) |
| 14 | Felis catus NELL1 isoform 2 (amino acid) |
| 15 | Canis lupis familiaris NELL1 (amino acid) |
| 16 | Ovis aries NELL1 (amino acid) |
| 17 | Homo sapiens NELL1 fragment (amino acid) |
| 18 | Equus caballus NELL1 fragment (amino acid) |
| 19 | Bos taurus NELL1 (amino acid) |

```
Homo sapiens NELL1 isoform 1 nucleotide sequence (SEQ ID NO: 1) and translated
amino acid sequence (SEQ ID NO: 2)
atatgcgagc gcagcacccg gcgctgccga gccacctccc ccgccgcccg ctagcaagtt       60
tggcggctcc aagccaggcg cgcctcagga tccaggctca tttgcttcca cctagcttcg      120
gtgcccctg ctaggcgggg accctcgaga gcg atg ccg atg gat ttg att tta       174
                                  Met Pro Met Asp Leu Ile Leu gtt gtg tgg ttc tgt gtg tgc act gcc agg aca gtg gtg ggc ttt ggg       222
Val Val Trp Phe Cys Val Cys Thr Ala Arg Thr Val Val Gly Phe Gly atg gac cct gac ctt cag atg gat atc gtc acc gag ctt gac ctt gtg       270
Met Asp Pro Asp Leu Gln Met Asp Ile Val Thr Glu Leu Asp Leu Val aac acc acc ctt gga gtt gct cag gtg tct gga atg cac aat gcc agc       318
Asn Thr Thr Leu Gly Val Ala Gln Val Ser Gly Met His Asn Ala Ser aaa gca ttt tta ttt caa gac ata gaa aga gag atc cat gca gct cct       366
Lys Ala Phe Leu Phe Gln Asp Ile Glu Arg Glu Ile His Ala Ala Pro cat gtg agt gag aaa tta att cag ctg ttc cgg aac aag agt gaa ttc       414
His Val Ser Glu Lys Leu Ile Gln Leu Phe Arg Asn Lys Ser Glu Phe
```

```
acc att ttg gcc act gta cag cag aag cca tcc act tca gga gtg ata      462
Thr Ile Leu Ala Thr Val Gln Gln Lys Pro Ser Thr Ser Gly Val Ile ctg tcc att cga gaa ctg gag cac agc tat ttt gaa ctg gag agc agt      510
Leu Ser Ile Arg Glu Leu Glu His Ser Tyr Phe Glu Leu Glu Ser Ser ggc ctg agg gat gag att cgg tat cac tac ata cac aat ggg aag cca      558
Gly Leu Arg Asp Glu Ile Arg Tyr His Tyr Ile His Asn Gly Lys Pro agg aca gag gca ctt cct tac cgc atg gca gat gga caa tgg cac aag      606
Arg Thr Glu Ala Leu Pro Tyr Arg Met Ala Asp Gly Gln Trp His Lys gtt gca ctg tca gtt agc gcc tct cat ctc ctg ctc cat gtc gac tgt      654
Val Ala Leu Ser Val Ser Ala Ser His Leu Leu Leu His Val Asp Cys aac agg att tat gag cgt gtg ata gac cct cca gat acc aac ctt ccc      702
Asn Arg Ile Tyr Glu Arg Val Ile Asp Pro Pro Asp Thr Asn Leu Pro cca gga atc aat tta tgg ctt ggc cag cgc aac caa aag cat ggc tta      750
Pro Gly Ile Asn Leu Trp Leu Gly Gln Arg Asn Gln Lys His Gly Leu ttc aaa ggg atc atc caa gat ggg aag atc atc ttt atg ccg aat gga      798
Phe Lys Gly Ile Ile Gln Asp Gly Lys Ile Ile Phe Met Pro Asn Gly tat ata aca cag tgt cca aat cta aat cac act tgc cca acc tgc agt      846
Tyr Ile Thr Gln Cys Pro Asn Leu Asn His Thr Cys Pro Thr Cys Ser gat ttc tta agc ctg gtg caa gga ata atg gat tta caa gag ctt ttg      894
Asp Phe Leu Ser Leu Val Gln Gly Ile Met Asp Leu Gln Glu Leu Leu gcc aag atg act gca aaa cta aat tat gca gag aca aga ctt agt caa      942
Ala Lys Met Thr Ala Lys Leu Asn Tyr Ala Glu Thr Arg Leu Ser Gln ttg gaa aac tgt cat tgt gag aag act tgt caa gtg agt gga ctg ctc      990
Leu Glu Asn Cys His Cys Glu Lys Thr Cys Gln Val Ser Gly Leu Leu tat cga gat caa gac tct tgg gta gat ggt gac cat tgc agg aac tgc     1038
Tyr Arg Asp Gln Asp Ser Trp Val Asp Gly Asp His Cys Arg Asn Cys act tgc aaa agt ggt gcc gtg gaa tgc cga agg atg tcc tgt ccc cct     1086
Thr Cys Lys Ser Gly Ala Val Glu Cys Arg Arg Met Ser Cys Pro Pro ctc aat tgc tcc cca gac tcc ctc cca gtg cac att gct ggc cag tgc     1134
Leu Asn Cys Ser Pro Asp Ser Leu Pro Val His Ile Ala Gly Gln Cys tgt aag gtc tgc cga cca aaa tgt atc tat gga gga aaa gtt ctt gca     1182
Cys Lys Val Cys Arg Pro Lys Cys Ile Tyr Gly Gly Lys Val Leu Ala gaa ggc cag cgg att tta acc aag agc tgt cgg gaa tgc cga ggt gga     1230
Glu Gly Gln Arg Ile Leu Thr Lys Ser Cys Arg Glu Cys Arg Gly Gly gtt tta gta aaa att aca gaa atg tgt cct cct ttg aac tgc tca gaa     1278
Val Leu Val Lys Ile Thr Glu Met Cys Pro Pro Leu Asn Cys Ser Glu aag gat cac att ctt cct gag aat cag tgc tgc cgt gtc tgt aga ggt     1326
Lys Asp His Ile Leu Pro Glu Asn Gln Cys Cys Arg Val Cys Arg Gly cat aac ttt tgt gca gaa gga cct aaa tgt ggt gaa aac tca gag tgc     1374
His Asn Phe Cys Ala Glu Gly Pro Lys Cys Gly Glu Asn Ser Glu Cys aaa aac tgg aat aca aaa gct act tgt gag tgc aag agt ggt tac atc     1422
Lys Asn Trp Asn Thr Lys Ala Thr Cys Glu Cys Lys Ser Gly Tyr Ile tct gtc cag gga gac tct gcc tac tgt gaa gat att gat gag tgt gca     1470
Ser Val Gln Gly Asp Ser Ala Tyr Cys Glu Asp Ile Asp Glu Cys Ala gct aag atg cat tac tgt cat gcc aat act gtg tgt gtc aac ctt cct     1518
Ala Lys Met His Tyr Cys His Ala Asn Thr Val Cys Val Asn Leu Pro ggg tta tat cgc tgt gac tgt gtc cca gga tac att cgt gtg gat gac     1566
Gly Leu Tyr Arg Cys Asp Cys Val Pro Gly Tyr Ile Arg Val Asp Asp ttc tct tgt aca gaa cac gat gaa tgt ggc agc ggc cag cac aac tgt     1614
Phe Ser Cys Thr Glu His Asp Glu Cys Gly Ser Gly Gln His Asn Cys gat gag aat gcc atc tgc acc aac act gtc cag gga cac agc tgc acc     1662
Asp Glu Asn Ala Ile Cys Thr Asn Thr Val Gln Gly His Ser Cys Thr
```

|     |     |
| --- | --- |
| tgc aaa ccg ggc tac gtg ggg aac ggg acc atc tgc aga gct ttc tgt<br>Cys Lys Pro Gly Tyr Val Gly Asn Gly Thr Ile Cys Arg Ala Phe Cys | 1710 |
| gaa gag ggc tgc aga tac ggt gga acg tgt gtg gct ccc aac aaa tgt<br>Glu Glu Gly Cys Arg Tyr Gly Gly Thr Cys Val Ala Pro Asn Lys Cys | 1758 |
| gtc tgt cca tct gga ttc aca gga agc cac tgc gag aaa gat att gat<br>Val Cys Pro Ser Gly Phe Thr Gly Ser His Cys Glu Lys Asp Ile Asp | 1806 |
| gaa tgt tca gag gga atc att gag tgc cac aac cat tcc cgc tgc gtt<br>Glu Cys Ser Glu Gly Ile Ile Glu Cys His Asn His Ser Arg Cys Val | 1854 |
| aac ctg cca ggg tgg tac cac tgt gag tgc aga agc ggt ttc cat gac<br>Asn Leu Pro Gly Trp Tyr His Cys Glu Cys Arg Ser Gly Phe His Asp | 1902 |
| gat ggg acc tat tca ctg tcc ggg gag tcc tgt att gac att gat gaa<br>Asp Gly Thr Tyr Ser Leu Ser Gly Glu Ser Cys Ile Asp Ile Asp Glu | 1950 |
| tgt gcc tta aga act cac acc tgt tgg aac gat tct gcc tgc atc aac<br>Cys Ala Leu Arg Thr His Thr Cys Trp Asn Asp Ser Ala Cys Ile Asn | 1998 |
| ctg gca ggg ggc ttt gac tgt ctc tgc ccc tct ggg ccc tcc tgc tct<br>Leu Ala Gly Gly Phe Asp Cys Leu Cys Pro Ser Gly Pro Ser Cys Ser | 2046 |
| ggt gac tgt cct cat gaa ggg ggg ctg aag cac aat ggc cag gtg tgg<br>Gly Asp Cys Pro His Glu Gly Gly Leu Lys His Asn Gly Gln Val Trp | 2094 |
| acc ttg aaa gaa gac agg tgt tct gtc tgc tcc tgc aag gat ggc aag<br>Thr Leu Lys Glu Asp Arg Cys Ser Val Cys Ser Cys Lys Asp Gly Lys | 2142 |
| ata ttc tgc cga cgg aca gct tgt gat tgc cag aat cca agt gct gac<br>Ile Phe Cys Arg Arg Thr Ala Cys Asp Cys Gln Asn Pro Ser Ala Asp | 2190 |
| cta ttc tgt tgc cca gaa tgt gac acc aga gtc aca agt caa tgt tta<br>Leu Phe Cys Cys Pro Glu Cys Asp Thr Arg Val Thr Ser Gln Cys Leu | 2238 |
| gac caa aat ggt cac aag ctg tat cga agt gga gac aat tgg acc cat<br>Asp Gln Asn Gly His Lys Leu Tyr Arg Ser Gly Asp Asn Trp Thr His | 2286 |
| agc tgt cag cag tgt cgg tgt ctg gaa gga gag gta gat tgc tgg cca<br>Ser Cys Gln Gln Cys Arg Cys Leu Glu Gly Glu Val Asp Cys Trp Pro | 2334 |
| ctc act tgc ccc aac ttg agc tgt gag tat aca gct atc tta gaa ggg<br>Leu Thr Cys Pro Asn Leu Ser Cys Glu Tyr Thr Ala Ile Leu Glu Gly | 2382 |
| gaa tgt tgt ccc cgc tgt gtc agt gac ccc tgc cta gct gat aac atc<br>Glu Cys Cys Pro Arg Cys Val Ser Asp Pro Cys Leu Ala Asp Asn Ile | 2430 |
| acc tat gac atc aga aaa act tgc ctg gac agc tat ggt gtt tca cgg<br>Thr Tyr Asp Ile Arg Lys Thr Cys Leu Asp Ser Tyr Gly Val Ser Arg | 2478 |
| ctt agt ggc tca gtg tgg acg atg gct gga tct ccc tgc aca acc tgt<br>Leu Ser Gly Ser Val Trp Thr Met Ala Gly Ser Pro Cys Thr Thr Cys | 2526 |
| aaa tgc aag aat gga aga gtc tgt tgt tct gtg gat ttt gag tgt ctt<br>Lys Cys Lys Asn Gly Arg Val Cys Cys Ser Val Asp Phe Glu Cys Leu | 2574 |
| caa aat aat tga agtatttaca gtggactcaa cgcagaagaa tggacgaaat<br>Gln Asn Asn * | 2626 |
| gaccatccaa cgtgattaag gataggaatc ggtagtttgg ttttttttgtt tgttttgttt | 2686 |
| ttttaaccac agataattgc caaagtttcc acctgaggac ggtgtttgga ggttgccttt | 2746 |
| tggacctacc actttgctca ttcttgctaa cctagtctag gtgacctaca gtgccgtgca | 2806 |
| tttaagtcaa tggttgttaa agaagtttc ccgtgttgta aatcatgttt cccttatcag | 2866 |
| atcatttgca aatacattta aatgatctca tggtaaatgt tgatgtattt tttggtttat | 2926 |
| tttgtgtact aacataatag agagagactc agctccttt atttattttg ttgatttatg | 2986 |
| gatcaaattc taaaataaag ttgcctgttg tgacttttgt cccatctact gcatacttag | 3046 |
| tgctgagatc cctgtaaaat gttttgatga aaatatgtat gtagagtcca gtcgcattat | 3106 |
| acatacattt catagtgctg aaccttctta aatgcctact cattcagctt aaacaggctg | 3166 |

-continued

| | |
|---|---|
| aagccaagta tgacaaagag gggaagggcc aaaaacataa tcaaagaata attttaaaga | 3226 |
| gaattcttgt ctctcttgca aaaaaaaaa | 3255 |

*Homo sapiens* NELL1 isoform 1 amino acid sequence (SEQ ID NO: 2)
Met Pro Met Asp Leu Ile Leu Val Val Trp Phe Cys Val Cys Thr Ala
Arg Thr Val Val Gly Phe Gly Met Asp Pro Asp Leu Gln Met Asp Ile
Val Thr Glu Leu Asp Leu Val Asn Thr Thr Leu Gly Val Ala Gln Val
Ser Gly Met His Asn Ala Ser Lys Ala Phe Leu Phe Gln Asp Ile Glu
Arg Glu Ile His Ala Ala Pro His Val Ser Glu Lys Leu Ile Gln Leu
Phe Arg Asn Lys Ser Glu Phe Thr Ile Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Leu Arg Glu Ile Arg Tyr His
Tyr Ile His Asn Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Val Asp Cys Asn Arg Ile Tyr Glu Arg Val Ile Asp
Pro Pro Asp Thr Asn Leu Pro Pro Gly Ile Asn Leu Trp Leu Gly Gln
Arg Asn Gln Lys His Gly Leu Phe Lys Gly Ile Ile Gln Asp Gly Lys
Ile Ile Phe Met Pro Asn Gly Tyr Ile Thr Gln Cys Pro Asn Leu Asn
His Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Ser Gln Leu Glu Asn Cys His Cys Glu Lys Thr
Cys Gln Val Ser Gly Leu Leu Tyr Arg Asp Gln Asp Ser Trp Val Asp
Gly Asp His Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ala Gly Gln Cys Cys Lys Val Cys Arg Pro Lys Cys Ile
Tyr Gly Gly Lys Val Leu Ala Glu Gly Gln Arg Ile Leu Thr Lys Ser
Cys Arg Glu Cys Arg Gly Gly Val Leu Val Lys Ile Thr Glu Met Cys
Pro Pro Leu Asn Cys Ser Glu Lys Asp His Ile Leu Pro Glu Asn Gln
Cys Cys Arg Val Cys Arg Gly His Asn Phe Cys Ala Glu Gly Pro Lys
Cys Gly Glu Asn Ser Glu Cys Lys Asn Trp Asn Thr Lys Ala Thr Cys
Glu Cys Lys Ser Gly Tyr Ile Ser Val Gln Gly Asp Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr
Val Gln Gly His Ser Cys Thr Cys Lys Pro Gly Tyr Val Gly Asn Gly
Thr Ile Cys Arg Ala Phe Cys Glu Glu Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ser Glu Gly Ile Ile Glu Cys
His Asn His Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Gly Phe Asp Cys Leu Cys
Pro Ser Gly Pro Ser Cys Ser Gly Asp Cys Pro His Glu Gly Gly Leu
Lys His Asn Gly Gln Val Trp Thr Leu Lys Glu Asp Arg Cys Ser Val
Cys Ser Cys Lys Asp Gly Lys Ile Phe Cys Arg Arg Thr Ala Cys Asp
Cys Gln Asn Pro Ser Ala Asp Leu Phe Cys Cys Pro Glu Cys Asp Thr
Arg Val Thr Ser Gln Cys Leu Asp Gln Asn Gly His Lys Leu Tyr Arg
Ser Gly Asp Asn Trp Thr His Ser Cys Gln Gln Cys Arg Cys Leu Glu
Gly Glu Val Asp Cys Trp Pro Leu Thr Cys Pro Asn Leu Ser Cys Glu
Tyr Thr Ala Ile Leu Glu Gly Glu Cys Cys Pro Arg Cys Val Ser Asp
Pro Cys Leu Ala Asp Asn Ile Thr Tyr Asp Ile Arg Lys Thr Cys Leu
Asp Ser Tyr Gly Val Ser Arg Leu Ser Gly Ser Val Trp Thr Met Ala
Gly Ser Pro Cys Thr Thr Cys Lys Cys Lys Asn Gly Arg Val Cys Cys
Ser Val Asp Phe Glu Cys Leu Gln Asn Asn

*Homo sapiens* NELL1 isoform 2 nucleotide sequence (SEQ ID NO: 3) and translated
amino acid sequence (SEQ ID NO: 4)

| | |
|---|---|
| atatgcgagc gcagcacccg gcgctgccga gccacctccc ccgccgcccg ctagcaagtt | 60 |
| tgcggctcc aagccaggcg cgcctcagga tccaggctca tttgcttcca cctagcttcg | 120 |
| gtgccccctg ctaggcgggg accctcgaga gcg atg ccg atg gat ttg att tta<br>                                         Met Pro Met Asp Leu Ile Leu | 174 |
| gtt gtg tgg ttc tgt gtg tgc act gcc agg aca gtg gtg ggc ttt ggg<br>Val Val Trp Phe Cys Val Cys Thr Ala Arg Thr Val Val Gly Phe Gly | 222 |
| atg gac cct gac ctt cag atg gat atc gtc acc gag ctt gac ctt gtg<br>Met Asp Pro Asp Leu Gln Met Asp Ile Val Thr Glu Leu Asp Leu Val | 270 |
| aac acc acc ctt gga gtt gct cag gtg tct gga atg cac aat gcc agc<br>Asn Thr Thr Leu Gly Val Ala Gln Val Ser Gly Met His Asn Ala Ser | 318 |
| aaa gca ttt tta ttt caa gac ata gaa aga gag atc cat gca gct cct<br>Lys Ala Phe Leu Phe Gln Asp Ile Glu Arg Glu Ile His Ala Ala Pro | 366 |
| cat gtg agt gag aaa tta att cag ctg ttc cgg aac aag agt gaa ttc<br>His Val Ser Glu Lys Leu Ile Gln Leu Phe Arg Asn Lys Ser Glu Phe | 414 |

-continued

| | |
|---|---|
| acc att ttg gcc act gta cag cag aag cca tcc act tca gga gtg ata<br>Thr Ile Leu Ala Thr Val Gln Gln Lys Pro Ser Thr Ser Gly Val Ile | 462 |
| ctg tcc att cga gaa ctg gag cac agc tat ttt gaa ctg gag agc agt<br>Leu Ser Ile Arg Glu Leu Glu His Ser Tyr Phe Glu Leu Glu Ser Ser | 510 |
| ggc ctg agg gat gag att cgg tat cac tac ata cac aat ggg aag cca<br>Gly Leu Arg Asp Glu Ile Arg Tyr His Tyr Ile His Asn Gly Lys Pro | 558 |
| agg aca gag gca ctt cct tac cgc atg gca gat gga caa tgg cac aag<br>Arg Thr Glu Ala Leu Pro Tyr Arg Met Ala Asp Gly Gln Trp His Lys | 606 |
| gtt gca ctg tca gtt agc gcc tct cat ctc ctg ctc cat gtc gac tgt<br>Val Ala Leu Ser Val Ser Ala Ser His Leu Leu Leu His Val Asp Cys | 654 |
| aac agg att tat gag cgt gtg ata gac cct cca gat acc aac ctt ccc<br>Asn Arg Ile Tyr Glu Arg Val Ile Asp Pro Pro Asp Thr Asn Leu Pro | 702 |
| cca gga atc aat tta tgg ctt ggc cag cgc aac caa aag cat ggc tta<br>Pro Gly Ile Asn Leu Trp Leu Gly Gln Arg Asn Gln Lys His Gly Leu | 750 |
| ttc aaa ggg atc atc caa gat ggg aag atc atc ttt atg ccg aat gga<br>Phe Lys Gly Ile Ile Gln Asp Gly Lys Ile Ile Phe Met Pro Asn Gly | 798 |
| tat ata aca cag tgt cca aat cta aat cac act tgc cca acc tgc agt<br>Tyr Ile Thr Gln Cys Pro Asn Leu Asn His Thr Cys Pro Thr Cys Ser | 846 |
| gat ttc tta agc ctg gtg caa gga ata atg gat tta caa gag ctt ttg<br>Asp Phe Leu Ser Leu Val Gln Gly Ile Met Asp Leu Gln Glu Leu Leu | 894 |
| gcc aag atg act gca aaa cta aat tat gca gag aca aga ctt agt caa<br>Ala Lys Met Thr Ala Lys Leu Asn Tyr Ala Glu Thr Arg Leu Ser Gln | 942 |
| ttg gaa aac tgt cat tgt gag aag act tgt caa gtg agt gga ctg ctc<br>Leu Glu Asn Cys His Cys Glu Lys Thr Cys Gln Val Ser Gly Leu Leu | 990 |
| tat cga gat caa gac tct tgg gta gat ggt gac cat tgc agg aac tgc<br>Tyr Arg Asp Gln Asp Ser Trp Val Asp Gly Asp His Cys Arg Asn Cys | 1038 |
| act tgc aaa agt ggt gcc gtg gaa tgc cga agg atg tcc tgt ccc cct<br>Thr Cys Lys Ser Gly Ala Val Glu Cys Arg Arg Met Ser Cys Pro Pro | 1086 |
| ctc aat tgc tcc cca gac tcc ctc cca gtg cac att gct ggc cag tgc<br>Leu Asn Cys Ser Pro Asp Ser Leu Pro Val His Ile Ala Gly Gln Cys | 1134 |
| tgt aag gtc tgc cga cca aaa tgt atc tat gga gga aaa gtt ctt gca<br>Cys Lys Val Cys Arg Pro Lys Cys Ile Tyr Gly Gly Lys Val Leu Ala | 1182 |
| gaa ggc cag cgg att tta acc aag agc tgt cgg gaa tgc cga ggt gga<br>Glu Gly Gln Arg Ile Leu Thr Lys Ser Cys Arg Glu Cys Arg Gly Gly | 1230 |
| gtt tta gta aaa att aca gaa atg tgt cct cct ttg aac tgc tca gaa<br>Val Leu Val Lys Ile Thr Glu Met Cys Pro Pro Leu Asn Cys Ser Glu | 1278 |
| aag gat cac att ctt cct gag aat cag tgc tgc cgt gtc tgt aga ggt<br>Lys Asp His Ile Leu Pro Glu Asn Gln Cys Cys Arg Val Cys Arg Gly | 1326 |
| cat aac ttt tgt gca gaa gga cct aaa tgt ggt gaa aac tca gag tgc<br>His Asn Phe Cys Ala Glu Gly Pro Lys Cys Gly Glu Asn Ser Glu Cys | 1374 |
| aaa aac tgg aat aca aaa gct act tgt gag tgc aag agt ggt tac atc<br>Lys Asn Trp Asn Thr Lys Ala Thr Cys Glu Cys Lys Ser Gly Tyr Ile | 1422 |
| tct gtc cag gga gac tct gcc tac tgt gaa gat att gat gag tgt gca<br>Ser Val Gln Gly Asp Ser Ala Tyr Cys Glu Asp Ile Asp Glu Cys Ala | 1470 |
| gct aag atg cat tac tgt cat gcc aat act gtg tgt gtc aac ctt cct<br>Ala Lys Met His Tyr Cys His Ala Asn Thr Val Cys Val Asn Leu Pro | 1518 |
| ggg tta tat cgc tgt gac tgt gtc cca gga tac att cgt gtg gat gac<br>Gly Leu Tyr Arg Cys Asp Cys Val Pro Gly Tyr Ile Arg Val Asp Asp | 1566 |
| ttc tct tgt aca gaa cac gat gaa tgt ggc agc ggc cag cac aac tgt<br>Phe Ser Cys Thr Glu His Asp Glu Cys Gly Ser Gly Gln His Asn Cys | 1614 |
| gat gag aat gcc atc tgc acc aac act gtc cag gga cac agc tgc acc<br>Asp Glu Asn Ala Ile Cys Thr Asn Thr Val Gln Gly His Ser Cys Thr | 1662 |

| | |
|---|---|
| tgc aaa ccg ggc tac gtg ggg aac ggg acc atc tgc aga gct ttc tgt<br>Cys Lys Pro Gly Tyr Val Gly Asn Gly Thr Ile Cys Arg Ala Phe Cys | 1710 |
| gaa gag ggc tgc aga tac ggt gga acg tgt gtg gct ccc aac aaa tgt<br>Glu Glu Gly Cys Arg Tyr Gly Gly Thr Cys Val Ala Pro Asn Lys Cys | 1758 |
| gtc tgt cca tct gga ttc aca gga agc cac tgc gag aaa gac att gat<br>Val Cys Pro Ser Gly Phe Thr Gly Ser His Cys Glu Lys Asp Ile Asp | 1806 |
| gaa tgt gcc tta aga act cac acc tgt tgg aac gat tct gcc tgc atc<br>Glu Cys Ala Leu Arg Thr His Thr Cys Trp Asn Asp Ser Ala Cys Ile | 1854 |
| aac ctg gca ggg ggc ttt gac tgt cto tgc ccc tct ggg ccc tcc tgc<br>Asn Leu Ala Gly Gly Phe Asp Cys Leu Cys Pro Ser Gly Pro Ser Cys | 1902 |
| tct ggt gac tgt cct cat gaa ggg ggg ctg aag cac aat ggc cag gtg<br>Ser Gly Asp Cys Pro His Glu Gly Gly Leu Lys His Asn Gly Gln Val | 1950 |
| tgg acc ttg aaa gaa gac agg tgt tct gtc tgc tcc tgc aag gat ggc<br>Trp Thr Leu Lys Glu Asp Arg Cys Ser Val Cys Ser Cys Lys Asp Gly | 1998 |
| aag ata ttc tgc cga cgg aca gct tgt gat tgc cag aat cca agt gct<br>Lys Ile Phe Cys Arg Arg Thr Ala Cys Asp Cys Gln Asn Pro Ser Ala | 2046 |
| gac cta ttc tgt tgc cca gaa tgt gac acc aga gtc aca agt caa tgt<br>Asp Leu Phe Cys Cys Pro Glu Cys Asp Thr Arg Val Thr Ser Gln Cys | 2094 |
| tta gac caa aat ggt cac aag ctg tat cga agt gga gac aat tgg acc<br>Leu Asp Gln Asn Gly His Lys Leu Tyr Arg Ser Gly Asp Asn Trp Thr | 2142 |
| cat agc tgt cag cag tgt cgg tgt ctg gaa gga gag gta gat tgc tgg<br>His Ser Cys Gln Gln Cys Arg Cys Leu Glu Gly Glu Val Asp Cys Trp | 2190 |
| cca cto act tgc ccc aac ttg agc tgt gag tat aca gct atc tta gaa<br>Pro Leu Thr Cys Pro Asn Leu Ser Cys Glu Tyr Thr Ala Ile Leu Glu | 2238 |
| ggg gaa tgt tgt ccc cgc tgt gtc agt gac ccc tgc cta gct gat aac<br>Gly Glu Cys Cys Pro Arg Cys Val Ser Asp Pro Cys Leu Ala Asp Asn | 2286 |
| atc acc tat gac atc aga aaa act tgc ctg gac agc tat ggt gtt tca<br>Ile Thr Tyr Asp Ile Arg Lys Thr Cys Leu Asp Ser Tyr Gly Val Ser | 2334 |
| cgg ctt agt ggc tca gtg tgg acg atg gct gga tct ccc tgc aca acc<br>Arg Leu Ser Gly Ser Val Trp Thr Met Ala Gly Ser Pro Cys Thr Thr | 2382 |
| tgt aaa tgc aag aat gga aga gtc tgt tgt tct gtg gat ttt gag tgt<br>Cys Lys Cys Lys Asn Gly Arg Val Cys Cys Ser Val Asp Phe Glu Cys | 2430 |
| ctt caa aat aat tga agtatttaca gtggactcaa cgcagaagaa tggacgaaat<br>Leu Gln Asn Asn * | 2485 |
| gaccatccaa cgtgattaag gataggaatc ggtagtttgg ttttttttgtt tgttttgttt | 2545 |
| ttttaaccac agataattgc caaagtttcc acctgaggac ggtgtttgga ggttgccttt | 2605 |
| tggacctacc actttgctca ttcttgctaa cctagtctag gtgacctaca gtgccgtgca | 2665 |
| tttaagtcaa tggttgttaa aagaagtttc ccgtgttgta aatcatgttt cccttatcag | 2725 |
| atcatttgca aatacattta aatgatctca tggtaaatgt tgatgtattt tttggtttat | 2785 |
| tttgtgtact aacataatag agagagactc agctcctttt atttattttg ttgatttatg | 2845 |
| gatcaaattc taaaataaag ttgcctgttg tgacttttgt cccatctact gcatacttag | 2905 |
| tgctgagatc cctgtaaaat gttttgatga aaatatgtat gtagagtcca gtcgcattat | 2965 |
| acatacattt catagtgctg aaccttctta aatgcctact cattcagctt aaacaggctg | 3025 |
| aagccaagta tgacaaagag gggaagggcc aaaaacataa tcaaagaata atttttaaaga | 3085 |
| gaattcttgt ctctcttgca aaaaaaaaa | 3114 |

*Homo sapiens* NELL1 isoform 2 amino acid sequence (SEQ ID NO: 4)
Met Pro Met Asp Leu Ile Leu Val Val Trp Phe Cys Val Cys Thr Ala
Arg Thr Val Val Gly Phe Gly Met Asp Pro Asp Leu Gln Met Asp Ile
Val Thr Glu Leu Asp Leu Val Asn Thr Thr Leu Gly Val Ala Gln Val
Ser Gly Met His Asn Ala Ser Lys Ala Phe Leu Phe Gln Asp Ile Glu
Arg Glu Ile His Ala Ala Pro His Val Ser Glu Lys Leu Ile Gln Leu

```
Phe Arg Asn Lys Ser Glu Phe Thr Ile Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Leu Arg Asp Glu Ile Arg Tyr His
Tyr Ile His Asn Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Val Asp Cys Asn Arg Ile Tyr Glu Arg Val Ile Asp
Pro Pro Asp Thr Asn Leu Pro Pro Gly Ile Asn Leu Trp Leu Gly Gln
Arg Asn Gln Lys His Gly Leu Phe Lys Gly Ile Ile Gln Asp Gly Lys
Ile Ile Phe Met Pro Asn Gly Tyr Ile Thr Gln Cys Pro Asn Leu Asn
His Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Ser Gln Leu Glu Asn Cys His Cys Glu Lys Thr
Cys Gln Val Ser Gly Leu Leu Tyr Arg Asp Gln Asp Ser Trp Val Asp
Gly Asp His Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ala Gly Gln Cys Cys Lys Val Cys Arg Pro Lys Cys Ile
Tyr Gly Gly Lys Val Leu Ala Glu Gly Gln Arg Ile Leu Thr Lys Ser
Cys Arg Glu Cys Arg Gly Gly Val Leu Val Lys Ile Thr Glu Met Cys
Pro Pro Leu Asn Cys Ser Glu Lys Asp His Ile Leu Pro Glu Asn Gln
Cys Cys Arg Val Cys Arg Gly His Asn Phe Cys Ala Glu Gly Pro Lys
Cys Gly Glu Asn Ser Glu Cys Lys Asn Trp Asn Thr Lys Ala Thr Cys
Glu Cys Lys Ser Gly Tyr Ile Ser Val Gln Asp Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr
Val Gln Gly His Ser Cys Thr Cys Lys Pro Gly Tyr Val Gly Asn Gly
Thr Ile Cys Arg Ala Phe Cys Glu Glu Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ala Leu Arg Thr His Thr Cys
Trp Asn Asp Ser Ala Cys Ile Asn Leu Ala Gly Gly Phe Asp Cys Leu
Cys Pro Ser Gly Pro Ser Cys Ser Gly Asp Cys Pro His Glu Gly Gly
Leu Lys His Asn Gly Gln Val Trp Thr Leu Lys Glu Asp Arg Cys Ser
Val Cys Ser Cys Lys Asp Gly Lys Ile Phe Cys Arg Arg Thr Ala Cys
Asp Cys Gln Asn Pro Ser Ala Asp Leu Phe Cys Cys Pro Glu Cys Asp
Thr Arg Val Thr Ser Gln Cys Leu Asp Gln Asn Gly His Lys Leu Tyr
Arg Ser Gly Asp Asn Trp Thr His Ser Cys Gln Gln Cys Arg Cys Leu
Glu Gly Glu Val Asp Cys Trp Pro Leu Thr Cys Pro Asn Leu Ser Cys
Glu Tyr Thr Ala Ile Leu Glu Gly Glu Cys Cys Pro Arg Cys Val Ser
Asp Pro Cys Leu Ala Asp Asn Ile Thr Tyr Asp Ile Arg Lys Thr Cys
Leu Asp Ser Tyr Gly Val Ser Arg Leu Ser Gly Ser Val Trp Thr Met
Ala Gly Ser Pro Cys Thr Thr Cys Lys Cys Lys Asn Gly Arg Val Cys
Cys Ser Val Asp Phe Glu Cys Leu Gln Asn Asn
```

*Equus caballus* NELL1 isoform 1 nucleotide sequence (SEQ ID NO: 5) and translated amino acid sequence (SEQ ID NO: 6)

```
atg ggc ttt ggg atg gac ccc gac ctt caa atg gat att atc acc gag       48
Met Gly Phe Gly Met Asp Pro Asp Leu Gln Met Asp Ile Ile Thr Glu ctc gac ctc gtg aac acc acc ctt gga gtc act cag gtg tcc gga ctg       96
Leu Asp Leu Val Asn Thr Thr Leu Gly Val Thr Gln Val Ser Gly Leu cac aat gcc agc aaa gca ttt tta ttt caa gat gta gag aga gag atc      144
His Asn Ala Ser Lys Ala Phe Leu Phe Gln Asp Val Glu Arg Glu Ile cat gca gcc cca cac gtg agt gag aaa tta att cag ctg ttc cgg aat      192
His Ala Ala Pro His Val Ser Glu Lys Leu Ile Gln Leu Phe Arg Asn aag agt gaa ttc acc ttt ttg gcc act gtg cag cag aag ccg tca act      240
Lys Ser Glu Phe Thr Phe Leu Ala Thr Val Gln Gln Lys Pro Ser Thr tca gga gtg ata ctg tcc att cga gaa ctg gaa aac agt tat ttt gaa      288
Ser Gly Val Ile Leu Ser Ile Arg Glu Leu Glu Asn Ser Tyr Phe Glu ctg gag agc agt ggc ctg aga gat gag att cga tat cac tac aca cac      336
Leu Glu Ser Ser Gly Leu Arg Asp Glu Ile Arg Tyr His Tyr Thr His aag ggg aag ccc agg aca gag gca ctt ccc tac cgg atg gcg gac gga      384
Lys Gly Lys Pro Arg Thr Glu Ala Leu Pro Tyr Arg Met Ala Asp Gly cgg tgg cac aag gtg gcg ctg tca gtt agc gcc tct cat ctc ctg ctc      432
Arg Trp His Lys Val Ala Leu Ser Val Ser Ala Ser His Leu Leu Leu cac atc gac tgc aac agg att tat gaa cgt gtg ata gac act cct gag      480
His Ile Asp Cys Asn Arg Ile Tyr Glu Arg Val Ile Asp Thr Pro Glu acc aac ctc ccc cca gga agc aat ttg tgg ctg ggt cag cga aac caa      528
Thr Asn Leu Pro Pro Gly Ser Asn Leu Trp Leu Gly Gln Arg Asn Gln
```

-continued

| | |
|---|---|
| aag cac ggc tta ttc aaa gga atc atc caa gat gga aaa atc atc ttc<br>Lys His Gly Leu Phe Lys Gly Ile Ile Gln Asp Gly Lys Ile Ile Phe | 576 |
| atg ccg aat gga tac ata aca cag tgt ccg aac ctg aat cgc act tgc<br>Met Pro Asn Gly Tyr Ile Thr Gln Cys Pro Asn Leu Asn Arg Thr Cys | 624 |
| cca acg tgc agt gat ttc tta agc ctg gtg caa gga atc atg gat tta<br>Pro Thr Cys Ser Asp Phe Leu Ser Leu Val Gln Gly Ile Met Asp Leu | 672 |
| caa gag ctt ctg gcc aag atg act gcg aaa cta aat tat gca gag aca<br>Gln Glu Leu Leu Ala Lys Met Thr Ala Lys Leu Asn Tyr Ala Glu Thr | 720 |
| cga ctt agt caa ttg gaa aac tgc cac tgc gag aag acc tgt caa gtg<br>Arg Leu Ser Gln Leu Glu Asn Cys His Cys Glu Lys Thr Cys Gln Val | 768 |
| agt gga ctg ctc tat aga gac cag gac tcc tgg gtt gat ggc gat cac<br>Ser Gly Leu Leu Tyr Arg Asp Gln Asp Ser Trp Val Asp Gly Asp His | 816 |
| tgt agg aac tgc acg tgc aaa agc ggc gct gtg aat tgt cgg agg atg<br>Cys Arg Asn Cys Thr Cys Lys Ser Gly Ala Val Glu Cys Arg Arg Met | 864 |
| tct tgt ccc cct ctc aat tgc tcc cca gac tcc ctc cct gtg cac gtt<br>Ser Cys Pro Pro Leu Asn Cys Ser Pro Asp Ser Leu Pro Val His Val | 912 |
| gcc ggc cag tgc tgt aag gtc tgc cga cca aaa tgt atc tac gga ggg<br>Ala Gly Gln Cys Cys Lys Val Cys Arg Pro Lys Cys Ile Tyr Gly Gly | 960 |
| aaa gtc ctt gca gaa ggc cag cgg att tta acc aag agc tgt cgg gaa<br>Lys Val Leu Ala Glu Gly Gln Arg Ile Leu Thr Lys Ser Cys Arg Glu | 1008 |
| tgc cga ggt gga gtt tta gtg aaa att aca gaa gcg tgc cct cct ttg<br>Cys Arg Gly Gly Val Leu Val Lys Ile Thr Glu Ala Cys Pro Pro Leu | 1056 |
| aac tgc tca gac aag gat cac att ctc cca gag aat cag tgc tgc agc<br>Asn Cys Ser Asp Lys Asp His Ile Leu Pro Glu Asn Gln Cys Cys Ser | 1104 |
| gtc tgc aga ggt cat aac ttt tgt gcg aaa gga cct aaa tgt ggt gaa<br>Val Cys Arg Gly His Asn Phe Cys Ala Lys Gly Pro Lys Cys Gly Glu | 1152 |
| aat tca gag tgc aaa aac tgg aat aca aaa gct act tgc gag tgc aag<br>Asn Ser Glu Cys Lys Asn Trp Asn Thr Lys Ala Thr Cys Glu Cys Lys | 1200 |
| aat ggt tat atc tct gtc cag ggg gac tcc gcc tac tgt gaa gat atc<br>Asn Gly Tyr Ile Ser Val Gln Gly Asp Ser Ala Tyr Cys Glu Asp Ile | 1248 |
| gat gag tgt gct gct aag atg cat tac tgt cgt gcc aat act gtg tgt<br>Asp Glu Cys Ala Ala Lys Met His Tyr Cys Arg Ala Asn Thr Val Cys | 1296 |
| gtc aac ctg cct ggg tta tat cgg tgt gac tgt gtc ccg gga tac att<br>Val Asn Leu Pro Gly Leu Tyr Arg Cys Asp Cys Val Pro Gly Tyr Ile | 1344 |
| cgc gtg gat gat ttc tct tgt aca gaa cat gac gaa tgt ggc agc ggg<br>Arg Val Asp Asp Phe Ser Cys Thr Glu His Asp Glu Cys Gly Ser Gly | 1392 |
| cag cac aac tgt gat gag aat gcc atc tgc acc aac act gtc cag gga<br>Gln His Asn Cys Asp Glu Asn Ala Ile Cys Thr Asn Thr Val Gln Gly | 1440 |
| cac agc tgc acc tgc aaa ccg ggc tac gtg ggg aat ggg acc agc tgc<br>His Ser Cys Thr Cys Lys Pro Gly Tyr Val Gly Asn Gly Thr Ser Cys | 1488 |
| aga gcg ttc tgc gaa gag ggc tgc aga tat ggc ggg aca tgc gtg gct<br>Arg Ala Phe Cys Glu Glu Gly Cys Arg Tyr Gly Gly Thr Cys Val Ala | 1536 |
| cct aac aaa tgt gtc tgt cct tct gga ttc aca gga agc cac tgt gag<br>Pro Asn Lys Cys Val Cys Pro Ser Gly Phe Thr Gly Ser His Cys Glu | 1584 |
| aaa gat att gat gaa tgt aca gag gga atc att gag tgc cac aac cat<br>Lys Asp Ile Asp Glu Cys Thr Glu Gly Ile Ile Glu Cys His Asn His | 1632 |
| tcc cgc tgc gtt aac ctg cca ggg tgg tac cac tgt gag tgc aga agc<br>Ser Arg Cys Val Asn Leu Pro Gly Trp Tyr His Cys Glu Cys Arg Ser | 1680 |
| ggt ttc cat gac gat ggg acc tat tca ctg tcc ggg gag tcc tgt att<br>Gly Phe His Asp Asp Gly Thr Tyr Ser Leu Ser Gly Glu Ser Cys Ile | 1728 |
| gac att gat gaa tgt gcc tta aga act cac acc tgt tgg aat gat tct<br>Asp Ile Asp Glu Cys Ala Leu Arg Thr His Thr Cys Trp Asn Asp Ser | 1776 |

-continued

| | |
|---|---|
| gcc tgc atc aac ttg gca ggg ggc ttc gac tgc ctg tgt ccc tca ggg<br>Ala Cys Ile Asn Leu Ala Gly Gly Phe Asp Cys Leu Cys Pro Ser Gly | 1824 |
| cca tcc tgc tct ggt gac tgc ccc cac gaa gga gga ctg aag cgc aac<br>Pro Ser Cys Ser Gly Asp Cys Pro His Glu Gly Gly Leu Lys Arg Asn | 1872 |
| ggg cag gtg tgg acc ctg aaa gaa gac agg tgt tct gtg tgt tcc tgc<br>Gly Gln Val Trp Thr Leu Lys Glu Asp Arg Cys Ser Val Cys Ser Cys | 1920 |
| aag gat ggg aag ata ttc tgc cga cgg aca gct tgt gat tgc cag aat<br>Lys Asp Gly Lys Ile Phe Cys Arg Arg Thr Ala Cys Asp Cys Gln Asn | 1968 |
| cca agc gtt gac ctt ttc tgt tgc cca gag tgt gac acc agg gtc aca<br>Pro Ser Val Asp Leu Phe Cys Cys Pro Glu Cys Asp Thr Arg Val Thr | 2016 |
| agt caa tgt tta gac caa aat gga cac aag ctc tat cga agt gga gac<br>Ser Gln Cys Leu Asp Gln Asn Gly His Lys Leu Tyr Arg Ser Gly Asp | 2064 |
| aat tgg act cac agc tgt cag cag tgc cgg tgt ctg gaa gga gag gta<br>Asn Trp Thr His Ser Cys Gln Gln Cys Arg Cys Leu Glu Gly Glu Val | 2112 |
| gat tgc tgg cca ctc act tgc ccc aga ttg agc tgt gag tac aca gcc<br>Asp Cys Trp Pro Leu Thr Cys Pro Arg Leu Ser Cys Glu Tyr Thr Ala | 2160 |
| atc ttg gaa ggg gag tgt tgt cca cgc tgt gtc agc gac ccc tgc ctg<br>Ile Leu Glu Gly Glu Cys Cys Pro Arg Cys Val Ser Asp Pro Cys Leu | 2208 |
| gcg gat aac atc gtc tat gac atc aga gaa act tgc ctg gac agc tat<br>Ala Asp Asn Ile Val Tyr Asp Ile Arg Glu Thr Cys Leu Asp Ser Tyr | 2256 |
| gga gtt tca agg ctt agt ggc tca gtg tgg aca ttg gct gga tct ccc<br>Gly Val Ser Arg Leu Ser Gly Ser Val Trp Thr Leu Ala Gly Ser Pro | 2304 |
| tgc acg acc tgc aaa tgc aag aat gga agt gtc tgc tgt tct gtg gat<br>Cys Thr Thr Cys Lys Cys Lys Asn Gly Ser Val Cys Cys Ser Val Asp | 2352 |
| ttg gag tgt ctt cat aat aat tga aggatttaaa atggactcat gatcgccaga<br>Leu Glu Cys Leu His Asn Asn * | 2406 |
| gaaaaatgga caaatgacca tccatgatga tgaaagaaca ggagttggtg tttttttac | 2466 |
| cacagacaat taccaaagtc tccgtctgag gaaggtgttt gcaggttgcc ttttggacct | 2526 |
| cccactctgc tcattcttgc taacctagtc taggtgacct acagtgcatt tcagtctatg | 2586 |
| gttgttaaaa gaagttttcc gtgttgtaaa tcacgtttcc cttaccaggt cattgcaaat | 2646 |
| acatttaaat gatttcatgg taaatgttga tgtatttttt gggtttattt tgtgtactaa | 2706 |
| cataatagag attcagctgc ttttatttat ttttttcttg acttttggat caaattcaac | 2766 |
| aaataaagtt gcctgttgtg atttt | 2791 |

*Equus caballus* NELL1 isoform 1 amino acid sequence (SEQ ID NO: 6)
Met Gly Phe Gly Met Asp Pro Asp Leu Gln Met Asp Ile Ile Thr Glu
Leu Asp Leu Val Asn Thr Thr Leu Gly Val Thr Gln Val Ser Gly Leu
His Asn Ala Ser Lys Ala Phe Leu Phe Gln Asp Val Glu Arg Glu Ile
His Ala Ala Pro His Val Ser Glu Lys Leu Ile Gln Leu Phe Arg Asn
Lys Ser Glu Phe Thr Phe Leu Ala Thr Val Gln Gln Lys Pro Ser Thr
Ser Gly Val Ile Leu Ser Ile Arg Glu Leu Glu Asn Ser Tyr Phe Glu
Leu Glu Ser Ser Gly Leu Arg Asp Glu Ile Arg Tyr His Tyr Thr His
Lys Gly Lys Pro Arg Thr Glu Ala Leu Pro Tyr Arg Met Ala Asp Gly
Arg Trp His Lys Val Ala Leu Ser Val Ser Ala Ser His Leu Leu Leu
His Ile Asp Cys Asn Arg Ile Tyr Glu Arg Val Ile Asp Thr Pro Glu
Thr Asn Leu Pro Pro Gly Ser Asn Leu Trp Leu Gly Gln Arg Asn Gln
Lys His Gly Leu Phe Lys Gly Ile Ile Gln Asp Gly Lys Ile Ile Phe
Met Pro Asn Gly Tyr Ile Thr Gln Cys Pro Asn Leu Asn Arg Thr Cys
Pro Thr Cys Ser Asp Phe Leu Ser Leu Val Gln Gly Ile Met Asp Leu
Gln Glu Leu Leu Ala Lys Met Thr Ala Lys Leu Asn Tyr Ala Glu Thr
Arg Leu Ser Gln Leu Glu Asn Cys His Cys Glu Lys Thr Cys Gln Val
Ser Gly Leu Leu Tyr Arg Asp Gln Asp Ser Trp Val Asp Gly Asp His
Cys Arg Asn Cys Thr Cys Lys Ser Gly Ala Val Glu Cys Arg Arg Met
Ser Cys Pro Pro Leu Asn Cys Ser Pro Asp Ser Leu Pro Val His Val
Ala Gly Gln Cys Cys Lys Val Cys Arg Pro Lys Cys Ile Tyr Gly Gly
Lys Val Leu Ala Glu Gly Gln Arg Ile Leu Thr Lys Ser Cys Arg Glu
Cys Arg Gly Gly Val Leu Val Lys Ile Thr Glu Ala Cys Pro Pro Leu
Asn Cys Ser Asp Lys Asp His Ile Leu Pro Glu Asn Gln Cys Cys Ser
Val Cys Arg Gly His Asn Phe Cys Ala Glu Gly Pro Lys Cys Gly Glu
Asn Ser Glu Cys Lys Asn Trp Asn Thr Lys Ala Thr Cys Glu Cys Lys

```
Asn Gly Tyr Ile Ser Val Gln Gly Asp Ser Ala Tyr Cys Glu Asp Ile
Asp Glu Cys Ala Ala Lys Met His Tyr Cys Arg Ala Asn Thr Val Cys
Val Asn Leu Pro Gly Leu Tyr Arg Cys Asp Cys Val Pro Gly Tyr Ile
Arg Val Asp Asp Phe Ser Cys Thr Glu His Asp Glu Cys Gly Ser Gly
Gln His Asn Cys Asp Glu Asn Ala Ile Cys Thr Asn Thr Val Gln Gly
His Ser Cys Thr Cys Lys Pro Gly Tyr Val Gly Asn Gly Thr Ser Cys
Arg Ala Phe Cys Glu Glu Gly Cys Arg Tyr Gly Gly Thr Cys Val Ala
Pro Asn Lys Cys Val Cys Pro Ser Gly Phe Thr Gly Ser His Cys Glu
Lys Asp Ile Asp Glu Cys Thr Glu Gly Ile Ile Glu Cys His Asn His
Ser Arg Cys Val Asn Leu Pro Gly Trp Tyr His Cys Glu Cys Arg Ser
Gly Phe His Asp Asp Gly Thr Tyr Ser Leu Ser Gly Glu Ser Cys Ile
Asp Ile Asp Glu Cys Ala Leu Arg Thr His Thr Cys Trp Asn Asp Ser
Ala Cys Ile Asn Leu Ala Gly Gly Phe Asp Cys Leu Cys Pro Ser Gly
Pro Ser Cys Ser Gly Asp Cys Pro His Glu Gly Gly Leu Lys Arg Asn
Gly Gln Val Trp Thr Leu Lys Glu Asp Arg Cys Ser Val Cys Ser Cys
Lys Asp Gly Lys Ile Phe Cys Arg Arg Thr Ala Cys Asp Cys Gln Asn
Pro Ser Val Asp Leu Phe Cys Cys Pro Glu Cys Asp Thr Arg Val Thr
Ser Gln Cys Leu Asp Gln Asn Gly His Lys Leu Tyr Arg Ser Gly Asp
Asn Trp Thr His Ser Cys Gln Gln Cys Arg Cys Leu Glu Gly Glu Val
Asp Cys Trp Pro Leu Thr Cys Pro Arg Leu Ser Cys Glu Tyr Thr Ala
Ile Leu Glu Gly Glu Cys Cys Pro Arg Cys Val Ser Asp Pro Cys Leu
Ala Asp Asn Ile Val Tyr Asp Ile Arg Glu Thr Cys Leu Asp Ser Tyr
Gly Val Ser Arg Leu Ser Gly Ser Val Trp Thr Leu Ala Gly Ser Pro
Cys Thr Thr Cys Lys Cys Lys Asn Gly Ser Val Cys Cys Ser Val Asp
Leu Glu Cys Leu His Asn Asn
```

*Equus caballus* NELL1 isoform 2 nucleotide sequence (SEQ ID NO: 7) and translated amino acid sequence (SEQ ID NO: 8)

```
atg ggc ttt ggg atg gac ccc gac ctt caa atg gat att atc acc gag       48
Met Gly Phe Gly Met Asp Pro Asp Leu Gln Met Asp Ile Ile Thr Glu ctc gac ctc gtg aac acc acc ctt gga gtc act cag gtg tcc gga ctg       96
Leu Asp Leu Val Asn Thr Thr Leu Gly Val Thr Gln Val Ser Gly Leu cac aat gcc agc aaa gca ttt tta ttt caa gat gta gag aga gag atc      144
His Asn Ala Ser Lys Ala Phe Leu Phe Gln Asp Val Glu Arg Glu Ile cat gca gcc cca cac gtg agt gag aaa tta att cag ctg ttc cgg aat      192
His Ala Ala Pro His Val Ser Glu Lys Leu Ile Gln Leu Phe Arg Asn aag agt gaa ttc acc ttt ttg gcc act gtg cag cag aag ccg tca act      240
Lys Ser Glu Phe Thr Phe Leu Ala Thr Val Gln Gln Lys Pro Ser Thr tca gga gtg ata ctg tcc att cga gaa ctg gaa aac agt tat ttt gaa      288
Ser Gly Val Ile Leu Ser Ile Arg Glu Leu Glu Asn Ser Tyr Phe Glu ctg gag agc agt ggc ctg aga gat gag att cga tat cac tac aca cac      336
Leu Glu Ser Ser Gly Leu Arg Asp Glu Ile Arg Tyr His Tyr Thr His aag ggg aag ccc agg aca gag gca ctt ccc tac cgg atg gcg gac gga      384
Lys Gly Lys Pro Arg Thr Glu Ala Leu Pro Tyr Arg Met Ala Asp Gly cgg tgg cac aag gtg gcg ctg tca gtt agc gcc tct cat ctc ctg ctc      432
Arg Trp His Lys Val Ala Leu Ser Val Ser Ala Ser His Leu Leu Leu cac atc gac tgc aac agg att tat gaa cgt gtg ata gac act cct gag      480
His Ile Asp Cys Asn Arg Ile Tyr Glu Arg Val Ile Asp Thr Pro Glu acc aac ctc ccc cca gga agc aat ttg tgg ctg ggt cag cga aac caa      528
Thr Asn Leu Pro Pro Gly Ser Asn Leu Trp Leu Gly Gln Arg Asn Gln aag cac ggc tta ttc aaa gga atc atc caa gat gga aaa atc atc ttc      576
Lys His Gly Leu Phe Lys Gly Ile Ile Gln Asp Gly Lys Ile Ile Phe atg ccg aat gga tac ata aca cag tgt ccg aac ctg aat cgc act tgc      624
Met Pro Asn Gly Tyr Ile Thr Gln Cys Pro Asn Leu Asn Arg Thr Cys cca acg tgc agt gat ttc tta agc ctg gtg caa gga atc atg gat tta      672
Pro Thr Cys Ser Asp Phe Leu Ser Leu Val Gln Gly Ile Met Asp Leu caa gag ctt ctg gcc aag atg act gcg aaa cta aat tat gca gag aca      720
Gln Glu Leu Leu Ala Lys Met Thr Ala Lys Leu Asn Tyr Ala Glu Thr cga ctt agt caa ttg gaa aac tgc cac tgc gag aag acc tgt caa gtg      768
Arg Leu Ser Gln Leu Glu Asn Cys His Cys Glu Lys Thr Cys Gln Val agt gga ctg cto tat aga gac cag gac tcc tgg gtt gat ggc gat cac      816
Ser Gly Leu Leu Tyr Arg Asp Gln Asp Ser Trp Val Asp Gly Asp His
```

| | | |
|---|---|---|
| tgt agg aac tgc acg tgc aaa agc ggc gct gtg gaa tgt cgg agg atg<br>Cys Arg Asn Cys Thr Cys Lys Ser Gly Ala Val Glu Cys Arg Arg Met | | 864 |
| tct tgt ccc cct ctc aat tgc tcc cca gac tcc ctc cct gtg cac gtt<br>Ser Cys Pro Pro Leu Asn Cys Ser Pro Asp Ser Leu Pro Val His Val | | 912 |
| gcc ggc cag tgc tgt aag gtc tgc cga cca aaa tgt atc tac gga ggg<br>Ala Gly Gln Cys Cys Lys Val Cys Arg Pro Lys Cys Ile Tyr Gly Gly | | 960 |
| aaa gtc ctt gca gaa ggc cag cgg att tta acc aag agc tgt cgg gaa<br>Lys Val Leu Ala Glu Gly Gln Arg Ile Leu Thr Lys Ser Cys Arg Glu | | 1008 |
| tgc cga ggt gga gtt tta gtg aaa att aca gaa gcg tgc cct cct ttg<br>Cys Arg Gly Gly Val Leu Val Lys Ile Thr Glu Ala Cys Pro Pro Leu | | 1056 |
| aac tgc tca gac aag gat cac att ctc cca gag aat cag tgc tgc agc<br>Asn Cys Ser Asp Lys Asp His Ile Leu Pro Glu Asn Gln Cys Cys Ser | | 1104 |
| gtc tgc aga ggt cat aac ttt tgt gcg aaa gga cct aaa tgt ggt gaa<br>Val Cys Arg Gly His Asn Phe Cys Ala Glu Gly Pro Lys Cys Gly Glu | | 1152 |
| aat tca gag tgc aaa aac tgg aat aca aaa gct act tgc gag tgc aag<br>Asn Ser Glu Cys Lys Asn Trp Asn Thr Lys Ala Thr Cys Glu Cys Lys | | 1200 |
| aat ggt tat atc tct gtc cag ggg gac tcc gcc tac tgt gaa gat atc<br>Asn Gly Tyr Ile Ser Val Gln Gly Asp Ser Ala Tyr Cys Glu Asp Ile | | 1248 |
| gat gag tgt gct gct aag atg cat tac tgt cgt gcc aat act gtg tgt<br>Asp Glu Cys Ala Ala Lys Met His Tyr Cys Arg Ala Asn Thr Val Cys | | 1296 |
| gtc aac ctg cct ggg tta tat cgg tgt gac tgt gtc ccg gga tac att<br>Val Asn Leu Pro Gly Leu Tyr Arg Cys Asp Cys Val Pro Gly Tyr Ile | | 1344 |
| cgc gtg gat gat ttc tct tgt aca gaa cat gac gaa tgt ggc agc ggg<br>Arg Val Asp Asp Phe Ser Cys Thr Glu His Asp Glu Cys Gly Ser Gly | | 1392 |
| cag cac aac tgt gat gag aat gcc atc tgc acc aac act gtc cag gga<br>Gln His Asn Cys Asp Glu Asn Ala Ile Cys Thr Asn Thr Val Gln Gly | | 1440 |
| cac agc tgc acc tgc aaa ccg ggc tac gtg ggg aat ggg acc agc tgc<br>His Ser Cys Thr Cys Lys Pro Gly Tyr Val Gly Asn Gly Thr Ser Cys | | 1488 |
| aga gcg ttc tgc gaa gag ggc tgc aga tat ggc ggg aca tgc gtg gct<br>Arg Ala Phe Cys Glu Glu Gly Cys Arg Tyr Gly Gly Thr Cys Val Ala | | 1536 |
| cct aac aaa tgt gtc tgt cct tct gga ttc aca gga agc cac tgt gag<br>Pro Asn Lys Cys Val Cys Pro Ser Gly Phe Thr Gly Ser His Cys Glu | | 1584 |
| aaa gac att gat gaa tgt gcc tta aga act cac acc tgt tgg aat gat<br>Lys Asp Ile Asp Glu Cys Ala Leu Arg Thr His Thr Cys Trp Asn Asp | | 1632 |
| tct gcc tgc atc aac ttg gca ggg ggc ttc gac tgc ctg tgt ccc tca<br>Ser Ala Cys Ile Asn Leu Ala Gly Gly Phe Asp Cys Leu Cys Pro Ser | | 1680 |
| ggg cca tcc tgc tct ggt gac tgc ccc cac gaa gga gga ctg aag cgc<br>Gly Pro Ser Cys Ser Gly Asp Cys Pro His Glu Gly Gly Leu Lys Arg | | 1728 |
| aac ggg cag gtg tgg acc ctg aaa gaa gac agg tgt tct gtg tgt tcc<br>Asn Gly Gln Val Trp Thr Leu Lys Glu Asp Arg Cys Ser Val Cys Ser | | 1776 |
| tgc aag gat ggg aag ata ttc tgc cga cgg aca gct tgt gat tgc cag<br>Cys Lys Asp Gly Lys Ile Phe Cys Arg Arg Thr Ala Cys Asp Cys Gln | | 1824 |
| aat cca agc gtt gac ctt ttc tgt tgc cca gag tgt gac acc agg gtc<br>Asn Pro Ser Val Asp Leu Phe Cys Cys Pro Glu Cys Asp Thr Arg Val | | 1872 |
| aca agt caa tgt tta gac caa aat gga cac aag ctc tat cga agt gga<br>Thr Ser Gln Cys Leu Asp Gln Asn Gly His Lys Leu Tyr Arg Ser Gly | | 1920 |
| gac aat tgg act cac agc tgt cag cag tgc cgg tgt ctg gaa gga gag<br>Asp Asn Trp Thr His Ser Cys Gln Gln Cys Arg Cys Leu Glu Gly Glu | | 1968 |
| gta gat tgc tgg cca ctc act tgc ccc aga ttg agc tgt gag tac aca<br>Val Asp Cys Trp Pro Leu Thr Cys Pro Arg Leu Ser Cys Glu Tyr Thr | | 2016 |
| gcc atc ttg gaa ggg gag tgt tgt cca cgc tgt gtc agc gac ccc tgc<br>Ala Ile Leu Glu Gly Glu Cys Cys Pro Arg Cys Val Ser Asp Pro Cys | | 2064 |

-continued

| | |
|---|---|
| ctg gcg gat aac atc gtc tat gac atc aga gaa act tgc ctg gac agc<br>Leu Ala Asp Asn Ile Val Tyr Asp Ile Arg Glu Thr Cys Leu Asp Ser | 2112 |
| tat gga gtt tca agg ctt agt ggc tca gtg tgg aca ttg gct gga tct<br>Tyr Gly Val Ser Arg Leu Ser Gly Ser Val Trp Thr Leu Ala Gly Ser | 2160 |
| ccc tgc acg acc tgc aaa tgc aag aat gga agt gtc tgc tgt tct gtg<br>Pro Cys Thr Thr Cys Lys Cys Lys Asn Gly Ser Val Cys Cys Ser Val | 2208 |
| gat ttg gag tgt ctt cat aat aat tga aggatttaaa atggactcat<br>Asp Leu Glu Cys Leu His Asn Asn * | 2255 |
| gatcgccaga gaaaaatgga caaatgacca | 2285 |

*Equus caballus* NELL1 isoform 2 amino acid sequence (SEQ ID NO: 8)
Met Gly Phe Gly Met Asp Pro Asp Leu Gln Met Asp Ile Ile Thr Glu
Leu Asp Leu Val Asn Thr Thr Leu Gly Val Thr Gln Val Ser Gly Leu
His Asn Ala Ser Lys Ala Phe Leu Phe Gln Asp Val Glu Arg Glu Ile
His Ala Ala Pro His Val Ser Glu Lys Leu Ile Gln Leu Phe Arg Asn
Lys Ser Glu Phe Thr Phe Leu Ala Thr Val Gln Gln Lys Pro Ser Thr
Ser Gly Val Ile Leu Ser Ile Arg Glu Leu Glu Asn Ser Tyr Phe Glu
Leu Glu Ser Ser Gly Leu Arg Asp Glu Ile Arg Tyr His Tyr Thr His
Lys Gly Lys Pro Arg Thr Glu Ala Leu Pro Tyr Arg Met Ala Asp Gly
Arg Trp His Lys Val Ala Leu Ser Val Ser Ala Ser His Leu Leu Leu
His Ile Asp Cys Asn Arg Ile Tyr Glu Arg Val Ile Asp Thr Pro Glu
Thr Asn Leu Pro Pro Gly Ser Asn Leu Trp Leu Gly Gln Arg Asn Gln
Lys His Gly Leu Phe Lys Gly Ile Ile Gln Asp Gly Lys Ile Ile Phe
Met Pro Asn Gly Tyr Ile Thr Gln Cys Pro Asn Leu Asn Arg Thr Cys
Pro Thr Cys Ser Asp Phe Leu Ser Leu Val Gln Gly Ile Met Asp Leu
Gln Glu Leu Leu Ala Lys Met Thr Ala Lys Leu Asn Tyr Ala Glu Thr
Arg Leu Ser Gln Leu Glu Asn Cys His Cys Glu Lys Thr Cys Gln Val
Ser Gly Leu Leu Tyr Arg Asp Gln Asp Ser Trp Val Asp Gly Asp His
Cys Arg Asn Cys Thr Cys Lys Ser Gly Ala Val Glu Cys Arg Arg Met
Ser Cys Pro Pro Leu Asn Cys Ser Pro Asp Ser Leu Pro Val His Val
Ala Gly Gln Cys Cys Lys Val Cys Arg Pro Lys Cys Ile Tyr Gly Gly
Lys Val Leu Ala Glu Gly Gln Arg Ile Leu Thr Lys Ser Cys Arg Glu
Cys Arg Gly Gly Val Leu Val Lys Ile Thr Glu Ala Cys Pro Pro Leu
Asn Cys Ser Asp Lys Asp His Ile Leu Pro Glu Asn Gln Cys Cys Ser
Val Cys Arg Gly His Asn Phe Cys Ala Glu Gly Pro Lys Cys Gly Glu
Asn Ser Glu Cys Lys Asn Trp Asn Thr Lys Ala Thr Cys Glu Cys Lys
Asn Gly Tyr Ile Ser Val Gln Gly Asp Ser Ala Tyr Cys Glu Asp Ile
Asp Glu Cys Ala Ala Lys Met His Tyr Cys Arg Ala Asn Thr Val Cys
Val Asn Leu Pro Gly Leu Tyr Arg Cys Asp Cys Val Pro Gly Tyr Ile
Arg Val Asp Asp Phe Ser Cys Thr Glu His Asp Glu Cys Gly Ser Gly
Gln His Asn Cys Asp Glu Asn Ala Ile Cys Thr Asn Thr Val Gln Gly
His Ser Cys Thr Cys Lys Pro Gly Tyr Val Gly Asn Gly Thr Ser Cys
Arg Ala Phe Cys Glu Glu Gly Cys Arg Tyr Gly Gly Thr Cys Val Ala
Pro Asn Lys Cys Val Cys Pro Ser Gly Phe Thr Gly Ser His Cys Glu
Lys Asp Ile Asp Glu Cys Ala Leu Arg Thr His Thr Cys Trp Asn Asp
Ser Ala Cys Ile Asn Leu Ala Gly Gly Phe Asp Cys Leu Cys Pro Ser
Gly Pro Ser Cys Ser Gly Asp Cys Pro His Glu Gly Gly Leu Lys Arg
Asn Gly Gln Val Trp Thr Leu Lys Glu Asp Arg Cys Ser Val Cys Ser
Cys Lys Asp Gly Lys Ile Phe Cys Arg Arg Thr Ala Cys Asp Cys Gln
Asn Pro Ser Val Asp Leu Phe Cys Cys Pro Glu Cys Asp Thr Arg Val
Thr Ser Gln Cys Leu Asp Gln Asn Gly His Lys Leu Tyr Arg Ser Gly
Asp Asn Trp Thr His Ser Cys Gln Gln Cys Arg Cys Leu Glu Gly Glu
Val Asp Cys Trp Pro Leu Thr Cys Pro Arg Leu Ser Cys Glu Tyr Thr
Ala Ile Leu Glu Gly Glu Cys Cys Pro Arg Cys Val Ser Asp Pro Cys
Leu Ala Asp Asn Ile Val Tyr Asp Ile Arg Glu Thr Cys Leu Asp Ser
Tyr Gly Val Ser Arg Leu Ser Gly Ser Val Trp Thr Leu Ala Gly Ser
Pro Cys Thr Thr Cys Lys Cys Lys Asn Gly Ser Val Cys Cys Ser Val
Asp Leu Glu Cys Leu His Asn Asn

*Mus muculus* NELL1 nucleotide sequence (SEQ ID NO: 9) and translated
amino acid sequence (SEQ ID NO: 10)

| | |
|---|---|
| gcgttggtgc gccctgcttg gcggggggcc tccggagcg atg ccg atg gat gtg<br>                                                                                               Met Pro Met Asp Val | 54 |
| att tta gtt ttg tgg ttc tgt gtg tgc acc gcc agg aca gtg ctg ggc<br>Ile Leu Val Leu Trp Phe Cys Val Cys Thr Ala Arg Thr Val Leu Gly | 102 |
| ttt ggg atg gac cct gac ctt cag atg gac atc atc act gaa ctt gac<br>Phe Gly Met Asp Pro Asp Leu Gln Met Asp Ile Ile Thr Glu Leu Asp | 150 |
| ctt gtg aac acc acc ctg ggc gtc act cag gtg gct gga cta cac aat<br>Leu Val Asn Thr Thr Leu Gly Val Thr Gln Val Ala Gly Leu His Asn | 198 |
| gcc agt aag gca ttt ctg ttt caa gat gta cag aga gag atc cac tca<br>Ala Ser Lys Ala Phe Leu Phe Gln Asp Val Gln Arg Glu Ile His Ser | 246 |

```
gcc cct cat gtg agt gag aag ctg atc cag cta ttc cgg aat aag agt      294
Ala Pro His Val Ser Glu Lys Leu Ile Gln Leu Phe Arg Asn Lys Ser gag ttt acc ttt ttg gct aca gtg cag cag aag ccg tcc acc tca ggg      342
Glu Phe Thr Phe Leu Ala Thr Val Gln Gln Lys Pro Ser Thr Ser Gly gtg ata ctg tcg atc cgg gag ctg gaa cac agc tat ttt gaa ctg gag      390
Val Ile Leu Ser Ile Arg Glu Leu Glu His Ser Tyr Phe Glu Leu Glu agc agt ggc cca aga gaa gag ata cgc tat cat tac atc cat ggc ggc      438
Ser Ser Gly Pro Arg Glu Glu Ile Arg Tyr His Tyr Ile His Gly Gly aag ccc agg act gag gcc ctt ccc tac cgc atg gcc gat gga cag tgg      486
Lys Pro Arg Thr Glu Ala Leu Pro Tyr Arg Met Ala Asp Gly Gln Trp cac aag gtc gcg ctg tct gtg agc gcc tct cac ctc cta ctc cat gtc      534
His Lys Val Ala Leu Ser Val Ser Ala Ser His Leu Leu Leu His Val gac tgc aat agg att tat gag cgt gtg ata gat cct ccg gag acc aac      582
Asp Cys Asn Arg Ile Tyr Glu Arg Val Ile Asp Pro Pro Glu Thr Asn ctt cct cca gga agc aat cta tgg ctt ggg caa cgt aat caa aag cat      630
Leu Pro Pro Gly Ser Asn Leu Trp Leu Gly Gln Arg Asn Gln Lys His ggc ttt ttc aaa gga atc atc caa gat ggc aag atc atc ttc atg ccg      678
Gly Phe Phe Lys Gly Ile Ile Gln Asp Gly Lys Ile Ile Phe Met Pro aac ggc ttc atc aca cag tgc cco aac cta aat cgc act tgc cca aca      726
Asn Gly Phe Ile Thr Gln Cys Pro Asn Leu Asn Arg Thr Cys Pro Thr tgc agt gat ttc ctg agc ctg gtt caa gga ata atg gat ttg caa gag      774
Cys Ser Asp Phe Leu Ser Leu Val Gln Gly Ile Met Asp Leu Gln Glu ctt ttg gcc aag atg act gca aaa ctg aat tat gca gag acg aga ctt      822
Leu Leu Ala Lys Met Thr Ala Lys Leu Asn Tyr Ala Glu Thr Arg Leu ggt caa ctg gaa aat tgc cac tgt gag aag acc tgc caa gtg agt ggg      870
Gly Gln Leu Glu Asn Cys His Cys Glu Lys Thr Cys Gln Val Ser Gly ctg ctc tac agg gac caa gac tcc tgg gta gat ggt gac aac tgc agg      918
Leu Leu Tyr Arg Asp Gln Asp Ser Trp Val Asp Gly Asp Asn Cys Arg aac tgc aca tgc aaa agt ggt gct gtg gag tgc cga agg atg tcc tgt      966
Asn Cys Thr Cys Lys Ser Gly Ala Val Glu Cys Arg Arg Met Ser Cys ccc cca ctc aac tgt tcc cca gac tca ctt cct gtg cat att tct ggc     1014
Pro Pro Leu Asn Cys Ser Pro Asp Ser Leu Pro Val His Ile Ser Gly caa tgt tgt aaa gtt tgc aga cca aaa tgt atc tat gga gga aaa gtt     1062
Gln Cys Cys Lys Val Cys Arg Pro Lys Cys Ile Tyr Gly Gly Lys Val ctt gct gag ggc cag cgg att tta acc aag acc tgc cgg gaa tgt cga     1110
Leu Ala Glu Gly Gln Arg Ile Leu Thr Lys Thr Cys Arg Glu Cys Arg ggt gga gtc ttg gta aaa atc aca gaa gct gcc cct cct ttg aac tgc     1158
Gly Gly Val Leu Val Lys Ile Thr Glu Ala Ala Pro Pro Leu Asn Cys tca gag aag gat cat att ctt ccg gag aac cag tgc tgc agg gtc tgc     1206
Ser Glu Lys Asp His Ile Leu Pro Glu Asn Gln Cys Cys Arg Val Cys cga ggt cat aac ttc tgt gca gaa gca cct aag tgt gga gaa aac tcg     1254
Arg Gly His Asn Phe Cys Ala Glu Ala Pro Lys Cys Gly Glu Asn Ser gaa tgc aaa aat tgg aat aca aaa gcg act tgt gag tgc aag aat gga     1302
Glu Cys Lys Asn Trp Asn Thr Lys Ala Thr Cys Glu Cys Lys Asn Gly tac atc tct gtc cag ggc aac tct gca tac tgt gaa gat atc gat gag     1350
Tyr Ile Ser Val Gln Gly Asn Ser Ala Tyr Cys Glu Asp Ile Asp Glu tgt gca gca aag atg cac tac tgt cat gcc aac acg gtg tgt gtc aac     1398
Cys Ala Ala Lys Met His Tyr Cys His Ala Asn Thr Val Cys Val Asn ttg ccg ggg tta tat cgc tgt gac tgc atc cca gga tac atc cgt gtg     1446
Leu Pro Gly Leu Tyr Arg Cys Asp Cys Ile Pro Gly Tyr Ile Arg Val gat gac ttc tct tgt acg gag cat gat gat tgt ggc agc gga caa cac     1494
Asp Asp Phe Ser Cys Thr Glu His Asp Asp Cys Gly Ser Gly Gln His
```

-continued

| | |
|---|---|
| aac tgt gac aaa aat gcc atc tgt acc aac aca gtc cag gga cac agc<br>Asn Cys Asp Lys Asn Ala Ile Cys Thr Asn Thr Val Gln Gly His Ser | 1542 |
| tgt acc tgc cag cca ggc tac gtg gga aat ggt act gtc tgc aaa gca<br>Cys Thr Cys Gln Pro Gly Tyr Val Gly Asn Gly Thr Val Cys Lys Ala | 1590 |
| ttc tgt gaa gag ggt tgc aga tac gga ggt acc tgt gtg gcc cct aac<br>Phe Cys Glu Glu Gly Cys Arg Tyr Gly Gly Thr Cys Val Ala Pro Asn | 1638 |
| aaa tgt gtc tgt cct tct gga ttc aca gga agc cac tgt gag aaa gat<br>Lys Cys Val Cys Pro Ser Gly Phe Thr Gly Ser His Cys Glu Lys Asp | 1686 |
| att gat gaa tgt gca gag gga ttc gtt gag tgc cac aac cac tcc cgc<br>Ile Asp Glu Cys Ala Glu Gly Phe Val Glu Cys His Asn His Ser Arg | 1734 |
| tgc gtt aac ctt cca ggg tgg tac cac tgt gag tgc aga agc ggt ttc<br>Cys Val Asn Leu Pro Gly Trp Tyr His Cys Glu Cys Arg Ser Gly Phe | 1782 |
| cat gac gat ggg acc tat tca ctg tcc ggg gag tcc tgc att gat att<br>His Asp Asp Gly Thr Tyr Ser Leu Ser Gly Glu Ser Cys Ile Asp Ile | 1830 |
| gat gaa tgt gcc tta aga act cac act tgt tgg aat gac tct gcc tgc<br>Asp Glu Cys Ala Leu Arg Thr His Thr Cys Trp Asn Asp Ser Ala Cys | 1878 |
| atc aac tta gca gga gga ttt gac tgc ctg tgt ccc tct ggg ccc tcc<br>Ile Asn Leu Ala Gly Gly Phe Asp Cys Leu Cys Pro Ser Gly Pro Ser | 1926 |
| tgc tct ggt gac tgt ccc cac gaa ggg ggg ctg aag cat aat ggg cag<br>Cys Ser Gly Asp Cys Pro His Glu Gly Gly Leu Lys His Asn Gly Gln | 1974 |
| gtg tgg att ctg aga gaa gac agg tgt tca gtc tgt tcc tgt aag gat<br>Val Trp Ile Leu Arg Glu Asp Arg Cys Ser Val Cys Ser Cys Lys Asp | 2022 |
| ggg aag ata ttc tgc cgg cgg aca gct tgt gat tgc cag aat cca aat<br>Gly Lys Ile Phe Cys Arg Arg Thr Ala Cys Asp Cys Gln Asn Pro Asn | 2070 |
| gtt gac ctt ttc tgc tgc cca gag tgt gac acc agg gtc act agc caa<br>Val Asp Leu Phe Cys Cys Pro Glu Cys Asp Thr Arg Val Thr Ser Gln | 2118 |
| tgt tta gat caa agc gga cag aag ctc tat cga agt gga gac aac tgg<br>Cys Leu Asp Gln Ser Gly Gln Lys Leu Tyr Arg Ser Gly Asp Asn Trp | 2166 |
| acc cac agc tgc cag cag tgc cga tgt ctg gaa gga gag gca gac tgc<br>Thr His Ser Cys Gln Gln Cys Arg Cys Leu Glu Gly Glu Ala Asp Cys | 2214 |
| tgg cct cta gct tgc cct agt ttg agc tgt gaa tac aca gcc atc ttt<br>Trp Pro Leu Ala Cys Pro Ser Leu Ser Cys Glu Tyr Thr Ala Ile Phe | 2262 |
| gaa gga gag tgt tgt ccc cgc tgt gtc agt gac ccc tgc ctg gct gat<br>Glu Gly Glu Cys Cys Pro Arg Cys Val Ser Asp Pro Cys Leu Ala Asp | 2310 |
| aat att gcc tat gac atc aga aaa act tgc ctg gac agc tct ggt att<br>Asn Ile Ala Tyr Asp Ile Arg Lys Thr Cys Leu Asp Ser Ser Gly Ile | 2358 |
| tcg agg ctg agc ggc gca gtg tgg aca atg gct gga tct ccc tgt aca<br>Ser Arg Leu Ser Gly Ala Val Trp Thr Met Ala Gly Ser Pro Cys Thr | 2406 |
| acc tgt caa tgc aag aat ggg aga gtc tgc tgc tct gtg gat ctg gtg<br>Thr Cys Gln Cys Lys Asn Gly Arg Val Cys Cys Ser Val Asp Leu Val | 2454 |
| tgt ctt gag aat aac tga agattttaaa tggactcatc acatgagaaa<br>Cys Leu Glu Asn Asn * | 2502 |
| atggacaaaa tgaccatcca acctgaggaa gaggaggggc tgatttcttt ttcttttaa | 2562 |
| ccacagtcaa ttaccaaagt ctccatcaga ggaaggcgtt tgggttgcct ttaccacttt | 2622 |
| gctcatcctt gctgacctag tctagatgcc tgcagtaccg tgtatttcgg tcgatggttg | 2682 |
| ttgagtctcc gtgctgtaaa tcacatttcc cttgtcagat catttacaga tacatttaaa | 2742 |
| ggattccatg ataaatgtta aagtaccttt tgtttatttt tgtgtaccaac ataatagaga | 2802 |
| cttggcacca | 2812 |

*Mus musculus* NELL1 amino acid sequence (SEQ ID NO: 10)
Met Pro Met Asp Val Ile Leu Val Leu Trp Phe Cys Val Cys Thr Ala
Arg Thr Val Leu Gly Phe Gly Met Asp Pro Asp Leu Gln Met Asp Ile
Ile Thr Glu Leu Asp Leu Val Asn Thr Thr Leu Gly Val Thr Gln Val -continued

```
Ala Gly Leu His Asn Ala Ser Lys Ala Phe Leu Phe Gln Asp Val Gln
Arg Glu Ile His Ser Ala Pro His Val Ser Glu Lys Leu Ile Gln Leu
Phe Arg Asn Lys Ser Glu Phe Thr Phe Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Pro Arg Glu Glu Ile Arg Tyr His
Tyr Ile His Gly Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Val Asp Cys Asn Arg Ile Tyr Glu Arg Val Ile Asp
Pro Pro Glu Thr Asn Leu Pro Pro Gly Ser Asn Leu Trp Leu Gly Gln
Arg Asn Gln Lys His Gly Phe Phe Lys Gly Ile Ile Gln Asp Gly Lys
Ile Ile Phe Met Pro Asn Gly Phe Ile Thr Gln Cys Pro Asn Leu Asn
Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Gly Gln Leu Glu Asn Cys His Cys Glu Lys Thr
Cys Gln Val Ser Gly Leu Leu Tyr Arg Asp Gln Asp Ser Trp Val Asp
Gly Asp Asn Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ser Gly Gln Cys Cys Lys Val Cys Arg Pro Lys Cys Ile
Tyr Gly Gly Lys Val Leu Ala Glu Gly Gln Arg Ile Leu Thr Lys Thr
Cys Arg Glu Cys Arg Gly Gly Val Leu Val Lys Ile Thr Glu Ala Cys
Pro Pro Leu Asn Cys Ser Glu Lys Asp His Ile Leu Pro Glu Asn Gln
Cys Cys Arg Val Cys Arg Gly His Asn Phe Cys Ala Glu Ala Pro Lys
Cys Gly Glu Asn Ser Glu Cys Lys Asn Trp Asn Thr Lys Ala Thr Cys
Glu Cys Lys Asn Gly Tyr Ile Ser Val Gln Gly Asn Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Ile Pro
Gly Tyr Ile Arg Val Asp Asp Phe Ser Cys Thr Glu His Asp Asp Cys
Gly Ser Gly Gln His Asn Cys Asp Lys Asn Ala Ile Cys Thr Asn Thr
Val Gln Gly His Ser Cys Thr Cys Gln Pro Gly Tyr Val Gly Asn Gly
Thr Val Cys Lys Ala Phe Cys Glu Gly Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ala Gly Phe Val Glu Cys
His Asn His Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Gly Phe Asp Cys Leu Cys
Pro Ser Gly Pro Ser Cys Ser Gly Asp Cys Pro His Glu Gly Gly Leu
Lys His Asn Gly Gln Val Trp Ile Leu Arg Glu Asp Arg Cys Ser Val
Cys Ser Cys Lys Asp Gly Lys Ile Phe Cys Arg Arg Thr Ala Cys Asp
Cys Gln Asn Pro Asn Val Asp Leu Phe Cys Cys Pro Glu Cys Asp Thr
Arg Val Thr Ser Gln Cys Leu Asp Gln Ser Gly Gln Lys Leu Tyr Arg
Ser Gly Asp Asn Trp Thr His Ser Cys Gln Gln Cys Arg Cys Leu Glu
Gly Glu Ala Asp Cys Trp Pro Leu Ala Cys Pro Ser Leu Ser Cys Glu
Tyr Thr Ala Ile Phe Glu Gly Glu Cys Cys Pro Arg Cys Val Ser Asp
Pro Cys Leu Ala Asp Asn Ile Ala Tyr Asp Ile Arg Lys Thr Cys Leu
Asp Ser Ser Gly Ile Ser Arg Leu Ser Gly Ala Val Trp Thr Met Ala
Gly Ser Pro Cys Thr Thr Cys Gln Cys Lys Asn Gly Arg Val Cys Cys
Ser Val Asp Leu Val Cys Leu Glu Asn Asn

Rattus norvegicus NELL1 nucleotide sequence (SEQ ID NO: 11) and translated
amino acid sequence (SEQ ID NO: 12)
aagcactggt ttcttgttag cgttggtgcg ccctgcttgg cggggggttct ccggagcg         58 atg ccg atg gat gtg att tta gtt ttg tgg ttc tgt gta tgc acc gcc        106
Met Pro Met Asp Val Ile Leu Val Leu Trp Phe Cys Val Cys Thr Ala agg aca gtg ttg ggc ttt ggg atg gac cct gac ctt cag ctg gac atc        154
Arg Thr Val Leu Gly Phe Gly Met Asp Pro Asp Leu Gln Leu Asp Ile atc tca gag ctc gac ctg gtg aac acc acc ctg gga gtc acg cag gtg        202
Ile Ser Glu Leu Asp Leu Val Asn Thr Thr Leu Gly Val Thr Gln Val gct gga ctg cac aac gcc agt aaa gca ttt cta ttt caa gat gta cag        250
Ala Gly Leu His Asn Ala Ser Lys Ala Phe Leu Phe Gln Asp Val Gln aga gag atc cat tcg gcc cct cac gtg agt gag aag ctg atc cag cta        298
Arg Glu Ile His Ser Ala Pro His Val Ser Glu Lys Leu Ile Gln Leu ttc cgg aat aag agc gag ttc acc ttt ttg gct aca gtg cag cag aaa        346
Phe Arg Asn Lys Ser Glu Phe Thr Phe Leu Ala Thr Val Gln Gln Lys cca tcc acc tca ggg gtg ata ctg tcc atc cgg gag ctg gag cac agc        394
Pro Ser Thr Ser Gly Val Ile Leu Ser Ile Arg Glu Leu Glu His Ser tat ttt gaa ctg gag agc agt ggc cca aga gaa gag ata cgc tac cat        442
Tyr Phe Glu Leu Glu Ser Ser Gly Pro Arg Glu Glu Ile Arg Tyr His tac ata cat ggt gga aag ccc agg act gag gcc ctt ccc tac cgc atg        490
Tyr Ile His Gly Gly Lys Pro Arg Thr Glu Ala Leu Pro Tyr Arg Met
```

```
gca gac gga caa tgg cac aag gtc gcg ctg tca gtg agc gcc tct cac       538
Ala Asp Gly Gln Trp His Lys Val Ala Leu Ser Val Ser Ala Ser His ctc ctg ctc cac atc gac tgc aat agg att tac gag cgt gtg ata gac       586
Leu Leu Leu His Ile Asp Cys Asn Arg Ile Tyr Glu Arg Val Ile Asp cct ccg gag acc aac ctt cct cca gga agc aat ctg tgg ctt ggg caa       634
Pro Pro Glu Thr Asn Leu Pro Pro Gly Ser Asn Leu Trp Leu Gly Gln cgt aac caa aag cat ggc ttt ttc aaa gga atc atc caa gat ggt aag       682
Arg Asn Gln Lys His Gly Phe Phe Lys Gly Ile Ile Gln Asp Gly Lys atc atc ttc atg ccg aat ggt ttc atc aca cag tgt ccc aac ctc aat       730
Ile Ile Phe Met Pro Asn Gly Phe Ile Thr Gln Cys Pro Asn Leu Asn cgc act tgc cca aca tgc agt gac ttc ctg agc ctg gtt caa gga ata       778
Arg Thr Cys Pro Thr Cys Ser Asp Phe Leu Ser Leu Val Gln Gly Ile atg gat ttg caa gag ctt ttg gcc aag atg act gca aaa ctg aat tat       826
Met Asp Leu Gln Glu Leu Leu Ala Lys Met Thr Ala Lys Leu Asn Tyr gca gag acg aga ctt ggt caa ctg gaa aat tgc cac tgt gag aag acc       874
Ala Glu Thr Arg Leu Gly Gln Leu Glu Asn Cys His Cys Glu Lys Thr tgc caa gtg agt ggg ctg ctc tac agg gac caa gac tcc tgg gtg gat       922
Cys Gln Val Ser Gly Leu Leu Tyr Arg Asp Gln Asp Ser Trp Val Asp ggt gac aac tgt ggg aac tgc acg tgc aaa agt ggt gcc gtg gag tgc       970
Gly Asp Asn Cys Gly Asn Cys Thr Cys Lys Ser Gly Ala Val Glu Cys cgc agg atg tcc tgt ccc ccg ctc aac tgt tcc ccg gac tca ctt cct      1018
Arg Arg Met Ser Cys Pro Pro Leu Asn Cys Ser Pro Asp Ser Leu Pro gtg cac att tcc ggc cag tgt tgt aaa gtt tgc aga cca aaa tgt atc      1066
Val His Ile Ser Gly Gln Cys Cys Lys Val Cys Arg Pro Lys Cys Ile tat gga gga aaa gtt ctt gct gag ggc cag cgg att tta acc aag acc      1114
Tyr Gly Gly Lys Val Leu Ala Glu Gly Gln Arg Ile Leu Thr Lys Thr tgc cgg gaa tgt cga ggt gga gtc ttg gta aaa atc aca gaa gct tgc      1162
Cys Arg Glu Cys Arg Gly Gly Val Leu Val Lys Ile Thr Glu Ala Cys cct cct ttg aac tgc tca gca aag gat cat att ctt cca gag aat cag      1210
Pro Pro Leu Asn Cys Ser Ala Lys Asp His Ile Leu Pro Glu Asn Gln tgc tgc agg gtc tgc cca ggt cat aac ttc tgt gca gaa gca cct aag      1258
Cys Cys Arg Val Cys Pro Gly His Asn Phe Cys Ala Glu Ala Pro Lys tgc gga gaa aac tcg gaa tgc aaa aat tgg aat aca aaa gca acc tgt      1306
Cys Gly Glu Asn Ser Glu Cys Lys Asn Trp Asn Thr Lys Ala Thr Cys gag tgc aag aat gga tac atc tct gtc cag ggc aac tct gca tac tgt      1354
Glu Cys Lys Asn Gly Tyr Ile Ser Val Gln Gly Asn Ser Ala Tyr Cys gaa gat att gat gag tgt gca gct aaa atg cac tat tgt cat gcc aac      1402
Glu Asp Ile Asp Glu Cys Ala Ala Lys Met His Tyr Cys His Ala Asn acc gtg tgt gtc aac ttg ccg ggg ttg tat cgc tgt gac tgc gtc cca      1450
Thr Val Cys Val Asn Leu Pro Gly Leu Tyr Arg Cys Asp Cys Val Pro ggg tac atc cgt gtg gat gac ttc tct tgt acg gag cat gat gat tgt      1498
Gly Tyr Ile Arg Val Asp Asp Phe Ser Cys Thr Glu His Asp Asp Cys ggc agc gga caa cac aac tgc gac aaa aat gcc atc tgt acc aac aca      1546
Gly Ser Gly Gln His Asn Cys Asp Lys Asn Ala Ile Cys Thr Asn Thr gtc cag gga cac agc tgc acc tgc cag ccg ggt tac gtg gga aat ggc      1594
Val Gln Gly His Ser Cys Thr Cys Gln Pro Gly Tyr Val Gly Asn Gly acc atc tgc aaa gca ttc tgt gaa gag ggt tgc aga tac gga ggt acc      1642
Thr Ile Cys Lys Ala Phe Cys Glu Glu Gly Cys Arg Tyr Gly Gly Thr tgt gtg gct cct aac aag tgt gtc tgt cct tct gga ttc acg gga agc      1690
Cys Val Ala Pro Asn Lys Cys Val Cys Pro Ser Gly Phe Thr Gly Ser cac tgt gag aaa gat att gat gaa tgc gca gag gga ttc gtt gaa tgc      1738
His Cys Glu Lys Asp Ile Asp Glu Cys Ala Glu Gly Phe Val Glu Cys
```

| | |
|---|---|
| cac aac tac tcc cgc tgt gtt aac ctg cca ggg tgg tac cac tgt gag<br>His Asn Tyr Ser Arg Cys Val Asn Leu Pro Gly Trp Tyr His Cys Glu | 1786 |
| tgc aga agc ggt ttc cat gac gat ggg acc tac tca ctg tcc ggg gag<br>Cys Arg Ser Gly Phe His Asp Asp Gly Thr Tyr Ser Leu Ser Gly Glu | 1834 |
| tcc tgc att gat atc gat gaa tgt gcc tta aga act cac act tgt tgg<br>Ser Cys Ile Asp Ile Asp Glu Cys Ala Leu Arg Thr His Thr Cys Trp | 1882 |
| aat gac tct gcc tgc atc aac tta gca gga gga ttt gac tgc ctg tgt<br>Asn Asp Ser Ala Cys Ile Asn Leu Ala Gly Gly Phe Asp Cys Leu Cys | 1930 |
| ccc tct ggg ccc tcc tgc tct ggt gac tgt ccc cac gaa gga ggg ctg<br>Pro Ser Gly Pro Ser Cys Ser Gly Asp Cys Pro His Glu Gly Gly Leu | 1978 |
| aag cat aat ggg cag gtg tgg att ctg aga gaa gac agg tgt tca gtc<br>Lys His Asn Gly Gln Val Trp Ile Leu Arg Glu Asp Arg Cys Ser Val | 2026 |
| tgt tcc tgc aag gat ggg aag ata ttc tgc cgg cgg aca gct tgt gat<br>Cys Ser Cys Lys Asp Gly Lys Ile Phe Cys Arg Arg Thr Ala Cys Asp | 2074 |
| tgc cag aat cca aat gtt gac ctt ttt tgc tgc cca gag tgc gat acc<br>Cys Gln Asn Pro Asn Val Asp Leu Phe Cys Cys Pro Glu Cys Asp Thr | 2122 |
| agg gtc acc agc caa tgt tta gat caa agt gga cag aag ctc tat cga<br>Arg Val Thr Ser Gln Cys Leu Asp Gln Ser Gly Gln Lys Leu Tyr Arg | 2170 |
| agt gga gac aac tgg acc cac agc tgc cag cag tgc cga tgt ctg gaa<br>Ser Gly Asp Asn Trp Thr His Ser Cys Gln Gln Cys Arg Cys Leu Glu | 2218 |
| gga gag gca gac tgc tgg cct ctg gct tgc cct agt ttg ggc tgt gaa<br>Gly Glu Ala Asp Cys Trp Pro Leu Ala Cys Pro Ser Leu Gly Cys Glu | 2266 |
| tac aca gcc atg ttt gaa ggg gag tgt tgt ccc cga tgt gtc agt gac<br>Tyr Thr Ala Met Phe Glu Gly Glu Cys Cys Pro Arg Cys Val Ser Asp | 2314 |
| ccc tgc ctg gct ggt aat att gcc tat gac atc aga aaa act tgc ctg<br>Pro Cys Leu Ala Gly Asn Ile Ala Tyr Asp Ile Arg Lys Thr Cys Leu | 2362 |
| gac agc ttt ggt gtt tcg agg ctg agc gga gcc gtg tgg aca atg gct<br>Asp Ser Phe Gly Val Ser Arg Leu Ser Gly Ala Val Trp Thr Met Ala | 2410 |
| gga tct cct tgt aca acc tgc aaa tgc aag aat ggg aga gtc tgc tgc<br>Gly Ser Pro Cys Thr Thr Cys Lys Cys Lys Asn Gly Arg Val Cys Cys | 2458 |
| tct gtg gat ctg gag tgt att gag aat aac tga agattttaaa tggactcgtc<br>Ser Val Asp Leu Glu Cys Ile Glu Asn Asn * | 2511 |
| acgtgagaaa atgggcaaaa tgatcatccc acctgaggaa gaagaggggc tgatttcttt | 2571 |
| ttcttttaa ccacagtcaa ttaccaaagt ctccatctga ggaaggcgtt tggattgcct | 2631 |
| ttgccacttt gctcatcctt gctgacctag tctagatgcc tgcagtaccg tgcatttcgg | 2691 |
| tcgatggttg ttgagtctca gtgttgtaaa tcgcatttcc ctcgtcagat catttacaga | 2751 |
| tacatttaaa ggggttccat gataaatgtt aatgtaactt tgtttatttt tgtgtactga | 2811 |
| cataatagag acttggcacc atttatttat ttttcttgat ttttggatca aattctaaaa | 2871 |
| ataaagttgc ctgttgcgaa aaaaaaaaaa aaaaaaaaaa aaaa | 2915 |

*Rattus norvegicus* NELL1 amino acid sequence (SEQ ID NO: 12)
Met Pro Met Asp Val Ile Leu Val Leu Trp Phe Cys Val Cys Thr Ala
Arg Thr Val Leu Gly Phe Gly Met Asp Pro Asp Leu Gln Leu Asp Ile
Ile Ser Glu Leu Asp Leu Val Asn Thr Thr Leu Gly Val Thr Gln Val
Ala Gly Leu His Asn Ala Ser Lys Ala Phe Leu Phe Gln Asp Val Gln
Arg Glu Ile His Ser Ala Pro His Val Ser Glu Lys Leu Ile Gln Leu
Phe Arg Asn Lys Ser Glu Phe Thr Phe Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Pro Arg Glu Glu Ile Arg Tyr His
Tyr Ile His Gly Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Ile Asp Cys Asn Arg Ile Tyr Glu Arg Val Ile Asp
Pro Pro Glu Thr Asn Leu Pro Pro Gly Ser Asn Leu Trp Leu Gly Gln
Arg Asn Gln Lys His Gly Phe Phe Lys Gly Ile Ile Gln Asp Gly Lys
Ile Ile Phe Met Pro Asn Gly Phe Ile Thr Gln Cys Pro Asn Leu Asn
Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr

```
Ala Glu Thr Arg Leu Gly Gln Leu Glu Asn Cys His Cys Glu Lys Thr
Cys Gln Val Ser Gly Leu Leu Tyr Arg Asp Gln Asp Ser Trp Val Asp
Gly Asp Asn Cys Gly Asn Cys Thr Cys Lys Ser Gly Ala Val Glu Cys
Arg Arg Met Ser Cys Pro Pro Leu Asn Cys Ser Pro Asp Ser Leu Pro
Val His Ile Ser Gly Gln Cys Cys Lys Val Cys Arg Pro Lys Cys Ile
Tyr Gly Gly Lys Val Leu Ala Glu Gly Gln Arg Ile Leu Thr Lys Thr
Cys Arg Glu Cys Arg Gly Gly Val Leu Val Lys Ile Thr Glu Ala Cys
Pro Pro Leu Asn Cys Ser Ala Lys Asp His Ile Leu Pro Glu Asn Gln
Cys Cys Arg Val Cys Pro Gly His Asn Phe Cys Ala Glu Ala Pro Lys
Cys Gly Glu Asn Ser Glu Cys Lys Asn Trp Asn Thr Lys Ala Thr Cys
Glu Cys Lys Asn Gly Tyr Ile Ser Val Gln Gly Asn Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Asp Cys
Gly Ser Gly Gln His Asn Cys Asp Lys Asn Ala Ile Cys Thr Asn Thr
Val Gln Gly His Ser Cys Thr Cys Gln Pro Gly Tyr Val Gly Asn Gly
Thr Ile Cys Lys Ala Phe Cys Glu Glu Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ala Glu Gly Phe Val Glu Cys
His Asn Tyr Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Gly Phe Asp Cys Leu Cys
Pro Ser Gly Pro Ser Cys Ser Gly Asp Cys Pro His Glu Gly Gly Leu
Lys His Asn Gly Gln Val Trp Ile Leu Arg Glu Asp Arg Cys Ser Val
Cys Ser Cys Lys Asp Gly Lys Ile Phe Cys Arg Arg Thr Ala Cys Asp
Cys Gln Asn Pro Asn Val Asp Leu Phe Cys Cys Pro Glu Cys Asp Thr
Arg Val Thr Ser Gln Cys Leu Asp Gln Ser Gly Gln Lys Leu Tyr Arg
Ser Gly Asp Asn Trp Thr His Ser Cys Gln Gln Cys Arg Cys Leu Glu
Gly Glu Ala Asp Cys Trp Pro Leu Ala Cys Pro Ser Leu Gly Cys Glu
Tyr Thr Ala Met Phe Glu Gly Glu Cys Cys Pro Arg Cys Val Ser Asp
Pro Cys Leu Ala Gly Asn Ile Ala Tyr Asp Ile Arg Lys Thr Cys Leu
Asp Ser Phe Gly Val Ser Arg Leu Ser Gly Ala Val Trp Thr Met Ala
Gly Ser Pro Cys Thr Thr Cys Lys Cys Lys Asn Gly Arg Val Cys Cys
Ser Val Asp Leu Glu Cys Ile Glu Asn Asn

Felis catus NELL1 isoform 1 amino acid sequence (SEQ ID NO: 13)
Met Pro Arg Asp Val Ile Leu Val Val Trp Phe Cys Val Cys Thr Ala
Arg Thr Val Val Gly Phe Gly Thr Asp Pro Asp Leu Val Asp Asp Ile
Ile Ala Glu Leu Asp Leu Val Asn Thr Thr Ala Gly Val Thr Gln Val
Ser Gly Leu His Asn Ala Ser Lys Ala Tyr Leu Phe Gln Glu Thr Glu
Arg Glu Ile His Ala Ala Pro His Val Ser Glu Lys Leu Ile Gln Leu
Phe Arg Asn Lys Ser Glu Phe Ser Phe Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Leu Arg Asp Glu Ile Arg Tyr His
Tyr Ile His Asn Gly Lys Pro Arg Thr Glu Ala Leu Pro Tyr Arg Met
Ala Asp Gly Gln Trp His Lys Val Ala Leu Ser Ile Ser Ala Ser His
Leu Leu Leu His Val Asp Cys Asn Arg Ile Tyr Glu Arg Val Ile Asp
Pro Pro Glu Thr Asn Leu Pro Pro Gly Ser Asn Val Trp Leu Gly Gln
Arg Asn Gln Lys His Gly Leu Phe Lys Gly Ile Ile Gln Asp Gly Lys
Ile Ile Phe Met Pro Asn Gly Tyr Ile Thr Gln Cys Pro Asn Leu Asn
Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Asn Gln Leu Glu Asn Cys His Cys Glu Lys Thr
Cys Gln Val Ser Gly Leu Leu Tyr Arg Asp Gln Asp Ser Trp Val Asp
Gly Asp His Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ala Gly Gln Cys Cys Lys Val Cys Arg Pro Lys Cys Ile
Tyr Gly Gly Lys Val Leu Ala Glu Gly Gln Arg Ile Leu Thr Lys Ser
Cys Arg Glu Cys Arg Gly Gly Val Leu Val Lys Ile Thr Asp Ala Cys
Pro Pro Leu Asn Cys Ser Glu Lys Asp His Ile Leu Pro Glu Asn Gln
Cys Cys Ser Val Cys Arg Gly His Asn Phe Cys Ala Glu Gly Pro Thr
Cys Gly Glu Asn Ser Glu Cys Lys Asn Trp Asn Thr Lys Ala Thr Cys
Glu Cys Lys Asn Gly Tyr Ile Ser Val Asn Gly Asp Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr
Val Gln Gly His Ser Cys Thr Cys Lys Pro Gly Tyr Val Gly Asn Gly
Thr Ile Cys Arg Ala Phe Cys Gln Glu Gly Cys Arg Tyr Gly Gly Thr
Cys Val Ser Pro Asn Lys Cys Val Cys Pro Ser Gly Phe Thr Gly Ser
His Cys Glu Lys Asp Ile Asp Glu Cys Thr Glu Gly Ile Ile Glu Cys
His Asn His Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Gly Phe Asp Cys Leu Cys
Pro Ser Gly Pro Ser Cys Ser Gly Asp Cys Pro His Glu Gly Gly Leu
Lys Arg Asn Gly Gln Val Trp Thr Leu Lys Glu Asp Arg Cys Ser Val
Cys Ser Cys Lys Asp Gly Lys Ile Phe Cys Arg Arg Thr Ala Cys Asp
```

-continued

```
Cys Gln Asn Pro Ser Val Asp Leu Phe Cys Cys Pro Glu Cys Asp Thr
Arg Val Thr Ser Gln Cys Leu Asp Gln Asn Gly His Lys Leu Tyr Arg
Ser Gly Asp Asn Trp Thr His Ser Cys Gln Gln Cys Arg Cys Leu Glu
Gly Glu Val Asp Cys Trp Pro Leu Thr Cys Pro Asn Leu Ser Cys Glu
Tyr Thr Ala Met Leu Glu Gly Glu Cys Cys Pro Arg Cys Val Ser Asp
Pro Cys Leu Ala Asp Asn Ile Ala Tyr Asp Ile Arg Lys Thr Cys Leu
Cys Gln Val Ser Gly Leu Leu Tyr Arg Asp Gln Asp Ser Trp Val Asp
Gly Asp His Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ala Gly Gln Cys Cys Lys Val Cys Arg Pro Lys Cys Ile
Tyr Gly Gly Lys Val Leu Ala Glu Gly Gln Arg Ile Leu Thr Lys Ser
Cys Arg Glu Cys Arg Gly Gly Val Leu Val Lys Ile Thr Asp Ala Cys
Pro Pro Leu Asn Cys Ser Glu Lys Asp His Ile Leu Pro Glu Asn Gln
Cys Cys Ser Val Cys Arg Gly His Asn Phe Cys Ala Glu Gly Pro Thr
Cys Gly Glu Asn Ser Glu Cys Lys Asn Trp Asn Thr Lys Ala Thr Cys
Glu Cys Lys Asn Gly Tyr Ile Ser Val Gln Gly Asp Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr
Val Gln Gly His Ser Cys Thr Cys Lys Pro Gly Tyr Val Gly Asn Gly
Thr Ile Cys Arg Ala Phe Cys Gln Glu Gly Cys Arg Tyr Gly Gly Thr
Cys Val Ser Pro Asn Lys Cys Val Cys Pro Ser Gly Phe Thr Gly Ser
His Cys Glu Lys Asp Ile Asp Glu Cys Ala Leu Arg Thr His Thr Cys
Trp Asn Asp Ser Ala Cys Ile Asn Leu Ala Gly Gly Phe Asp Cys Leu
Cys Pro Ser Gly Pro Ser Cys Ser Gly Asp Cys Pro His Glu Gly Gly
Leu Lys Arg Asn Gly Gln Val Trp Thr Leu Lys Glu Asp Arg Cys Ser
Val Cys Ser Cys Lys Asp Gly Lys Ile Phe Cys Arg Arg Thr Ala Cys
Asp Cys Gln Asn Pro Ser Val Asp Leu Phe Cys Cys Pro Glu Cys Asp
Thr Arg Val Thr Ser Gln Cys Leu Asp Gln Asn Gly His Lys Leu Tyr
Arg Ser Gly Asp Asn Trp Thr His Ser Cys Gln Gln Cys Arg Cys Leu
Glu Gly Glu Val Asp Cys Trp Pro Leu Thr Cys Pro Asn Leu Ser Cys
Glu Tyr Thr Ala Met Leu Glu Gly Glu Cys Cys Pro Arg Cys Val Ser
Asp Pro Cys Leu Ala Asp Asn Ile Ala Tyr Asp Ile Arg Lys Thr Cys
Leu Asp Ser Tyr Gly Ile Ser Arg Leu Ser Gly Ala Val Trp Thr Met
Ala Gly Ser Pro Cys Thr Thr Cys Lys Cys Lys Asn Gly Ser Val Cys
Cys Ser Val Asp Leu Glu Cys Leu His Asn Asn
```

*Felis catus* NELL1 isoform 2 amino acid sequence (SEQ ID NO: 14)
```
Met Pro Arg Asp Val Ile Leu Val Val Trp Phe Cys Val Cys Thr Ala
Arg Thr Val Leu Gly Phe Gly Met Asp Pro Asp Leu Gln Leu Asp Ile
Ile Ser Glu Leu Asp Leu Val Asn Thr Thr Leu Gly Val Thr Gln Val
Ala Gly Leu His Asn Ala Ser Lys Ala Phe Leu Phe Gln Asp Val Val
Arg Glu Ile His Ser Ala Pro His Val Ser Glu Lys Leu Ile Gln Leu
Phe Arg Asn Lys Ser Glu Phe Thr Phe Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Pro Arg Glu Val Ile Arg Tyr His
Tyr Ile His Gly Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Ile Asp Cys Asn Arg Ile Tyr Glu Arg Val Ile Asp
Pro Pro Glu Thr Asn Leu Pro Pro Gly Ser Asn Leu Trp Leu Gly Gln
Arg Asn Gln Lys His Gly Phe Phe Lys Gly Ile Ile Gln Asp Gly Lys
Ile Ile Phe Met Pro Asn Gly Phe Ile Thr Gln Cys Pro Asn Leu Asn
Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Gly Gln Leu Glu Asn Cys His Cys Glu Lys Thr
Cys Gln Val Ser Gly Leu Leu Tyr Arg Asp Gln Asp Ser Trp Val Asp
Gly Asp Asn Cys Gly Asn Cys Thr Cys Lys Ser Gly Ala Val Glu Cys
Arg Arg Met Ser Cys Pro Pro Leu Asn Cys Ser Pro Asp Ser Leu Pro
Val His Ile Ser Gly Gln Cys Cys Lys Val Cys Arg Pro Lys Cys Ile
Tyr Gly Gly Lys Val Leu Ala Glu Gly Gln Arg Ile Leu Thr Lys Thr
Cys Arg Glu Cys Arg Gly Gly Val Leu Val Lys Ile Thr Glu Ala Cys
Pro Pro Leu Asn Cys Ser Ala Lys Asp His Ile Leu Pro Glu Asn Gln
Cys Cys Arg Val Cys Pro Gly His Asn Phe Cys Ala Glu Ala Pro Lys
Cys Gly Glu Asn Ser Glu Cys Lys Asn Trp Asn Thr Lys Ala Thr Cys
Glu Cys Lys Asn Gly Tyr Ile Ser Val Gln Gly Asn Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Asp Cys
Gly Ser Gly Gln His Asn Cys Asp Lys Asn Ala Ile Cys Thr Asn Thr
Val Gln Gly His Ser Cys Thr Cys Gln Pro Gly Tyr Val Gly Asn Gly
Thr Ile Cys Lys Ala Phe Cys Glu Glu Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ala Glu Gly Phe Val Glu Cys
His Asn Tyr Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Gly Phe Asp Cys Leu Cys
Pro Ser Gly Pro Ser Cys Ser Gly Asp Cys Pro His Glu Gly Gly Leu
```

Lys His Asn Gly Gln Val Trp Ile Leu Arg Glu Asp Arg Cys Ser Val
Cys Ser Cys Lys Asp Gly Lys Ile Phe Cys Arg Arg Thr Ala Cys Asp
Cys Gln Asn Pro Asn Val Asp Leu Phe Cys Cys Pro Glu Cys Asp Thr
Arg Val Thr Ser Gln Cys Leu Asp Gln Ser Gly Gln Lys Leu Tyr Arg
Ser Gly Asp Asn Trp Thr His Ser Cys Gln Gln Cys Arg Cys Leu Glu
Gly Glu Ala Asp Cys Trp Pro Leu Ala Cys Pro Ser Leu Gly Cys Glu
Tyr Thr Ala Met Phe Glu Gly Glu Cys Cys Pro Arg Cys Val Ser Asp
Pro Cys Leu Ala Gly Asn Ile Ala Tyr Asp Ile Arg Lys Thr Cys Leu
Asp Ser Phe Gly Val Ser Arg Leu Ser Gly Ala Val Trp Thr Met Ala
Gly Ser Pro Cys Thr Thr Cys Lys Cys Lys Asn Gly Arg Val Cys Cys
Ser Val Asp Leu Glu Cys Ile Glu Asn Asn

*Canis lupis* familiaris NELL1 amino acid sequence (SEQ ID NO: 15)
Met Thr Ser Thr Ser Phe Leu Leu Trp Leu Gly Cys Val His Asn Thr
Lys Phe Pro Phe Pro Leu Val Leu Val Thr Arg Ala Ile Val Val Val
Val Val Glu Val Val Gly Val Gly Ser Pro Gly Val Arg Ile Arg Ser
Ser Gln Leu Glu Asn Cys His Cys Glu Lys Thr Cys Gln Val Ser Gly
Leu Leu Tyr Arg Asp Gln Asp Ser Trp Val Asp Gly His Cys Arg
Asn Cys Thr Cys Lys Gly Gly Ala Val Glu Cys Arg Arg Met Ser Cys
Pro Pro Leu Asn Cys Ser Pro Asp Ser Leu Pro Val His Ile Ala Gly
Gln Cys Cys Lys Val Cys Arg Pro Lys Cys Ile Tyr Gly Gly Arg Val
Leu Ala Glu Gly Gln Arg Ile Leu Thr Lys Ser Cys Arg Glu Cys Arg
Gly Gly Val Leu Val Lys Ile Thr Asp Ala Cys Pro Pro Leu Asn Cys
Ser Glu Lys Asp His Ile Leu Pro Glu Asn Gln Cys Cys Ser Val Cys
Arg Gly His Asn Phe Cys Ala Glu Gly Pro Lys Cys Gly Glu Asn Ser
Glu Cys Lys Asn Trp Asn Thr Lys Ala Thr Cys Glu Cys Lys Asn Gly
Tyr Ile Ser Val Gln Gly Asp Ser Ala Tyr Cys Glu Asp Ile Asp Glu
Cys Ala Ala Lys Met His Tyr Cys His Ala Asn Thr Val Cys Val Asn
Leu Pro Gly Leu Tyr Arg Cys Asp Cys Val Pro Gly Tyr Ile Arg Val
Asp Asp Phe Ser Cys Thr Glu His Asp Glu Cys Gly Ser Gly Gln His
Asn Cys Asp Glu Asn Ala Ile Cys Thr Asn Thr Val Arg Gly His Ser
Cys Thr Cys Lys Pro Gly Tyr Val Gly Asn Gly Thr Ile Cys Arg Ala
Phe Cys Gln Glu Gly Cys Arg Tyr Gly Gly Ser Cys Val Ser Pro Asn
Lys Cys Val Cys Pro Ser Gly Phe Thr Gly Ser His Cys Glu Lys Asp
Ile Asp Glu Cys Thr Glu Gly Ile Ile Glu Cys His Asn His Ser Arg
Cys Val Asn Leu Pro Gly Trp Tyr His Cys Glu Cys Arg Ser Gly Phe
His Asp Asp Gly Thr Tyr Ser Leu Ser Gly Glu Ser Cys Ile Asp Ile
Asp Glu Cys Ala Leu Arg Thr His Thr Cys Trp Asn Asp Ser Ala Cys
Ile Asn Leu Ala Gly Gly Phe Asp Cys Leu Cys Pro Ser Gly Pro Ser
Cys Ser Gly Asp Cys Pro His Glu Gly Gly Leu Lys Arg Asn Gly Gln
Val Trp Thr Leu Lys Glu Asp Arg Cys Ser Val Cys Ser Cys Lys Asp
Gly Lys Ile Leu Cys Arg Arg Thr Ala Cys Asp Cys Gln Asn Pro Ser
Val Asp Leu Phe Cys Cys Pro Glu Cys Asp Thr Arg Val Thr Ser Gln
Cys Leu Asp Gln Asn Gly His Lys Leu Tyr Arg Ser Gly Asp Asn Trp
Thr His Ser Cys Gln Gln Cys Arg Cys Leu Glu Gly Glu Val Asp Cys
Trp Pro Leu Thr Cys Pro Asn Leu Ser Cys Glu Tyr Thr Ala Ile Leu
Glu Gly Glu Cys Cys Pro Arg Cys Val Ser Asp Pro Cys Leu Ala Asp
Asn Ile Ala Tyr Asp Ile Arg Lys Thr Cys Leu Asp Ser Tyr Gly Ile
Gly Asp His Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ala Gly Gln Cys Cys Lys Val Cys Arg Pro Lys Cys Ile
Tyr Gly Gly Lys Val Leu Ala Glu Gly Gln Arg Ile Leu Ser Lys Asn
Cys Gln Glu Cys Arg Gly Gly Val Leu Val Lys Ile Thr Glu Ala Cys
Pro Leu Leu Asn Cys Ser Glu Lys Asp His Ile Leu Pro Glu Asn Gln
Cys Cys Ser Val Cys Arg Gly His Asn Phe Cys Ala Glu Gly Pro Lys
Cys Gly Glu Asn Ser Glu Cys Lys Asn Trp Asn Thr Lys Ala Thr Cys
Glu Cys Lys Asn Gly Tyr Ile Ser Val Gln Gly Asp Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Asp Cys
Gly Ser Gly Gln His Asn Cys Asp Glu Asn Ala Ile Cys Thr Asn Thr
Val Gln Gly His Ser Cys Thr Cys Lys Pro Gly Tyr Val Gly Asn Gly
Thr Ile Cys Arg Ala Phe Cys Glu Glu Gly Cys Arg Tyr Gly Gly Thr
Cys Met Ala Pro Asn Lys Cys Val Cys Pro Ser Gly Phe Thr Gly Ser
His Cys Glu Lys Asp Ile Asp Glu Cys Ala Glu Gly Ile Ile Glu Cys
His Ser His Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Val Asp Ile Asp Glu Cys Ala Leu Thr His Thr Cys Trp
Asn Asp Ser Ala Cys Ile Asn Leu Ala Gly Gly Phe Asp Cys Leu Cys
Pro Ser Gly Pro Ser Cys Ser Gly Asp Cys Pro His Glu Gly Gly Leu
Lys Arg Asn Gly Gln Val Trp Thr Leu Lys Glu Asp Arg Cys Ser Val
Cys Ser Cys Lys Asp Gly Lys Ile Phe Cys Arg Arg Thr Ala Cys Asp
Cys Gln Asn Pro Ser Val Asp Leu Phe Cys Cys Pro Glu Cys Asp Thr
Arg Val Thr Ser Gln Cys Leu Asp Gln Asn Gly Asn Lys Leu Tyr Arg
Ser Gly Asp Asn Trp Thr His Ser Cys Gln Gln Cys Arg Cys Leu Glu
Gly Glu Val Asp Cys Trp Pro Leu Thr Cys Pro Ser Leu Ser Cys Glu
Tyr Thr Thr Ile Leu Glu Gly Glu Cys Cys Pro Arg Cys Val Ser Asp
Pro Cys Leu Ala Asp Asn Ile Ala Tyr Asp Ile Arg Lys Thr Cys Leu
Asp Ser Tyr Gly Leu Ser Arg Leu Ser Gly Ser Val Trp Thr Met Ala

```
Gly Ser Pro Cys Thr Thr Cys Lys Cys Lys Asn Gly Ser Val Cys Cys
Ser Val Asp Leu Glu Cys Leu His Asn Asn
```

*Ovis aries* NELL1 amino acid sequence (SEQ ID NO: 16)
```
Met Pro Met Asp Val Ile Leu Val Leu Trp Phe Cys Val Cys Thr Ala
Arg Thr Val Leu Gly Phe Gly Met Asp Pro Asp Leu Gln Leu Asp Ile
Ile Ser Glu Leu Asp Leu Val Asn Thr Thr Leu Gly Val Thr Gln Val
Ala Gly Leu His Asn Ala Ser Lys Ala Phe Leu Phe Gln Asp Val Gln
Arg Glu Ile His Ser Ala Pro His Val Ser Glu Lys Leu Ile Gln Leu
Phe Arg Asn Lys Ser Glu Phe Thr Phe Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Pro Arg Glu Glu Ile Arg Tyr His
Tyr Ile His Gly Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Ile Asp Cys Asn Arg Ile Tyr Glu Arg Val Ile Asp
Pro Pro Glu Thr Asn Leu Pro Pro Gly Ser Asn Leu Trp Leu Gly Gln
Arg Asn Gln Lys His Gly Phe Phe Lys Gly Ile Ile Gln Asp Gly Lys
Ile Ile Phe Met Pro Asn Gly Phe Ile Thr Gln Cys Pro Asn Leu Asn
Arg Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Gly Gln Leu Glu Asn Cys His Cys Glu Lys Thr
Cys Gln Val Ser Gly Leu Leu Tyr Arg Asp Gln Asp Ser Trp Val Asp
Gly Asp Asn Cys Gly Asn Cys Thr Cys Lys Ser Gly Ala Val Glu Cys
Arg Arg Met Ser Cys Pro Pro Leu Asn Cys Ser Pro Asp Ser Leu Pro
Val His Ile Ser Gly Gln Cys Cys Lys Val Cys Arg Pro Lys Cys Ile
Tyr Gly Gly Lys Val Leu Ala Glu Gly Gln Arg Ile Leu Thr Lys Thr
Cys Arg Glu Cys Arg Gly Gly Val Leu Val Lys Ile Thr Glu Ala Cys
Pro Pro Leu Asn Cys Ser Ala Lys Asp His Ile Leu Pro Glu Asn Gln
Cys Cys Arg Val Cys Pro Gly His Asn Phe Cys Ala Glu Ala Pro Lys
Cys Gly Glu Asn Ser Glu Cys Lys Asn Trp Asn Thr Lys Ala Thr Cys
Glu Cys Lys Asn Gly Tyr Ile Ser Val Gln Gly Asn Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Asp Cys
Gly Ser Gly Gln His Asn Cys Asp Lys Asn Ala Ile Cys Thr Asn Thr
Val Gln Gly His Ser Cys Thr Cys Gln Pro Gly Tyr Val Gly Asn Gly
Thr Ile Cys Lys Ala Phe Cys Glu Glu Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ala Glu Gly Phe Val Glu Cys
His Asn Tyr Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Phe Asp Arg Cys Leu Cys
Pro Ser Gly Pro Ser Cys Ser Gly Asp Cys Pro His Glu Gly Gly Leu
Lys His Asn Gly Gln Val Trp Ile Leu Arg Glu Asp Arg Cys Ser Val
Cys Ser Cys Lys Asp Gly Lys Ile Phe Cys Arg Arg Thr Ala Cys Asp
Cys Gln Asn Pro Asn Val Asp Leu Phe Cys Cys Pro Glu Cys Asp Thr
Arg Val Thr Ser Gln Cys Leu Asp Gln Ser Gly Gln Lys Leu Tyr Arg
Ser Gly Asp Asn Trp Thr His Ser Cys Gln Gln Cys Arg Cys Leu Glu
Gly Glu Ala Asp Cys Trp Pro Leu Ala Cys Pro Ser Leu Gly Cys Glu
Tyr Thr Ala Met Phe Glu Gly Glu Cys Cys Pro Arg Cys Val Ser Asp
Pro Cys Leu Ala Gly Asn Ile Ala Tyr Asp Ile Arg Lys Thr Cys Leu
Asp Ser Phe Gly Val Ser Arg Leu Ser Gly Ala Val Trp Thr Met Ala
Gly Ser Pro Cys Thr Thr Cys Lys Cys Lys Asn Gly Arg Val Cys Cys
Ser Val Asp Leu Glu Cys Ile Glu Asn Asn
```

*Homo sapiens* NELL1 fragment amino acid sequence (SEQ ID NO: 17)
```
Phe Gly Met Asp Pro Asp Leu Gln Met Asp Ile
Val Thr Glu Leu Asp Leu Val Asn Thr Thr Leu Gly Val Ala Gln Val
Ser Gly Met His Asn Ala Ser Lys Ala Phe Leu Phe Gln Asp Ile Glu
Arg Glu Ile His Ala Ala Pro His Val Ser Glu Lys Leu Ile Gln Leu
Phe Arg Asn Lys Ser Glu Phe Thr Ile Leu Ala Thr Val Gln Gln Lys
Pro Ser Thr Ser Gly Val Ile Leu Ser Ile Arg Glu Leu Glu His Ser
Tyr Phe Glu Leu Glu Ser Ser Gly Leu Arg Asp Glu Ile Arg Tyr His
Tyr Ile His Asn Gly Lys Pro Arg Thr Glu Ala Leu Pro Tyr Arg Met
Ala Asp Gly Gln Trp His Lys Val Ala Leu Ser Val Ser Ala Ser His
Leu Leu Leu His Val Asp Cys Asn Arg Ile Tyr Glu Arg Val Ile Asp
Pro Pro Asp Thr Asn Leu Pro Pro Gly Ile Asn Leu Trp Leu Gly Gln
Arg Asn Gln Lys His Gly Leu Phe Lys Gly Ile Ile Gln Asp Gly Lys
Ile Ile Phe Met Pro Asn Gly Tyr Ile Thr Gln Cys Pro Asn Leu Asn
His Thr Cys Pro Thr Cys Ser Asp Phe Leu Ser Leu Val Gln Gly Ile
Met Asp Leu Gln Glu Leu Leu Ala Lys Met Thr Ala Lys Leu Asn Tyr
Ala Glu Thr Arg Leu Ser Gln Leu Glu Asn Cys His Cys Glu Lys Thr
Cys Gln Val Ser Gly Leu Leu Tyr Arg Asp Gln Asp Ser Trp Val Asp
Gly Asp His Cys Arg Asn Cys Thr Cys Lys Ser Gly Ala Val Glu Cys
Arg Arg Met Ser Cys Pro Pro Leu Asn Cys Ser Pro Asp Ser Leu Pro
Val His Ile Ala Gly Gln Cys Cys Lys Val Cys Arg Pro Lys Cys Ile
Tyr Gly Gly Lys Val Leu Ala Glu Gly Gln Arg Ile Leu Thr Lys Ser
Cys Arg Glu Cys Arg Gly Gly Val Leu Val Lys Ile Thr Glu Met Cys
```

-continued

```
Pro Pro Leu Asn Cys Ser Glu Lys Asp His Ile Leu Pro Glu Asn Gln
Cys Cys Arg Val Cys Arg Gly His Asn Phe Cys Ala Glu Gly Pro Lys
Cys Gly Glu Asn Ser Glu Cys Lys Asn Trp Asn Thr Lys Ala Thr Cys
Glu Cys Lys Ser Gly Tyr Ile Ser Val Gln Gly Asp Ser Ala Tyr Cys
Glu Asp Ile Asp Glu Cys Ala Ala Lys Met His Tyr Cys His Ala Asn
Thr Val Cys Val Asn Leu Pro Gly Leu Tyr Arg Cys Asp Cys Val Pro
Gly Tyr Ile Arg Val Asp Asp Phe Ser Cys Thr Glu His Asp Glu Cys
Gly Ser Gly Gln His Asn Cys Asp Glu Asn Ala Ile Cys Thr Asn Thr
Val Gln Gly His Ser Cys Thr Cys Lys Pro Gly Tyr Val Gly Asn Gly
Thr Ile Cys Arg Ala Phe Cys Glu Glu Gly Cys Arg Tyr Gly Gly Thr
Cys Val Ala Pro Asn Lys Cys Val Cys Pro Ser Gly Phe Thr Gly Ser
His Cys Glu Lys Asp Ile Asp Glu Cys Ser Glu Gly Ile Ile Glu Cys
His Asn His Ser Arg Cys Val Asn Leu Pro Gly Trp Tyr His Cys Glu
Cys Arg Ser Gly Phe His Asp Asp Gly Thr Tyr Ser Leu Ser Gly Glu
Ser Cys Ile Asp Ile Asp Glu Cys Ala Leu Arg Thr His Thr Cys Trp
Asn Asp Ser Ala Cys Ile Asn Leu Ala Gly Gly Phe Asp Cys Leu Cys
Pro Ser Gly Pro Ser Cys Ser

Equus caballus NELL1 fragment amino acid sequence (SEQ ID NO: 18)
Phe Gly Met Asp Pro Asp Leu Gln Met Asp Ile Ile Thr Glu
Leu Asp Leu Val Asn Thr Thr Leu Gly Val Thr Gln Val Ser Gly Leu
His Asn Ala Ser Lys Ala Phe Leu Phe Gln Asp Val Glu Arg Glu Ile
His Ala Ala Pro His Val Ser Glu Lys Leu Ile Gln Leu Phe Arg Asn
Lys Ser Glu Phe Thr Phe Leu Ala Thr Val Gln Gln Lys Pro Ser Thr
Ser Gly Val Ile Leu Ser Ile Arg Glu Leu Glu Asn Ser Tyr Phe Glu
Leu Glu Ser Ser Gly Leu Arg Asp Glu Ile Arg Tyr His Tyr Thr His
Lys Gly Lys Pro Arg Thr Glu Ala Leu Pro Tyr Arg Met Ala Asp Gly
Arg Trp His Lys Val Ala Leu Ser Val Ser Ala Ser His Leu Leu Leu
His Ile Asp Cys Asn Arg Ile Tyr Glu Arg Val Ile Asp Thr Pro Glu
Thr Asn Leu Pro Pro Gly Ser Asn Leu Trp Leu Gly Gln Arg Asn Asn
Lys His Gly Leu Phe Lys Gly Ile Ile Gln Asp Gly Lys Ile Ile Phe
Met Pro Asn Gly Tyr Ile Thr Gln Cys Pro Asn Leu Asn Arg Thr Cys
Pro Thr Cys Ser Asp Phe Leu Ser Leu Val Gln Gly Ile Met Asp Leu
Gln Glu Leu Leu Ala Lys Met Thr Ala Lys Leu Asn Tyr Ala Glu Thr
Arg Leu Ser Gln Leu Glu Asn Cys His Cys Glu Lys Thr Cys Gln Val
Ser Gly Leu Leu Tyr Arg Asp Gln Asp Ser Trp Val Asp Gly Asp His
Cys Arg Asn Cys Thr Cys Lys Ser Gly Ala Val Glu Cys Arg Arg Met
Ser Cys Pro Pro Leu Asn Cys Ser Pro Asp Ser Leu Pro Val His Val
Ala Gly Gln Cys Cys Lys Val Cys Arg Pro Lys Cys Ile Tyr Gly Gly
Lys Val Leu Ala Glu Gly Gln Arg Ile Leu Thr Lys Ser Cys Arg Glu
Cys Arg Gly Gly Val Leu Val Lys Ile Thr Glu Ala Cys Pro Pro Leu
Asn Cys Ser Asp Lys Asp His Ile Leu Pro Glu Asn Gln Cys Cys Ser
Val Cys Arg Gly His Asn Phe Cys Ala Glu Gly Pro Lys Cys Gly Glu
Asn Ser Glu Cys Lys Asn Trp Asn Thr Lys Ala Thr Cys Glu Cys Lys
Asn Gly Tyr Ile Ser Val Gln Gly Asp Ser Ala Tyr Cys Glu Asp Ile
Asp Glu Cys Ala Ala Lys Met His Tyr Cys Arg Ala Asn Thr Val Cys
Val Asn Leu Pro Gly Leu Tyr Arg Cys Asp Cys Val Pro Gly Tyr Ile
Arg Val Asp Asp Phe Ser Cys Thr Glu His Asp Glu Cys Gly Ser Gly
Gln His Asn Cys Asp Glu Asn Ala Ile Cys Thr Asn Thr Val Gln Gly
His Ser Cys Thr Cys Lys Pro Gly Tyr Val Gly Asn Gly Thr Ser Cys
Arg Ala Phe Cys Glu Glu Gly Cys Arg Tyr Gly Gly Thr Cys Val Ala
Pro Asn Lys Cys Val Cys Pro Ser Gly Phe Thr Gly Ser His Cys Glu
Lys Asp Ile Asp Glu Cys Thr Glu Gly Ile Ile Glu Cys His Asn His
Ser Arg Cys Val Asn Leu Pro Gly Trp Tyr His Cys Glu Cys Arg Ser
Gly Phe His Asp Asp Gly Thr Tyr Ser Leu Ser Gly Glu Ser Cys Ile
Asp Ile Asp Glu Cys Ala Leu Arg Thr His Thr Cys Trp Asn Asp Ser
Ala Cys Ile Asn Leu Ala Gly Gly Phe Asp Cys Leu Cys Pro Ser Gly
Pro Ser Cys Ser Bos taurus NELL1 amino acid sequence (SEQ ID NO: 19)
Met Ala Leu Cys Ser Phe Ser Val Val Gly Phe Gly Leu Asp Pro Asp
Leu Gln Leu Asp Ile Ile Thr Glu Leu Asp Leu Val Asn Thr Thr Leu
Gly Val Thr Gln Val Ser Gly Leu His Asn Thr Ser Lys Ala Phe Leu
Phe Gln Asp Ala Glu Arg Glu Ile His Ala Ala Pro His Val Ser Glu
Lys Leu Ile Gln Leu Phe Arg Asn Lys Ser Glu Phe Thr Phe Leu Ala
Thr Val Gln Gln Lys Pro Ser Thr Ser Gly Val Ile Leu Ser Ile Arg
Glu Leu Glu His Ser Tyr Phe Glu Leu Glu Ser Ser Gly Leu Arg Asp
Glu Ile Arg Tyr His Tyr Val His Ser Gly Arg Pro Arg Thr Glu Ala
Leu Pro Tyr Arg Leu Ala Asp Gly Gln Trp His Arg Val Ala Leu Ser
Val Ser Ala Ser His Leu Leu Leu His Ile Asp Cys Asn Arg Ile Tyr
Glu Arg Val Ile Asp Pro Pro Glu Thr Asn Leu Pro Pro Gly Ser Asn
Leu Trp Leu Gly Gln Arg Asn Gln Lys His Gly Leu Phe Lys Gly Ile
Ile Gln Asp Gly Lys Ile Ile Phe Met Pro Asn Gly Tyr Ile Thr Gln
Cys Pro Asn Leu Asn Arg Thr Cys Pro Thr Cys Ser Asp Phe Leu Ser
Leu Val Gln Gly Ile Met Asp Leu Gln Glu Leu Leu Ala Lys Met Thr
Ala Lys Leu Asn Tyr Ala Glu Thr Arg Leu Ser Gln Leu Glu Asn Cys
His Cys Glu Lys Thr Cys Gln Val Ser Gly Leu Leu Tyr Arg Asp Gln
Asp Ser Trp Val Asp Gly Asp His Cys Arg Asn Cys Thr Cys Lys Ser
Gly Ala Val Glu Cys Arg Arg Met Ser Cys Pro Pro Leu Asn Cys Ser
```

-continued

```
Pro Asp Ser Leu Pro Val His Ile Ala Gly Glu Cys Cys Lys Val Cys
Arg Pro Lys Cys Ile Tyr Gly Gly Lys Val Leu Ala Glu Gly Gln Arg
Ile Leu Ser Lys Ser Cys Gln Glu Cys Arg Gly Gly Val Leu Val Lys
Ile Thr Glu Ala Cys Pro Leu Leu Asn Cys Ser Glu Lys Asp His Ile
Leu Pro Glu Asn Gln Cys Cys Ser Val Cys Arg His Asn Phe Cys
Ala Glu Gly Pro Lys Cys Gly Glu Asn Ser Glu Cys Lys Asn Trp Asn
Thr Lys Ala Thr Cys Glu Cys Lys Asn Gly Tyr Ile Ser Val Gln Gly
Asp Ser Ala Tyr Cys Glu Asp Ile Asp Glu Cys Ala Ala Lys Met His
Tyr Cys His Ala Asn Thr Val Cys Val Asn Leu Pro Gly Leu Tyr Arg
Cys Asp Cys Val Pro Gly Tyr Ile Arg Val Asp Asp Phe Ser Cys Thr
Glu His Asp Asp Cys Gly Ser Gly Gln His Asn Cys Asp Glu Asn Ala
Ile Cys Thr Asn Thr Val Gln Gly His Ser Cys Thr Cys Lys Pro Gly
Tyr Val Gly Asn Gly Thr Ile Cys Arg Gly Met Pro Glu Val Gly Pro
Pro Arg Ala Leu Leu Asn Ser Leu Asp Leu Gly Phe Leu Ser Phe Ser
Lys Glu Ala Leu Ala Val Gly Met Ile Thr Leu Glu Gly Asn Ile Val
Ala Lys Ser Phe Thr Asp Asp Glu Thr Leu Val Glu Arg Gly Arg Glu
Lys Val Ile Ala Leu Leu Phe Ser Trp Leu His Lys Glu Lys Leu Ser
Leu Glu Asn Leu Arg Asp Ile Tyr Cys Lys Ala Asn Ser Leu Val Gly
Leu Asp His Leu Pro Gln Arg
```

EXAMPLES

The present invention, thus generally described, will be understood more readily by reference to the following Examples, which are provided by way of illustration and are not intended to be limiting of the instant invention. The Examples are not intended to represent that the experiments below are all experiments performed.

Example 1

Cloning and Expression of Recombinant Horse NELL1 Peptides

Various Nell1 polypeptides were designed based on the horse (*Equus caballus*) reference sequence: XP_001505306.1 GI: 149719523 (Aug. 14, 2013). The horse protein sequence has recently been updated in the NCBI database as XP_014597419 (Nov. 20, 2015).

The "full-length" version coding sequence begins at amino acid (aa) #3 which is the start of the signaling sequence till the last amino acid (#791) and contains all predicted conserved protein domains. Three variant NELL1 proteins were designed such that certain specific N- or C-terminal domain(s) was/were missing and the alternative form was shorter in size than the full-length version (Table 2). These four different recombinant NELL1 proteins were manufactured using a high-throughput wheat germ cell-free translation system (commercial Cell-Free System (CFS) In Vitro Wheat Germ System developed by Abnova Corporation, Taipei, Taiwan). The gene sequence was cloned in a plasmid vector that was transcribed and then translated in vitro in a wheat germ extract containing all 20 different amino acids. This protein expression system was pioneered by Yaeta Endo and later developed into a high throughput format (Madin et al. (2000) *Proc. Natl. Acad. Sci. U.S.A.* 97(2):559-564; Sawasaki et al. (2000) *Nucleic Acids Symp Ser* 44:9-10; Sawasaki et al. (2002) *Proc. Natl. Acad. Sci. U.S.A.* 99(23):14652-14657; and Endo and Sawasaki (2003) *Biotechnol. Adv.* 21(8):695-713). Purification of the products was accomplished by binding of the NELL1 protein tagged with glutathione S-transferase (GST) to an anti-GST resin. The products were eluted in 50 mM Tris-HCl, 10 mM reduced glutathione, pH 8.0.

TABLE 2

Description of recombinant horse NELL1 peptides.

| NELL1 Protein Description | Deleted Domains | MW (kDa)* | Concentration (µg/µl) | Purity (%) |
|---|---|---|---|---|
| NELL1 aa 3-791 (full-length) | None | 112.42 | 0.09 | 87.22 |
| NELL1 aa 252-791 | Entire N-terminal thrombospondin domain | 85.03 | 0.05 | 56.27 |
| NELL1 aa 3-612 | Two C-terminal von Willebrand factor C (VWC) domains | 92.73 | 0.13 | 89.44 |
| NELL1 aa 34-612 | Initial part of N-terminal thrombospondin domain and 2 C-terminal VWC domains | 89.32 | 0.17 | 65.82 |

*includes GST-tag of 26 kDa

To determine purity, 0.5 microgram protein was loaded in a lane on a 12.5% SDS-PAGE gel and stained with Coomassie Blue. BioSpectrum AC® Imaging System with software-VisionWorksLS V6.8 was employed to determine the purities by calculating the ratio of the major expected band for each protein variant relative to other minor bands. The value of concentration is the index of yield. The higher the concentration, the more yield is obtained. If a polypeptide has <0.1 µg/µl, the protein is considered difficult to produce and purify.

The full-length horse NELL1 protein (aa 3-791) has both lower concentration/yield and purity (0.09 µg/µl; 87.22%), compared to the NELL1 variant with 3-612 amino acid sequence (0.13 µg/µl; 89.44%). The other NELL1 variants (MW=85.03 kDa and MW=89.32) have very low concentration/yield and/or purity and were not deemed optimal for testing further for biological activity in vivo.

Additional independent preparations of variant and full-length NELL1 proteins were produced and utilized to check biological activity using in vitro (e.g. elution of protein from two scaffolds and wound healing scratch assays) and in vivo experiments (e.g. horse body wound healing study). Several preparations of amounts ranging from 20 micrograms-2.5 milligrams consistently yielded levels of concentration and purities similar to those obtained in the first experiment→90% for the NELL1 variant #3-612 and 85-87% for the full-length (FIGS. 2A-2D).

Example 2

Effects of NELL1 Peptide on an In Vitro Model of Tendon Injury and Repair

There are several in vitro systems that can be utilized to demonstrate the efficacy of NELL1 in tendon repair and regeneration. These strategies make use of precursor or stem cells that give rise to tendons and can show that addition of NELL1 protein stimulates proliferation, differentiation, gene expression of key genes in tendon formation and/or migration of these cells.

The effects of NELL1 in the in vitro model of tendon injury and repair as described in Nemoto et al. (2013) *J Equine Sci* 24(2):17-24 are determined as follows. Fibroblasts are obtained from tendon explants dissected and minced into pieces from the superficial digital flexor tendon of healthy adult horses at the time of slaughter. Treatment with 0.1% type I collagenase (37 degrees, 20 minutes) will degrade the collagen holding cells in the tendon ECM, thereby releasing cells. Cells are cultured on Dulbecco's Modified Eagle Medium [with 10% fetal bovine serum, 100 U/ml penicillin G, 100 microgram/ml streptomycin] at 5% $CO_2$, 37° C. to sub-confluence. Cell cultures are dispersed with 0.1% trypsin in PBS and sub-cultured close to confluence (~4 days in 12-well plates), then used for the classic scratch assay. Five parallel 0.1 mm "scratches" are made (1000 microliter blue pipette tip) in each cell culture plate, simulating a "wound gap" or injury in the cell sheet.

NELL1 protein, at varying doses, is added to three cultures per dose (15 gaps or wounds per dose measured). Three cultures are designated as negative controls. Initial doses for testing based on other in vitro studies with NELL1 are (ng/mL): 10, 31.6, 100, 316, 1000, and 3160.

The gaps are examined and measured every other day until they are closed. Data is analyzed to determined rates of closure and which treatment(s) exhibited the best and fastest healing.

The experiment described above is repeated and instead of quantitative measurements of gap closure, samples are cultured and harvested at various time points (after 0, 12, 24, 28 and 78 hrs post NELL1 treatment) for RNA extraction, cDNA synthesis and gene expression analysis. Genes that are biomarkers for tendon proliferation and migration are assessed. Examples of such genes are: Collagen 1, Collagen III, Tenascin C, and COMP.

Example 3

NELL1 Peptide Promotes Cell Migration and Wound Healing in Human Fibroblasts In Vitro The effects of two NELL1 proteins (full-length and variant 3-612aa) on cell migration and wound healing were tested and compared using in vitro models of primary human fibroblasts: adult dermal fibroblasts, type 1 diabetes dermal fibroblasts, and ligament fibroblasts. Three doses of both NELL1 proteins (full-length and variant 3-612aa) were tested on wound healings assays for each cell type using 4-6 replicates per dose: 100 ng/ml, 200 ng/ml, 300 ng/ml. Human fibroblasts were cultured in typical fibroblast growth media (FGM) supplemented with fetal bovine serum (FBS) and various growth factors. Cells in the logarithmic growing phase were cultured overnight in 96-well plates to make cell monolayers. Wound areas (750-micron wide) were generated in the middle of the cell monolayers in a consistent manner using an IncuCyte WoundMaker® 96 (Essen Bioscience, Michigan, U.S.A.). After treatment, cells were incubated and observed in an IncuCyte® Live-Cell Analysis System (Essen Bioscience, Michigan, U.S.A.). Images of cell migration and wound closure were captured using phase contrast microscopy each hour over a 24-hour period. Wound areas, cell confluence and healing rates (average velocity of cells moving into gap) were measured and data was analyzed using GraphPad Prism 7.0.

Figure 3A:
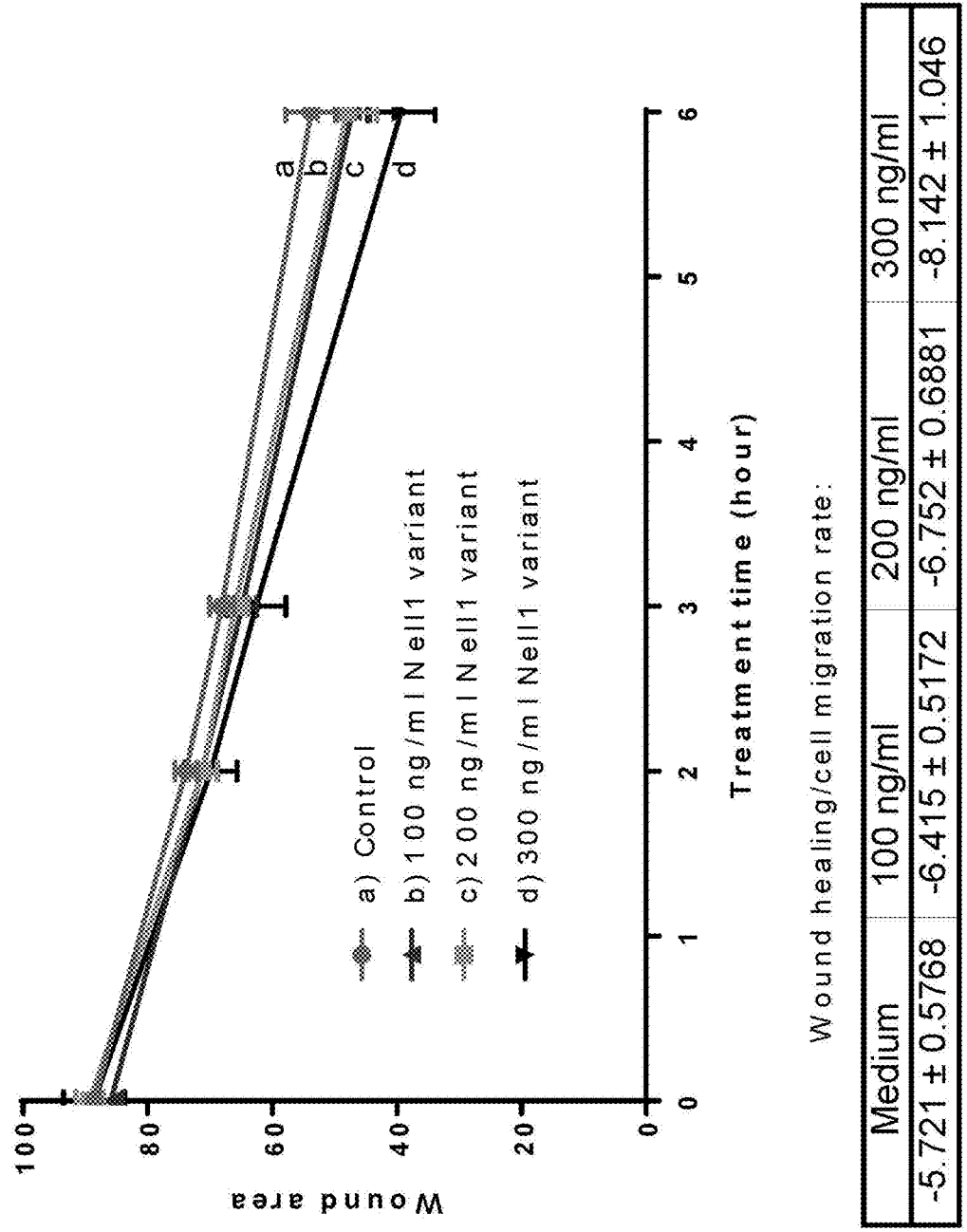
FIGS. 3A-3D depict effects of full-length NELL1 protein (aa3-791) or a NELL1 protein variant (aa3-612) on wound healing assays using diabetic dermal fibroblasts (FIGS. 3A and 3B), normal dermal fibroblasts (FIG. 3C), and normal ligament fibroblasts (FIG. 3D).
Figure 3B:
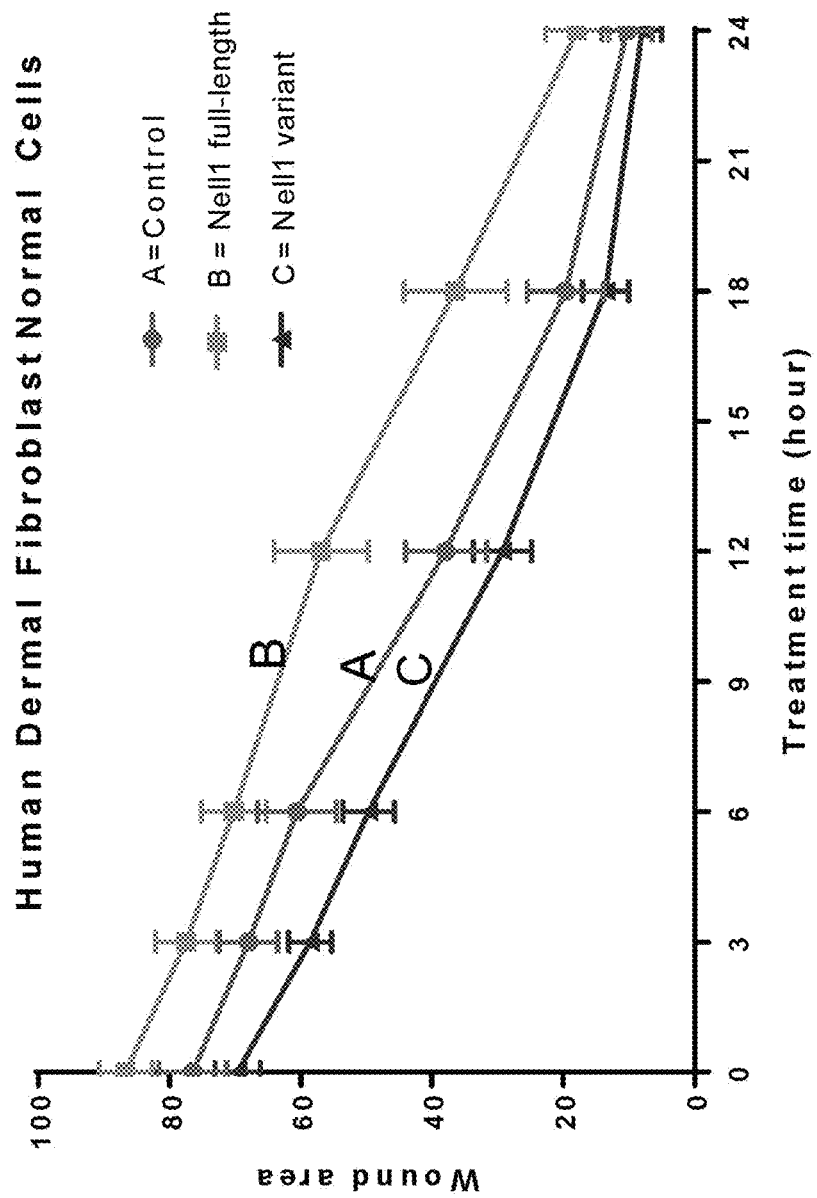
Figure 3C:
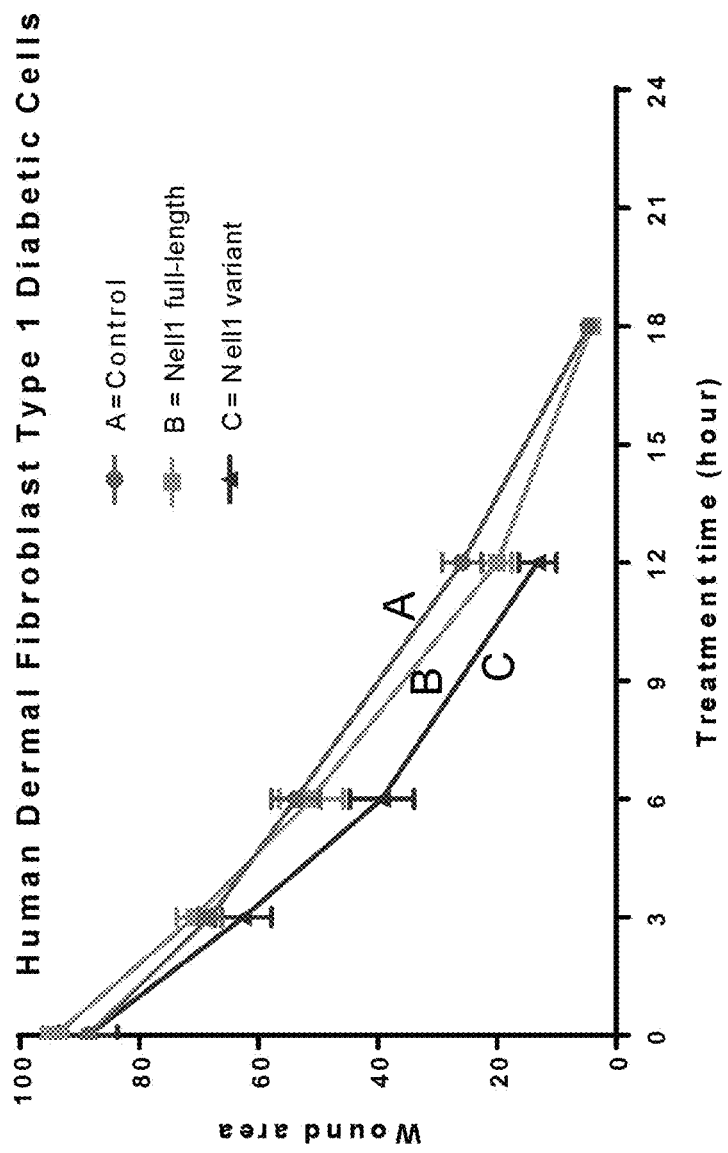
Figure 3D:
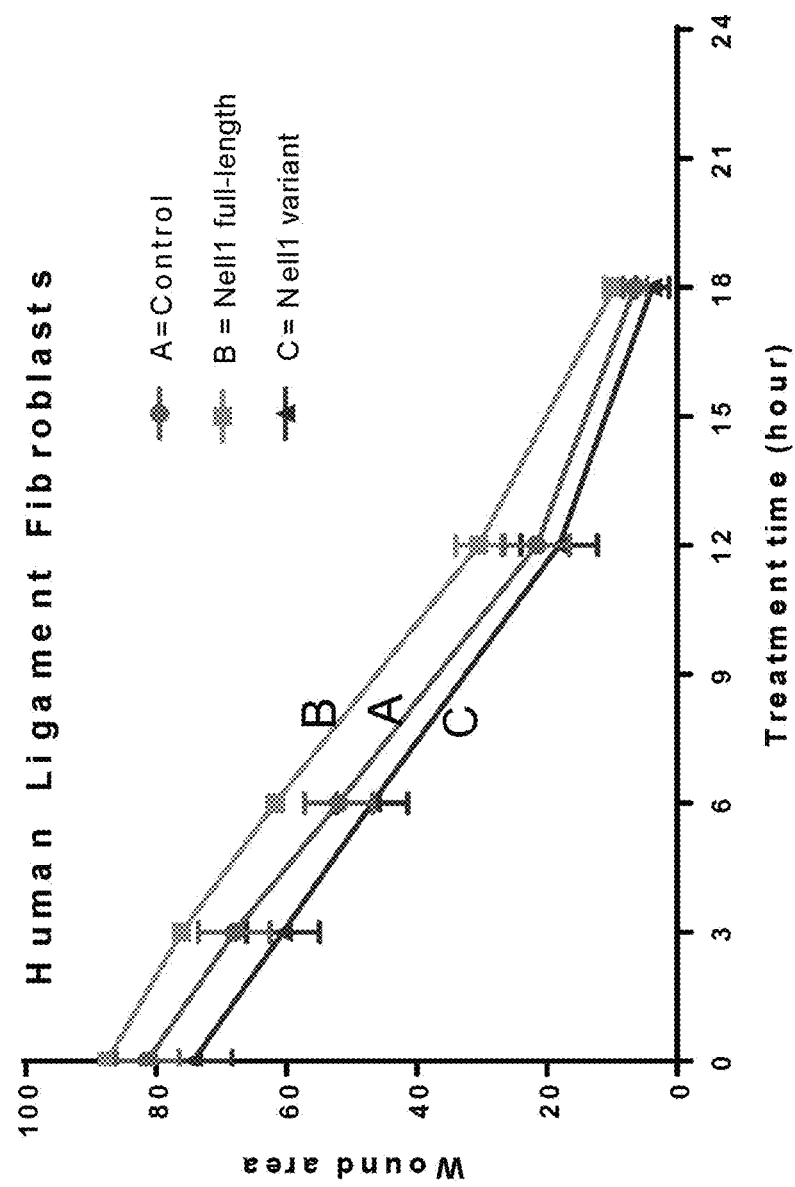

Not only did the NELL1 variant protein increase the rate of normal human dermal fibroblast cell migration, but also the migration of type 1 diabetes dermal fibroblast cells and in a dose dependent manner compared to the full-length NELL1 protein and control untreated cells, with the highest dose tested showing the highest increase in wound closure (FIGS. 3A-3C). The mean migration rates were: 5.7, 6.4, 6.8, and 8.1 for medium control, 100, 200, and 300 ng/ml of NELL1 variant, respectively. Treatment with the NELL1 variant at the highest dose tested (300 ng/ml) also showed increased wound healing in ligament-derived fibroblasts compared to untreated controls (FIG. 3D).

Although full-length NELL1 protein did not promote closure of the wound areas in these initial studies, an alternative dosage of full-length NELL1 protein or alternative culture conditions, for example, growth of the fibroblasts in serum-free medium, might be necessary in order to exhibit such an effect.

Methods

Cells.

The following primary cells were purchased: normal human dermal fibroblasts (ixcells Biotech, Cat. #10HU-014), type 1 diabetes human dermal fibroblasts (ixcells Biotech, Cat. #10HU-014), and normal human ligament fibroblasts (ScienCell Research Lab, Inc., Cat. #2630).

Primary cultures of these human fibroblasts were established in complete Fibroblast Growth Medium (FGM; ScienCell Research Laboratories; Cat. #2301) and incubated in a humidified 37° C., 5% $CO_2$ incubator. The FGM was supplemented with 10% heat-inactivated fetal bovine serum (FBS), penicillin (100 units/ml), streptomycin (100 µg/ml), and other growth factors, according to the protocol of the cell suppliers.

Human Fibroblast Monolayer Scratch (Wound Healing) Assay.

96-well plates were coated with a thin layer of biomatrix according to cell types. The cell numbers were optimized/titrated per well in the plate for each type of cells. Cells were seeded in the log growing phase into each well (maximum of 100 µL per well) on 96-well microplates and cells were incubated overnight in a humidified 37° C., $CO_2$ incubator to form 100% confluent cell monolayers.

An IncuCyte® WoundMaker device/platform was used to create homogeneous, 750-micron wide scratch wounds in the middle of the cell monolayers on 96-well microplates, by strictly following the IncuCyte® WoundMaker protocol. The medium with cell debris was removed immediately after wounding/scratching by gentle aspiration on the side of each well. Each well was carefully replenished with 100 µL per well of fresh pre-warmed medium and any cell debris removed by gentle aspiration on the side of each well. Each well (free of debris) was replenished with 50 µL per well of fresh pre-warmed medium, or 50 µL per well of fresh medium with NELL1 protein (full-length or NELL1 3-612aa variant) with the appropriate concentration to achieve the required dose in each well. Four dosages were tested in at least 4 replicates per treatment: untreated Control (0), 100 ng/mL, 200 ng/mL and 300 ng/mL for each of the NELL1 full-length protein and the NELL1 variant protein. Plates were gently tapped to mix.

The plate with cells was incubated in an IncuCyte® Live-Cell Analysis System. Phase contrast images of cell migration towards the empty space in the wounded area were captured/recorded (10× magnification, digitally zoomed) at time of 0 (start), and then every other hour post wounding and treatments. The time courses of migration of cells in an IncuCyte® Live-Cell Analysis System were recorded. The total pixel of cells in the wounded area before and after treatments was measured using the IncuCyte™ Software. The following calculations were made from the data:

Wound area at timepoints (Tn)—the area between wound boundaries over time

Cell confluence area=Wound area (T0)–Wound area (Tn)

Relative cell confluence in the wound=Cell confluence in the wound/total wound area*100

Wound healing rate=the average velocity at which the cells collectively move into the wound gap; is the absolute value of the slope of curve fitting of cell confluence areas over the times (dA/dt) before 50% cell confluency.

Data were analyzed and plotted out using GraphPad Prism 7.0 (San Diego, Calif.).

Example 4

Effects of NELL1 Peptide on an In Vivo Model of Equine Tendon/Ligament Injury

Tendon injury animal models are well established in horses because of the great demand for treatments of tendon damage, especially in valuable racehorses and show/dressage horses (Schramme et al. (2010) *Vet Comp Orthop Traumatol* 358-365; Estrada et al. (2014) *Vet Comp Orthop Traumatol* 358-365; Nixon et al. (2008) *Am J Vet Res* 69:928-937; Watts et al. (2012) *EVJ* 44(5):576-586). The most common model of damage to the Superficial Digital Flexor Tendon (SDFT) is a good model for the human Achilles tendon, a significant and common injury in human patients. Equine SDFT tendonitis can be created chemically using collagenase or via surgical means.

The following study is performed on a surgically induced SDFT tendonitis equine model.

Twenty-four healthy adult horses are selected and randomly assigned into four groups with six horses per group. The dosing of NELL1 is extrapolated from wound healing studies in horses based on the amount of protein per area of injury. Group 1 is administered saline solution as a control. Group 2 is administered dose 1 (400 micrograms of NELL1). Group 3 is administered dose 2 (800 micrograms of NELL1) and Group 4 is administered dose 3 (1600 micrograms of NELL1).

After general anesthesia, a core lesion of 8 cm in the SDFT of a randomized forelimb is generated with a 3.5 mm synovial resector under ultrasound imaging. Operated limbs are bandaged for two weeks post-operation until sutures are removed. Horses are confined to a stall during this two week period.

NELL1 treatment is administered under sedation via intralesional injection guided by ultrasound imaging, once at seven days post-injury.

Rehabilitation is performed on a treadmill after two weeks with the length of time walking steadily increasing (10 mins/day during weeks 3-6, 20 mins/day during weeks 7-10, 30 mins/day during weeks 11-14, 40 mins/day during weeks 15-20). During weeks 21-22, rehabilitation will be 35 mins/day walking and 5 mins/day trotting. Rehab during weeks 23-24 will consist of 30 mins/day walking and 10 mins/day trotting.

Healing is assessed by a variety of techniques: a) regular ultrasound evaluation at 2-weeks, 4-weeks, 6-weeks, 8-weeks, 12-weeks, 16-weeks, 20-weeks and 24-weeks; b) histological examination of tendons at the end of study; and c) gene expression via quantitative RTPCR techniques of tendon-specific genes (collagen types I, III, decorin, cartilage oligomeric protein (COMP) and Tenascin C.

Example 5

NELL1 Peptide Promotes Healing of Body Wounds in Horse

In order to test the efficacy of the NELL1 protein in healing soft tissue injuries in a large animal model with economic/commercial veterinary significance, purified, recombinant, horse NELL1, full-length protein (NFL) and a variant domain-specific form (NV1) were administered to body wounds of horses. NFL spans amino acids 3-791 of the horse NELL1 protein and contains all the known/predicted domains of the horse NELL1 protein, while NV1 contains amino acids 3-612 and does not contain the last two von willebrand factor domains at the C-terminus of the protein.

Six circular 4-cm diameter wounds (3/side) were created surgically on the thorax of 8 adult female horses to evaluate wound healing. Two days after wounding, during the first dressing change, wounds were treated with one of the following: control—volume equal to that of sterile saline that was used to dilute the stock NELL1 protein; dose 1 (95.2 µg/4-cm wound) of NFL or NV1; or dose 2 (190.4 µg/4-cm wound) of NFL or NV1. NELL1 was delivered by directly infusing a biodegradable, commercially available calcium alginate dressing. Wound healing was assessed over a period of 42 days using a 3-D imaging system (Eykona camera; Bowling et al. (2008) The Eykona Wound Measurement System: Modernizing Wound Measurement for the 21$^{st}$ Century. 12$^{th}$ *Malvern Diabetic Foot Conference,* UK8, May 14-16; and Bowling et al. (2009) *Diabetic Medicine* 26(1):93-96). Researchers administering the treatment and performing the regular wound healing measurements were blinded to the treatment and dosage given to a wound.

Statistical analyses indicated significant healing effects for the variant NELL1 protein that enhanced healing based on the remaining inner unhealed wound area at the end of the study (Day 42 post-treatment). In contrast, there were no statistically significant differences observed between untreated control wounds and those treated with the full-length NELL1 protein (NFL). Interestingly, from days 3-14 post-treatment, wounds treated with NFL had consistently lower unhealed areas compared to controls, but these effects were not increased or sustained until the end of the study.

Six general health parameters were monitored daily throughout the study to evaluate safety: body temperature, pulse rate, respiratory rates, defecation, appetite and behavior/attitude (irritability, aggressiveness or unusual behavior). Results indicated that both NFL and NV1 NELL1 proteins did not elicit adverse effects in the test subjects and therefore, is a safe product to use for wound healing in horses.

This initial equine study suggested that healing effects might be boosted with a second application of the NELL1 protein within the second week. There were strong trends of increased wound healing observed from days 3-14 with both NELL1 proteins, but these trends were not sustained for the full-length NELL1. Future wide range dose optimization studies might provide a statistically significant effect with full-length NELL1 and also enhance the observed effects of the variant NELL1 protein.

Methods

Horses.

Eight mixed-breed, female adult horses, 8 to 15 years old, weighing 453-589 kgs, free of any clinically detectable medical disorder, were housed in individual stalls and were kept under constant conditions (i.e., temperature, feeding, cleaning) throughout the study. They were examined daily for signs of discomfort, lameness, and illness. Horses were randomly assigned numbers (referred to as treatment identification numbers) 1 through 8, and based on their number, received pre-determined grid pattern of wounds, outlined in FIG. 4, and treatments, listed in Table 3.

Wounding Protocol and Treatment Groups.

Figure 4:
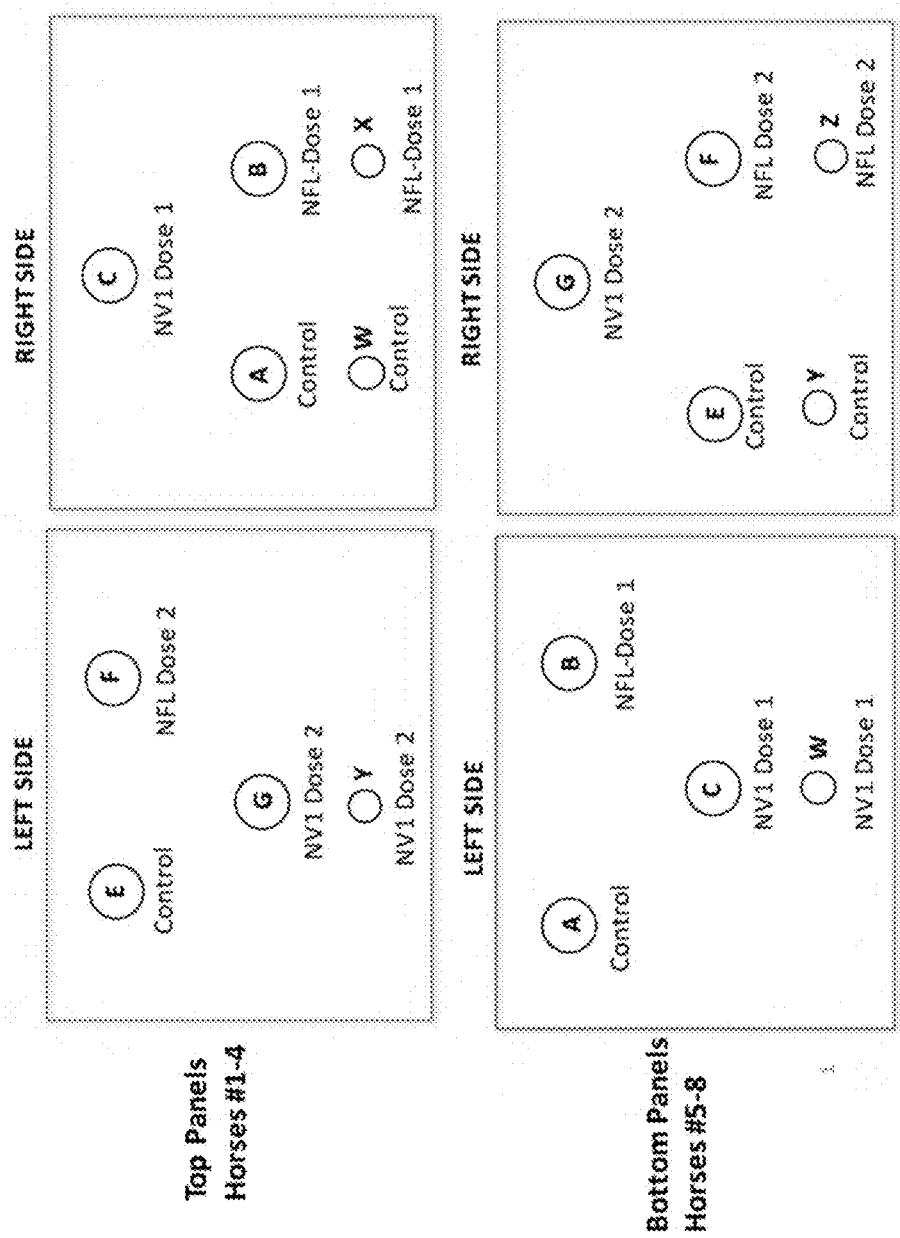
FIG. 4 provides an illustration of the wound grid on each side of the horses indicating the three 4-cm diameter (A, B, C or E, F, G) and the 2-cm diameter cutaneous wounds (W, Y, W and X, or Y and Z) and treatments with control, full-length NELL1 (NFL), or NELL1 variant (NV1). Top grids were for horses 1-4 and the bottom grids were for horses 5-8.
Figure 5:
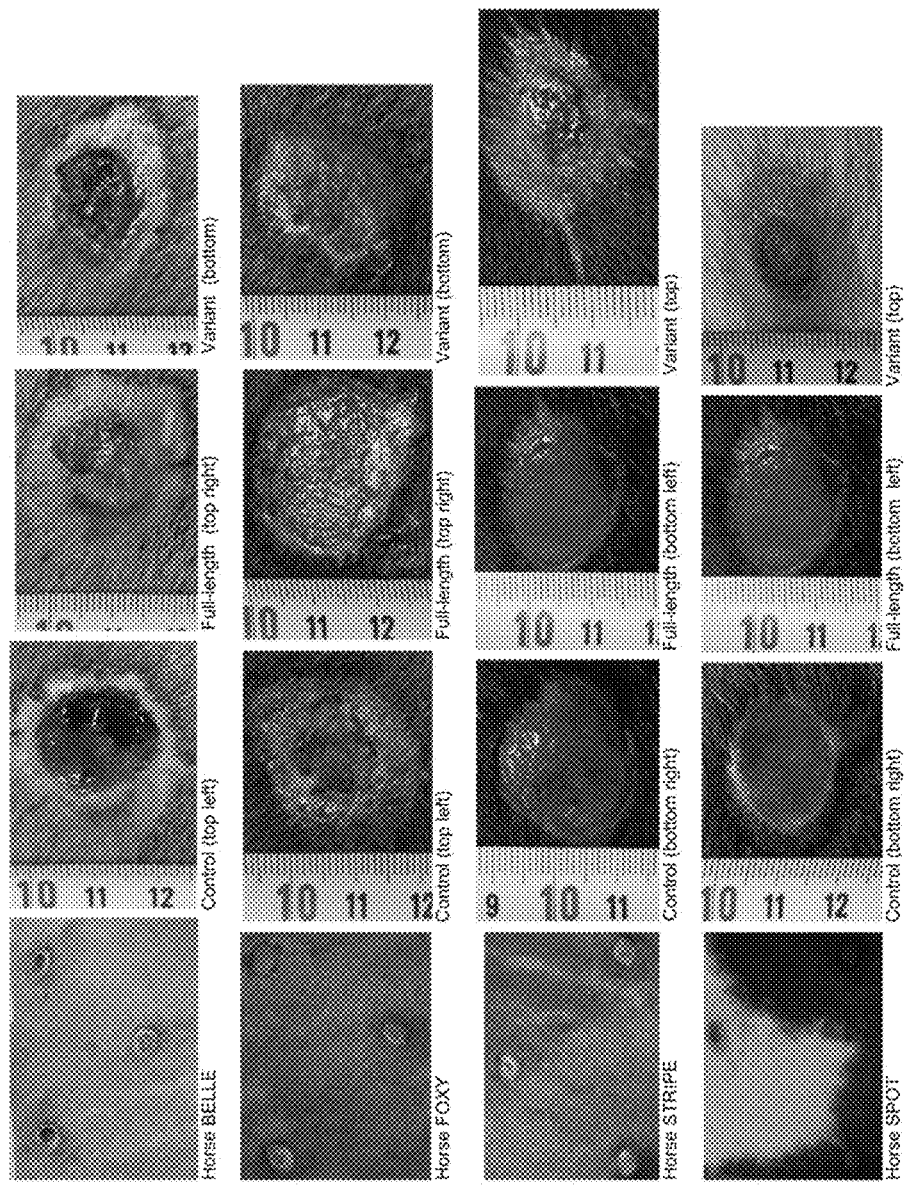
FIG. 5 shows horse body wounds at day 42 post-treatment showing improved healing with NELL1 variant (NV1) compared to full-length NELL1 (NFL) and controls.

All procedures were carried out according to approved IACUC protocol (UTK-IACUC No. 2247-0314). The wound model used was a modification of an established equine model (Schumacher et al. (1992) *Am J Vet Res* 53(9):1568-1571; Gomez et al. (2004) *The Canadian Journal of Veterinary Research* 68:49-55; and Morgan et al. (2009) *J Am Vet Med Assoc* 234(9):1-8). On day 0, each horse was sedated with detomidine HCl (0.006-0.012 mg/kg) and butorphanol (0.006-0.012 mg/kg). Hair on the right and left sides of the thorax was removed with clippers, and the sides of the thorax were prepared for aseptic surgery. Sites of wounds were desensitized with a local anesthetic (2% mepivacaine HCl) subcutaneously. Three, 4-cm diameter and one or two, 2-cm diameter, circular, full-thickness, cutaneous defects were created on the dorsal aspect of the right and left sides of the thorax (FIG. 4). The 4-cm diameter wounds were created at least 8 cm apart from each other, and 2-cm diameter biopsy wounds were created at least 4 cm ventral to the most ventral 4-cm diameter wound(s). All wounds were created using sterilized, 4-cm and 2-cm diameter, stainless steel, custom-made, biopsy punches. 4-cm diameter wounds were allowed to heal over 42 days and were assessed qualitatively and by quantitative measurements (FIG. 5). The large wounds were arranged in a triangular pattern, as illustrated in FIG. 4, designed to prevent solutions applied to the dorsally located wounds from migrating by gravity to the ventral wounds. The smaller wounds generated for biopsy were located directly ventral to the ventral large wounds and were treated identically to the large wounds. Biopsy tissues were collected for future molecular analyses.

Wounds were covered with a sterile, alginate dressing cut to the size of the wound. The dressings were held in place with a sterile, non-adhesive dressing (Telfa Pad, Johnson & Johnson, New Brunswick, N.J.), which was stapled to the skin beneath it. Each side of the thorax was covered with a large, sterile combine to compress the wound and to absorb exudate, if any, from the wound. The dressings and the combines were held in place with a custom-made, belly bandage (Boa Abdominal Bandage; Wire 2 Wire Vet Products, LLC, Lexington, Ky.) positioned over the right and left sides over the thorax, directly over the wounds. Horses received phenylbutazone (2.2 mg/kg, IV) before surgery and for 1 day after surgery (2.2 mg/kg, orally, q12 h).

On day 2 after wounding, the alginate dressings were carefully removed. NELL1 protein of the appropriate dose (FIG. 4, Table 3) or sterile isotonic saline solution (control) was loaded into the alginate dressing cut to the size of the wound. The NELL1-soaked dressing or the isotonic saline solution-soaked dressing was laid directly on the wound and covered with a fresh, sterile, non-absorbent non-adhesive dressing, which was stapled to the skin beneath it. The dressings were removed 2 days later, and thereafter, the wounds were dressed twice weekly with a sterile combine pad applied to each side of the thorax and held in place with the belly bandage. FIG. 4 illustrates the position and designations of the wounds, and Table 3 indicates the treatment applied to each wound.

TABLE 3

NELL1 form and dosage for treatment of horse wounds.

| Horse # | 4-cm diameter wound | 2-cm diameter wound for biopsy | Treatment | Dose |
|---|---|---|---|---|
| 1-4 | A-right side | | Control | NA |
|  | B-right side | | NELL1, full-length (NFL) | 1 = 95.2 µg |
|  | C-right side | | NELL1, Variant 1 (NV1) | 1 = 95.2 µg |
|  |  | W-right side | Control | NA |
|  |  | X-right side | NFL | 1 = 23.7 µg |
|  | E-left side | | Control | NA |
|  | F-left side | | NFL | 2 = 190.4 µg |
|  | G-left side | | NV1 | 2 = 190.4 µg |
|  |  | Y-left side | NV1 | 2 = 47.4 µg |
| 5-8 | A-left side | | control | |
|  | B-left side | | NFL | 1 = 95.2 µg |
|  | C-left side | | NV1 | 1 = 95.2 µg |
|  |  | W-left side | NV1 | 1 = 23.7 µg |
|  | E-right side | | Control | NA |
|  | F-right side | | NFL | 2 = 190.4 µg |
|  | G-right side | | NV1 | 2 = 190.4 µg |
|  |  | Y-right side | Control | NA |
|  |  | Z-right side | NFL | 2 = 47.4 µg |

Following the treatment groups shown in Table 3, the total samples per group were:
Control = 16 big (4-cm) wounds
NFL Dose 1 = 8 big wounds
NV1 Dose 1 = 8 big wounds
NFL Dose 2 = 8 big wounds
NV1 Dose 2 = 8 big wounds Horse NELL1 Protein and Variants.

Purified recombinant horse NELL1 proteins were manufactured as described in Example 1. The efficacy of two forms of NELL1 protein in treating equine wounds was tested. These two forms were the full-length protein (aa3-791), designated as NFL, and one shorter domain-specific variant (aa3-612), designated as NV1. The NELL1 proteins were stored in buffered solution and shipped frozen in dry ice from Abnova Corp. for storage at −80° C. until ready for use. These proteins were used within 4 weeks of delivery.

Dosage and Delivery.

Wounds were treated with a control (isotonic saline solution), NELL1 full-length protein, or the NELL1 variant protein two days after wounding, during the first dressing change. Control treatment was phosphate buffered saline (PBS). Dose 1 (i.e., NELL1 full-length protein) was 95.2 micrograms per 4-cm diameter circular wound, and Dose 2 (i.e., NELL1 variant protein) was 190.4 micrograms per 4-cm diameter wound.

NELL1 proteins were thawed on ice, proper concentrations were prepared, and the buffered NELL1 proteins were loaded/pipetted directly into the selected dressing. The NELL1 protein was loaded in a volume of 2400 µL for application to each of all of the 4-cm diameter wounds, and in a volume of 600 µL for application to each of the 2-cm diameter wounds. These volumes were determined by loading the dressings cut to the sizes of the wounds and by testing various volumes of phosphate-buffered isotonic saline solution to determine maximum loading volume without the solution dripping from the dressing. A 100-mm diameter sterile plastic Petri dish was used for each dressing, and all protein-soaked dressings were prepared under sterile conditions in a tissue culture hood. Each Petri dish was labelled with the horse treatment identification number and the type and dose of the protein applied.

Evaluation of Wound Healing 3-D Imaging.

Wound measurements were taken from images obtained from a digital, 3-D wound imaging device that enables rapid, secure, repeatable collection of wound data (TOMI 3D, Eykona Medical, USA). Images were acquired at the following time points: time of wounding, initial treatment, each dressing change (i.e., twice weekly), and at the termination of study.

Data Analyses.

All images were downloaded onto a computer with image analysis software developed by Eykona. The images were then analyzed individually using a trace-area function in the software. The outer most margin of the wound was measured first and the area recorded in $mm^2$. These values were recorded over the various time points to determine the rate of wound contraction. The inner area, or non-epithelialized area, was then measured in similar fashion by tracing the area outlined by the epithelial margin. These values were recorded over time and used to calculate the rate of epithelialization.

Because there was some degree of variation in the initial size of the wounds, all measurements were normalized on a percent scale so that the initial wound measurement reflected 100% of the size of the wound. Changes in the overall area of the wound and of the epithelialized area were then subsequently expressed as a percentage. Rates of contraction and epithelialization were expressed as $mm^2/day$.

Rate of contraction was calculated by subtracting the area of the wound at one time-point from the determined area of the wound at the previous time-point and then dividing the difference in area by the number of days between those two time-points. An overall rate of contraction was calculated by subtracting the final area of the wound from the initial area of the wound and dividing the difference by the total number of days between those two time-points. The area of epithelialization for each 4-cm diameter wound was calculated by subtracting the area of the wound from the area of granulation tissue, and the rate of epithelialization was then calculated in similar fashion by subtracting the area of epithelialization at one time-point from the area of epithelialization at the previous time-point and then dividing the difference in area by the number of days between those two time-points.

Results and Discussion

Overall Health Effects of NELL1 Protein.

All horses were monitored daily throughout the study period. No adverse effects on the health and behavior of the horses were observed. The temperature, pulse and respiratory rates, defecation, appetite, and attitude of the horses were monitored daily and were within normal limits throughout the 42-day study.

Delivery of NELL1 Protein Via Calcium Alginate Dressing.

This study is the first in which NELL1 protein was administered into soft tissue injuries in horses using a calcium alginate dressing. The selection of this dressing was based upon a previous in vitro study comparing the release of NELL1 protein from a collagen and a calcium alginate commercial dressing. The elution profiles suggested that in a calcium alginate carrier, the NELL1 protein is released within 2-3 days. In this in vivo study, at day 3 post-treatment there was no visual evidence of the dressing and no abnormal acute inflammatory reactions were observed.

Effects of NELL1 on Wound Healing (Days 3-42, Rates of Wound Healing, Epithelialization and Contraction).

For all data analyses, at a given time point, the total area of the wound, the inner area (i.e. the area filled with granulation tissue) and the epithelialized area (i.e., the difference between the total area and the inner area) were calculated for each 4-cm diameter wound of each horse from images obtained at the time of each bandage change. Each measurement was represented as a change in $mm^2$ relative to the previous measurement.

Data was also normalized to account for variation in wound sizes at day 0 and considers that all wounds are at 100% value (all unhealed areas) before treatment.

Figure 6:
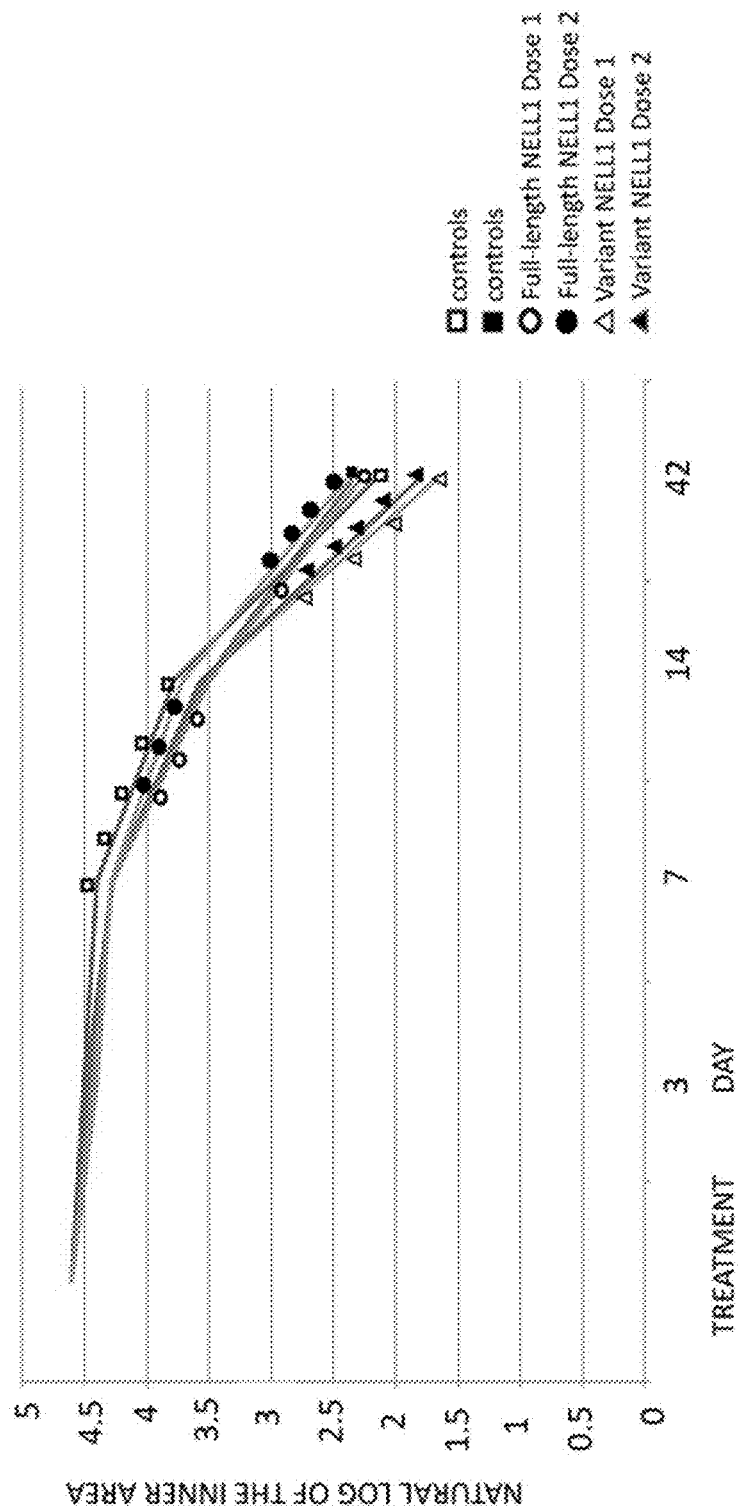
FIG. 6 shows a graph of the natural log values of the inner area in horse wounds that remain unhealed on days post-treatment with full-length (lines 3 and 4) or variant NELL1 protein (lines 5 and 6) and untreated control wounds (lines 1 and 2).

For statistical analyses, cumulative data from each treatment group were analyzed. Initially, standard T-TEST using Microsoft Excel (Windows 7) was used to compare these changes, and the p values were calculated. At day 42 (last day of observation/end of experimental part), analyses of normalized data of inner area (unhealed) indicated strong trends in the wounds treated with the variant NELL1 form ($p=0.08$ for both Dose 1 and Dose 2; $p=0.04$ for all wounds treated with the variant regardless of dose). Data shows that horse wounds at Day 42 treated with NELL1 variant showed faster healing (smaller unhealed inner area) compared to control. The wounds have smaller areas that remain unhealed and the variation/standard deviation was consistently lower in wounds treated with the smaller NELL1 variant compared to controls and those treated with the full-length form (FIGS. 5 and 6 and Table 4).

TABLE 4

Healing of 4-cm horse body wounds based on the remaining unhealed inner area at various days post-treatment with a degradable calcium alginate dressing infused with saline solution (untreated controls), full-length (amino acids #3-791) or variant (amino acids #3-612) horse NELL1 protein.

| | OBSERVATIONS (N) | MEAN ($mm^2$) | STANDARD DEVIATION |
|---|---|---|---|
| CONTROL (UNTREATED) | | | |
| Day 3 (T3) | 16 | 90.1 | 5.9 |
| Day 7 (T7) | 16 | 76.7 | 10.5 |
| Day 14 (T14) | 16 | 39.2 | 9.5 |
| Day 42 (T42) | 16 | 9.8 | 5.4 |
| FULL-LENGTH NELL1: DOSE 1 | | | |
| T3 | 8 | 85.8 | 4.9 |
| T7 | 8 | 71.1 | 9.7 |
| T14 | 8 | 32.1 | 6.2 |
| T42 | 8 | 10.3 | 7.9 |
| FULL-LENGTH NELL1: DOSE 2 | | | |
| T3 | 8 | 81.7 | 7.5 |
| T7 | 8 | 72.3 | 10.9 |
| T14 | 8 | 41.0 | 6.5 |
| T42 | 8 | 11.0 | 9.9 |
| VARIANT NELL1 (aa #3-612): DOSE 1 | | | |
| T3 | 8 | 85.3 | 8.6 |
| T7 | 8 | 72.3 | 8.4 |
| T14 | 8 | 31.2 | 14.6 |
| T42 | 8 | 5.5 | 3.9 |

TABLE 4-continued

Healing of 4-cm horse body wounds based on the remaining unhealed inner area at various days post-treatment with a degradable calcium alginate dressing infused with saline solution (untreated controls), full-length (amino acids #3-791) or variant (amino acids #3-612) horse NELL1 protein.

| | OBSERVATIONS (N) | MEAN (mm$^2$) | STANDARD DEVIATION |
|---|---|---|---|
| VARIANT NELL1 (aa #3-612): DOSE 2 | | | |
| T3 | 8 | 86.8 | 5.7 |
| T7 | 8 | 72.2 | 4.3 |
| T14 | 8 | 35.5 | 4.0 |
| T42 | 8 | 6.2 | 2.8 |

Wounds treated with full-length NELL1 did not show significant differences or trend towards better healing at day 42. Interestingly, wounds treated with full-length NELL1 showed significant differences in having a smaller inner unhealed area with Dose 2 at 3 days post-treatment (p=0.03)

Because wound healing is not a linear process and previous reports suggested plotting log-transformed values, data was converted into log values and plotted (Gelfand et al. (2002) *The Society for Investigative Dermatology* 119: 1420-1425). These log values were then used for graphical representation of the data (FIG. 6). Consistent with the initial analyses, the graphs for wounds treated with the smaller variant showed a trend for better healing from the controls and at after day 14, these wounds start to heal faster than the other treatment groups.

In addition to the standard T-test, additional statistical tools and approaches were used to analyze the data. A mixed-model ANOVA was used to analyze the data to factor in fixed and random effects and the study design where a single horse was given several different treatments (2 NELL1 protein forms and 2 doses per form).

When treatments were analyzed individually, there are significant differences by the mean rate of healing through time and these time patterns differ by treatment. This was also observed for the other parameters such as rate of contraction, rate of epithelialization, and overall healing rate. The mixed model ANOVA analyses confirmed the earlier results where treatment with NELL1 variant showed faster healing (smaller unhealed inner area) compared to control.

SUMMARY AND CONCLUSIONS

NELL1 horse proteins did not elicit any adverse effects on the wounds, over-all health and behavior of the horses. Horse NELL1 protein is deemed to be a safe product in the manner delivered and dosages tested in this study. This is the first known application of the horse NELL1 protein into an animal model.

NELL1 protein can be effectively and efficiently delivered into horse body wounds via a calcium alginate biodegradable dressing. The dressing enables delivery into the soft tissue injury within three days, wherein the entire dressing was completely absorbed into the wounds (by visual/macroscopic examination). This study represents the first known test in vivo of a calcium alginate dressing to administer NELL1 protein into soft tissue injuries.

NELL1 variant protein exhibited effects that promoted wound healing as measured by the remaining inner unhealed area assessed at day 42 post-treatment. The standard deviation for treatment at both doses was very low compared to either control or full-length NELL. There was no statistically significant difference between the two tested doses.

There were no statistically significant effects nor strong trends for control wounds or those treated with full-length NELL1 (except for day 3 post-treatment for NFL Dose 2, p=0.03) and the variations were large for both of these groups compared to the NELL1 variant form.

The mixed model analysis indicated that the pattern of healing over time was significantly different between the various treatment groups. The log graphs of inner unhealed area size for the different groups showed that the NELL1 variant treated wounds started differentiation or separation from the other treatments after day 14. These data suggested that perhaps a re-application of the NELL1 protein (before the end of 14 days) might sustain the effects beyond the initial weeks and yield more dramatic effects than initially observed in this study.

Those skilled in the art will further appreciate that the present invention may be embodied in other specific forms without departing from the spirit or central attributes thereof. In that the foregoing description of the present invention discloses exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A NELL1 peptide fragment or variant thereof having at least 95% sequence identity to SEQ ID NO: 17 or 18, wherein said NELL1 peptide fragment or variant thereof has at least one of the properties selected from the group consisting of:
   a) enhanced efficacy in tissue regeneration,
   b) enhanced promotion of wound healing,
   c) easier purification,
   d) higher yield, and
   e) less aggregate formation,
      when compared to the fragment's respective full-length NELL1 protein; and
   wherein said NELL1 peptide fragment or variant thereof lacks the carboxy-terminal 179 amino acid residues of the fragment's respective full-length NELL1 protein.

2. The NELL1 peptide fragment or variant thereof of claim 1, wherein said NELL1 peptide fragment comprises the amino acid sequence set forth in SEQ ID NO: 17 or 18.

3. The NELL1 peptide fragment or variant thereof of claim 1, wherein said NELL1 peptide fragment consists of the amino acid sequence set forth in SEQ ID NO: 17 or 18.

4. A pharmaceutical composition comprising the NELL1 peptide fragment or variant thereof of any one of claims 1, 2, and 3.

5. The pharmaceutical composition of claim 4, wherein said NELL1 peptide fragment or variant thereof is incorporated into a drug eluting device, scaffold, matrix, or sutures.

6. The pharmaceutical composition of claim 5, wherein said NELL1 peptide fragment or variant thereof is incorporated into a hydrogel, calcium alginate wound dressing, or calcium alginate matrix.

7. A kit comprising the NELL1 peptide fragment or variant thereof of any one of claims 1, 2, and 3.

* * * * *